(12) United States Patent
Elmén

(10) Patent No.: US 8,440,637 B2
(45) Date of Patent: May 14, 2013

(54) COMBINATION TREATMENT FOR THE TREATMENT OF HEPATITIS C VIRUS INFECTION

(75) Inventor: Joacim Elmén, Malmö (SE)

(73) Assignee: Santaris Pharma A/S, Hørsholm (DK)

( * ) Notice: Subject to any disclaimer, the term of this patent is extended or adjusted under 35 U.S.C. 154(b) by 336 days.

(21) Appl. No.: 12/681,591

(22) PCT Filed: Oct. 3, 2008

(86) PCT No.: PCT/DK2008/000345
§ 371 (c)(1),
(2), (4) Date: Jul. 26, 2010

(87) PCT Pub. No.: WO2009/043354
PCT Pub. Date: Apr. 9, 2009

(65) Prior Publication Data
US 2010/0280099 A1     Nov. 4, 2010

Related U.S. Application Data

(60) Provisional application No. 60/977,497, filed on Oct. 4, 2007, provisional application No. 60/979,217, filed on Oct. 11, 2007, provisional application No. 61/028,062, filed on Feb. 12, 2008.

(30) Foreign Application Priority Data

Jul. 17, 2008   (EP) .................................. 08104780

(51) Int. Cl.
*C12N 15/11*     (2006.01)
*A61K 48/00*    (2006.01)
*C07H 21/02*    (2006.01)
*C07H 21/04*    (2006.01)

(52) U.S. Cl.
USPC ......................................... 514/44 A; 536/24.5

(58) Field of Classification Search ..... 514/44; 536/24.5
See application file for complete search history.

(56) References Cited

U.S. PATENT DOCUMENTS

| | | |
|---|---|---|
| 4,914,210 A | 4/1990 | Levenson et al. |
| 4,920,115 A | 4/1990 | Nestler et al. |
| 4,962,029 A | 10/1990 | Levenson et al. |
| 5,919,795 A | 7/1999 | Chang et al. |
| 6,030,785 A | 2/2000 | Katze et al. |
| 6,121,283 A | 9/2000 | Chang et al. |

(Continued)

FOREIGN PATENT DOCUMENTS

| EP | 0 699 751 A1 | 3/1996 |
|---|---|---|
| EP | 1 099 442 A2 | 5/2001 |

(Continued)

OTHER PUBLICATIONS

Beaucage, L. and Iyer, R., "Advances in the Synthesis of Oligonucleotides by the Phosphoramidite Approach," *Tetrahedron* 48:2223-2311, Pergamon Press, United Kingdom (1992).

(Continued)

*Primary Examiner* — Terra Cotta Gibbs
(74) *Attorney, Agent, or Firm* — Sterne, Kessler, Goldstein & Fox P.L.L.C.

(57) ABSTRACT

The present invention relate to the use of a combination of an inhibitor of miR-122 and an inhibitor of VLDL assembly, for the treatment of HCV, hyperlipidemia and hypercholesterolemia.

14 Claims, 37 Drawing Sheets

U.S. PATENT DOCUMENTS

| | | | |
|---|---|---|---|
| 6,284,458 B1 | 9/2001 | Anderson et al. | |
| 6,423,489 B1 | 7/2002 | Anderson et al. | |
| 6,433,159 B1 | 8/2002 | Anderson | |
| 7,087,229 B2 | 8/2006 | Zhao et al. | |
| 7,307,067 B2 | 12/2007 | Sarnow et al. | |
| 8,163,708 B2 | 4/2012 | Elmen et al. | |
| 2003/0068320 A1 | 4/2003 | Dingivan | |
| 2004/0204356 A1 | 10/2004 | Guenzler-Pukall et al. | |
| 2005/0069522 A1 | 3/2005 | Colonno et al. | |
| 2005/0182005 A1 | 8/2005 | Tuschl et al. | |
| 2005/0227934 A1 | 10/2005 | Stoffel et al. | |
| 2005/0261218 A1 | 11/2005 | Esau et al. | |
| 2006/0035212 A1 | 2/2006 | Balakireva | |
| 2006/0035858 A1 | 2/2006 | Geary et al. | |
| 2006/0040989 A1 | 2/2006 | Meerpoel et al. | |
| 2006/0058266 A1 | 3/2006 | Manoharan et al. | |
| 2006/0185027 A1 | 8/2006 | Bartel et al. | |
| 2006/0265771 A1 | 11/2006 | Lewis et al. | |
| 2007/0049547 A1 | 3/2007 | Esau et al. | |
| 2009/0082297 A1 | 3/2009 | Lioy et al. | |
| 2009/0143326 A1 | 6/2009 | Obad et al. | |
| 2009/0298916 A1 | 12/2009 | Kauppinen et al. | |
| 2010/0004320 A1 | 1/2010 | Elmen et al. | |
| 2010/0298410 A1 | 11/2010 | Obad et al. | |
| 2010/0330035 A1 | 12/2010 | Hildebrandt-Eriksen et al. | |
| 2011/0077288 A1 | 3/2011 | Kauppinen et al. | |

FOREIGN PATENT DOCUMENTS

| | | |
|---|---|---|
| EP | 0 662 157 B1 | 6/2001 |
| EP | 1 222 309 B1 | 7/2005 |
| EP | 1747023 B1 | 1/2011 |
| EP | 1931782 B1 | 1/2011 |
| WO | WO 95/30746 A1 | 11/1995 |
| WO | WO 99/14226 A2 | 3/1999 |
| WO | WO 00/56746 A2 | 9/2000 |
| WO | WO 00/56748 A1 | 9/2000 |
| WO | WO 00/66604 A2 | 11/2000 |
| WO | WO 01/23613 A1 | 4/2001 |
| WO | WO 01/25248 A2 | 4/2001 |
| WO | WO 02/28875 A2 | 4/2002 |
| WO | WO 02/081494 A1 | 10/2002 |
| WO | WO 02/094250 A2 | 11/2002 |
| WO | WO 03/006475 A2 | 1/2003 |
| WO | WO 03/011887 A2 | 2/2003 |
| WO | WO 03/029459 A2 | 4/2003 |
| WO | WO 03/070750 A2 | 8/2003 |
| WO | WO 03/095467 A1 | 11/2003 |
| WO | WO 2004/044181 A2 | 5/2004 |
| WO | WO 2004/046160 A2 | 6/2004 |
| WO | WO 2004/069991 A2 | 8/2004 |
| WO | WO 2004/076622 A2 | 9/2004 |
| WO | WO 2005/013901 A2 | 2/2005 |
| WO | WO 2005/013905 A2 | 2/2005 |
| WO | WO 2005/023986 A2 | 3/2005 |
| WO | WO 2005/054494 A2 | 6/2005 |
| WO | WO 2005/058824 A2 | 6/2005 |
| WO | WO 2005/061710 A1 | 7/2005 |
| WO | WO 2005/078139 A2 | 8/2005 |
| WO | WO 2005/079397 A2 | 9/2005 |
| WO | WO 2005/098029 A2 | 10/2005 |
| WO | WO 2005/103298 A2 | 11/2005 |
| WO | WO 2005/107816 A2 | 11/2005 |
| WO | WO 2006/010423 A2 | 2/2006 |
| WO | WO 2006/020676 A2 | 2/2006 |
| WO | WO 2006/020768 A2 | 2/2006 |
| WO | WO 2006/027776 A2 | 3/2006 |
| WO | WO 2006/036916 A2 | 4/2006 |
| WO | WO 2006/053430 A1 | 5/2006 |
| WO | WO 2006/069584 A2 | 7/2006 |
| WO | WO 2006/093526 A2 | 9/2006 |
| WO | WO 2006/112872 A2 | 10/2006 |
| WO | WO 2006/113910 A2 | 10/2006 |
| WO | WO 2006/133022 A2 | 12/2006 |
| WO | WO 2006/137941 A2 | 12/2006 |
| WO | WO 2007/021896 A2 | 2/2007 |
| WO | WO 2007/027775 A2 | 3/2007 |
| WO | WO 2007/027894 A2 | 3/2007 |
| WO | WO 2007/031081 A2 | 3/2007 |
| WO | WO 2007/031091 A2 | 3/2007 |
| WO | WO 2007/090073 A2 | 8/2007 |
| WO | WO 2007/112753 A2 | 10/2007 |
| WO | WO 2007/112754 A2 | 10/2007 |
| WO | WO 2007/134181 A2 | 11/2007 |
| WO | WO 2007/146511 A2 | 12/2007 |
| WO | WO 2008/025025 A2 | 2/2008 |
| WO | WO 2008/034122 A2 | 3/2008 |
| WO | WO 2008/034123 A2 | 3/2008 |
| WO | WO 2008/046911 A2 | 4/2008 |
| WO | WO 2008/057234 A2 | 5/2008 |
| WO | WO 2008/061537 A2 | 5/2008 |
| WO | WO 2008/074328 A2 | 6/2008 |
| WO | WO 2008/091703 A2 | 7/2008 |
| WO | WO 2008/113832 A2 | 9/2008 |
| WO | WO 2008/124384 A2 | 10/2008 |
| WO | WO 2008/150729 A2 | 12/2008 |
| WO | WO 2008/154401 A2 | 12/2008 |
| WO | WO 2009/020771 A2 | 2/2009 |
| WO | WO 2009/032083 A1 | 3/2009 |
| WO | WO 2009/043353 A2 | 4/2009 |
| WO | WO/2009/043354 | 4/2009 |
| WO | WO/2009/109665 | 9/2009 |
| WO | WO/2010/000665 | 1/2010 |
| WO | WO 2010/012667 A1 | 2/2010 |
| WO | WO/2011/048125 | 4/2011 |

OTHER PUBLICATIONS

Beaucage, L. and Iyer, R., "The Synthesis of Modified Oligonucleotides by the Phosphoramidite Approach and Their Applications," *Tetrahedron 49*:6123-6194, Pergamon Press, United Kingdom (1993).

Boutla, A., et al., "Developmental defects by antisense-mediated inactivation of micro-RNAs 2 and 13 in *Drosophila* and the identification of putative target genes," *Nucleic Acids Res. 31*:4973-4980, Oxford University Press, United Kingdom (2003).

Crooke, S., "Chapter 3: In Vitro Cellular Uptake, Distribution, and Metabolism of Oligonucleotides," in *Antisense Research and Application 131*:103-140, Springer-Verlag, Berlin, Germany (1998).

Dass, C., "Vehicles for oligonucleotide delivery to tumors," *J. Pharm. Pharmacol. 54*:3-27, Pharmaceutical Press, United Kingdom (2002).

Davidson, N. and Shelness, G., "Apolipoprotein B: mRNA Editing, Lipoprotein Assembly, and Presecretory Degradation," *Annu. Rev. Nutr. 20*:169-193, Annual Reviews, United States (2000).

Elmén, J., et al., "LNA-mediated microRNA silencing in non-human primates," *Nature 452*:896-900, Nature Publishing Group, United Kingdom (2008).

Elmén, J., et al., "LNA-mediated microRNA silencing in non-human primates," [Supplementary Information] *Nature 452*, 33 pages, Nature Publishing Group, United Kingdom (2008).

Esau, C., et al., "MicroRNA-143 Regulates Adipocyte Differentiation," *J. Biol. Chem. 279*:52361-52365, American Society for Biochemistry and Molecular Biology, United States (2004).

Freier, S. and Altmann, K.-H., "The ups and downs of nucleic acid duplex stability: structure—stability studies on chemically-modified DNA: RNA duplexes," *Nucleic Acids Res. 25*:4429-4443, Oxford University Press, United Kingdom (1997).

Heid, C., et al., "Real Time Quantitative PCR," *Genome Res. 6*:986-994, Cold Spring Harbor Laboratory Press, United States (1996).

Huang, H., et al., "Hepatitis C virus production by human hepatocytes dependent on assembly and secretion of very low-density lipoproteins," *Proc. Natl. Acad. Sci. U.S.A. 104*:5848-5853, National Academy of Sciences, United States (2007).

Hutton, J., "Renaturation kinetics and thermal stability of DNA in aqueous solutions of formamide and urea," *Nucleic Acids Res. 4*:3537-3555, Oxford University Press, United Kingdom (1977).

Jopling, C., "Modulation of Hepatitis C Virus RNA Abundance by a Liver-Specific MicroRNA," *Science 309*:1577-1571, American Assn. for the Advancement of Science, United States (2005).

Lecellier, C.-H., et al., "A Cellular MicroRNA Mediates Antiviral Defense in Human Cells," *Science 308*:557-560, American Assn. for the Advancement of Science, United States (2005).

Lecellier, C.-H., et al., "A Cellular MicroRNA Mediates Antiviral Defense in Human Cells," [Supporting Online Material] *Science* 308:557-560, American Assn. for the Advancement of Science, United States (2005).

Naguibneva, I., et al., "The microRNA *miR-181* targets the homeobox protein Hox-A11 during mammalian myoblast differentiation," *Nature Cell Biol.* 8:1-7, Nature Publishing Group, United States (2006).

Pedersen, D., et al., "Preparation of LNA Phosphoramidites," *Synthesis* 6:802-808, Thieme/Academic Press, Germany (2002).

Pedersen, D., and Koch, T., "Analogues of LNA (Locked Nucleic Acid). Synthesis of the 2'Thio-LNA Thymine and 5-Methyl Cytosine Phosphoramidites," *Synthesis* 4:578-582, Thieme/Academic Press, Germany (2003).

Randall, G., et al., "Cellular cofactors affecting hepatitis C virus infection and replication," *Proc. Natl. Acad. Sci. USA* 104:12884-12889, National Academy of Sciences, United States (2007).

Rosenbohm, C., et al., "Synthesis of 2'-amino-LNA: a new strategy," *Org. Biomol. Chem.* 1:655-663, Royal Society of Chemistry, United Kingdom (2003).

Singh, S. and Wengel, J., "Synthesis of Novel Bicyclo[2.2.1] Ribonucleosides: 2'-Amino- and 2'-Thio-LNA Monomeric Nucleosides," *J. Org. Chem.* 63:6078-6079, American Chemical Society, United States (1998).

Sørensen, M., et al.,"α-L-*ribo*-Configured Locked Nucleic Acid (α-L-LNA): Synthesis and Properties," *J. Am. Chem. Soc.* 124:2164-2176, American Chemical Society, United States (2002).

Uhlmann, E., "Recent advances in the medicinal chemistry of antisense oligonucleotides," *Curr. Opin. Drug Discov. Develop.* 3:203-213, Thomson Reuters (Scientific) Ltd., United Kingdom (2000).

International Search Report for International Application No. PCT/DK2007/000168, European Patent Office, mailed on Jan. 28, 2008.

International Search Report for International Application No. PCT/DK2008/000345, European Patent Office, mailed on Jul. 10, 2009.

The Written Opinion of the International Searching Authority for International Application No. PCT/DK2008/000345, European Patent Office, mailed on Apr. 7, 2010.

International Search Report for International Application No. PCT/DK2008/000344, European Patent Office, mailed on Jul. 10, 2009.

International Search Report for International Application No. PCT/EP2009/052728, European Patent Office, mailed on Jul. 31, 2009.

International Search Report for International Application No. PCT/DK2007/000169, European Patent Office, mailed on Mar. 7, 2008.

Co-pending U.S. Appl. No. 12/245,544, filed Oct. 3, 2008, United States Patent Office, Alexandria, VA., United States (Not Published).

Co-pending U.S. Appl. No. 12/400,625, filed Mar. 9, 2009, United States Patent Office, Alexandria, VA., United States (Not Published).

Co-pending U.S. Appl. No. 12/681,587, filed Apr. 2, 2010 , United States Patent Office, Alexandria, VA., United States (Not Published).

Co-pending U.S. Appl. No. 12/767,631, filed Apr. 26, 2010 , United States Patent Office, Alexandria, VA., United States (Not Published).

Abelson, J., et al., "Sequence Variants in *SLITRK1* Are Associated with Tourette's Syndrome," *Science* 310:317-320, American Association for the Advancement of Science, United States (2005).

Agrawal, S., "Importance of nucleotide sequence and chemical modifications of antisense oligonucleotides," *Biochim. Biophys. Acta* 1489:53-68, Elsevier, Netherlands (1999).

Agrawal, S. and Zhao, Q., "Antisense therapeutics," *Curr. Opin. Chem. Biol.* 2:519-528, Elsevier, United Kingdom (1998).

Agrawal, S., et al., "Mixed-backbone oligonucleotides as second generation antisense oligonucleotides: In vitro and in vivo studies," *Proc. Natl. Acad. Sci. USA* 94:2620-2625, National Academy of Sciences, United States (1997).

Agrawal, S., et al., "Pharmacokinetics, biodistribution, and stability of oligodeoxynucleotide phosphorothioates in mice," *Proc. Natl. Acad. Sci. USA* 88:7595-7599, National Academy of Sciences, United States (1991).

Akhtar, S., "Antisense Technology: Selection and Delivery of Optimally Acting Antisense Oligonucleotides," *J. Drug Target.* 5:225-234, Informa Healthcare, United States (1998).

Alvarez-Garcia, I. and Miska, E., "MicroRNA functions in animal development and human disease," *Development* 132:4653-4662, The Company of Biologists, Ltd., United Kingdom (2005).

Ambros, V., "The functions of animal microRNAs," *Nature* 431:350-355, Nature Publishing Group, United Kingdom (2004).

Ameres, S., et al., "Molecular Basis for Target RNA Recognition and Cleavage by Human RISC," *Cell* 130:101-112, Cell Press, United States (2007).

Asangani, I., et al., "MicroRNA-21 (miR-21) post-transcriptionally downregulates tumor suppressor Pdcd4 and stimulates invasion, intravasation and metastasis in colorectal cancer," *Oncogene* 27:2128-2136, Nature Publishing Group, United Kingdom (2008).

Bai, S., et al., "MicroRNA-122 inhibits tumorigenic Properties of Hepatocellular Carcinoma Cells and Sensitizes These Cells to Sorafenib," *J. Biol. Chem.* 284:32015-32027, American Society for Biochemistry and Molecular Biology, United States (2009).

Bartel, D., "MicroRNAs: Genomics, Biogenesis, Mechanism, and Function," *Cell* 116:281-297, Cell Press, United States (2004).

Bartenschlager, R. and Pietschmann, T., "Efficient hepatitis C virus cell culture system: What a difference the host cell makes," *Proc. Natl. Acad. Sci. USA* 102:9739-9740, National Academy of Sciences, United States (2005).

Bartosch, B., et al., "Cell Entry of Hepatitis C Virus Requires a Set of Co-receptors That Include the CD81 Tetraspanin and the SR-B1 Scavenger Receptor," *J. Biol. Chem.* 278:41624-41630, American Society for Biochemistry and Molecular Biology, United States (2003).

Bennett, C., "MicroRNAs as therapeutic targets," Abstracts of Papers, 234th ACS National Meeting, Aug. 19-23, 2007, Boston, MA, United States, CARB-047, Database: CAPLUS (2007), 1 page.

Bennett, C., et al., "Antisense Oligonucleotide-based Therapeutics," in *Gene and Cell Therapy*, 2nd Ed., pp. 347-374, Templeton, N., ed., Marcel Dekker, Inc., United States (2004).

Bhat, B., et al., "2'-O-Methoxyethyl/2'-Fluoro Modified Oligonucleotides Result in More Potent Inhibition of micro RNA-122 in Vivo: A Target Implicated in HCV Replication," *Nucleic Acids Symposium Series* 52:69, Oxford University Press, United Kingdom (2008).

Boehm, M. and Slack, F., "A Developmental Timing MicroRNA and Its Target Regulate Life Span in *C. elegans*," *Science* 310:1954-1957, American Association for the Advancement of Science, United States (2005).

Boutla, A., et al., "Short 5'-phosphorylated double-stranded RNAs induce RNA interference in *Drosophila*," *Curr. Biol.* 11:1776-1780, Cell Press, United States (2001).

Braasch, D., et al., "Antisense inhibition of gene expression in cells by oligonucleotides incorporating locked nucleic acids: effect of mRNA target sequence and chimera design," *Nucleic Acids Res.* 30:5160-5167, Oxford University Press, United Kingdom (2002).

Branch, A., "A good antisense molecule is hard to find," *Trends Biochem. Sci.* 23:45-50, Elsevier Science Ltd., United Kingdom (1998).

Branch, A. and Rice, C.,"Antisense Gets a Grip on miR-122 in Chimpanzees," *Sci. Transl. Med.* 2:1-4, American Association for the Advancement of Science, United States (2010).

Brennecke, J., et al., "*bantam* Encodes a Developmentally Regulated microRNA that Controls Cell Proliferation and Regulates the Proapoptotic Gene *hid* in *Drosophila*," *Cell* 113:25-36, Cell Press, United States (2003).

Brennecke, J., et al., "Principles of MicroRNA-Target Recognition," *PLoS Biology* 3:E85/0404-E85/0418, Public Library of Science, United States (2005).

Calin, G. and Croce, C., "MicroRNA signatures in human cancers," *Nat. Rev. Cancer* 6:857-866, Nature Publishing Group, United Kingdom (2006).

Calin, G., et al., "A MicroRNA Signature Associated with Prognosis and Progression in Chronic Lymphocytic Leukemia," *N. Engl. J. Med.* 353:1793-1801, Massachusetts Medical Society, United States (2005).

Calin, G., et al., "Frequent deletions and down-regulation of micro-RNA genes *miR15* and *miR16* at 13q14 in chronic lymphocytic leukemia," *Proc. Natl. Acad. Sci. USA* 99:15524-15529, National Academy of Sciences, United States (2002).

Calin, G., et al., "Human microRNA genes are frequently located at fragile sites and genomic regions involved in cancers," *Proc. Natl. Acd. Sci. USA 101*:2999-3004, National Academy of Sciences, United States (2004).

Chan, J., et al.,"MicroRNA-21 Is an Antiapoptotic Factor in Human Glioblastoma Cells," *Cancer Res. 65*:6029-6033, American Association for Cancer Research, United States (2005).

Chang, J., et al., "Liver-Specific MicroRNA miR-122 Enhances the Replication of Hepatitis C Virus in Nonhepatic Cells," *J. Virol. 82*:8215-8223, American Society For Microbiology, United States (2008).

Chang, J., et al., "miR-122, a Mammalian Liver-Specific microRNA, is Processed from hcr mRNA and May Downregulate the High Affinity Cationic Amino Acid Transporter CAT-1," *RNA Biol. 1*:106-113, Landes Bioscience, United States (2004).

Chen, X., "A MicroRNA as a Translational Repressor of *APETALA2* in *Arabidopsis* Flower Development," *Science 303*:2022-2025, American Association for the Advancement of Science, United States (2004).

Chen, J., et al., "The role of microRNA-1 and micro-RNA-133 in skeletal muscle proliferation and differentiation," *Nat. Genet. 38*:228-233, Nature Publishing Company, United States (2005).

Cheng, A., et al., "Antisense inhibition of human miRNAs and indications for an involvement of miRNA in cell growth and apoptosis," *Nucleic Acids Res. 33*:1290-1297, Oxford University Press, United Kingdom (2005).

Choi, W., et al., "Target Protectors Reveal Dampening and Balancing of Nodal Agonist and Antagonist by miR-430," *Science 318*:271-274, American Association for the Advancement of Science, United States (2007).

Christensen, U. and Pedersen, E., "Intercalating nucleic acids containing insertions of 1-*O*-(1-pyrenylmethyl)glycerol: stabilisation of dsDNA and discrimination of DNA over RNA," *Nucleic Acids Res. 30*:4918-4925, Oxford University Press, United Kingdom (2002).

Connolly, E., et al., "Elevated Expression of the miR-17-92 Polycistron and miR-21 in Hepadnavirus-Associated Hepatocellular Carcinoma Contributes to the Malignant Phenotype," *Am. J. Pathol. 173*:856-864, American Society for Investigative Pathology, United States (2008).

Cook, P., "Antisense Medicinal Chemistry," in *Antisense Research & Application*, Crooke, S., ed.,vol. 131, pp. 51-101, Springer-Verlag, Germany (1998).

Corsten, M., et al., "MicroRNA-21 Knockdown Disrupts Glioma Growth In vivo and Displays Synergistic Cytotoxicity with Neural Precursor Cell-Delivered S-TRAIL in Human Gliomas," *Cancer Res. 67*:8994-9000, American Association for Cancer Research, United States (2007).

Coulouarn, C., et al., "Loss of miR-122 expression in liver cancer correlates with suppression of the hepatic phenotype and gain of metastatic properties," *Oncogene 28*:3526-36, Nature Publishing Group, United Kingdom (2009).

Crooke, S., "An overview of Progress in Antisense Therapeutics," *Antisense & Nucleic Acid Drug Development 8*:115-122, Mary Ann Liebert, Inc., United States (1998).

Crooke, S., "Basic Principles of Antisense Technology," in *Antisense Drug Technology, Principles, Strategies and Applications*, Crooke, S., ed, pp. 1-18, Marcel Dekker, Inc., NY, United States (2001).

Crooke, S.,"Mechanisms of Antisense Drug Action, an Introduction," in *Antisense Drug Technology, Principles, Strategies and Applications*, Crooke, S., ed., pp. 5-45, Taylor & Francis LLC, United Kingdom (2008).

Czech, M., "MicroRNAs as Therapeutic Targets," *N. Engl. J. Med. 354*:1194-1195, Massachusetts Medical Society, United States (2006).

Davis, S., et al., "Improved targeting of miRNA with antisense oligonucleotides," *Nucleic Acids Res. 34*:2294-2304, Oxford University Press, United Kingdom (2006).

Davis, S., et al., "Potent inhibition of microRNA in vivo without degradation," *Nucleic Acids Res. 37*:70-77, Oxford University Press, United Kingdom (2008).

Davis, S., et al., "Potent inhibition of microRNA in vivo without degradation," *Nucleic Acids Res. 37*:70-77, [Supplementary data], Oxford University Press, United Kingdom (2008).

Deere, J., et al., "Antisense Prosphorodiamidate Morpholino Oligomer Length and Target Position Effects on Gene-Specific Inhibition in *Eschericia coli*," *Antimicrob. Agents Chemother. 49*:249-255, American Society for Microbiology, United States (2005).

D. Young & Co., Investigation of teachings of WO2008/061537 and WO2008/151639, Jan. 2009, 22 pages.

Díaz-Toledano, R., et al., "In vitro characterization of a miR-122-sensitive double-helical switch element in the 5' region of hepatitis C virus RNA," *Nucl. Acids Res. 37*:5498-5510, Oxford University Press, United Kingdom (2009).

Eis, P., et al., "Accumulation of miR-155 and *BIC* RNA in human B cell lymphomas," *Proc. Natl. Acad. Sci. USA 102*: 3627-3632, National Academy of Sciences, United States (2005).

Eisenberg, I., et al., "Distinctive patterns of microRNA expression in primary muscular disorders," *Proc. Natl. Acad. Sci. USA 104*:17016-17021, National Academy of Sciences, United States (2007).

Elbashir, S., et al., "Analysis of gene function in somatic mammalian cells using small interfering RNAs," *Methods 26*:199-213, Academic Press, United States (2002).

Elmén, J., et al., "Antagonism of microRNA-122 in mice by systematically administered LNA-antimiR leads to up-regulation of a large set of predicted target mRNAs in the liver," *Nucleic Acids Res. 36*:1153-1162, Oxford University Press, United Kingdom (2008).

Elmén, J., et al., "LNA-antimiRs: Promising candidates for therapeutic intervention of disease-related microRNAs," [Conference abstract] Nov. 1-2, 2006, MicroRNAs: Biology to Development and Disease, Peterhouse, University of Cambridge, United Kingdom (2006), 1 page.

Elmén, J., et al., "LNA-antimiRs: Promising candidates for therapeutic intervention of disease-related microRNAs," [Poster] 71st Symposium on Quantitative Biology: Regulatory RNAs, Cold Spring Harbor, NY, United States, May 31-Jun. 5, 2006, 1 page.

Elmén, J., et al., "LNA-antimiRs: Promising candidates for therapeutic intervention of disease-related microRNAs," [Presentation abstract], 71st Symposium on Quantitative Biology: Regulatory RNAs, May 31-Jun. 5, 2006, Cold Spring Harbor, NY, United States, 1 page.

Elmén, J., et al., "Locked nucleic acid containing antisense oligonucleotides enhance inhibition of HIV-1 genome dimerization and inhibit virus replication," *FEBS Letters 578*:285-290, Elsevier B.V., Netherlands (2004).

Esau, C., "Inhibition of microRNA with antisense oligonucleotides," *Methods 44*:55-60, Academic Press, United States (2008).

Esau, C. and Monia, B., "Therapeutic potential for microRNAs," *Adv. Drug Deliv. Rev.59*:101-114, Elsevier Science Publishers, B.V., Netherlands (2007).

Esau, C., et al., "Identification of microRNAs involved in adipocyte development using second-generation antisense oligonucleotides in an in vitro adipocyte differentiation model," [Poster abstract] siRNAs and miRNAs Keystone Symposium, Keystone Resort, Apr. 14-19, 2004, Colorado, United States, 1 page.

Esau, C., et al., "MicroRNA-143 Regulates Adipocyte Differentiation," [Supplementary Methods], *J. Biol. Chem. 279*, 25 pages, American Society for Biochemistry and Molecular Biology, United States (2004).

Esau, C., et al., "miR-122 regulation of lipid metabolism revealed by in vivo antisense targeting," *Cell Metab. 3*:87-98, Cell Press, United States (2006).

Esau, C., et al., "miR-122 regulation of lipid metabolism revealed by in vivo antisense targeting," [Supplemental data], *Cell Metab. 3*, Cell Press, United States (2006), 1 page.

Esquela-Kerscher, A. and Slack, F., "Oncomirs-microRNAs with a role in cancer," *Nat. Rev. Cancer 6*:259-269, Nature Publishing Group, United Kingdom (2006).

Fabani, M. and Gait, M., "miR-122 targeting with LNA/2'-*O*-methyl oligonucleotide mixmers, peptide nucleic acids (PNA), and PNA-peptide conjugates," *RNA 14*:336-346, Cold Spring Harbor Laboratory Press, United States (2008).

U.S. Department of Health and Human Services, Food and Drug Administration, Center for Drug Evaluation and Research (CDER),"Guidance for Industry Antiviral Product Development—Conducting and Submitting Virology Studies to the Agency," Jun. 2006, Clinical Antimicrobial, 17 pages.

Feld, J. and Hoofnagle, J., "Mechanism of action of interferon and ribavirin in treatment of hepatitis C," *Nature* 436:967-972, Nature Publishing Group, United Kingdom (2005).

Feld, J., et al., "Ribavirin Improves Early Response to Pegirterferon Through Improved Interferon Signaling," *Gastroenterology* 139:154-162, W.B. Saunders, United States (2010).

Fluiter, K., et al., "In vivo tumor growth inhibition and biodistribution studies of locked nucleic acid (LNA) antisense oligonucleotides," *Nucleic Acids Res.* 31:953-962, Oxford University Press, United Kingdom (2003).

Fornari, F., et al., "MiR-122/Cyclin G1 Interaction Modulates p53 Activity and Affects Doxorubicin Sensitivity of Human Hepatocarcinoma Cells," *Cancer Res.* 69:5761-5767, American Association for Cancer Research, United States (2009).

Frankel, L., et al., "Programmed Cell Death 4 (PDCD4) Is an Important Functional Target of the MicroRNA *miR-21* in Breast Cancer Cells," *J. Biol. Chem.* 283:1026-1033, The American Society for Biochemistry and Molecular Biology, Inc., United States (2008).

Freier, S., "Methods of Selecting Sites in RNA for Antisense Targeting," in *Antisense Drug Technology*, Crooke, S., ed., CRC Press, United States (2001).

Frieden, M. and Ørum, H., "Locked Nucleic Acid Holds Promise in the Treatment of Cancer," *Curr. Pharmac. Design* 14:1138-1142, Bentham Science Publishers, Netherlands (2008).

Frieden, M., et al., "Expanding the design horizon of antisense oligonucleotides with alpha-L-LNA," *Nucleic Acids Res.* 31:6365-6372, Oxford University Press, United Kingdom (2003).

Gabriely, G., et al., "MicroRNA 21 Promotes Glioma Invasion by Targeting Matrix Metalloproteinase Regulators," *Molec. Cell. Biol.* 28:5369-5380, American Society for Microbiology, United States (2008).

Galardi, S., et al., "miR-221 and miR-222 Expression Affects the Proliferation Potential of Human Prostate Carcinoma Cell Lines by Targeting p27$^{Kip1}$," *J. Biol. Chem.* 282:23716-23724, The American Society for Biochemistry and Molecular Biology, Inc., United States (2007).

Geary, R., et al., "Pharmacokinetic Properties of 2'-*O*-(2-Methoxyethyl)-Modified Oligonucleotide Analogs in Rats," *J. Pharm. Exper. Therap.* 296:890-897, The American Society for Pharmacology and Experimental Therapeutics, United States (2001).

Gentleman, R., et al., "Bioconductor: open software development for computational biology and bioinformatics," *Genome Biol.* 5:R80, BioMed Central Ltd., United Kingdom (2004).

Gerwitz, A., et al., "Nucleic Acid Therapeutics: State of the Art and Future Prospects," *Blood* 92:712-736, American Society of Hematology, United States (1998).

Giles, R., et al., "Selecting optimal oligonucleotide composition for maximal antisense effect following streptolysin O-mediated delivery into human leukaemia cells," *Nucleic Acid Res.* 26:1567-1575, Oxford University Press, United Kingdom (1998).

Giraldez, A., et al., "MicroRNAs Regulate Brain Morphogenesis in Zebrafish," *Science* 308:833-838, American Association for the Advancement of Science, United States (2005).

Girard, M., et al., "miR-122, a paradigm for the role of microRNAs in the liver," *J. Hepatol.* 48:648-656, Elsevier, United Kingdom (2008).

Gramantieri, L., et al., "Cyclin G1 is a Target of miR-122a, a MicroRNA Frequently Down-regulated in Human Hepatocellular Carcinoma," *Cancer Res.* 64:6092-6099, American Association for Cancer Research, United States (2007).

Greene, T. and Wuts, P., "Protective Groups in Organic Synthesis," [Table of Contents], 3rd ed., John Wiley & Sons, Chichester, England (1999).

Griffiths-Jones, S., "The microRNA Registry," *Nucleic Acids Res.* 32:D109-D111, [Database issue], Oxford University Press, United Kingdom (2004).

Griffiths-Jones, S., et al., "miRBase: microRNA sequences, targets and gene nomenclature," *Nucleic Acids Res.* 34:D140-D144, [Database issue], Oxford University Press, United Kingdom (2006).

Grimm, D. and Kay, M., "Therapeutic application of RNAi: is mRNA targeting finally ready for prime time?," *J. Clinic. Invest.* 117:3633-3641, American Society for Clinical Investigation, United States (2007).

Grimson, A., et al., "MicroRNA Targeting Specificity in Mammals: Determinants beyond Seed Pairing," *Mol. Cell.* 27:91-105, Elsevier, Inc., Netherlands (2007).

Hanecak, R., et al., "Antisense Oligonucleotide Inhibition of Hepatitis C Virus Gene Expression in Transformed Hepatocytes," *J. Virol.* 70:5203-5212, American Society For Microbiology, United States (1996).

Haussecker, D. and Kay, M., "miR-122 Continues to Blaze the Trail for MicroRNA Therapeutics," *Mol. Ther.* 18:240-242, Nature Publishing Group, United States (2010).

He, L., et al., "A microRNA polycistron as a potential human oncogene," *Nature* 435:828-833, Nature Publishing Group, United Kingdom (2005).

Henke, J., et al., "microRNA-122 stimulates translation of hepatitis C virus RNA," *EMBO J.* 27:3300-3310, Nature Publishing Group, United Kingdom (2008).

Hildebrandt-Eriksen, E. et al., "A Unique Therapy for HCV Inhibits microRNA-122 in Humans and Results in HCV Suppression in Chronically Infected Chimpanzees: Results from Primate and First-in-Human Studies," *Hepatology LB19*, 50:12A, Wiley, United States (2009).

Hogrefe, R., "An Antisense Oligonucleotide Primer," *Antisense Nucleic Acid Drug Dev.* 9:351-357, Mary Ann Liebert, Inc., United States (1999).

Hornstein, E., et al., "The microRNA *miR-196* acts upstream of Hoxb8 and Shh in limb development," *Nature* 438:671-674, Nature Publishing Group, United Kingdom (2005).

Horwich, M. and Zamore, P., "Design and delivery of antisense oligonucleotides to block microRNA function in cultured *Drosophila* and human cells," *Nature Protocols* 3:1537-1549, Nature Publishing Group, United Kingdom (2008).

Hu, Q., "Subcellular trafficking of antisense oligonucleotides and down-regulation of *bcl-2* gene expression in human melanoma cells using a fusogenic liposome delivery system," *Nucleic Acid Res.* 30:3632-3641, Oxford University Press, United Kingdom (2002).

Huber, W., et al., "Variance stabilization applied to microarray data calibration and to the quantification of differential expression," *Bioinformatics* 18:S96-S104, Oxford University Press, United Kingdom (2002).

Hutvágner, G., et al., "A Cellular Function for the RNA-Interference Enzyme Dicer in the Maturation of the *let-7* Small Temporal RNA," *Science* 293:834-838, American Association for the Advancement of Science, United States (2001).

Hutvágner, G., et al., "Sequence-Specific Inihibition of Small RNA Function," *PLoS Biology* 2:0465-0475, Public Library of Science, United States (2004).

Hutvágner, G., et al., "Sequence-specific inhibition of small RNA function," [Poster abstract], siRNAs and miRNAs Keystone Symposium, Apr. 14-19, 2004, Keystone Resort, Colorado, United States, 1 page.

Hwang, H., et al., "Cell—cell contact globally activates microRNA biogenesis," *Proc. Natl. Acad. Sci. USA* 106:7016-7021, National Academy of Sciences, United States (2009).

Ikeda, M., et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," *J. Virol.* 76:2997-3006, American Society for Microbiology, United States (2002).

Iliopoulos, D., et al., "MicroRNA-370 controls the expression of MicroRNA-122 and Cpt1α and affects lipid metabolism," *J. Lipid. Res.* 51:1513-1523, American Society for Biochemistry and Molecular Biology, United States (2010).

Iorio, M., et al., "MicroRNA Gene Expression Deregulation in Human Breast Cancer," *Cancer Res.* 65:7065-7070, American Association for Cancer Research, United States (2005).

Ittig, D., et al., "Nuclear antisense effects in cyclophilin A pre-mRNA splicing by oligonucleotides: a comparison of tricyclo-DNA with LNA," *Nucleic Acids Res.* 32:346-353, Oxford University Press, United Kingdom (2004).

Jackson, A. and Linsley, P., "The Therapeutic Potential of microRNA Modulation," Discoverymedicine.com, accessed at http://www.discoverymedicine.com/Aimee-Jackson/2010/04/10/the-therapeutic-potential-of-microma-modulation/, accessed on May 5, 2010, 7 pages.

Jepsen, J. and Wengel, J., "LNA-Antisense rivals siRNA for gene silencing," *Curr. Opin. Drug Discov. Develop.* 7:188-194,Thomson Reuters (Scientific) Ltd., United Kingdom (2004).

Jepsen, J., et al ., "Locked Nucleic Acid: A Potent Nucleic Acid Analog in Therapeutics and Biotechnology," *Oligonucleotides* 14:130-146, Mary Ann Liebert, Inc., United States (2004).

Jin, P., et al., "RNA and microRNAs in fragile X mental retardation," *Nat. Cell Biol.* 6:1048-1053, Nature Publishing Group, United States (2004).

Johansson, H., et al., "Target-specific arrest of mRNA translation by antisense 2'-O-alkyloligoribonucleotides," *Nucleic Acids Res.* 22:4591-4598, Oxford University Press, United Kingdom (1994).

Johnson, C., et al., "The *let-7* MicroRNA Represses Cell Proliferation Pathways in Human Cells," *Cancer Res.* 67:7713-7722, American Association for Cancer Research, United States (2007).

Johnson, S., et al., "*RAS* Is Regulated by the *let-7* MicroRNA Family," *Cell 120*: 635-647, Cell Press, United States (2005).

Johnston, Jr., R., and Hobert, O., "A microRNA controlling left/right neuronal asymmetry in *Caenorhabditis elegans*," *Nature* 426:845-849, Nature Publishing Group, United Kingdom (2003).

Jopling, C., et al., "Position-Dependent Function for a Tandem MicroRNA miR-122-Binding Site Located in the Hepatitis C Virus RNA Genome," *Cell Host and Microbe* 4:77-85, Cell Press, United States (2008).

Jopling, C., "Regulation of hepatitis C virus by microRNA-122," *Biochem. Soc. Trans.* 36:1220-1223, Portland Press, United Kingdom (2008).

Jopling, C., et al., "Liver-specific microRNA122 Regulates Hepatitis C Viral RNA Abundance," pp. 124, Translational Control 2004 Meeting, Sep. 7-12, 2004, Cold Spring Harbor Laboratory, Cold Spring Harbor, NY, United States.

Jopling, C., et al., "Positive and Negative Modulation of Viral and Cellular mRNAs by Liver-specific MicroRNA miR-122," Cold Spring Harbor Symposia on Quantitative Biology, May 31-Jun. 5, 2006, vol. 71, pp. 369-376, Cold Spring Laboratory Press, United States.

Kauppinen, S., "Antagonizing microRNAs for therapeutics," *Hum. Gene Ther.* 19:1063, M.A. Liebert, United States (2008).

Kauppinen, S., et al., "Locked Nucleic Acid: High-Affinity Targeting of Complementary RNA for RNomics," in *Handbook of Experimental Pharmacology*, vol. 173, pp. 405-422, Springer-Verlag, Berlin, Germany (2006).

Kauppinen, S., et al., "Locked nucleic acid (LNA): High affinity targeting of RNA for diagnostics and therapeutics," *Drug Discovery Today: Technologies* 2:287-290, Elsevier, Ltd., Netherlands (2005).

Kaur, H., et al., "LNA-modified oligonucleotides effectively drive intramolecular-stable hairpin to intermolecular-duplex state," *Biochem. Biophys. Res. Comm.* 352:118-122, Academic Press, United States (2007).

Ketting, R., et al., "Dicer functions in RNA interference and in synthesis of small RNA involved in developmental timing in *C. elegans*," *Genes Dev.* 15:2654-2659, Cold Spring Harbor Laboratory Press, United States (2001).

Khan, A., et al., "Transfection of small RNAs globally perturbs gene regulation by endogenous microRNAs," *Nat. Biotechnol.* 27:549-555, Nature Publishing Group, United States (2009).

Kinberger, G., et al., "Design, synthesis and in vivo results of chemically-modified antisense oligonucleotides targeting microRNA-122," Abstracts of Papers, 234th ACS National Meeting and Exposition, Boston, Massachusetts, United States, Aug. 19-23, 2007, 1 page.

Klein, M., et al., "Homeostatic regulation of MeCP2 expression by a CREB-induced microRNA," *Nat. Neurosci.*10:1513-1514, Nature Publishing Group, United States (2007).

Kloosterman, W. and Plasterk, R., "The Diverse Functions of MicroRNAs in Animal Development and Disease," *Dev. Cell* 11:441-450, Elsevier, Inc., Netherlands (2006).

Kloosterman, W., et al., "In situ detection of miRNAs in animal embryos using LNA-modified oligonucleotide probe," *Nat. Methods* 3:27-29, Nature Publishing Group, United States (2006).

Kloosterman, W., et al., "Substrate requirements for *let-7* function in the developing zebrafish embryo," *Nucleic Acids Res.* 32:6284-6291, Oxford University Press, United Kingdom (2004).

Kocerha, J., et al., "MicroRNA-219 modulates NMDA receptor-mediated neurobehavioral dysfunction," *Proc. Natl. Acad. Sci. USA* 106:3507-3512, National Academy of Sciences, United States (2009).

Kocherha, J., et al., "microRNAs in CNS Disorders," *Neuromol. Med.* 11:162-172, Humana Press, United States (2009).

Koch, T., and Ørum, H., "Locked Nucleic Acid," in *Antisense Drug Technology, Principles, Strategies and Applications*, Crooke, S., ed., pp. 519-564, Taylor & Francis Group, United Kingdom (2008).

Koch, T., et al., "Locked Nucleic Acid: Properties and Therapeutic Aspects," in *Therapeutic Oligonucleotides*, Kurreck, J., ed., pp. 103-141, Royal Society of Chemistry, Cambridge, United Kingdom (2008).

Krukemeyer, M., et al., "Description of B Lymphocytes and Plasma Cells, Complement, and Chemokines/Receptors in Acute Liver Allograft Rejection," *Transplantation* 78:65-70, Lippincott Williams & Wilkins, United States (2004).

Krützfeldt, J., et al., "Specificity of microRNAs in vivo with 'antagomirs,'" *Nature Letters* 438:685-689, Nature Publishing Group, United Kingdom (2005).

Krützfeldt, J., et al., "Specificity, duplex degradation and subcellular localization of antagomirs," *Nucleic Acids Res.* 35:2885-2892, Oxford University Press, United Kingdom (2007).

Krützfeldt, J., et al., "Strategies to determine the biological function of microRNAs," *Nat. Genet.* 38:S14-S19, Nature Publishing Group, United Kingdom (2006).

Kurreck, J., et al., "Design of antisense oligonucleotides stabilized by locked nucleic acids," *Nucleic Acids Res.* 30:1911-1918, Oxford University Press, United Kingdom (2002).

Kutay, H., et al., "Downregulation of miR-122 in the Rodent and Human Hepatocellular Carcinomas," *J. Cell. Biol.* 99:671-678, Wiley-Liss, United States (2006).

Kwon, C., et al., "MicroRNA1 influences cardiac differentiation in *Drosophila* and regulates Notch signaling," *Proc. Natl. Acad. Sci. USA* 102:18986-18991, National Academy of Sciences, United States (2005).

Lagos-Quintana, M., et al., "Identification of Novel Genes Coding for Small Expressed RNAs," *Science* 294:853-858, American Association for the Advancement of Science, United States (2001).

Lagos-Quintana, M., et al., "Identification of Tissue-Specific MicroRNAs from Mouse," *Curr. Biol.* 12:735-739, Elsevier Science Ltd., Netherlands (2002).

Landthaler, M., et al., "Sequence-specific inhibition of microRNA and siRNA-induced RNA silencing" [Poster abstract], siRNAs and miRNAs Keystone Symposium, Keystone Resort, Apr. 14-19, 2004, Colorado, United States, 1 page.

Landthaler, M., et al., "The Human DiGeorge Syndrome Critical Region Gene 8 and Its *D. melanogaster* Homolog Are Required for miRNA Biogenesis," *Curr. Biol.* 14:2162-2167, Elsevier Ltd., Netherlands (2004).

Lanford, R., et al., "Antagonizing MicroRNA-122 and Treatment of Hepatitis C Virus Infection," *Hepatology* 51:1461-1465, Wiley, United States (2010).

Lanford, R., et al., "Antiviral Effect and Virus-Host Interactions in Response to Alpha Interferon, Gamma Interferon, Poly(I)-poly(C), Tumor Necrosis Factor Alpha, and Ribavirin in Hepatitis C Virus Subgenomic Replicons," *J. Virol.* 77:1092-1104, American Society For Microbiology, United States (2003).

Lanford, R., et al., "Lack of Response to Exogenous Interferon-α in the Liver of Chimpanzees Chronically Infected with Hepatitis C Virus," *Hepatology* 46:999-1008, Wiley, United States (2007).

Lanford, R., et al., "The Accelerating Pace of HCV Research: A Summary of the 15th International Symposium on Hepatitis C Virus and Related Viruses," *Gastroenterology* 136:9-16, W.B. Saunders, United States (2009).

Lanford, R., et al., "Therapeutic Silencing of MicroRNA-122 in Primates with Chronic Hepatitis C Virus Infection," *Science* 327:198-201, American Association for the Advancement of Science, United States (2010).

Leaman, D., et al., "Antisense-Mediated Depletion Reveals Essential and Specific Functions of MicroRNAs in *Drosophila* Development," *Cell* 121:1097-1108, Elsevier Inc., United States (2005).

Leaman, D., et al., "MiRNA function in *Drosophila* development," [Poster abstract], siRNAs and miRNAs Keystone Symposium, Keystone Resort, Apr. 14-19, 2004, Colorado, United States, , 1 page.

Lee, Y. and Dutta, A. "The tumor suppressor microRNA *let-7* represses the HMGA2 oncogene" *Genes Dev.* 21:1025-1030, Cold Spring Harbor Laboratory Press, United States (2007).

Lee, Y., et al., "Depletion of Human Micro-RNA miR-125b Reveals That It Is Critical for the Proliferation of Differentiated Cells but Not for the Down-regulation of Putative Targets during Differentiation," *J. Biol. Chem.* 280:16635-16641, The American Society for Biochemistry and Molecular Biology, Inc., United States (2005).

Lee, Y., et al., "The nuclear RNase III Drosha initiates microRNA processing," *Nature* 425:415-419, Nature Publishing Group, United Kingdom (2003).

Le Sage, C., et al., "Regulation of the p27$^{Kip1}$ tumor suppressor by miR-221 and miR-222 promotes cancer cell proliferation," *Cell* 6:3699-3708, Nature Publishing Group, United Kingdom (2007).

Lewis, B., et al., "Conserved Seed Pairing, Often Flanked by Adenosines, Indicates that Thousands of Human Genes are MicroRNA Targets," *Cell* 120:15-20, Elsevier, Inc., Netherlands (2005).

Li, X. and Carthew, R., "A microRNA Mediates EGF Receptor Signaling and Promotes Photoreceptor Differentiation in the *Drosophila* Eye," *Cell* 123:1267-1277, Cell Press, United States (2005).

Lim, L., et al., "Microarray analysis shows that some microRNAs downregulate large numbers of target mRNAs," *Nature* 433:769-773, Nature Publishing Group, United Kingdom (2005).

Lima, W., et al., "Combinatorial Screening and Rational Optimization for Hybridization to Folded Hepatitis C Virus RNA of Oligonucleotides with Biological Antisense Activity," *J. Biol. Chem.* 272:626-638, American Society for Biochemistry and Molecular Biology, United States (1997).

Lindenbach, B., et al., "Complete Replication of Hepatitis C Virus in Cell Culture," *Science* 309:623-626, American Association for the Advancement of Science, United States (2005).

Lisziewicz, J., et al., "Long-term treatment of human immunodeficiency virus-infected cells with antisense oligonucleotide phosphorothioates," *Proc. Natl. Acad. Sci. USA* 90:3860-3864, National Academy of Sciences, United States (1993).

Liu, J., et al., "The microRNAs of *Caenorhabditis elegans*," [Powerpoint slides], 36 slides, Sep. 22, 2004.

Love, T., et al., "Not miR-ly small RNAs: Big potential for microRNAs in therapy," *J. Allergy. Clin. Immunol.* 121:309-319, Mosby, United States (2008).

Lu, J., et al., "MicroRNA expression profiles classify human cancers," *Nature* 435:834-838, Nature Publishing Group, United Kingdom (2005).

Lupberger, J., et al., "RNAi—A powerful tool to unravel hepatitis C virus-host interactions within the infectious live cycle," *J. Hepatol.* 48:523-525, Elsevier, United Kingdom (2007).

Machlin, E., et al., "Masking the 5' terminal nucleotides of the hepatitis C virus genome by an unconventional microRNA-target RNA complex," *Proc. Natl. Acad. Sci. USA* 108:3193-3198, National Academy of Sciences, USA (2011).

McLeod, B., et al., "The 'real world' utility of miRNA patents: lessons learned from expressed sequence tags," *Nat. Biotechnol.* 29:129-133, Nature Publishing Group, United Kingdom (2011).

Manoharan, M., et al., "Novel Functionalization of the Sugar Moiety of Nucleic Acids for Multiple Labeling in the Minor Groove," *Tetrahedron Lett.* 34:7171-7174, Pergamon Press, PLC., United Kingdom (1991).

Martinez, J., et al., "Single-Stranded Antisense siRNAs Guide Target RNA Cleavage in RNAi," *Cell* 110:563-574, Cell Press, United States (2002).

Matz, M., et al., "Early post-transplant urinary IP-10 expression after kidney transplantation is predictive of short- and long-term graft function," *Kidney Int.* 69:1683-1690, Nature Publishing Group, United States (2006).

Mayr, C., et al., "Disrupting the Pairing Between *let-7* and *Hmga2* Enhances Oncogenic Transformation," *Science* 315:1576-1579, American Association for the Advancement of Science, United States (2007).

McManus, M., and Sharp, P., "Gene Silencing In Mammals By Small Interfering RNAs," *Nat. Rev. Genet.* 3:737-747, Nature Publishing Group, United Kingdom (2002).

Meister, G., et al., "Sequene-specific inhibition of microRNA- and siRNA-induced RNA silencing," *RNA* 10:544-550, Cold Spring Harbor Press, United States (2004).

Metzler, M., et al., "High Expression of Precursor MircoRNA-155/BIC RNA in Children with Burkitt Lymphoma," *Genes Chromosomes Cancer* 39:167-169, Wiley-Liss, United States (2004).

Michael, M., et al., "Reduced Accumulation of Specific MicroRNAs in Colorectal Neoplasia," *Mol. Cancer Res.* 1:882-891, American Association for Cancer Research, United States (2003).

Mirnezami, A., et al., "MicroRNAs: Key players in carcinogenesis and novel therapeutic targets," *Eur. J. Surg. Oncol.* 35:339-347, Elsevier, Netherlands (2009).

Miska, E., et al., "Most *Caenorhabditis elegans* microRNAs Are Individually Not Essential for Development or Viability," *PLoS Genet.* 3:e215/2395-2403, Public Library of Science, United States (2007).

Moore, S., "'Antisense' touted as medical hope, but critics ask if promise is reasonable," Wall Street Journal (Eastern edition), New York, NY, United States, May 10, 1996, pp. A5A, 6 pages (1996).

Möröy, T., et al., "Structure and expression of *hcr*, a locus rearranged with *c-myc* in a woodchuck hepatocellular carcinoma," *Oncogene* 4:59-65, Nature Publishing Group, United Kingdom (1989).

Mourelatos, Z., et al., "miRNPs: a novel class of ribonucleoproteins containing numerous microRNAs," *Genes Dev.* 16:720-728, Cold Spring Harbor Laboratory Press, United States (2002).

Naguibneva, I., et al., "An LNA-based loss-of-function assay for micro-RNAs," *Biomed. Pharmacother.* 60:633-638, Elsevier Ltd., United Kingdom (2006).

Naguibneva, I., et al., "MicroRNAs in terminal muscle differentiation," [Poster abstract], siRNAs and miRNAs Keystone Symposium, Keystone Resort, Colorado United States, Apr. 14-19, 2004, 1 page.

Naguibneva, I., et al., "The microRNA miR-181 targets the homeobox protein Hox-A11 during mammalian myoblast differentiation," *Nature Cell Biol.* 8:278-284 [Supplementary Information], Nature Publishing Group, United States (2006).

Nelson, P., "The microRNA world: small is mighty," *Trends Biochem. Sci.* 28:534-540, Elsevier Ltd., United Kingdom (2003).

Neuman, B., et al., "Antisense Morpholino-Oligomers Directed against the 5' End of the Genome Inhibit Coronavirus Proliferation and Growth," *J. Virol.* 78:5891-5899, American Society for Microbiology, United States (2004).

Nielsen, S., et al., "Association between Hepatitis C Virus and Very-Low-Density Lipoprotein (VLDL)/LDL Analyzed in Iodixanol Density Gradients," *J. Virol.* 80:2418-2428, American Society for Microbiology, United States (2006).

Niepmann, M., "Activation of hepatitis C virus translation by a liver-specific microRNA," *Cell Cycle* 8:1473-1477, Landes Bioscience, United States (2009).

Norman, K. and Sarnow, P., "Hepatitis C virus' Achilles' heel-dependence on liver-specific microRNA miR-122," *Cell Res.* 20:247-249, Nature Publishing Group, United Kingdom (2010).

Norman, K. and Sarnow, P., "Modulation of Hepatitis C Virus RNA Abundance and the Isoprenoid Biosynthesis Pathway by MicroRNA miR-122 Involves Distinct Mechanisms," *J. Virol.* 84:666-670, American Society for Microbiology, United States (2010).

Nulf, C. and Corey, D., "Intracellular inhibition of hepatitis C virus (HCV) internal ribosomal entry site (IRES)-dependent translation by peptide nucleic acids (PNAs) and locked nucleic acids (LNAs)," *Nucleic Acids Res.* 32:3792-3798, Oxford University Press, United Kingdom (2004).

Obad, S., et al., "Targeting of cancer-associated microRNAs using short LNA-antimiR oligonucleotides," *European Journal of Cancer Supplements* 6:142, 20th Meeting of the European Association for Cancer Research, Lyon, France, Jun. 5-8, 2008.

Ørom, U., et al., "LNA-modified oligonucleotides mediate specific inhibition of microRNA function," *Gene* 372:137-141, Elsevier, Inc., Netherlands (2006).

Ouellet, D., et al., "MicroRNAs in Gene Regulation: When the Smallest Governs It All," Article ID 69616, *J. Biomed. Biotechnol.* 2006:1-20, Hindawi Publishing Corporation, United States (2006).

Pan, Q., et al., "New therapeutic opportunities for Hepatitis C based on small RNA," *World J. Gastroenterol.* 13:4431-4436, Baishideng Pub., China (2007).

Pan, Q., et al., "Prospects of RNAi and microRNA-based therapies for hepatitis C," *Expert Opin. Biol. Ther.*9:713-724, Informa Healthcare, United Kingdom (2009).

Park, J., et al., "Antisense Inhibition of microRNA-21 or-221 Arrests Cell Cycle, Induces Apoptosis, and Sensitizes the Effects of Gemcitabine in Pancreatic Adenocarcinoma," *Pancreas* 38:e190-e199, Lippincott Williams & Wilkins, United States (2009).

Pasquinelli, A., et al., "Conservation of the sequence and temporal expression of *let-7* heterochronic regulatory RNA," *Nature* 408:86-89, Nature Publishing Group, United Kingdom (2000).

Paushkin, S., et al., "The SMN complex, an assemblyosome of ribonucleoproteins," *Curr. Opin. Cell Biol.* 14:305-312, Elsevier Science Ltd., United Kingdom (2002).

Pavio, N. and Lai, M., "The hepatitis C virus persistence: how to evade the immune system?," *J. Biosci.* 28:287-304, Springer, India (2003).

Pedersen, I., et al., "Interferon modulation of cellular microRNAs as an antiviral mechanism," *Nature* 449:919-923, Nature Publishing Group, United Kingdom (2007).

Petri, A., et al., "MicroRNA Silencing in Primates: Towards Development of Novel Therapeutics," *Cancer Res.* 69:393-395, American Association for Cancer Research, United States (2009).

Pietschmann, T., et al., "Construction and characterization of infectious intragenotypic and intergenotypic hepatitis C virus chimeras," *Proc. Natl. Acad. Sci. USA* 103:7408-7413, National Academy of Sciences, United States (2006).

Pietschmann, T., et al., "Production of Infectious Genotype 1b Virus Particles in Cell Culture and Impairment by Replication Enhancing Mutations," *PLoS Pathogens* 5:1-14, Public Library of Science, United States (2009).

Poy, M., "A pancreatic islet-specific microRNA regulates insulin secretion," *Nature* 432:226-230, Nature Publishing Group, United Kingdom (2004).

Prakash, T., et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med. Chem.* 53:1636-1650, American Chemical Society, United States (2010).

Regulus Therapeutic, Press release, "Regulus Therapeutics and GlaxoSmithKline Establish New Collaboration to Develop and Commercialize microRNA Therapeutics Targeting miR-122," Feb. 25, 2010, 2 pages.

Roberts, A. and Jopling, C., "Targeting viral infection by microRNA inhibition," *Genome Biology* 1:201, Biomed Central Ltd., United Kingdom (2010), 4 pages.

Robertson, B., et al., "Specificity and functionality of microRNA inhibitors," *Silence* 1:10, BioMed Central, United Kingdom (2010), 34 pages.

Saeed, A., et al., "TM4: A Free, Open-Source System for Microarray Data Management and Analysis," *BioTechniques* 34:374-378, Informa Healthcare USA, Inc., United Kingdom (2003).

Samuel, D., "Hepatitis C, Interferon, and Risk of Rejection After Liver Transplantation," *Liver Transpl.* 10:868-887, Wiley InterScience, United States (2004).

SantarisPharma, In House Memo to Attorney at Horton, dated Jan. 27, 2009, Santaris Memo 2009, 4 pages.

SantarisPharma, "LNA-antimiRs—Towards Effective MircoRNA Antagonists," *Nature Genet.* 38, microRNA Supplement, Jun. 2006 [Powerpoint slide], 1 page.

Sarasin-Filipowicz, M., et al., "Decreased levels of microRNA miR-122 in individuals with hepatitis C responding poorly to interferon therapy," *Nature Med.* 15:31-33, Nature Publishing Company, United States (2009).

Sarnow, P., et al., "MicroRNAs: expression, avoidance and subversion by vertebrate viruses," *Nat. Rev. Microbiol.* 4:651-659, Nature Publishing Group, United Kingdom (2006).

Sazani, P., et al., "Nuclear antisense effects of neutral, anionic and cationic oligonucleotide analogs," *Nucleic Acids. Res.* 29:3965-3974, Oxford University Press, United Kingdom (2001).

Schwarz, D., et al., "Evidence that siRNAs Function as Guides, Not Primers, in the *Drosophila* and Human RNAi Pathways," *Mol. Cell* 10:537-548, Cell Press, United States (2002).

Seth, P., et al., "Synthesis and Biophysical Evaluation of 2',4'-Constrained 2'O-Methoxyethyl and 2',4'-Constrained 2'O-Ethyl Nucleic Acid Analogues," *J. Org. Chem.* 75:1569-1581, American Chemical Society, United States (2010).

Shan, Y., et al., "An Antagomir of Mir-122 Down-Regulates Hepatitis C Virus Infection and Up-Regulates Heme Oxygenase-1 Expression in Human Hepatocytes," *Gastroenterology* 132:T1649, pp. A824, W.B. Saunders, United States (2007).

Shan, Y., et al., "Reciprocal Effects of Micro-RNA-122 on Expression of Heme Oxygenase-1 and Hepatitis C Virus Genes in Human Hepatocytes," *Gastroentrology* 133:1166-1174, W.B. Saunders, United States (2007).

Shan, Y., et al., "Reciprocal Effects of Micro-RNA-122 on Expression of Heme Oxygenase-1 and Hepatitis C Virus Genes in Human Hepatocytes," Hepatology 80A. AASLD abstract #181. Wiley, United States (2006).

Soifer, H., et al., "microRNAs in Disease and Potential Therapeutic Applications," *Mol. Ther.* 15:2070-2079, The American Society of Gene Therapy, United States (2007).

Sokol, N. and Ambros,V., "Mesodermally expressed *Drosophila microRNA-1* is regulated by Twist and is required in muscles during larval growth," *Gene Dev.* 19:2343-2354, Cold Spring Harbor Laboratory Press, United States (2005).

Song, J., et al., "Crystal Structure of Argonaute and Its Implications for RISC Slicer Activity," *Science* 305:1434-1437, American Association for the Advancement of Science, United States (2004).

Stark, A., et al., "Identification of Drosophila MicroRNA Targets," *PLoS Biology* 1: 397-409, Academic Press, United States (2003).

Stein, C., "How to Design an Antisense Oligodeoxynucleotide Experiment: A Consensus Approach," *Antisense Nucleic Acid Drug Dev.* 8:129-132, Mary Ann Liebert, Inc., United States (1998).

Stenvang, J. and Kauppinen S., "MicroRNAs as targets for antisense-based therapeutics," *Expert. Opin. Biol. Ther.* 8:59-81, Informa Healthcare, United Kingdom (2008).

Stenvang, J., et al., "Targeting of microRNAs for therapeutics," *Biochem. Soc. Trans.* 36:1197-1200, Portland Press on the behalf of The Biochemical Society, United Kingdom (2008).

Swayze, E., et al., "Antisense oligonucleotides containing locked nucleic acid improve potency but cause significant hepatotoxicity in animals," *Nucleic Acids Res.* 35:687-700, Oxford University Press, United Kingdom (2007).

Tallet-Lopez, B., et al., "Antisense oligonucleotides targeted to the domain IIId of the hepatitis C virus IRES compete with 40S ribosomal subunit binding and prevent in vitro translation," *Nucleic Acids Res.* 31:734-742, Oxford University Press, United Kingdom (2003).

Tam, W., "Identification and characterization of human *BIC*, a gene on chromosome 21 that encodes a noncoding RNA," *Gene* 274:157-167, Elsevier, Netherlands (2001).

Tijsterman, M., et al., "RNA Helicase MUT-14-Depedent Gene Silencing Triggered in *C. elegans* by Short Antisense RNAs," *Science* 295:694-697, American Association for the Advancement of Science, United States (2002).

Timmerman, L., "Regulus, the MicroRNA Child of Isis and Alnylam, Strikes Potential $150M Deal with Glaxo," Xconomy.com, accessed at: http://www.xconomy.com/san-diego/2010/02/25/regulus-the-microrna-child-of-isis-and-alnylam-strikes-potential-150m-deal-with-glaxo/, accessed on Feb. 25, 2010, 2 pages.

Triboulet, R., et al., "Suppression of MicroRNA-Silencing Pathway by HIV-1 During Virus Replication," *Science 315*:1579-1582, American Association for the Advancement of Science, United States (2007).

Tsai, W., et al., "MicroRNA-122, a Tumor Suppressor MicroRNA that Regulates Intrahepatic Metastasis of Hepatocellular Carcinoma," *Hepatology 49*:1571-1582, Wiley, United States (2009).

Tsuchiya, Y., et al., "MicroRNA Regulates the Expression of Human Cytochrome P450 1B1," *Cancer Res. 66*:9090-9098, American Association for Cancer Research, United States (2006).

Uhlmann, E. and Peyman, A., "Antisense Oligonucleotides: A New Therapeutic Principle," *Chem. Rev. 90*:543-584, American Chemical Society, United States (1990).

Válóczi, A., et al., "Sensitive and specific detection of microRNAs by northern blot analysis using LNA-modified oligonucleotide probes," *Nucleic Acids Res. 32*:e175, Oxford University Press, United Kingdom (2004).

van Rooij, E. and Olson, E., "MicroRNAs: powerful new regulators of heart disease and provocative therapeutic targets," *J. Clinic. Invest. 117*:2369-2376, American Society for Clinical Investigation, United States (2007).

van Rooij, E., et al., "Control of Stress-Dependent Cardiac Growth and Gene Expression by a MicroRNA," *Science 316*:575-579, American Association for the Advancement of Science, United States (2007).

Wagner, R., "Gene inhibition using antisense oligodeoxynucleotides," *Nature 372*:333-335, Nature Publishing Group, United Kingdom (1994).

Wagner, R., et al., "Potent and selective inhibition of gene expression by an antisense heptanucleotide," *Nat. Biotechnol. 14*:840-844, Nature Publishing Group, United Kingdom (1996).

Wahlestedt, C., et al., "Potent and nontoxic antisense oligonucleotides containing locked nucleic acids," *Proc. Natl. Acad. Sci. USA 97*:5633-5638, National Academy of the Sciences, United States (2000).

Wakita, T., et al., "Production of infectious hepatitis C virus in tissue culture from a cloned viral genome," *Nat. Med. 11*:791-796, Nature Publishing Company, United States (2005).

Wakita, T., et al., and Pietschmann, T., et al., Abstracts Nos. O-33 and O-34, 11th International Symposium on HCV & Related Viruses, Heidelberg, Germany, Oct. 3-7, 2004, 1 page.

Walter, T., et al., "Rejection Under Alpha Interferon Therapy in Liver Transplant Recipients," *Am. J. Transplant. 7*:177-184, Blackwell Munksgaard, Denmark (2007).

Wang, X., et al., "MicroRNA-122a functions as a novel tumor suppressor downstream of adenomatous polyposis coli in gastrointestinal cancers," *Biochem. Biophys. Res. Comm. 387*:376-380, Academic Press, United States (2009).

Wang, Z., et al., "miRNAs at the heart of the matter," *J. Mol. Med. 86*:771-783, Springer International, Germany (2008).

Watanabe, T., et al., "Plasma Protein Binding of an Antisense Oligonucleotide Targeting Human ICAM-I (ISIS 2302)," *Oligonucleotides 16*:169-180, Mary Ann Liebert, Inc., United States (2006).

Wehner, K. and Sarnow, P., "Regulation of mRNA molecules by microRNAs," in *Translational Control in Biology & Medicine, Cold Spring Harbor Monograph Series*, vol. 48, pp. 297-318, Cold Spring Harbor Laboratory Press, NY, United States (2007).

Weiler, J., et al., "Anti-miRNA oligonucleotides (AMOs): ammunition to target miRNAs implicated in human disease?," *Gene Ther. 13*:496-502, Nature Publishing Group, United Kingdom (2006).

Wengel, J., "LNA (Locked Nucleic Acid)," in *Antisense Drug Technology, Principles, Strategies and Applications*, Crooke, S., ed. pp. 339-357, Marcel Dekker, Inc., New York (2001).

Wengel, J., et al., "Chemistry of locked nucleic acids (LNA): Design, synthesis, and bio-physical properties," *Lett. Pept. Sci. 10*:237-253, Kluwer Academic Publishers, Germany (2004).

Wienholds, E., et al., "MicroRNA Expression in Zebrafish Embryonic Development," *Science 309*:310-311, American Association for the Advancement of Science, United States (2005).

Worm, J., et al., "Silencing of microRNA-155 in mice during acute inflammatory response leads to depression of c/ebp Beta and down-regulation of G-CSF," *Nucleic Acids Res. 37*:5784-5792, Oxford University Press, United Kingdom (2009).

Wu, X., et al., "miR-122 affects the viability of apoptosis of hepatocellular carcinoma cells," *Scand. J. Gastroenter. 44*:1332-1339, Informa Healthcare, United Kingdom (2009).

Xiao, J., et al., "Novel Approaches for Gene-Specific Interference Via Manipulating Actions of MicroRNAs: Examination on the Pacemaker Channel Genes HCN2 and HCN4," *J. Cell. Physiol. 212*:285-292, Wiley-Liss, New York, United States (2007).

Xie, Z., et al., "Transmission of Hepatitis C Virus Infection to Tree Shrews," *Virology 244*:513-520, Academic Press, New York, United States (1998).

Yang, B., et al., "The muscle-specific microRNA *miR-1* regulates cardiac arrhythmogenic potential by targeting *GJA1* and *KCNJ2*," *Nat. Med. 13*:486-491, Nature Publishing Company, United States (2007).

Yekta, S., et al., "MicroRNA-Directed Cleavage of *HOXB8* mRNA," *Science 304*:594-596, American Association for the Advancement of Science, United States (2004).

Yi, M. and Lemon, S., "Adaptive Mutations Producing Efficient Replication of Genotype 1a Hepatitis C Virus RNA in Normal Huh7 Cells," *J. Virol. 78*:7904-7915, American Society for Microbiology, United States (2004).

Yi-Ping, L., et al., "MicroRNA-122 antagonism against hepatitis C virus genotypes 1-6 and reduced efficacy by host RNA insertion or mutations in the HCV 5' UTR," *Proc. Natl. Acad. Sci. USA 108*:4991-4996, National Academy of Sciences, United States (2011).

Yu, J., et al., "RNA interference by expression of short-interfering RNAs and hairpin RNAs in mammalian cells," *Proc. Natl. Acad. Sci. USA 99*:6047-6052, National Academy of Sciences, United States (2002).

Zamecnik, P. and Stephenson, M., "Inhibition of Rous sarcoma virus replication and cell transformation by a specific oligodeoxynucleotide," *Proc. Natl. Acad. Sci. USA 75*:280-284, National Academy of Sciences, United States (1978).

Zhang, H., et al., "Antisense Oligonucleotide Inhibition of Hepatitis C Virus (HCV) Gene Expression in Livers of Mice Infected with an HCV-Vaccinia Virus Recombinant," *Antimicrob. Agents and Chemoth. 43*:347-353, American Society for Microbiology, United States (1999).

Zhao, Y., et al., "Serum response factor regulates a muscle-specific microRNA that targets *Hand2* during cardiogenesis," *Nature 436*:214-220, Nature Publishing Group, United Kingdom (2005).

Zhong, J. et al., "Robust hepatitis C virus infection in vitro," *Proc. Natl. Acad. Sci. USA 102*:9294-9299, National Academy of Sciences, United States (2005).

Baofeng Y., et al. P.R.C patent application No. 200710072002, Extract from SIPO database, accessed on Jun. 6, 2007, 1 page.

Response and Amended Claims dated Sep. 17, 2007 in Office Action mailed on Mar. 16, 2007, U.S. Appl. No. 10/909,125, Esau et al., filed Jul. 30, 2004, 14 pages.

Response from Applicant dated May 13, 2008, in Office Action mailed Nov. 13, 2007 on U.S. Appl. No. 10/909,125, Esau et al., filed Jul. 30, 2004, 10 pages.

Response and Amended Claims dated Aug. 4, 2009, in reply to Office Action mailed on Mar. 16, 2007 in U.S. Appl. No. 10/909,125, 12 pages.

Response to Office Action mailed Sep. 13, 2006, in U.S. Appl. No. 11/122,328, Sarnow et al., filed May 3, 2005, 11 pages.

International Search Report and Written Opinion for International Appl. No. PCT/DK2007/000169, European Patent Office, Netherlands, mailed on Mar. 7, 2008, 8 pages.

International Search Report for International Appl. No. PCT/EP2007/060703, European Patent Office, Netherlands, mailed on Aug. 13, 2008, 5 pages.

International Search Report for International Appl. No. PCT/EP2008/053309, European Patent Office, Netherlands, mailed on Jul. 18, 2008, 3 pages.

International Search Report for International Appl. No. PCT/EP2008/066920, European Patent Office, Netherlands, mailed on Jun. 17, 2009, 5 pages.

Bartenschlager, R. and Lohmann, V., "Replication of hepatitis C virus," J. Gen. Virol. 81:1631-1648, Great Britain (2000).

Jannsen, H., et al., "A Randomized, Double-blind, Placebo (PLB) Controlled Safety and Anti-viral Proof of Concept Study of Miravirsen (MIR), an Oligonucleotide Targeting miR-122, In Treatment Naive Patients with Genotype 1 (GT1) Chronic HCV Infection," (Abstract) American Association for the Study of Liver Diseases (AASLD) 2011 Annual Meetinq Abstract, Nov. 7, 2011, San Francisco, California, 1 page.

"Declaration of Dr. Susanna Obad," from File History of European Patent No. 1747023, dated Sep. 27, 2011, 4 pages.

"Declaration under 37 CFR 1.132 of Dr. Christine Esau," dated Apr. 15, 2011, from the File History of U.S. Appl. No. 11/513,102, filed Aug. 29, 2006, 5 pages.

"Exclusive License and Nonexclusive Option Agreement Between Glaxo Group Limited and Regulus Therapeutics Inc.," Isis Pharmaceutics (Confidential), Exhibit 10.2, License Agreement, 56 pages, Feb. 24, 2010.

McNair, T., "Cholesterol," BBC Health, accessed at: http://www.bbc.co.uk/health/physical_health/conditions/cholesterol1.shtml, accessed at Nov. 7, 2011, 3 pages.

"Opposition against European Patent No. 1 931 782 B1 granted to Isis Pharmaceuticals Inc.," Document No. G0119EP, Santaris Pharma A/S, Oct. 4, 2011, 46 pages.

Opposition Statement by Santaris Pharma A/S to EP-B-1747023, in the name of The Board of Trustees of the Leland Stanford Junior University, 94 pages, 2011.

Santaris Pharma A/S report new clinical data from miravirsen Phase 2a study to treat Hepatitis C in late-breaking oral presentation at the AASLD annual meeting, (Press Release) American Association for the Study of Liver Diseases (AASLD) 2011 Annual Meeting Abstract, Nov. 7, 2011, San Francisco, California, 2 pages.

Kluiver, J. et al., "BIC and miR-155 are highly expressed in Hodgkin, primary mediastinal and diffuse large B cell lymphomas," Journal of Pathology 207:243-249, Wiley Interscience, United States (2005).

Lin, C., et al., "mir-122 targets an anti-apoptotic gene, Bcl-w in human hepatocellular carcinoma cell lines," Biochem. Biophys. Res. Comm. 375:315-320, Academic Press, United States (2008.

Office Action mailed on Jul. 13, 2010 in U.S. Appl. No. 12/296,084, inventors Elmen et al., filed Sep. 10, 2009.

Office Action mailed on Nov. 5, 2010 in U.S. Appl. No. 12/400,625, inventors Kauppinen et al., fled Mar. 9, 2009.

Office Action mailed on Aug. 25, 2011 in U.S. Appl. No. 12/245,544, inventors Obad et al., filed Oct. 3, 2008, 38 pages.

Office Action mailed on Aug. 3, 2011 in U.S. Appl. No. 12/295,960, inventors Elmén, et al., filed Mar. 30, 2009, 43 pages.

Office Action mailed on Nov. 22, 2011 in U.S. Appl. No. 12/400,625, inventors Kauppinen, et al., filed Mar. 9, 2009, 42 pages.

Office Action mailed on Dec. 30, 2011 in U.S. Appl. No. 12/921,339, inventors Kauppinen et al., filed Nov. 29, 2010, 25 pages.

Office Action mailed on May 10, 2012 in U.S. Appl. No. 13/006,099, inventors Elmen et al., filed Jan. 13, 2011, 12 pages.

Office Action mailed on May 2, 2012 in U.S. Appl. No. 12/400,625, inventors Kauppinen, et al., filed Mar. 9, 2009, 35 pages.

Office Action mailed on May 25, 2012 in U.S. Appl. No. 12/767,631, inventors Hildebrant-Eriksen, et al., filed Apr. 26, 2010, 19 pages.

Office Action mailed on Oct. 25, 2011 in U.S. Appl. No. 12/767,631, inventors Hildebrant-Eriksen, et al., filed Apr. 26, 2010, 15 pages.

Co-pending U.S. Appl. No. 12/921,339, filed Sep. 7, 2010, United States Patent Office, Alexandria, VA., United States (now published as US 2011-0077288 A1).

Co-pending U.S. Appl. No. 12/296,084, filed Sep. 10, 2009, United States Patent Office, Alexandria, VA., United States (now published as US 2010-0004320 A1).

Co-pending U.S. Appl. No. 12/400,625, filed Mar. 9, 2009 United States Patent Office, Alexandria, VA., United States (now published as US 2009-0298916 A1).

Co-pending U.S. Appl. No. 13/006,099, filed Jan. 13, 2011 United States Patent Office, Alexandria, VA., United States (now published as 2012-0083596 A1).

Co-pending U.S. Appl. No. 13/057,146, filed Jul. 24, 2009, United States Patent Office, Alexandria, Va, United States (now published as US 2011-0146216 A1).

Co-pending U.S. Appl. No. 13/415,685, filed Mar. 8, 2012, United States Patent Office, Alexandria, Va, United States (Not Published).

Implication of High-Affinity Hybridization by Locked Nucleic Acid Oligomers for Inhibition of Human Telomerase, Biochemistry 41:9973-9981, ACS Publications, United States (2002).

Advisory Action mailed on Oct. 25, 2012, in U.S. Appl. No. 12/767,631, filed Apr. 26, 2010, 3 pages.

Berezikov, et al. "Approaches to microRNA discovery," Nature Genetics Supplement 38:S2-S7, Nature Publishing Group, United Kingdom (2006).

Doench, et al. "Specificity of microRNA target selection in translational repression," Genes & Development 18:504-511, Cold Spring Harbor Laboratory Press, United States (2004).

Engels et al. "Principles and effects of microRNA-mediated post-transcriptional gene regulation", Oncogene 25:6163-6169, Nature Publishing Group, United Kingdom (2006).

Fluiter, et al. "On the in vitro and in vivo properties of four locked nucleic acid nucleotides incorporated into an anti-H-Ras antisense oligonucleotide," ChemBioChem. 6:1104-1109, Wiley-VCH Verlag GmbH & Co., Germany (2005).

Hornstein, et al. "Canalization of development by microRNAs," Nature Genetics Supplement 38:S20-S24, Nature Publishing Group, United Kingdom (2006).

Rajewsky, "MicroRNA target predictions in animals," Nature Genetics Supplement 38:S8-S13 , Nature Publishing Group, United Kingdom (2006).

Roberts, et al. "Efficient and persistent splice switching by systemically delivered LNA oligonucleotides in mice," Molecular Therapy 14:471—(2006).

Office Action mailed on Sep. 20, 2012, in U.S. Appl. No. 13/006,099, inventors Elmen et al., filed Jan. 13, 2011, 12 pages.

Office Action mailed on Sep. 10, 2012, in U.S. Appl. No. 12/921,339, inventors Kauppinen et al., filed Nov. 29, 2010, 7 pages.

Office Action mailed on Nov. 2, 2012, in U.S. Appl. No. 13/057,146, inventors Worm et al., filed Apr. 28, 2011, 7 pages.

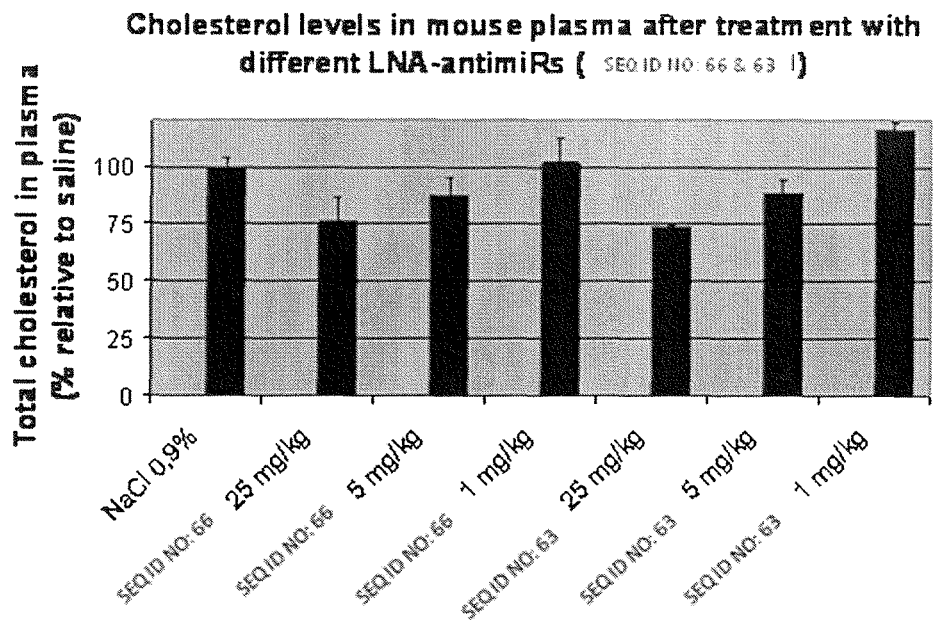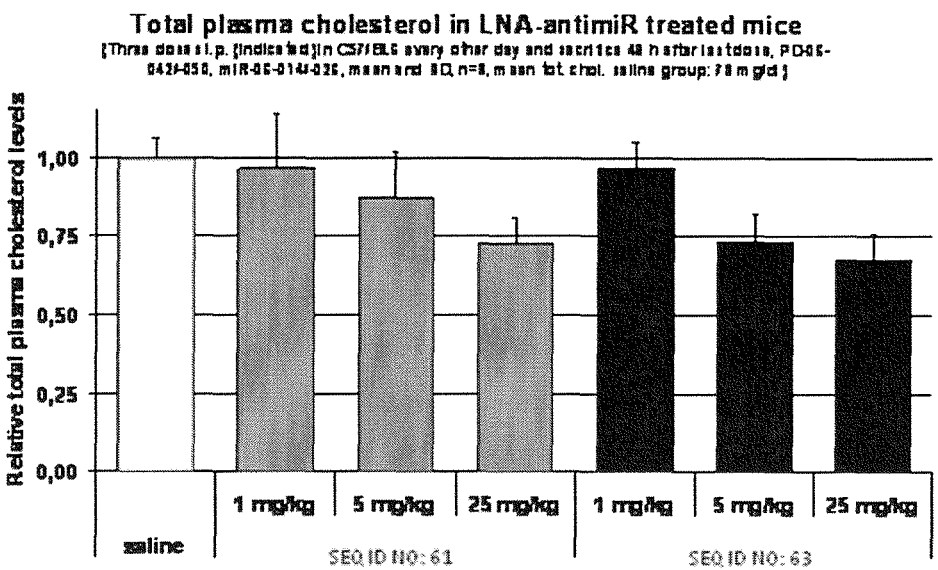
Figure 3 (A and B)

SEQUENCE LISTING

<160> NUMBER OF SEQ ID NOS: 103

<210> SEQ ID NO 1
<211> LENGTH: 16
<212> TYPE: DNA
<213> ORGANISM: artificial
<220> FEATURE:
<223> OTHER INFORMATION: antisense motif

<400> SEQUENCE: 1
cagcattggt attcag                                                          16

<210> SEQ ID NO 2
<211> LENGTH: 15
<212> TYPE: DNA
<213> ORGANISM: artificial
<220> FEATURE:
<223> OTHER INFORMATION: antisense motif

<400> SEQUENCE: 2
cagcattggt attca                                                           15

<210> SEQ ID NO 3
<211> LENGTH: 15
<212> TYPE: DNA
<213> ORGANISM: artificial
<220> FEATURE:
<223> OTHER INFORMATION: antisense motif

<400> SEQUENCE: 3
agcattggta ttcag                                                           15

<210> SEQ ID NO 4
<211> LENGTH: 14
<212> TYPE: DNA
<213> ORGANISM: artificial
<220> FEATURE:
<223> OTHER INFORMATION: antisense motif

<400> SEQUENCE: 4
cagcattggt attc                                                            14

<210> SEQ ID NO 5
<211> LENGTH: 14
<212> TYPE: DNA
<213> ORGANISM: artificial
<220> FEATURE:
<223> OTHER INFORMATION: antisense motif

<400> SEQUENCE: 5
agcattggta ttca                                                            14

<210> SEQ ID NO 6
<211> LENGTH: 14
<212> TYPE: DNA
<213> ORGANISM: artificial
<220> FEATURE:
<223> OTHER INFORMATION: antisense motif

<400> SEQUENCE: 6
gcattggtat tcag                                                            14

<210> SEQ ID NO 7
<211> LENGTH: 13
<212> TYPE: DNA

```
<213> ORGANISM: artificial
<220> FEATURE:
<223> OTHER INFORMATION: antisense motif

<400> SEQUENCE: 7
cagcattggt att                                                        13

<210> SEQ ID NO 8
<211> LENGTH: 13
<212> TYPE: DNA
<213> ORGANISM: artificial
<220> FEATURE:
<223> OTHER INFORMATION: antisense motif

<400> SEQUENCE: 8
agcattggta ttc                                                        13

<210> SEQ ID NO 9
<211> LENGTH: 13
<212> TYPE: DNA
<213> ORGANISM: artificial
<220> FEATURE:
<223> OTHER INFORMATION: antisense motif

<400> SEQUENCE: 9
gcattggtat tca                                                        13

<210> SEQ ID NO 10
<211> LENGTH: 13
<212> TYPE: DNA
<213> ORGANISM: artificial
<220> FEATURE:
<223> OTHER INFORMATION: antisense motif

<400> SEQUENCE: 10
cattggtatt cag                                                        13

<210> SEQ ID NO 11
<211> LENGTH: 12
<212> TYPE: DNA
<213> ORGANISM: artificial
<220> FEATURE:
<223> OTHER INFORMATION: antisense motif

<400> SEQUENCE: 11
cagcattggt at                                                         12

<210> SEQ ID NO 12
<211> LENGTH: 12
<212> TYPE: DNA
<213> ORGANISM: artificial
<220> FEATURE:
<223> OTHER INFORMATION: antisense motif

<400> SEQUENCE: 12
agcattggta tt                                                         12

<210> SEQ ID NO 13
<211> LENGTH: 12
<212> TYPE: DNA
<213> ORGANISM: artificial
<220> FEATURE:
<223> OTHER INFORMATION: antisense motif

<400> SEQUENCE: 13
gcattggtat tc                                                         12
```

```
<210> SEQ ID NO 14
<211> LENGTH: 12
<212> TYPE: DNA
<213> ORGANISM: artificial
<220> FEATURE:
<223> OTHER INFORMATION: antisense motif

<400> SEQUENCE: 14
cattggtatt ca                                                              12

<210> SEQ ID NO 15
<211> LENGTH: 12
<212> TYPE: DNA
<213> ORGANISM: artificial
<220> FEATURE:
<223> OTHER INFORMATION: antisense motif

<400> SEQUENCE: 15
attggtattc ag                                                              12

<210> SEQ ID NO 16
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate linkage
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: LNA methyl cytosine
<220> FEATURE:
<221> NAME/KEY: misc_feature
<222> LOCATION: (12)..(15)
<223> OTHER INFORMATION: LNA
<220> FEATURE:
<221> NAME/KEY: misc_feature
<222> LOCATION: (13)..(13)
<223> OTHER INFORMATION: LNA methyl cytosine

<400> SEQUENCE: 16
agcattggta ttcag                                                           15

<210> SEQ ID NO 17
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(13)
<223> OTHER INFORMATION: phosphorothioate linkages
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: LNA methyl cytosine
<220> FEATURE:
<221> NAME/KEY: misc_feature
<222> LOCATION: (12)..(14)
<223> OTHER INFORMATION: LNA
<220> FEATURE:
```

```
<221> NAME/KEY: misc_feature
<222> LOCATION: (13)..(13)
<223> OTHER INFORMATION: LNA methyl cytosine

<400> SEQUENCE: 17
agcattggta ttca                                                       14

<210> SEQ ID NO 18
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (2)..(13)
<223> OTHER INFORMATION: phosphorothioate linkages
<220> FEATURE:
<221> NAME/KEY: misc_feature
<222> LOCATION: (3)..(3)
<223> OTHER INFORMATION: LNA methyl cytosine
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(13)
<223> OTHER INFORMATION: LNA methyl cytosine

<400> SEQUENCE: 18
agcattggta ttca                                                       14

<210> SEQ ID NO 19
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(13)
<223> OTHER INFORMATION: phosphorothioate linkage
<220> FEATURE:
<221> NAME/KEY: misc_feature
<222> LOCATION: (3)..(3)
<223> OTHER INFORMATION: LNA methyl cytosine
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(13)
<223> OTHER INFORMATION: LNA methyl cytosine

<400> SEQUENCE: 19
agcattggta ttca                                                       14

<210> SEQ ID NO 20
<211> LENGTH: 14
<212> TYPE: DNA
```

-continued

```
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: phosphorothioate linkages
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: LNA methyl cytocine
<220> FEATURE:
<221> NAME/KEY: misc_feature
<222> LOCATION: (4)..(14)
<223> OTHER INFORMATION: phosphorothioate linkages
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(13)
<223> OTHER INFORMATION: LNA methyl cytocine

<400> SEQUENCE: 20
agcattggta ttca                                                           14

<210> SEQ ID NO 21
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(11)
<223> OTHER INFORMATION: phosphorothioate linkages
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: LNA methyl cytocine
<220> FEATURE:
<221> NAME/KEY: misc_feature
<222> LOCATION: (12)..(14)
<223> OTHER INFORMATION: phosphorothioate linkages
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(13)
<223> OTHER INFORMATION: LNA methyl cytocine

<400> SEQUENCE: 21
agcattggta ttca                                                           14

<210> SEQ ID NO 22
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: phosphorothioate linkages
<220> FEATURE:
```

```
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: LNA methyl cytosine
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(14)
<223> OTHER INFORMATION: phosphorothioate linkages
<220> FEATURE:
<221> NAME/KEY: misc_feature
<222> LOCATION: (13)..(13)
<223> OTHER INFORMATION: LNA methyl cytosine

<400> SEQUENCE: 22
agcattggta ttca                                              14

<210> SEQ ID NO 23
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: phosphoro thioate linkages
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: LNA methyl cytosine
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(13)
<223> OTHER INFORMATION: LNA methyl cytosine
<220> FEATURE:
<221> NAME/KEY: misc_feature
<222> LOCATION: (13)..(14)
<223> OTHER INFORMATION: phosphoro thioate linkages

<400> SEQUENCE: 23
agcattggta ttca                                              14

<210> SEQ ID NO 24
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (2)..(13)
<223> OTHER INFORMATION: phosphorothioate linkages
<220> FEATURE:
<221> NAME/KEY: misc_feature
<222> LOCATION: (3)..(3)
<223> OTHER INFORMATION: LNA methyl cytosine
<220> FEATURE:
```

```
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(13)
<223> OTHER INFORMATION: LNA methyl cytosine

<400> SEQUENCE: 24
agcattggta ttca                                                          14

<210> SEQ ID NO 25
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(12)
<223> OTHER INFORMATION: phosphorothioate linkages
<220> FEATURE:
<221> NAME/KEY: misc_feature
<222> LOCATION: (3)..(3)
<223> OTHER INFORMATION: LNA methyl cytosine
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (13)..(13)
<223> OTHER INFORMATION: LNA methyl cytosine

<400> SEQUENCE: 25
agcattggta ttca                                                          14

<210> SEQ ID NO 26
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(13)
<223> OTHER INFORMATION: phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 26
gcattggtat tca                                                           13

<210> SEQ ID NO 27
<211> LENGTH: 13
<212> TYPE: DNA
```

```
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(12)
<223> OTHER INFORMATION: phosphorothioate linkages
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 27
gcattggtat tca                                                          13

<210> SEQ ID NO 28
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (3)..(13)
<223> OTHER INFORMATION: phosphorothioate linkages
<220> FEATURE:
<221> NAME/KEY: misc_feature
<222> LOCATION: (11)..(13)
<223> OTHER INFORMATION: LNA

<400> SEQUENCE: 28
gcattggtat tca                                                          13

<210> SEQ ID NO 29
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(10)
<223> OTHER INFORMATION: phosphorothioate linkages
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
```

```
<221> NAME/KEY: misc_feature
<222> LOCATION: (11)..(13)
<223> OTHER INFORMATION: phosphorothioate linkages
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 29
gcattggtat tca                                                         13

<210> SEQ ID NO 30
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(11)
<223> OTHER INFORMATION: phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(13)
<223> OTHER INFORMATION: phosphorothioate linkages
<220> FEATURE:
<221> NAME/KEY: misc_feature
<222> LOCATION: (12)..(12)
<223> OTHER INFORMATION: LNA methyl cytosine

<400> SEQUENCE: 30
gcattggtat tca                                                         13

<210> SEQ ID NO 31
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(12)
<223> OTHER INFORMATION: LNA methyl cytosine
```

```
<400> SEQUENCE: 31
gcattggtat tca                                                          13

<210> SEQ ID NO 32
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(12)
<223> OTHER INFORMATION: phosphorothioate linkages
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 32
gcattggtat tca                                                          13

<210> SEQ ID NO 33
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(11)
<223> OTHER INFORMATION: phosphorothioate linkages
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 33
gcattggtat tca                                                          13

<210> SEQ ID NO 34
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: phosphorothioate linkages
<220> FEATURE:
```

```
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(12)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 34
gcattggtat tc                                                          12

<210> SEQ ID NO 35
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(12)
<223> OTHER INFORMATION: phosphorothioate linkages
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(12)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 35
gcattggtat tc                                                          12

<210> SEQ ID NO 36
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (3)..(12)
<223> OTHER INFORMATION: phosphorothioate linkages
<220> FEATURE:
<221> NAME/KEY: misc_feature
<222> LOCATION: (11)..(12)
<223> OTHER INFORMATION: LNA
<220> FEATURE:
```

-continued

```
<221> NAME/KEY: misc_feature
<222> LOCATION: (12)..(12)
<223> OTHER INFORMATION: LNA methyl cytosine

<400> SEQUENCE: 36
gcattggtat tc                                                              12

<210> SEQ ID NO 37
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(10)
<223> OTHER INFORMATION: phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(12)
<223> OTHER INFORMATION: phosphorothioate linkages
<220> FEATURE:
<221> NAME/KEY: misc_feature
<222> LOCATION: (11)..(12)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 37
gcattggtat tc                                                              12

<210> SEQ ID NO 38
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(11)
<223> OTHER INFORMATION: phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(12)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 38
gcattggtat tc                                                              12

<210> SEQ ID NO 39
<211> LENGTH: 12
<212> TYPE: DNA
```

```
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(11)
<223> OTHER INFORMATION: phosphorothioate linkages
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (11)..(12)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 39
gcattggtat tc                                                              12

<210> SEQ ID NO 40
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: LNA methyl cytosine
<220> FEATURE:
<221> NAME/KEY: misc_feature
<222> LOCATION: (3)..(10)
<223> OTHER INFORMATION: phosphorothioate linkages
<220> FEATURE:
<221> NAME/KEY: misc_feature
<222> LOCATION: (11)..(12)
<223> OTHER INFORMATION: LNA
<220> FEATURE:
<221> NAME/KEY: misc_feature
<222> LOCATION: (12)..(12)
<223> OTHER INFORMATION: LNA methyl cytosine

<400> SEQUENCE: 40
gcattggtat tc                                                              12

<210> SEQ ID NO 41
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: misc_feature
<222> LOCATION: (1)..(3)
<223> OTHER INFORMATION: Oxy LNA
<220> FEATURE:
<221> NAME/KEY: misc_feature
<222> LOCATION: (1)..(1)
<223> OTHER INFORMATION: Oxy LNA methyl cytosine
<220> FEATURE:
```

```
<221> NAME/KEY: misc_feature
<222> LOCATION: (13)..(15)
<223> OTHER INFORMATION: Oxy LNA
<220> FEATURE:
<221> NAME/KEY: misc_feature
<222> LOCATION: (14)..(14)
<223> OTHER INFORMATION: Oxy LNA methyl cytosine

<400> SEQUENCE: 41
cagcattggt attca                                                   15

<210> SEQ ID NO 42
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: phosphorothioate linkages
<220> FEATURE:
<221> NAME/KEY: misc_feature
<222> LOCATION: (1)..(2)
<223> OTHER INFORMATION: Oxy LNA
<220> FEATURE:
<221> NAME/KEY: misc_feature
<222> LOCATION: (12)..(13)
<223> OTHER INFORMATION: Oxy LNA
<220> FEATURE:
<221> NAME/KEY: misc_feature
<222> LOCATION: (13)..(13)
<223> OTHER INFORMATION: Oxy LNA methyl cytosine

<400> SEQUENCE: 42
agcattggta ttca                                                    14

<210> SEQ ID NO 43
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: phosphorothioate linkages
<220> FEATURE:
<221> NAME/KEY: misc_feature
<222> LOCATION: (1)..(2)
<223> OTHER INFORMATION: Oxy LNA
<220> FEATURE:
<221> NAME/KEY: misc_feature
<222> LOCATION: (11)..(13)
<223> OTHER INFORMATION: Oxy LNA
<220> FEATURE:
<221> NAME/KEY: misc_feature
<222> LOCATION: (13)..(13)
<223> OTHER INFORMATION: Oxy LNA methyl cytosine

<400> SEQUENCE: 43
agcattggta ttca                                                    14

<210> SEQ ID NO 44
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: phosphorothioate linkages
<220> FEATURE:
```

```
<221> NAME/KEY: misc_feature
<222> LOCATION: (1)..(3)
<223> OTHER INFORMATION: Oxy LNA
<220> FEATURE:
<221> NAME/KEY: misc_feature
<222> LOCATION: (3)..(3)
<223> OTHER INFORMATION: Oxy LNA methyl cytosine
<220> FEATURE:
<221> NAME/KEY: misc_feature
<222> LOCATION: (11)..(13)
<223> OTHER INFORMATION: Oxy LNA
<220> FEATURE:
<221> NAME/KEY: misc_feature
<222> LOCATION: (13)..(13)
<223> OTHER INFORMATION: Oxy LNA methyl cytosine

<400> SEQUENCE: 44
agcattggta ttca                                                       14

<210> SEQ ID NO 45
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: phosphorothioate linkages
<220> FEATURE:
<221> NAME/KEY: misc_feature
<222> LOCATION: (1)..(1)
<223> OTHER INFORMATION: Oxy LNA
<220> FEATURE:
<221> NAME/KEY: misc_feature
<222> LOCATION: (11)..(12)
<223> OTHER INFORMATION: Oxy LNA
<220> FEATURE:
<221> NAME/KEY: misc_feature
<222> LOCATION: (12)..(12)
<223> OTHER INFORMATION: Oxy LNA methyl cytosine

<400> SEQUENCE: 45
gcattggtat tc                                                         12

<210> SEQ ID NO 46
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: phosphorothioate linkages
<220> FEATURE:
<221> NAME/KEY: misc_feature
<222> LOCATION: (1)..(2)
<223> OTHER INFORMATION: Oxy LNA
<220> FEATURE:
<221> NAME/KEY: misc_feature
<222> LOCATION: (2)..(2)
<223> OTHER INFORMATION: Oxy LNA methyl cytosine
<220> FEATURE:
<221> NAME/KEY: misc_feature
<222> LOCATION: (10)..(12)
<223> OTHER INFORMATION: Oxy LNA
<220> FEATURE:
<221> NAME/KEY: misc_feature
<222> LOCATION: (12)..(12)
<223> OTHER INFORMATION: Oxy LNA methyl cytosine

<400> SEQUENCE: 46
gcattggtat tc                                                         12
```

```
<210> SEQ ID NO 47
<211> LENGTH: 10
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(10)
<223> OTHER INFORMATION: phosphorothioate linkages
<220> FEATURE:
<221> NAME/KEY: misc_feature
<222> LOCATION: (1)..(1)
<223> OTHER INFORMATION: Oxy LNA
<220> FEATURE:
<221> NAME/KEY: misc_feature
<222> LOCATION: (10)..(10)
<223> OTHER INFORMATION: Oxy LNA

<400> SEQUENCE: 47
gcattggtat                                                          10

<210> SEQ ID NO 48
<211> LENGTH: 10
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(10)
<223> OTHER INFORMATION: phosphorothioate linkages
<220> FEATURE:
<221> NAME/KEY: misc_feature
<222> LOCATION: (1)..(2)
<223> OTHER INFORMATION: Oxy LNA
<220> FEATURE:
<221> NAME/KEY: misc_feature
<222> LOCATION: (2)..(2)
<223> OTHER INFORMATION: Oxy LNA methyl cytosine
<220> FEATURE:
<221> NAME/KEY: misc_feature
<222> LOCATION: (9)..(10)
<223> OTHER INFORMATION: Oxy LNA

<400> SEQUENCE: 48
gcattggtat                                                          10

<210> SEQ ID NO 49
<211> LENGTH: 10
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(10)
<223> OTHER INFORMATION: phosphorothioate linkages
<220> FEATURE:
<221> NAME/KEY: misc_feature
<222> LOCATION: (1)..(2)
<223> OTHER INFORMATION: Oxy LNA
<220> FEATURE:
<221> NAME/KEY: misc_feature
<222> LOCATION: (2)..(2)
<223> OTHER INFORMATION: Oxy LNA methyl cytosine
<220> FEATURE:
<221> NAME/KEY: misc_feature
<222> LOCATION: (8)..(10)
<223> OTHER INFORMATION: Oxy LNA

<400> SEQUENCE: 49
gcattggtat                                                          10
```

```
<210> SEQ ID NO 50
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (12)..(13)
<223> OTHER INFORMATION: LNA

<400> SEQUENCE: 50
agcattggta ttca                                                    14

<210> SEQ ID NO 51
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA

<400> SEQUENCE: 51
agcattggta ttca                                                    14

<210> SEQ ID NO 52
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (11)..(13)
<223> OTHER INFORMATION: LNA

<400> SEQUENCE: 52
agcattggta ttca                                                    14

<210> SEQ ID NO 53
<211> LENGTH: 14
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 53
agcattggta ttca                                                    14
```

```
<210> SEQ ID NO 54
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (11)..(12)
<223> OTHER INFORMATION: LNA

<400> SEQUENCE: 54
gcattggtat tc                                                              12

<210> SEQ ID NO 55
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(12)
<223> OTHER INFORMATION: LNA

<400> SEQUENCE: 55
gcattggtat tc                                                              12

<210> SEQ ID NO 56
<211> LENGTH: 12
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (10)..(12)
<223> OTHER INFORMATION: LNA

<400> SEQUENCE: 56
gcattggtat tc                                                              12

<210> SEQ ID NO 57
<211> LENGTH: 10
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (10)..(10)
<223> OTHER INFORMATION: LNA

<400> SEQUENCE: 57
gcattggtat                                                                 10
```

```
<210> SEQ ID NO 58
<211> LENGTH: 23
<212> TYPE: RNA
<213> ORGANISM: homo sapiens

<400> SEQUENCE: 58
uggaguguga caauguguu ugu                                              23

<210> SEQ ID NO 59
<211> LENGTH: 23
<212> TYPE: RNA
<213> ORGANISM: homo sapiens

<400> SEQUENCE: 59
uguuuguggu aacaguguga ggu                                             23

<210> SEQ ID NO 60
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: phosphorothioate linkages
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 60
ccattgtcac actcca                                                     16

<210> SEQ ID NO 61
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: phosphorothioate linkages
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
```

<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 61
ccattgtcac actcca                                                     16

<210> SEQ ID NO 62
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: phosphorothioate linkages
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 62
ccattgtcac actcca                                                     16

<210> SEQ ID NO 63
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 63
ccattgtcac actcc                                                      15

<210> SEQ ID NO 64
<211> LENGTH: 15
<212> TYPE: DNA

```
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 64
ccattctgac cctac                                                    15

<210> SEQ ID NO 65
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: phosphorothioate linkages
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 65
ccattgtctc aatcca                                                   16

<210> SEQ ID NO 66
<211> LENGTH: 13
<212> TYPE: DNA
<213> ORGANISM: artificial
<220> FEATURE:
<223> OTHER INFORMATION: LNA oligomer
<220> FEATURE:
```

```
<221> NAME/KEY: misc_feature
<222> LOCATION: (1)..(13)
<223> OTHER INFORMATION: phosphorothioate linkages
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(13)
<223> OTHER INFORMATION: LNA

<400> SEQUENCE: 66
attgtcacac tcc                                                          13

<210> SEQ ID NO 67
<211> LENGTH: 23
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (20)..(23)
<223> OTHER INFORMATION: LNA

<400> SEQUENCE: 67
acaaacacca ttgtcacact cca                                               23

<210> SEQ ID NO 68
<211> LENGTH: 23
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (7)..(14)
<223> OTHER INFORMATION: LNA

<400> SEQUENCE: 68
acaaacacca ttgtcacact cca                                               23

<210> SEQ ID NO 69
<211> LENGTH: 23
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
```

```
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA
<220> FEATURE:
<221> NAME/KEY: misc_feature
<222> LOCATION: (18)..(18)
<223> OTHER INFORMATION: LNA
<220> FEATURE:
<221> NAME/KEY: misc_feature
<222> LOCATION: (21)..(21)
<223> OTHER INFORMATION: LNA

<400> SEQUENCE: 69
acaaacacca ttgtcacact cca                                          23

<210> SEQ ID NO 70
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (5)..(7)
<223> OTHER INFORMATION: LNA
<220> FEATURE:
<221> NAME/KEY: misc_feature
<222> LOCATION: (10)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 70
ccattgtcac actcc                                                   15

<210> SEQ ID NO 71
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(5)
<223> OTHER INFORMATION: LNA
<220> FEATURE:
<221> NAME/KEY: misc_feature
<222> LOCATION: (7)..(10)
<223> OTHER INFORMATION: LNA
<220> FEATURE:
<221> NAME/KEY: misc_feature
<222> LOCATION: (12)..(13)
<223> OTHER INFORMATION: LNA

<400> SEQUENCE: 71
attgtcacac tcc                                                     13
```

```
<210> SEQ ID NO 72
<211> LENGTH: 11
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (5)..(8)
<223> OTHER INFORMATION: LNA
<220> FEATURE:
<221> NAME/KEY: misc_feature
<222> LOCATION: (10)..(11)
<223> OTHER INFORMATION: LNA

<400> SEQUENCE: 72
tgtcacactc c                                                          11

<210> SEQ ID NO 73
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(15)
<223> OTHER INFORMATION: high affinity nucleotide analogues
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (2)..(2)
<223> OTHER INFORMATION: 2'MOE
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (4)..(5)
<223> OTHER INFORMATION: 2'MOE
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (8)..(9)
<223> OTHER INFORMATION: 2'MOE
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (11)..(11)
<223> OTHER INFORMATION: 2'MOE
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (13)..(13)
<223> OTHER INFORMATION: 2'MOE
<220> FEATURE:
<221> NAME/KEY: misc_feature
<222> LOCATION: (14)..(15)
<223> OTHER INFORMATION: LNA
```

```
<400> SEQUENCE: 73
ccattgtcac actcc                                                    15

<210> SEQ ID NO 74
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (2)..(2)
<223> OTHER INFORMATION: 2'Fluoro
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (4)..(4)
<223> OTHER INFORMATION: 2'Fluoro
<220> FEATURE:
<221> NAME/KEY: misc_feature
<222> LOCATION: (4)..(5)
<223> OTHER INFORMATION: 2'Fluoro
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (8)..(9)
<223> OTHER INFORMATION: 2'Fluoro
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (11)..(11)
<223> OTHER INFORMATION: 2'Fluoro
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (13)..(13)
<223> OTHER INFORMATION: 2'Fluoro
<220> FEATURE:
<221> NAME/KEY: misc_feature
<222> LOCATION: (14)..(15)
<223> OTHER INFORMATION: LNA

<400> SEQUENCE: 74
ccattgtcac actcc                                                    15

<210> SEQ ID NO 75
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
```

```
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 75
tgcatggatt tgcaca                                                    16

<210> SEQ ID NO 76
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 76
tgcatggatt tgcac                                                     15

<210> SEQ ID NO 77
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (13)..(13)
<223> OTHER INFORMATION: LNA

<400> SEQUENCE: 77
catggatttg cac                                                       13
```

<210> SEQ ID NO 78
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 78
tgcatggatt tgcac                                              15

<210> SEQ ID NO 79
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA

<400> SEQUENCE: 79
catggatttg cac                                                13

<210> SEQ ID NO 80
<211> LENGTH: 13
<212> TYPE: DNA

```
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(13)
<223> OTHER INFORMATION: LNA

<400> SEQUENCE: 80
catggatttg cac                                                        13

<210> SEQ ID NO 81
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 81
tgcatggatt tgcac                                                      15

<210> SEQ ID NO 82
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
```

```
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (9)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 82
tgcatggatt tgcaca                                                   16

<210> SEQ ID NO 83
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 83
ccattgtcac actcca                                                   16

<210> SEQ ID NO 84
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
```

```
<221> NAME/KEY: misc_feature
<222> LOCATION: (14)..(14)
<223> OTHER INFORMATION: LNA

<400> SEQUENCE: 84
ccattgtaac tctcca                                                      16

<210> SEQ ID NO 85
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 85
ccattgtcac actcca                                                      16

<210> SEQ ID NO 86
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 86
ccattgtcac actcc                                                       15

<210> SEQ ID NO 87
<211> LENGTH: 13
<212> TYPE: DNA
<213> ORGANISM: artificial
<220> FEATURE:
<223> OTHER INFORMATION: LNA oligomer
<220> FEATURE:
```

```
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA

<400> SEQUENCE: 87
attgtcacac tcc                                                              13

<210> SEQ ID NO 88
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 88
ccattgtcac actcc                                                            15

<210> SEQ ID NO 89
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (13)..(13)
<223> OTHER INFORMATION: LNA
```

```
<400> SEQUENCE: 89
attgtcacac tcc                                                          13

<210> SEQ ID NO 90
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA

<400> SEQUENCE: 90
attgtcacac tcc                                                          13

<210> SEQ ID NO 91
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(13)
<223> OTHER INFORMATION: LNA

<400> SEQUENCE: 91
attgtcacac tcc                                                          13

<210> SEQ ID NO 92
<211> LENGTH: 15
<212> TYPE: DNA
<213> ORGANISM: artificial
<220> FEATURE:
<223> OTHER INFORMATION: LNA oligomer
<220> FEATURE:
```

```
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 92
ccattgtcac actcc                                                    15

<210> SEQ ID NO 93
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 93
ccattgtcac actcca                                                   16

<210> SEQ ID NO 94
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 94
ccattgtcac actcca                                                   16
```

<210> SEQ ID NO 95
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 95
tcacgattag cattaa                                                        16

<210> SEQ ID NO 96
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 96
atcacgatta gcatta                                                        16

<210> SEQ ID NO 97
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:

```
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (13)..(13)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 97
tcacgattag cattaa                                                     16

<210> SEQ ID NO 98
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 98
atcacgatta gcatta                                                     16

<210> SEQ ID NO 99
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (2)..(2)
<223> OTHER INFORMATION: LNA
<220> FEATURE:
```

```
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 99
gagccgaacg aacaa                                                          15

<210> SEQ ID NO 100
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (12)..(12)
<223> OTHER INFORMATION: LNA

<400> SEQUENCE: 100
gccgaacgaa caa                                                            13

<210> SEQ ID NO 101
<211> LENGTH: 15
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
```

-continued

```
<221> NAME/KEY: misc_feature
<222> LOCATION: (13)..(13)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 101
gagccgaacg aacaa                                                       15

<210> SEQ ID NO 102
<211> LENGTH: 13
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (13)..(13)
<223> OTHER INFORMATION: LNA

<400> SEQUENCE: 102
gccgaacgaa caa                                                         13

<210> SEQ ID NO 103
<211> LENGTH: 16
<212> TYPE: DNA
<213> ORGANISM: artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: phosphorothioate linkages
<220> FEATURE:
<221> NAME/KEY: misc_feature
<222> LOCATION: (1)..(3)
<223> OTHER INFORMATION: OXY LNA
<220> FEATURE:
<221> NAME/KEY: misc_feature
<222> LOCATION: (1)..(1)
<223> OTHER INFORMATION: OXY LNA methyl cytosine
<220> FEATURE:
<221> NAME/KEY: misc_feature
<222> LOCATION: (13)..(15)
<223> OTHER INFORMATION: OXY LNA
<220> FEATURE:
<221> NAME/KEY: misc_feature
```

```
-continued
<222> LOCATION: (14)..(14)
<223> OTHER INFORMATION: OXY LNA methyl cytosine

<400> SEQUENCE: 103
cagcattggt attcag                                                16
```

COMBINATION TREATMENT FOR THE TREATMENT OF HEPATITIS C VIRUS INFECTION

This application is the U.S. National Stage of International Application No. PCT/DK2008/000345, filed Oct. 3, 2008, which claims the benefit of U.S. Provisional Application Nos.: 60/977,497, filed Oct. 4, 2007; 60/979,217, filed Oct. 11, 2007; and 61/028,062, filed Feb. 12, 2008; and European Patent Application No. 08104780, filed Jul. 17, 2008, all of which are incorporated herein by reference in their entirety.

REFERENCE TO A SEQUENCE LISTING SUBMITTED ELECTRONICALLY VIA EFS-WEB

The content of the electronically submitted sequence listing (Name: Sequence_Listing.txt, Size: 45,500 bytes; and Date of Creation: Apr. 2, 2010) is herein incorporated by reference in its entirety.

FIELD OF THE INVENTION

The present invention provides compositions and methods useful for treatment of hepatitis C virus infection. In particular, this invention relates to the use of a combination of compounds, one which is capable of inhibiting miR-122 and another which is capable of inhibiting Apo-B100 or alternatively of inhibiting another molecule in the VLDL assembly pathway. Inhibition of miR-122 in combination with inhibition of the VLDL assembly pathway, i.e. Apo-B100 is beneficial for the treatment of hepatitis C virus infection.

BACKGROUND

Around 150-200 million people around the world are chronically infected with Hepatitis C virus (HCV). The infection can cause liver inflammation (hepatitis) that is often asymptomatic, but ensuing chronic hepatitis can result later in cirrhosis (fibrotic scarring of the liver) and liver cancer.

The hepatitis C virus (HCV) is spread by blood-to-blood contact with an infected person's blood. The symptoms can be medically managed, and a proportion of patients can be cleared of the virus by a long course of anti-viral medicines. Although early medical intervention is helpful, people with HCV infection often experience mild symptoms, and consequently do not seek treatment. In the U.S., those with a history of intravenous drug use, inhaled drug usage, tattoos, or who have been exposed to blood via unsafe sex or social practices are at increased risk of acquiring this disease. Hepatitis C is the leading cause of liver transplantation in the United States.

MiR-122 is a liver specific microRNA, well conserved within vertebrates. MiR-122 is involved in cholesterol metabolism (Esau et al. 2005) and it has recently been shown that miR-122 is important for hepatitis C(HCV) replication (Jopling et al. 2005).

The sequence of miR-122 is well conserved between different mammalian species (mirbase, Sanger Center, UK).

```
>hsa-miR-122 MIMAT0000421
UGGAGUGUGACAAUGGUGUUUG

>mmu-miR-122 MIMAT0000246
UGGAGUGUGACAAUGGUGUUUG

>rno-miR-122 MIMAT0000827
UGGAGUGUGACAAUGGUGUUUG
```

-continued
```
>dre-miR-122 MIMAT0001818
UGGAGUGUGACAAUGGUGUUUG

>xtr-miR-122 MIMAT0003585
UGGAGUGUGACAAUGGUGUUUGU

>gga-miR-122 MIMAT0001190
UGGAGUGUGACAAUGGUGUUUGU

>bta-miR-122 MIMAT0003849
UGGAGUGUGACAAUGGUGUUUG
```

Joplin et al. also show that blocking miR-122 by an oligonucleotide inhibits HCV genomic replication. miR-122 interacts with a target sequences in the 5'UTR and 3'UTR of the virus, mutations in these sites reduce virus replication. Both the 5'UTR and 3'UTR miR-122 target site is conserved in the HCV genotypes 1a, 1b, 2, 3, 4, 5, and 6. This suggests that all HCV genotype replication can be reduced by blocking miR-122. It has also recently been shown that genotype 2 replication is blocked by targeting miR-122 with a complementary oligonucleotide (Randall et al. PNAS 2007).

A second cellular factor of importance for the ability of HCV to replicate in mammalian cells is the VLDL assembly pathway (Huang et al. 2007). VLDL assembly is important for packaging/release of the viral particles from the host cell. Reducing the VLDL assembly also reduce release of HCV particles.

One factor of particular significance in the VLDL assembly pathway is Apolipoprotein B (also known as ApoB, apolipoprotein B-100; ApoB-100, apolipoprotein B-48; ApoB-48 and Ag(x) antigen). ApoB is a large glycoprotein that serves an indispensable role in the assembly and secretion of lipids and in the transport and receptor-mediated uptake and delivery of distinct classes of lipoproteins. ApoB plays an important role in the regulation of circulating lipoprotein levels, and is therefore relevant in terms of atherosclerosis susceptibility which is highly correlated with the ambient concentration of apolipoprotein B-containing lipoproteins. See Davidson and Shelness (Annul Rev. Nutr., 2000, 20, 169-193) for further details of the two forms of ApoB present in mammals, their structure and medicinal importance of ApoB.

Two forms of apolipoprotein B exist in mammals. ApoB-100 represents the full-length protein containing 4536 amino acid residues synthesized exclusively in the human liver (Davidson and Shelness, Annul Rev. Nutr., 2000, 20, 169-193). A truncated form known as ApoB-48 is colinear with the amino terminal 2152 residues and is synthesized in the small intestine of all mammals (Davidson and Shelness, Annul Rev. Nutr., 2000, 20, 169-193).

The basis by which the common structural gene for apolipoprotein B produces two distinct protein isoforms is a process known as RNA editing. A site specific cytosine-to-uracil editing reaction produces a UAA stop codon and translational termination of apolipoprotein B to produce ApoB-48 (Davidson and Shelness, Annul Rev. Nutr., 2000, 20, 169-193). +

About 70% of all infected establish chronic infection. Current antiviral therapy against HCV consist of interferon in combination with ribavirin, which is effective in some patients, however a large group do not respond or do not tolerate the treatment. Therefore, a need for novel treatment modalities for HCV exists. The present invention provides a novel combination treatment for HCV, comprising an inhibitor of miR-122 in combination with an inhibitor of ApoB-100 or an inhibitor of the VLDL assembly pathway. The combination treatment provided lead to a reduction of two endogenous host factors miR-122 and the VLDL pathway (or APOB-100) that are needed for the full replication of HCV.

Implementation of a treatment that does not directly target the virus, but rather inhibits host factors that are important for HCV replication in the host cell, will reduce the problem related to the high mutation rate of an RNA/RNA replicating virus, which could increase the probability of escape mutations and resistance to therapies that target the virus directly.

The invention relates to the combination of compounds which modulate (suitably inhibit) VLDL assembly, and compounds which inhibit miR-122 function, and that by utilizing both compounds in medical treatment or prevention of HCV infection, an improved treatment is achieved. Whilst not wishing to be bound to any specific theory, we consider that by combating the virus at two different steps in its lifecycle leads to synergy in inhibition and less resistance to drugs.

SUMMARY OF THE INVENTION

The present invention provides a novel combination treatment for hepatitis C virus infection, utilizing the combined effects of blocking miR-122 and VLDL/apoB.

The composition consist of any agent reducing/blocking miR-122 (such as but not limited to LNA-antimiR blocking miR-122 (LNA containing antisense oligonucleotide targeting miR-122, LNA-antimiR-122) or any other oligonucleotide targeting miR-122 or a an agent generally blocking the microRNA pathway and the function) in combination with any agent reducing/blocking VLDL assembly (such as an LNA antisense oligonucleotide reducing ApoB100, or siRNA blocking ApoB100, or other current drugs reducing VLDL assembly/pathway for example MTP (microsomal triglyceride transfer protein) inhibitors (such as BMS-2101038 used by Huang et al. 2007), or any other agent reducing/blocking the VLDL assembly/pathway). It is also possible that this could be combined with additional antiviral agents.

In one embodiment, the present invention utilizes antisense oligonucleotide, such as Locked Nucleic Acid (LNA) oligomeric compounds for modulating VLDL assembly in example by inhibiting apolipoprotein B expression, including inhibition of the alternative isoform of apolipoprotein B ApoB-48.

In a further embodiment, which may be the same or different, the invention utilizes molecules which interfere with the function of microRNA-122 (miR-122), so called antimirs which target miR-122, such as antisense oligonucleotides, including Locked Nucleic Acid (LNA) oligomeric compounds to provide efficient blocking of miR-122.

miR-122 is involved in, and is even considered essential for the replication of HCV in human liver cells.

The invention provides for a medicament which comprises a miR-122 inhibitor, an inhibitor of VLDL assembly, and a suitable pharmacologically acceptable carrier.

Suitably, the medicament is for the treatment of HCV infection.

It will be recognized that the miR-122 inhibitor and the inhibitor of VLDL assembly are not, preferably, the same compound, but are different compounds. In this respect it is preferable that the VLDL assembly inhibitor is not a direct inhibitor of miR-122, such as a antisense oligonucleotide to miR-122.

The invention also provides for a method for the preparation of a medicament said method comprising admixing said miR-122 inhibitor, said inhibitor of VLDL assembly, and said suitable pharmacologically acceptable carrier.

The invention further provides for a kit for the treatment of HCV infection comprising a miR-122 inhibitor and an inhibitor of VLDL assembly according to any one of the preceding claims.

The use of a miR-122 inhibitor according to any one of the preceding claims, and an inhibitor of VLDL assembly according to any one of the preceding claims, (or the kit according to claim 18) for the preparation of a medicament for the treatment or prevention of HCV infection.

In one embodiment said treatment or prevention is for the prevention of post transplantation reinfection.

In one embodiment the use the medicament is made for treatment of patients that may be or are resistant to other existing treatment, such as interferon and/or ribavirin treatment.

In one embodiment the medicament is administered parentally.

In one embodiment, the medicament is administered intravenously or intramuscularly or intraperitoneally.

In one embodiment, the miR-122 inhibitor and the inhibitor of VLDL assembly are administered simultaneously in a combined dosage regimen.

In one embodiment, the miR-122 inhibitor and the inhibitor of VLDL assembly are administered simultaneously in separate dosage regimens.

In one embodiment, the miR-122 inhibitor and the inhibitor of VLDL assembly are to be administered separately in two different dosage forms.

The invention further provides for a method for treatment or of prevention of HCV infection in a patient, said method comprising the steps of administering the medicament according to the invention to a patient in need thereof, optionally using the administration routes, or for the purpose, referred to herein.

The invention further provides for a method for the concurrent down-regulation of VDLD assembly and miR-122 and/or HCV infection in a mammalian or human cell, said method comprising administering a miR-122 inhibitor and an inhibitor of VLDL assembly to said cell.

The invention further provides for a method for the concurrent down-regulation of ApoB and miR-122 and/or HCV infection in a mammalian or human cell, said method comprising administering a miR-122 inhibitor, and an inhibitor of ApoB to the preceding claims to said cell.

In the above methods of concurrent down-regulation, the cell typically comprises miR-122 and optionally HCV, and may suitably comprises the mRNA encoding ApoB-100 (or alternative VDLD or mRNA target as referred to herein).

The invention further provides a miR-122 inhibitor as a medicament for the treatment of HCV infection in patients treated with an APOB-100 inhibitor.

The invention further provides an APOB-100 inhibitor as a medicament for the treatment of HCV infection in patients treated with a miR-122 inhibitor.

The invention further provides the use of the medicaments and compositions of the invention, wherein the medicament is for the prevention of post transplantation reinfection.

The invention further provides the use of the medicaments and compositions of the invention, wherein the medicament is for prophylactic treatment.

The invention further provides the use of the medicaments and compositions of the invention, wherein the medicament is for treatment of patients infected with HCV, wherein said treatment is not prophylactic or for the prevention of post transplantation reinfection.

The invention further provides for any one of the above medicaments and compositions, wherein the medicament is made for treatment of patients that are resistant to other existing treatment, such as interferon and/or ribavirin treatment.

The invention further provides the above medicaments and compositions, wherein the APOB-100 antagonist, is an oligonucleotide complementary to all or part of the APOB-100 mRNA sequence, or is an inhibitor of MTP.

The invention further provides the above medicaments and compositions, wherein the apoB-100 antagonist is an oligonucleotide that contains one or more LNA residues.

The invention further provides medicaments and compositions comprising an antisense apoB-100 oligonucleotide comprising one or more LNA residues, wherein the oligonucleotide contains one or more mismatches.

The invention further provides medicaments and compositions as described above, wherein the miR-122 inhibitor is an oligonucleotide that is complementary to all or part of the miR-122 RNA sequence.

The invention further provides medicaments and compositions as described above, wherein the miR-122 inhibitor is an antisense oligonucleotide comprising a sequence that is complementary to the miR-122 seed sequence.

The invention further provides medicaments and compositions as described above, wherein the miR-122 inhibitor is SEQ ID NO: 63.

The invention further provides medicaments and compositions as described above, wherein the miR-122 inhibitor is an oligonucleotide that contains one or more LNA residues.

The invention further provides medicaments and compositions as described above, wherein the miR-122 inhibitor is an antisense oligonucleotide containing one or more mismatches.

The invention further provides medicaments and compositions as described above, wherein the medicament is administered parentally.

The invention further provides medicaments and compositions as described above, wherein the medicament is administered intravenously or intramuscularly or intraperitoneally.

The invention further provides medicaments and compositions as described above, wherein the miR-122 inhibitor and the APOB-100 inhibitor are administered simultaneously in a combined dosage regimen.

The invention further provides medicaments and compositions as described above, wherein the miR-122 inhibitor and the APOB-100 inhibitor are administered simultaneously in separate dosage regimens.

The invention further provides medicaments and compositions as described above, wherein the medicaments and compositions are made for use in combination with treatment with interferon and/or ribavirin.

The invention further provides for a method of treating a subject suffering from HCV infection, the method comprising the step of administering a pharmaceutical composition as defined herein to the subject in need thereof.

BRIEF DESCRIPTION OF THE DRAWINGS

FIG. 3. Assessment of plasma cholesterol levels in LNA-antimiR-122a treated mice compared to the control mice that received saline.

DETAILED DESCRIPTION OF THE INVENTION

Terms Used in the Description

Figure 1:
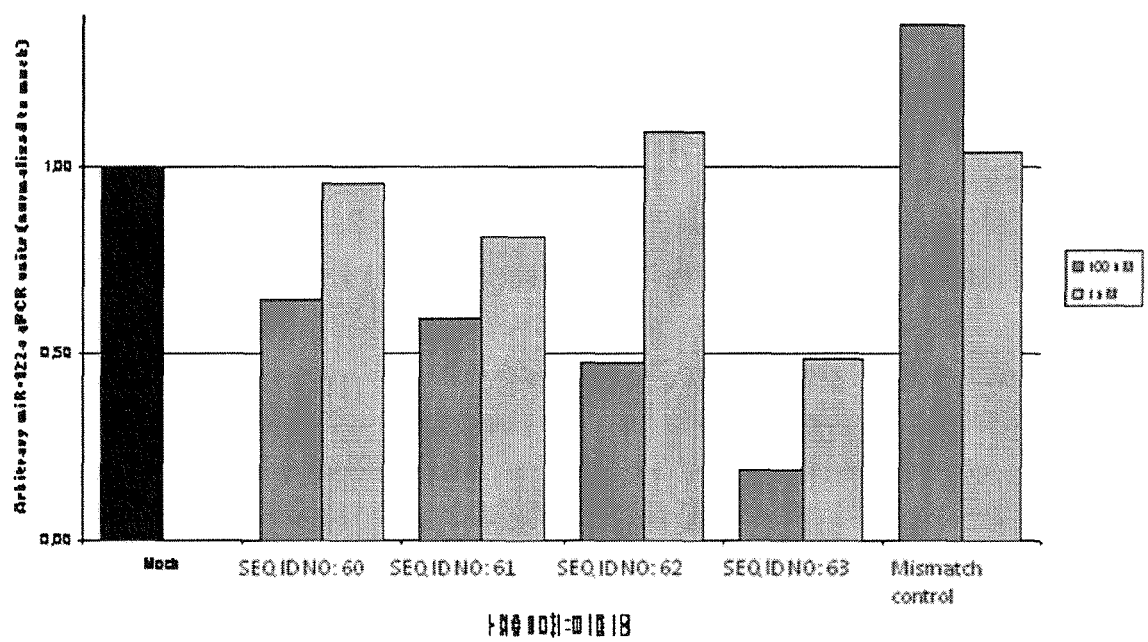
FIG. 1. The effect of treatment with different LNA antimiR oligonucleotides on target nucleic acid expression in the miR-122a expressing cell line Huh-7. Shown are amounts of miR-122a (arbitrary units) derived from miR-122a specific qRT-PCR as compared to untreated cells (mock). The LNA anti-miR oligonucleotides were used at two concentrations, 1 and 100 nM, respectively. Included is also a mismatch control (SEQ ID NO: 64) to SEQ ID NO: 63.

"HCV" means hepatitis C virus.

The terms "Oligomeric compound", which is interchangeable with the term "oligonucleotide", "oligo", and "oligonucleotide compound", refer, in the context of the present invention, to an oligomer, i.e. a nucleic acid polymer (e.g. ribonucleic acid (RNA) or deoxyribonucleic acid (DNA)) or nucleic acid analogue of those known in the art, preferably Locked Nucleic Acid (LNA), or a mixture thereof). This term includes oligonucleotides composed of naturally occurring nucleobases, sugars and internucleoside (backbone) linkages as well as oligonucleotides having non-naturally-occurring portions which function similarly or with specific improved functions. Fully or partly modified or substituted oligonucleotides are often preferred over native forms because of several desirable properties of such oligonucleotides, such as for instance, the ability to penetrate a cell membrane, good resistance to extra- and intracellular nucleases, high affinity and specificity for the nucleic acid target. The LNA analogue is particularly preferred, for example, regarding the above-mentioned properties. Therefore, in a highly preferable embodiment, the terms "oligomeric compound", "oligonucleotide", "oligo" and "oligonucleotide compound" according to the invention, are compounds which are built up of both nucleotide and nucleotide analogue units, such as LNA units to form a polymeric compound of between 12-50 nucleotides/nucleotide analogues (oligomer).

By the term "unit" is understood a monomer.

In one embodiment the inhibitor of inhibitor of VLDL assembly, is an inhibitor of a molecule involved in, such as a molecule regulating, VLDL assembly, such as in non limiting example, a molecule selected from the group consisting of apoB-48, apoB-100, apoC, apoE, MTP (microsomal transfer protein), TGH (triacylglycerol hydrolase), ACAT2 (liver and intestine acyl-COA:cholesterol acyl transferase), Phospholipase D, iPLA2 (cytosolic calcium-independent phospholipase A2).

In one embodiment the inhibitor of VLDL assembly is an inhibitor of ApoB.

In one embodiment the inhibitor of VLDL assembly is an inhibitor of MTP (microsomal transfer protein)

In one embodiment the inhibitor of VLDL assembly is an antisense oligomeric compound which comprises a nucleobase sequence which is complementary to a corresponding region of the mRNA which encodes said molecule involved in VLDL assembly.

In one embodiment the inhibitor of VLDL assembly is, selected from the ApoB-100 inhibitors, such as those referred to herein, such as SEQ ID NO: 31, SEQ ID NO: 26 or SEQ ID NO: 103 or any one of the compounds disclosed in Table 1.

In one embodiment the antisense oligomeric compound which inhibits VLDL assembly has a length of between 10 and 23 nucleobases, such as 10, 11, 12, 13, 14, 15, 16, 17, 18, 19, 20, 21, 22 or 23 nucleobases.

In one embodiment the antisense oligomeric compound which inhibits VLDL assembly is a gapmer oligonucleotide which consist or comprises of a nucleobase sequence of formula 5' A-B-C 3' or, optionally 5' A-B-C-D 3', wherein: Region A consist or comprises of between 1 and 5 nucleotide analogues; region B comprises of 7, 8, 9, 10, 11 or 12 nucleobases which, when formed in a duplex with a complementary mRNA are capable of recruiting RNAseH, such as DNA nucleotide unit; region C consist or comprises of between 1 and 5 nucleotide analogues; and when present region D consists of 1, 2, or 3 DNA units.

In one embodiment the nucleotide analogues present in regions A and C are independently selected from the group consisting of 2'-O-alkyl-RNA unit, 2'-OMe-RNA unit, 2'-amino-DNA unit, 2'-fluoro-DNA unit, LNA unit, PNA unit, HNA unit, and INA unit.

In one embodiment the nucleotide analogues present in regions A and C are all the same, and are preferably LNA units.

ApoB Inhibiting Compounds for Use in the Invention.

LNA-apoB-antisense: An LNA containing antisense oligonucleotide targeting apoB100

ApoB100 inhibiting compounds useful in the present invention include but is not limited to compounds such as those disclosed in WO2007/031081, U.S. Pat. No. 4,920,115, U.S. Pat. No. 5,919,795, U.S. Pat. No. 6,121,283, EP1099442, US2006040989, WO2005058824, WO2006010423, US2006035858, WO2006020676, WO2006036916, WO2006053430, WO2006113910, US20050712211, WO2000097662, WO2003011887 and WO2004044181 which are hereby all incorporated by reference. Especially preferred are the compounds disclosed in U.S. 60/896,419 and U.S. 60/977,409, the entire specification which are also incorporated by reference.

Further compounds which may be useful in the present invention are disclosed in WO2006/036916, WO2003/011887, WO2004/044181, all of which are also incorporated by reference.

In this section relating to apoB inhibiting compounds for use in the invention, SEQ ID NO refers to those listed in Table 1 of example 2.

The apoB-100 inhibiting compounds of the present invention preferably employs oligomeric compounds, particularly antisense oligonucleotides, for use in modulating the function of nucleic acid molecules encoding apolipoprotein B (such as Apo-B100 and/or ApoB-48). The modulation is ultimately a change in the amount of apolipoprotein B produced. In one embodiment this is accomplished by providing oligomeric compounds, which specifically hybridise with nucleic acids, such as messenger RNA, which encodes apolipoprotein B. The modulation preferably results in the inhibition of the expression of apolipoprotein B, i.e. leads to a decrease in the number of functional proteins produced.

Oligomeric compounds, which modulate expression of the target, are identified through experimentation or though rational design based on sequence information on the target and know-how on how best to design an oligonucleotide compound against a desired target. The sequences of these compounds are preferred embodiments of the invention. Likewise, the sequence motifs in the target to which these preferred oligomeric compounds are complementary (referred to as "hot spots") are preferred sites for targeting.

In one embodiment, the antisense oligomeric compound which inhibits VLDL assembly has a length of between 10 and 23 nucleobases, such as 10, 11, 12, 13, 14, 15, 16, 17, 18, 19, 20, 21, 22 or 23 nucleobases. Typically, the nucleobases form a contiguous nucleobase sequence. In one embodiment, the oligomeric compound which inhibits VLDL assembly consists of a total of 10-15 nucleobases, wherein the nucleobase sequence of said compound is present in SEQ ID NO 1, wherein said compound comprises at least 3 nucleotide analogues.

In one embodiment, the antisense oligomeric compound which inhibits VLDL assembly is a gapmer oligonucleotide which consist or comprises of a nucleobase sequence of formula 5' A-B-C 3' or, optionally 5' A-B-C-D 3', wherein: Region A consist or comprises of between 1 and 5 nucleotide analogues; region B comprises of 7, 8, 9, 10, 11 or 12 nucleobases which, when formed in a duplex with a complementary mRNA are capable of recruiting RNAseH, such as DNA nucleotide unit; region C consist or comprises of between 1 and 5 nucleotide analogues; and when present region D consists of 1, 2, or 3 DNA units.

The gapmer may comprises or consists, in a 5' to 3' direction i) region A: a stretch of 2-4 nucleotide analogues, followed by ii) region B: a stretch of 6-11 nucleotides (such as DNA nucleotides), which is followed by iii) region C: a stretch of 2-4 nucleotide analogues, and optionally iv) one or two nucleotides (D).

In one embodiment region A has a length of 1 nucleotide analogues.

In one embodiment region A has a length of 2 nucleotide analogues.

In one embodiment region A has a length of 3 nucleotide analogues.

In one embodiment region A has a length of 4 nucleotide analogues.

In one embodiment region C has a length of 1 nucleotide analogues.

In one embodiment region C has a length of 2 nucleotide analogues.

In one embodiment region C has a length of 3 nucleotide analogues.

In one embodiment region C has a length of 4 nucleotide analogues.

In one embodiment region B has a length of between 7 and 10 nucleotides (such as DNA nucleotides), such as 8 or 9 nucleosides (such as DNA nucleotides).

In one embodiment the compound which inhibits VLDL assembly has a length of from 12-15 nucleobases.

In one embodiment the compound which inhibits VLDL assembly has a length of 12, 13, or 14 nucleobases.

In one embodiment the nucleobase sequence of the compound which inhibits VLDL assembly comprises a internucleobase linkage group selected from the group consisting of a phosphate group, a phosphodiester group, a phosphorothioate group and a boranophosphate group, the internucleoside linkage may be —O—P(O)$_2$—O—, —O—P(O, S)—O—. The same linkage groups may be used in the inhibitor of miR-122.

In one embodiment, the internucleobase linkage groups between the nucleobase units of the nucleobase sequence of the compound which inhibits VLDL assembly are independently selected from either phosphorothioate or phosphodiester linkage groups. The same linkage groups may be used in the inhibitor of miR-122.

In one embodiment region A comprises at least one phosphodiester linkage between two nucleotide analogue units, or a nucleotide analogue unit and a nucleotide unit. It will be understood that the linkage group between a nucleotide analogue and a nucleotide unit in this context refers to the linkage group between regions A and B.

In one embodiment region C comprises at least one phosphodiester linkage between two nucleotide analogue units, or a nucleotide analogue unit and a nucleotide unit. It will be understood that the linkage group between a nucleotide analogue and a nucleotide unit in this context refers to the linkage group between regions B and C.

In one embodiment the internucleotide linkages between the nucleotides of region B are phosphorothioate.

In one embodiment the internucleobase linkage between the 3' nucleotide analogue of A and the 5' nucleotide of region B is a phosphorothioate.

In one embodiment the internucleobase linkage between the 3' nucleotide of region B and the 5' nucleotide analogue of region C is a phosphorothioate.

In one embodiment the internucleobase linkage between the 3' nucleotide analogue of A and the 5' nucleotide of region B is a phosphodiester.

In one embodiment the internucleobase linkage between the 3' nucleotide of region B and the 5' nucleotide analogue of region C is a phosphodiester.

In one embodiment the internucleobase linkage between the two 5' nucleotide analogues of region A are phosphodiester.

In one embodiment the internucleobase linkage between the two 3' nucleotide analogues of region C are phosphodiester.

In one embodiment the internucleobase linkage between the two 3' nucleotide analogues of region A are phosphodiester.

In one embodiment the internucleobase linkage between the two 5' nucleotide analogues of region C are phosphodiester.

In one embodiment region A has a length of 4 nucleotide analogues and internucleobase linkage between the two middle nucleotide analogues of region A are phosphodiester.

In one embodiment region C has a length of 4 nucleotide analogues and internucleobase linkage between the two middle nucleotide analogues of region C are phosphodiester.

In one embodiment all the internucleobase linkages between nucleotide analogues present in the compound of the invention are phosphodiester.

In one embodiment, such as the embodiments referred to above, as suitable and where not specifically indicated all remaining internucleobase linkages are either phosphodiester or phosphorothioate, or in one separate embodiment a mixture thereof.

In one embodiment all the internucleobase linkage groups are phosphorothioate.

In one embodiment the nucleotide analogues present within the compound which inhibits VLDL assembly, such as in regions A and C are independently selected from the group consisting of: 2'-O-alkyl-RNA monomers, 2'-amino-DNA monomers, 2'-fluoro-DNA monomers, LNA monomers, arabino nucleic acid (ANA) monomers, 2'-fluoro-ANA monomers, HNA monomers, INA monomers.

In one embodiment the nucleotide analogues are independently selected from the group consisting of 2'-MOE-RNA (2'-O-methoxyethyl-RNA), 2'Fluoro-DNA, and LNA.

In one embodiment at least one of said nucleotide analogues is a locked nucleic acid (LNA).

In one embodiment at least one of said nucleotide analogues is 2'-MOE-RNA, such as 2, 3, 4, 5, 6, 7 or 8 2'-MOE-RNA nucleobase units.

In one embodiment at least one of said nucleotide analogues is 2'-fluoro DNA, such as 2, 3, 4, 5, 6, 7 or 8 2'-fluoro-DNA nucleobase units.

In one embodiment 2, 3, 4, 5, 6, 7 or 8 of the nucleotide analogues are LNA and any remaining nucleotide analogue may be selected from the groups of nucleotide analogues referred to any one of claims 26-30.

In one embodiment all the nucleotide analogues are LNA.

In one embodiment the LNA nucleotide analogues present within the compound which inhibits VLDL assembly is/are selected from beta-D-oxy-LNA, alpha-L-oxy-LNA, beta-D-amino-LNA and beta-D-thio-LNA.

In one embodiment the nucleobase sequence selected from the group consisting of SEQ ID NOS 2, 3, 4, 5, 6, 7, 8, 9, 10, 11, 12, 13, 14, 15.

In one embodiment the compound which inhibits VLDL assembly is selected from the group consisting of SEQ ID NO: 17, 18, 19, 20, 21, 22, 23, 24 and 25.

In one embodiment the compound which inhibits VLDL assembly is selected from the group consisting of SEQ ID NO: 26, 27, 28, 29, 30, 31, 32, and 33.

In one embodiment the compound which inhibits VLDL assembly is selected from the group consisting of SEQ ID NO 34, 35, 36, 37, 38, 39 and 40.

The invention also refers to a conjugate comprising the compound which inhibits VLDL assembly and at least one non-nucleotide or non-polynucleotide moiety covalently attached to said compound.

In one embodiment referring to the conjugate, the non-nucleotide or non-polynucleotide moiety consists or comprise a sterol group such as cholesterol.

The medicament may, in one embodiment, further comprise at least one cholesterol-lowering compound.

Suitable cholesterol lowering compounds may be selected from a compound is selected from the group consisting of bile salt sequestrant resins (e.g., cholestyramine, colestipol, and colesevelam hydrochloride), HMGCoA-reductase inhibitors (e.g., lovastatin, cerivastatin, prevastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), implitapide, inhibitors of bile acid transporters (apical sodium-dependent bile acid transporters), regulators of hepatic CYP7a, estrogen replacement therapeutics (e.g., tamoxifen), and anti-inflammatories (e.g., glucocorticoids). Combinations with statins may be particularly preferred.

In a preferred embodiment, the oligonucleotides are capable of hybridising against the target nucleic acid, such as an ApoB mRNA or miR-122, to form a duplex with a Tm of at least 37° C., such as at least 40° C., at least 50° C., at least 55° C., or at least 60° C. In one aspect the Tm is between 37° C. and 80° C., such as between 40 or 50 and 70° C. Measurement of $T_m$ A 3 μM solution of the compound in 10 mM sodium phosphate/100 mM NaCl/0.1 nM EDTA, pH 7.0 is mixed with its complement DNA or RNA oligonucleotide at 3 μM concentration in 10 mM sodium phosphate/100 mM NaCl/0.1 nM EDTA, pH 7.0 at 90° C. for a minute and allowed to cool down to room temperature. The melting curve of the duplex is then determined by measuring the absorbance at 260 nm with a heating rate of 1° C./min. in the range of 25 to 95° C. The $T_m$ is measured as the maximum of the first derivative of the melting curve.

The oligomeric compounds are preferably antisense oligomeric compounds, also referred to as 'antisense oligonucleotides' and 'antisense inhibitors'.

The antisense inhibitors are preferably single stranded oligonucleotides. The single stranded oligonucleotides are preferably complementary to the corresponding region of the target nucleic acid.

Typically, single stranded 'antisense' oligonucleotides specifically interact with the mRNA of the target gene, causing either targeted degradation of the mRNA, for example via the RNaseH mechanism, or otherwise preventing translation.

In one embodiment the oligomeric compound according to the invention may target the DNA encoding mammalian ApoB.

The term "nucleobase" as used herein refers to DNA and RNA nucleotides and nucleotide analogues thereof.

The oligomeric compound according to the invention preferably comprises at least three nucleotide analogues. The at least three nucleotide analogues are preferably locked nucleic acid nucleotide analogues, and the oligomeric compound which comprises such nucleotide analogues are referred to herein as "LNA oligomeric compound", "LNA oligonucleotide compound" and "LNA oligonucleotide".

Suitable nucleotide analogues for use in the oligonucleotide referred to herein are independently selected from the group consisting of: 2'-O-alkyl-RNA monomers, 2'-amino-DNA monomers, 2'-fluoro-DNA monomers, LNA monomers, arabino nucleic acid (ANA) monomers, 2'-fluoro-ANA monomers, HNA monomers, INA monomers.

2'-O-methoxyethyl-RNA, 2'-fluoro-DNA monomers and LNA are preferred and as such the oligonucleotide of the invention may comprise nucleotide analogues which are independently selected from these three types of analogue, or may comprise of only one type selected from the three types. In a most preferred embodiment the oligonucleotide comprises only LNA nucleotide analogues and nucleotides (RNA or DNA, most preferably DNA nucleotides).

The invention refers to an oligomeric compound, consisting of 10-15, such as 11-15, 12-15, 13-15, in particular 12-14 nucleobases wherein the nucleobase sequence is present in SEQ ID NO. 1. The list of such sequences is given in Table 1. Preferred groups of sequences present in SEQ ID NO 1 are SEQ ID NO: 4-15.

The terms "corresponding to"/"corresponds to" refer to the comparison between the combined sequence of nucleotides and nucleotide analogues of the oligomeric compound of the invention, or subsequence thereof, and the equivalent nucleotide sequence of, e.g. Apolipoprotein B nucleic acid sequence (i.e. the nucleic acid target). Nucleotide analogues are compared directly to their equivalent nucleotides. The compounds of the invention may therefore have a sequence which is present (i.e. corresponds to) in the human ApoB sequence, i.e. SEQ ID NO 1.

Preferred groups of sequences present in SEQ ID NO 1 are SEQ ID NO: 4-15. Preferred ApoB antisense oligonucleotide sequences for use in the invention:

SEQ ID NO: 31: 5'-$G_s^o$ $^mC_s^o$ $a_s$ $t_s$ $t_s$ $g_s$ $g_s$ $t_s$ $a_s$ $t_s$ $T_s^o$ $^mC^o$ $A^o$-3'

SEQ ID NO: 26: 5'-$G_s^o$ $^mC_s^o$ $a_s$ $t_s$ $t_s$ $g_s$ $g_s$ $t_s$ $a_s$ $t_s$ $T_s^o$ $^mC_s^o$ $A^o$-3'

SEQ ID NO: 103: 5'-$^mC_s^o$ $A_s^o$ $G_s^o$ $c_s$ $a_s$ $t_s$ $t_s$ $g_s$ $g_s$ $t_s$ $a_s$ $t_s$ $T_s^o$ $^mC_s^o$ $A_s^o$ g-3'

In another preferred embodiment, the VLDL assembly inhibitor to be used in combination with a miR-122 inhibitor, is an inhibitor of MTP, such as BMS-2101038 (Huan et al. 2007, PNAS, vol 104 (14) page 5848-5853).

In another preferred embodiment, the VLDL assembly inhibitor to be used in combination with a miR-122 inhibitor, is an inhibitor of a molecule important for VLDL assembly, such as in non limiting example apoB-48, apoB-100, apoC, apoE, MTP (microsomal transfer protein), TGH (triacylglycerol hydrolase), ACAT2 (liver and intestine acyl-COA:cholesterol acyl transferase), Phospholipase D, iPLA2 (cytosolic calcium-independent phospholipase A2).

MiR-122 Inhibiting Compounds for Use in the Invention.

In one embodiment the miR-122 inhibitor is an antisense oligonucleotide

In one embodiment the miR-122 inhibitor has a length of between 8 and 23 nucleobases, such as 8, 9, 10, 11, 12, 13, 14, 15, 16, 17, 18, 19, 20, 21, 22 or 23 nucleobases.

In one embodiment the miR-122 inhibitor comprises or consists of a contiguous nucleobase sequence which is complementary to the corresponding region of miR-122, and may optionally comprise 1, 2 or 3 mismatches with said corresponding region.

In one embodiment the miR-122 inhibitor is SEQ ID NO: 63, or any other of the miR-122 inhibitors (antimirs) as described herein.

In one embodiment the miR-122 inhibitor and/or the inhibitor of VLDL assembly comprises one or more nucleotide analogue units (monomer), such as a nucleotide analogue selected from the group consisting of 2'-O-alkyl-RNA unit, 2'-OMe-RNA unit, 2'-amino-DNA unit, 2'-fluoro-DNA unit, LNA unit, PNA unit, HNA unit, and INA unit.

Suitable miR-122 inhibitors which may be, in some embodiment, be used in the present invention are disclosed in WO2005/107816A2, WO 2007/021896, WO 2007/0049547, and WO 2006/020768—all of which are hereby incorporated by reference. Further miR-122 inhibiting compounds useful in the present invention includes but are not limited to those disclosed in WO03/029459, US2005/0182005, US2005/0227934, US20050261218, Boutla et al. 2003 (Nucleic Acids Research 31: 4973-4980), Lecellier et al. *Science* 2005, 308, 557-560, Naguibneva et al. *Nature Cell Biology* 2006 8 (3), 278-84 all of which are hereby incorporated by reference It is preferred that the miR-122 inhibitor is an LNA oligomer, i.e. a LNA-antimiR-122: An LNA containing antisense oligonucleotide targeting miR-122:

SEQ ID in this section relating to miR-122 refers to those that may be found in Table 2 of example 3, and on page 52 in Table A.

Specially preferred miR-122 inhibiting compounds, are disclosed in PCT/DK2007/000168 and PCT/DK2007/000169 both of which are hereby incorporated by reference.

The miR-122 inhibiting oligonucleotide (antisense oligonucleotide) is typically single stranded. It will therefore be understood that within the context of the invention the term oligonucleotide may be used interchangeably with the term single stranded oligonucleotide.

In one embodiment, the miR-122 inhibiting oligonucleotide are short (single stranded) oligonucleotides, of length of between 8 and 17 nucleobases in length, such as between 10 and 17 nucleobases which are complementary to human microRNA-122. The short oligonucleotides are particularly effective at alleviating miRNA-122 repression in vivo. It is found that the incorporation of high affinity nucleotide analogues into the oligonucleotides results in highly effective anti-microRNA molecules which appear to function via the formation of almost irreversible duplexes with the miRNA target, rather than RNA cleavage based mechanisms, such as mechanisms associated with RNaseH or RISC.

It is highly preferable that miR-122 inhibiting oligonucleotide, comprises a region of contiguous nucleobase sequence which is 100% complementary to the human microRNA-122 seed region.

It is preferable that single stranded oligonucleotide according to the invention is complementary to the mature human microRNA-122 sequence.

In one embodiment, the miR-122 inhibiting oligonucleotide does not comprise a nucleobase at the 3' end that corresponds to the first 5' end nucleotide of the target microRNA.

In one embodiment, the first nucleobase of the miR-122 inhibiting oligonucleotide, counting from the 3' end, is a nucleotide analogue, such as an LNA unit.

In one embodiment, the second nucleobase of the miR-122 inhibiting oligonucleotide, counting from the 3' end, is a nucleotide analogue, such as an LNA unit.

In one embodiment, the ninth and/or the tenth nucleotide of miR-122 inhibiting oligonucleotide counting from the 3' end, is a nucleotide analogue, such as an LNA unit.

In one embodiment, the ninth nucleobase of the miR-122 inhibiting oligonucleotide, counting from the 3' end is a nucleotide analogue, such as an LNA unit.

In one embodiment, the tenth nucleobase of miR-122 inhibiting oligonucleotide, counting from the 3' end is a nucleotide analogue, such as an LNA unit.

In one embodiment, both the ninth and the tenth nucleobase of miR-122 inhibiting oligonucleotide, calculated from the 3' end is a nucleotide analogue, such as an LNA unit.

In one embodiment, miR-122 inhibiting oligonucleotide, does not comprise a region of more than 5 consecutive DNA nucleotide units. In one embodiment, miR-122 inhibiting oligonucleotide, does not comprise a region of more than 6 consecutive DNA nucleotide units.

In one embodiment, miR-122 inhibiting oligonucleotide, does not comprise a region of more than 7 consecutive DNA nucleotide units. In one embodiment, miR-122 inhibiting oligonucleotide, does not comprise a region of more than 8 consecutive DNA nucleotide units. In one embodiment, miR-122 inhibiting oligonucleotide, does not comprise a region of more than 3 consecutive DNA nucleotide units. In one embodiment, miR-122 inhibiting oligonucleotide, does not comprise a region of more than 2 consecutive DNA nucleotide units.

In one embodiment, miR-122 inhibiting oligonucleotide, comprises at least region consisting of at least two consecutive nucleotide analogue units, such as at least two consecutive LNA units.

In one embodiment, miR-122 inhibiting oligonucleotide, comprises at least region consisting of at least three consecutive nucleotide analogue units, such as at least three consecutive LNA units.

In one embodiment, miR-122 inhibiting oligonucleotide, does not comprise a region of more than 7 consecutive nucleotide analogue units, such as LNA units. In one embodiment, miR-122 inhibiting oligonucleotide, does not comprise a region of more than 6 consecutive nucleotide analogue units, such as LNA units. In one embodiment, miR-122 inhibiting oligonucleotide, does not comprise a region of more than 5 consecutive nucleotide analogue units, such as LNA units. In one embodiment, miR-122 inhibiting oligonucleotide, does not comprise a region of more than 4 consecutive nucleotide analogue units, such as LNA units. In one embodiment, miR-122 inhibiting oligonucleotide, does not comprise a region of more than 3 consecutive nucleotide analogue units, such as LNA units. In one embodiment, miR-122 inhibiting oligonucleotide, does not comprise a region of more than 2 consecutive nucleotide analogue units, such as LNA units.

In one embodiment, the first or second 3' nucleobase of miR-122 inhibiting oligonucleotide, corresponds to the second 5' nucleotide of the microRNA sequence.

In one embodiment, nucleobase units 1 to 6 (inclusive) of miR-122 inhibiting oligonucleotide, as measured from the 3' end the region of miR-122 inhibiting oligonucleotide, are complementary to the microRNA seed region sequence.

In one embodiment, nucleobase units 1 to 7 (inclusive) of miR-122 inhibiting oligonucleotide, as measured from the 3' end the region of miR-122 inhibiting oligonucleotide, are complementary to the microRNA seed region sequence.

In one embodiment, nucleobase units 2 to 7 (inclusive) of miR-122 inhibiting oligonucleotide, as measured from the 3' end the region of miR-122 inhibiting oligonucleotide, are complementary to the microRNA seed region sequence.

In one embodiment, miR-122 inhibiting oligonucleotide, comprises at least one nucleotide analogue unit, such as at least one LNA unit, in a position which is within the region complementary to the miRNA seed region. miR-122 inhibiting oligonucleotide, may, in one embodiment comprise at between one and 6 or between 1 and 7 nucleotide analogue units, such as between 1 and 6 and 1 and 7 LNA units, in a position which is within the region complementary to the miRNA seed region.

In one embodiment, the nucleobase sequence of miR-122 inhibiting oligonucleotide, which is complementary to the sequence of the microRNA seed region, is selected from the group consisting of (X) Xxxxxx, (X) xXxxxx, (X) xxXxxx, (X) xxxXxx, (X) xxxxXx and (X) xxxxxX, as read in a 3'-5' direction, wherein "X" denotes a nucleotide analogue, (X) denotes an optional nucleotide analogue, such as an LNA unit, and "x" denotes a DNA or RNA nucleotide unit.

In one embodiment, miR-122 inhibiting oligonucleotide, comprises at least two nucleotide analogue units, such as at least two LNA units, in positions which are complementary to the miRNA seed region.

In one embodiment, the nucleobase sequence of miR-122 inhibiting oligonucleotide, which is complementary to the sequence of the microRNA seed region, is selected from the group consisting of (X) XXxxxx, (X) XxXxxx, (X) XxxXxx, (X) XxxxXx, (X) XxxxxX, (X) xXXxxx, (X) xXxXxx, (X) xXxxXx, (X) xXxxxX, (X) xxXXxx, (X) xxXxXx, (X) xxXxxX, (X) xxxXXx, (X) xxxXxX and (X) xxxxXX, wherein "X" denotes a nucleotide analogue, such as an LNA unit, (X) denotes an optional nucleotide analogue, such as an LNA unit, and "x" denotes a DNA or RNA nucleotide unit.

In one embodiment, miR-122 inhibiting oligonucleotide, comprises at least three nucleotide analogue units, such as at least three LNA units, in positions which are complementary to the miRNA seed region.

In one embodiment, the nucleobase sequence of miR-122 inhibiting oligonucleotide, which is complementary to the sequence of the microRNA seed region, is selected from the group consisting of (X) XXXxxx, (X) xXXXxx, (X) xxXXXx, (X) xxxXXX, (X) XXxXxx, (X) XXxxXx, (X) XXxxxX, (X) xXXxXx, (X) xXXxxX, (X) xxXXxX, (X) XxXXxx, (X) XxxXXx, (X) XxxxXX, (X) xXxXXx, (X) xXxxXX, (X) xXxXxX and (X) XxXxXx, wherein "X" denotes a nucleotide analogue, such as an LNA unit, (X) denotes an optional nucleotide analogue, such as an LNA unit, and "x" denotes a DNA or RNA nucleotide unit.

In one embodiment, miR-122 inhibiting oligonucleotide, comprises at least four nucleotide analogue units, such as at least four LNA units, in positions which are complementary to the miRNA seed region.

In one embodiment the nucleobase sequence of miR-122 inhibiting oligonucleotide, which is complementary to the sequence of the microRNA seed region, is selected from the group consisting of (X) xxXXX, (X) xXxXXX, (X) xXXxXX, (X) xXXXxX, (X) xXXXXx, (X) XxxXXX, (X) XxXxXX, (X) XxXXxX, (X) XxXXXx, (X) XXxxXX, (X) XXxXxX, (X) XXxXXx, (X) XXXxxX, (X) XXXxXx, and (X) XXXXxx, wherein "X" denotes a nucleotide analogue, such as an LNA unit, (X) denotes an optional nucleotide analogue, such as an LNA unit, and "x" denotes a DNA or RNA nucleotide unit.

In one embodiment, miR-122 inhibiting oligonucleotide, comprises at least five nucleotide analogue units, such as at least five LNA units, in positions which are complementary to the miRNA seed region.

In one embodiment, the nucleobase sequence of miR-122 inhibiting oligonucleotide, which is complementary to the sequence of the microRNA seed region, is selected from the group consisting of (X) xXXXXX, (X) XxXXXX, (X) XXxXXX, (X) XXXxXX, (X) XXXXxX and (X) XXXXXx, wherein "X" denotes a nucleotide analogue, such as an LNA unit, (X) denotes an optional nucleotide analogue, such as an LNA unit, and "x" denotes a DNA or RNA nucleotide unit.

In one embodiment, miR-122 inhibiting oligonucleotide, comprises six or seven nucleotide analogue units, such as six or seven LNA units, in positions which are complementary to the miRNA seed region.

In one embodiment, the nucleobase sequence of miR-122 inhibiting oligonucleotide, which is complementary to the sequence of the microRNA seed region, is selected from the group consisting of XXXXXX, XxXXXXX, XXxXXXX, XXXxXXX, XXXXxXX, XXXXXxX and XXXXXXx, wherein "X" denotes a nucleotide analogue, such as an LNA unit, such as an LNA unit, and "x" denotes a DNA or RNA nucleotide unit.

In one embodiment, the two nucleobase motif at position 7 to 8, counting from the 3' end of miR-122 inhibiting oligonucleotide, is selected from the group consisting of xx, XX, xX and Xx, wherein "X" denotes a nucleotide analogue, such as an LNA unit, such as an LNA unit, and "x" denotes a DNA or RNA nucleotide unit.

In one embodiment, the two nucleobase motif at position 7 to 8, counting from the 3' end of miR-122 inhibiting oligonucleotide, is selected from the group consisting of XX, xX and Xx, wherein "X" denotes a nucleotide analogue, such as an LNA unit, such as an LNA unit, and "x" denotes a DNA or RNA nucleotide unit.

In one embodiment, miR-122 inhibiting oligonucleotide, comprises at least 12 nucleobases and wherein the two nucleobase motif at position 11 to 12, counting from the 3' end of miR-122 inhibiting oligonucleotide, is selected from the group consisting of xx, XX, xX and Xx, wherein "X" denotes a nucleotide analogue, such as an LNA unit, such as an LNA unit, and "x" denotes a DNA or RNA nucleotide unit.

In one embodiment, miR-122 inhibiting oligonucleotide, comprises at least 12 nucleobases and wherein the two nucleobase motif at position 11 to 12, counting from the 3' end of miR-122 inhibiting oligonucleotide, is selected from the group consisting of XX, xX and Xx, wherein "X" denotes a nucleotide analogue, such as an LNA unit, such as an LNA unit, and "x" denotes a DNA or RNA nucleotide unit.

In one embodiment, miR-122 inhibiting oligonucleotide, comprises at least 13 nucleobases and wherein the three nucleobase motif at position 11 to 13, counting from the 3' end, is selected from the group consisting of xxx, Xxx, xXx, xxX, XXx, XxX, xXX and XXX, wherein "X" denotes a nucleotide analogue, such as an LNA unit, such as an LNA unit, and "x" denotes a DNA or RNA nucleotide unit.

In one embodiment, the three nucleobase motif at position 11 to 13, counting from the 3' end of miR-122 inhibiting oligonucleotide, is selected from the group consisting of Xxx, xXx, xxX, XXx, XxX, XxX and XXX, wherein "X" denotes a nucleotide analogue, such as an LNA unit, such as an LNA unit, and "x" denotes a DNA or RNA nucleotide unit.

In one embodiment, miR-122 inhibiting oligonucleotide, comprises at least 14 nucleobases and wherein the four nucleobase motif at positions 11 to 14, counting from the 3' end, is selected from the group consisting of xxxx, Xxxx, xXxx, xxXx, xxxX, XXxx, XxXx, XxxX, xXXx, xXxX, xxXX, XXXx, XxXX, xXXX, XXxX and XXXX wherein "X" denotes a nucleotide analogue, such as an LNA unit, such as an LNA unit, and "x" denotes a DNA or RNA nucleotide unit.

In one embodiment, the four nucleobase motif at position 11 to 14 of miR-122 inhibiting oligonucleotide, counting from the 3' end, is selected from the group consisting of Xxxx, xXxx, xxXx, xxxX, XXxx, XxXx, XxxX, xXXx, xXxX, xxXX, XXXx, XxXX, xXXX, XXxX and XXXX, wherein "X" denotes a nucleotide analogue, such as an LNA unit, and "x" denotes a DNA or RNA nucleotide unit.

In one embodiment, miR-122 inhibiting oligonucleotide, comprises 15 nucleobases and the five nucleobase motif at position 11 to 15, counting from the 3' end, is selected from the group consisting of Xxxxx, xXxxx, xxXxx, xxxXx, xxxxX, XXxxx, XxXxx, XxxXx, XxxxX, xXXxx, xXxXx, xXxxX, xxXXx, xxXxX, xxxXX, XXXxx, XXxXx, XXxxX, xXXXx, xxXXX, XXxXX, XxXxX, XXXXx, XXXxX, XXxXX, XxXXX, xXXXX, and XXXXX wherein "X" denotes a nucleotide analogue, such as an LNA unit, such as an LNA unit, and "x" denotes a DNA or RNA nucleotide unit.

In one embodiment, miR-122 inhibiting oligonucleotide, comprises 16 nucleobases and the six nucleobase motif at positions 11 to 16, counting from the 3' end, is selected from the group consisting of Xxxxxx, xXxxxx, xxXxxx, xxxXxx, xxxxXx, xxxxxX, XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX, xxxxXX, XXXxxx, XXxXxx, XXxxXx, XXxxxX, XxXXxx, XxXxXx, XxXxxX, XxxXXx, XxxXxX, xXXXxx, xXXxXx, xXXxxX, xXxXXx, xXxXxX, xXxxXX, xxXXXx, xxXXxX, xxXxXX, xxxXXX, XXXXxx, XXXxXx, XXXxxX, XXxXXx, XXxXxX, XXxxXX, XxXXxX, XxXxXX, XxxXXX, xXXXXx, xXXXxX, xXXxXX, xXxXXX, xXXXXX, XxXXXX, XXxXXX, XXXxXX, XXXXxX, XXXXXx, and XXXXXX wherein "X" denotes a nucleotide analogue, such as an LNA unit, such as an LNA unit, and "x" denotes a DNA or RNA nucleotide unit.

In one embodiment, the six nucleobase motif at positions 11 to 16 of miR-122 inhibiting oligonucleotide, counting from the 3' end, is xxXxxX, wherein "X" denotes a nucleotide analogue, such as an LNA unit, such as an LNA unit, and "x" denotes a DNA or RNA nucleotide unit.

In one embodiment, the three 5' most nucleobases, is selected from the group consisting of Xxx, xXx, xxX, XXx, XxX, xXX and XXX, wherein "X" denotes a nucleotide analogue, such as an LNA unit, such as an LNA unit, and "x" denotes a DNA or RNA nucleotide unit.

In one embodiment, x" denotes a DNA unit.

In one embodiment, miR-122 inhibiting oligonucleotide, comprises a nucleotide analogue unit, such as an LNA unit, at the 5' end.

In one embodiment, the nucleotide analogue units, such as X, are independently selected form the group consisting of: 2'-O-alkyl-RNA unit, 2'-OMe-RNA unit, 2'-amino-DNA unit, 2'-fluoro-DNA unit, LNA unit, PNA unit, HNA unit, INA unit.

In one embodiment, all the nucleobases of miR-122 inhibiting oligonucleotide, of the invention are nucleotide analogue units.

In one embodiment, the nucleotide analogue units, such as X, are independently selected form the group consisting of: 2'-OMe-RNA units, 2'-fluoro-DNA units, and LNA units.

In one embodiment, miR-122 inhibiting oligonucleotide, comprises said at least one LNA analogue unit and at least one further nucleotide analogue unit other than LNA.

In one embodiment, the non-LNA nucleotide analogue unit or units are independently selected from 2'-OMe RNA units and 2'-fluoro DNA units.

In one embodiment, miR-122 inhibiting oligonucleotide, consists of at least one sequence XYX or YXY, wherein X is LNA and Y is either a 2'-OMe RNA unit and 2'-fluoro DNA unit.

In one embodiment, the sequence of nucleobases of miR-122 inhibiting oligonucleotide, consists of alternative X and Y units.

In one embodiment, miR-122 inhibiting oligonucleotide, comprises alternating LNA and DNA units (Xx) or (xX).

In one embodiment, miR-122 inhibiting oligonucleotide, comprises a motif of alternating LNA followed by 2 DNA units (Xxx), xXx or xxX.

In one embodiment, at least one of the DNA or non-LNA nucleotide analogue units are replaced with a LNA nucleobase in a position selected from the positions identified as LNA nucleobase units in any one of the embodiments referred to above.

In one embodiment, "X" donates an LNA unit.

In one embodiment, miR-122 inhibiting oligonucleotide, comprises at least 2 nucleotide analogue units, such as at least 3 nucleotide analogue units, such as at least 4 nucleotide analogue units, such as at least 5 nucleotide analogue units, such as at least 6 nucleotide analogue units, such as at least 7 nucleotide analogue units, such as at least 8 nucleotide analogue units, such as at least 9 nucleotide analogue units, such as at least 10 nucleotide analogue units.

In one embodiment, miR-122 inhibiting oligonucleotide, comprises at least 2 LNA units, such as at least 3 LNA units, such as at least 4 LNA units, such as at least 5 LNA units, such as at least 6 LNA units, such as at least 7 LNA units, such as at least 8 LNA units, such as at least 9 LNA units, such as at least 10 LNA units.

In one embodiment wherein at least one of the nucleotide analogues, such as LNA units, is either cytosine or guanine, such as between 1-10 of the of the nucleotide analogues, such as LNA units, is either cytosine or guanine, such as 2, 3, 4, 5, 6, 7, 8, or 9 of the of the nucleotide analogues, such as LNA units, is either cytosine or guanine.

In one embodiment at least two of the nucleotide analogues such as LNA units is either cytosine or guanine. In one embodiment at least three of the nucleotide analogues such as LNA units is either cytosine or guanine. In one embodiment at least four of the nucleotide analogues such as LNA units is either cytosine or guanine. In one embodiment at least five of the nucleotide analogues such as LNA units is either cytosine or guanine. In one embodiment at least six of the nucleotide analogues such as LNA units is either cytosine or guanine. In one embodiment at least seven of the nucleotide analogues such as LNA units is either cytosine or guanine. In one embodiment at least eight of the nucleotide analogues such as LNA units is either cytosine or guanine.

In a preferred embodiment the nucleotide analogues have a higher thermal duplex stability a complementary RNA nucleotide than the binding affinity of an equivalent DNA nucleotide to said complementary RNA nucleotide.

In one embodiment, the nucleotide analogues confer enhanced serum stability to the single stranded oligonucleotide.

In one embodiment, miR-122 inhibiting oligonucleotide, forms an A-helix conformation with a complementary single stranded RNA molecule.

A duplex between two RNA molecules typically exists in an A-form conformation, where as a duplex between two DNA molecules typically exits in a B-form conformation. A duplex between a DNA and RNA molecule typically exists in a intermediate conformation (A/B form). The use of nucleotide analogues, such as beta-D-oxy LNA can be used to promote a more A form like conformation. Standard circular dichromisms (CD) or NMR analysis is used to determine the form of duplexes between the oligonucleotides of the invention and complementary RNA molecules.

As recruitment by the RISC complex is thought to be dependant upon the specific structural conformation of the miRNA/mRNA target, the oligonucleotides according to the present invention may, in one embodiment form a A/B—form duplex with a complementary RNA molecule.

However, we have also determined that the use of nucleotide analogues which promote the A-form structure can also be effective, such as the alpha-L isomer of LNA.

In one embodiment, miR-122 inhibiting oligonucleotide, forms an A/B-form conformation with a complementary single stranded RNA molecule.

In one embodiment, miR-122 inhibiting oligonucleotide, forms an A-from conformation with a complementary single stranded RNA molecule.

In one embodiment, miR-122 inhibiting oligonucleotide, does not mediate RNAseH based cleavage of a complementary single stranded RNA molecule. Typically a stretch of at least 5 (typically not effective of RNAse H recruitment), more preferably at least 6, more preferably at least 7 or 8 consecutive DNA nucleobases (or alternative nucleobases which can recruit RNAseH, such as alpha L-amino LNA) are required in order for an oligonucleotide to be effective in recruitment of RNAseH.

EP 1 222 309 provides in vitro methods for determining RNaseH activity, which may be used to determine the ability to recruit RNaseH. A compound is deemed capable of recruiting RNase H if, when provided with the complementary RNA target, it has an initial rate, as measured in pmol/l/min, of at least 1%, such as at least 5%, such as at least 10% or less than 20% of the equivalent DNA only oligonucleotide, with no 2' substitutions, with phosphorothiote linkage groups between all nucleotides in the oligonucleotide, using the methodology provided by Example 91-95 of EP 1 222 309.

A compound is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphiothiote linkage groups between all nucleotides in the oligonucleotide, using the methodology provided by Example 91-95 of EP 1 222 309.

In a highly preferred embodiment, miR-122 inhibiting oligonucleotide, of the invention is capable of forming a duplex with a complementary single stranded RNA nucleic acid molecule (typically of about the same length of said single stranded oligonucleotide) with phosphodiester internucleoside linkages, wherein the duplex has a $T_m$ of at least about 60° C., indeed it is preferred that miR-122 inhibiting oligonucleotide, is capable of forming a duplex with a complementary single stranded RNA nucleic acid molecule with phosphodiester internucleoside linkages, wherein the duplex has a $T_m$ of between about 70° C. to about 95° C., such as a $T_m$ of between about 70° C. to about 90° C., such as between about 70° C. and about 85° C.

In one embodiment, miR-122 inhibiting oligonucleotide, is capable of forming a duplex with a complementary single stranded DNA nucleic acid molecule with phosphodiester internucleoside linkages, wherein the duplex has a $T_m$ of between about 50° C. to about 95° C., such as between about 50° C. to about 90° C., such as at least about 55° C., such as at least about 60° C., or no more than about 95° C.

MiR-122 inhibiting oligonucleotide, may, in one embodiment have a length of between 14-16 nucleobases, including 15 nucleobases.

In one embodiment, the LNA unit or units are independently selected from the group consisting of oxy-LNA, thio-LNA, and amino-LNA, in either of the D-β and L-α configurations or combinations thereof.

In one specific embodiment the LNA units may be an ENA nucleobase.

In one the embodiment the LNA units are beta D oxy-LNA.

In one embodiment the LNA units are in alpha-L amino LNA.

In a preferable embodiment, miR-122 inhibiting oligonucleotide, comprises between 3 and 17 LNA units.

In one embodiment, miR-122 inhibiting oligonucleotide, comprises at least one internucleoside linkage group which differs from phosphate.

In one embodiment, miR-122 inhibiting oligonucleotide, comprises at least one phosphorothioate internucleoside linkage.

In one embodiment, miR-122 inhibiting oligonucleotide, comprises phosphodiester and phosphorothioate linkages.

In one embodiment, the all the internucleoside linkages are phosphorothioate linkages.

In one embodiment, miR-122 inhibiting oligonucleotide, comprises at least one phosphodiester internucleoside linkage.

In one embodiment, all the internucleoside linkages of miR-122 inhibiting oligonucleotide, of the invention are phosphodiester linkages.

In one embodiment, pharmaceutical composition according to the invention comprises a carrier such as saline or buffered saline.

In one embodiment, the method for the synthesis of a single stranded oligonucleotide targeted against a human microRNA, is performed in the 3' to 5' direction a-f.

The method for the synthesis of miR-122 inhibiting oligonucleotide, may be performed using standard solid phase oligonucleotide synthesis.

LNA-Containing miR-122 Antisense Oligonucleotides Useful in the Methods and Compositions of Invention While LNA units and non-LNA units may be combined in a number of ways to form oligonucleotides, it has surprisingly been found by the inventors of the present invention that a certain core DNA sequence and a certain presence of LNA units in said DNA sequence results in a particularly high inhibition of microRNA. This presence of LNA units in said core sequence of the oligonucleotides of the present invention made said oligonucleotides highly nuclease resistant.

The nucleotides outside the core sequence may be both LNA units and/or non-LNA units. In one embodiment, the non-LNA units outside the core sequence are DNA units.

The miR-122 Core Sequence

In order for the miR-122 inhibiting oligonucleotide to inhibit miR-122 as efficiently as possible there needs to be a certain degree of complementarity between the antisense oligonucleotide of the present invention and the corresponding miR-122 sequence.

It is particularly important for the miR-122 inhibiting oligonucleotide to be complementary with positions 3 to 8, counting from the 5' end, of the corresponding target microRNA. Nucleotide 1, counting from the 5' end, in some of the target microRNAs is a non-pairing base and is most likely hidden in a binding pocket in the Ago 2 protein. Accordingly, the oligonucleotide of the invention may or may not have a nucleotide in position 1, counting from the 3' end, corresponding to nucleotide 1, counting from the 5' end, of the corresponding target microRNA. In some cases, the first two nucleotides, counting from the 5' end, of the corresponding target microRNA may be left unmatched.

The core sequence is therefore a DNA sequence from positions one to six, two to seven or positions three to eight, counting from the 3' end, corresponding to positions three to eight, counting from the 5' end, of the corresponding target microRNA.

miR-122a

The sequence of miR-122a from positions three to eight, counting from the 5' end, is gagugu (see miRBase entry HGNC:MIRN122A). The corresponding DNA sequence is ctcaca.

Accordingly, in one aspect of the present invention relates to an oligonucleotide, such as an oligonucleotide having a length of from 12 to 26 nucleotides having the DNA sequence from positions one to six, two to seven or three to eight, preferably from positions two to seven or three to eight, counting from the 3' end:

ctcaca, wherein at least one, such as one, preferably at least two, such as two or three, DNA units in said sequence have been substituted by their corresponding LNA unit.

One embodiment relates to the miR-122 inhibiting oligonucleotide as described above having a DNA sequence from positions one to seven, two to eight or three to nine, preferably from positions two to eight or three to nine, counting from the 3' end:

ctcacac, wherein at least one, such as one, preferably at least two, such as two, more preferably at least three, such as three or four, DNA units in said sequence have been substituted by their corresponding LNA unit.

In another embodiment, miR-122 inhibiting oligonucleotide has a DNA sequence from positions one to eight, two to nine or three to ten, preferably from positions two to nine or three to ten, counting from the 3' end:

ctcacact, wherein at least one, such as one, preferably at least two, such as two, more preferably at least three, such as three or four, DNA units in said sequence have been substituted by their corresponding LNA unit.

In yet another embodiment, miR-122 inhibiting oligonucleotide has a DNA sequence from positions one to nine, two to ten or three to eleven, preferably from positions two to ten or three to eleven, counting from the 3' end:

ctcacactg, wherein at least one, such as one, preferably at least two, such as two, more preferably at least three, such as three, even more preferably at least four, such as four or five, DNA units in said sequence have been substituted by their corresponding LNA unit.

Modification of Nucleotides in the Core Sequence

As mentioned above, in the core sequence of miR-122 inhibiting oligonucleotide at least one, such as one, preferably at least two, such as two or three, DNA units in said sequence have been substituted by their corresponding LNA unit. The present inventors have further found that inhibition of the target microRNAs may be further increased by making sure that two LNA units in said core sequence are separated by at least one DNA unit.

Accordingly, one embodiment miR-122 inhibiting oligonucleotide as described above, wherein at least two, such as two or three, DNA units from positions one to six, two to seven or three to eight, preferably from positions two to seven or three to eight, counting from the 3' end, have been substituted by their corresponding LNA unit and wherein the LNA units are separated by at least one DNA unit.

The present inventors have also found that inhibition of target microRNAs may be even further increased by making sure that two LNA units in the core sequence are separated by at most two DNA units. Accordingly, in one embodiment the miR-122 inhibiting oligonucleotide as described above, wherein the number of consecutive DNA units from positions one to six, two to seven or three to eight, preferably from positions two to seven or three to eight, counting from the 3' end, is at most two.

Said findings apply to the core sequence per se, i.e. the finding applies to the positions of the oligonucleotides of the present invention corresponding to the core sequence. Hence, another embodiment relates to the oligonucleotide as described above, wherein at least two, such as two, three or four, DNA units from positions one to seven, two to eight or three to nine, preferably from positions two to eight or three to nine, counting from the 3' end, have been substituted by their corresponding LNA unit and wherein the LNA units are separated by at least one DNA unit. A further embodiment relates to the oligonucleotide as described above, wherein the number of consecutive DNA units from positions one to seven, two to eight or three to nine, preferably from positions two to eight or three to nine, counting from the 3' end, is at most two.

Yet another embodiment relates to the oligonucleotide as described above, wherein at least two, such as two, three or four, DNA units from positions one to eight, two to nine or three to ten, preferably from positions two to nine or three to ten, counting from the 3' end, have been substituted by their corresponding LNA unit and wherein the LNA units are separated by at least one DNA unit. Yet a further embodiment relates to the oligonucleotide as described above, wherein the number of consecutive DNA units from positions one to eight, two to nine or three to ten, preferably from positions two to nine or three to ten, counting from the 3' end, is at most two.

Still another embodiment relates to the oligonucleotide as described above, wherein at least two, such as two, three, four or five, DNA units from positions one to nine, two to ten or three to eleven, preferably from positions two to ten or three to eleven, counting from the 3' end, have been substituted by their corresponding LNA unit and wherein the LNA units are separated by at least one DNA unit. Still a further embodiment relates to the oligonucleotide as described above, wherein the number of consecutive DNA units from positions one to nine, two to ten or three to eleven, preferably from positions two to ten or three to eleven, counting from the 3' end, is at most two.

Modification of Nucleotides Outside the Core Sequence

As mentioned above, the nucleotides outside the core sequence may be both LNA units and/or non-LNA units. In one embodiment, the invention relates to the oligonucleotide as described above, wherein the number of LNA units outside the core sequence is at least one, such as one, two, three or four, and wherein said LNA units are separated by at least one non-LNA unit. In a further embodiment, the substitution pattern outside the core sequence is such that the number of consecutive non-LNA units outside the core sequence is at most two.

Modification of Nucleotides in Positions 3 to 8, Counting from the 3' End.

In the following embodiments which refer to the modification of nucleotides in positions 3 to 8, counting from the 3° end, the LNA units may be replaced with other nucleotide analogues, such as those referred to herein. "X" may, therefore be selected from the group consisting of 2'-O-alkyl-RNA unit, 2'-OMe-RNA unit, 2'-amino-DNA unit, 2'-fluoro-DNA unit, LNA unit, PNA unit, HNA unit, INA unit. "x" is preferably DNA or RNA, most preferably DNA.

In an interesting embodiment of the invention, the miR-122 inhibiting oligonucleotide are modified in positions 3 to 8, counting from the 3' end. The design of this sequence may be defined by the number of non-LNA units present or by the number of LNA units present. In a preferred embodiment of the former, at least one, such as one, of the nucleotides in positions three to eight, counting from the 3' end, is a non-LNA unit. In another embodiment, at least two, such as two, of the nucleotides in positions three to eight, counting from the 3' end, are non-LNA units. In yet another embodiment, at least three, such as three, of the nucleotides in positions three to eight, counting from the 3' end, are non-LNA units. In still another embodiment, at least four, such as four, of the nucleotides in positions three to eight, counting from the 3' end, are non-LNA units. In a further embodiment, at least five, such as five, of the nucleotides in positions three to eight, counting from the 3' end, are non-LNA units. In yet a further embodiment, all six nucleotides in positions three to eight, counting from the 3' end, are non-LNA units. In a preferred embodiment, said non-LNA unit is a DNA unit.

Alternatively defined, in a preferred embodiment, the miR-122 inhibiting oligonucleotide comprises at least one LNA unit in positions three to eight, counting from the 3' end. In an embodiment thereof, the miR-122 inhibiting oligonucleotide comprises one LNA unit in positions three to eight, counting from the 3' end. The substitution pattern for the nucleotides in positions three to eight, counting from the 3' end, may be selected from the group consisting of Xxxxxx, xXxxxx, xxXxxx, xxxXxx, xxxxXx and xxxxxX, wherein "X" denotes an LNA unit and "x" denotes a non-LNA unit.

In another embodiment, the miR-122 inhibiting oligonucleotide comprises at least two LNA units in positions three to eight, counting from the 3' end. In an embodiment thereof, the miR-122 inhibiting oligonucleotide comprises two LNA units in positions three to eight, counting from the 3' end. The substitution pattern for the nucleotides in positions three to eight, counting from the 3' end, may be selected from the group consisting of XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX and xxxxXX, wherein "X" denotes an LNA unit and "x" denotes a non-LNA unit. In a preferred embodiment, the substitution pattern for the nucleotides in positions three to eight, counting from the 3' end, is selected from the group consisting of XxXxxx, XxxXxx, XxxxXx, XxxxxX, xXxXxx, xXxxXx, xXxxxX, xxXxXx, xxXxxX and xxxXxX, wherein "X" denotes an LNA unit and "x" denotes a non-LNA unit. In a more preferred embodiment, the substitution pattern for the nucleotides in positions three to eight, counting from the 3' end, is selected from the group consisting of xXxXxx, xXxxXx, xXxxxX, xxXxXx, xxXxxX and xxxXxX, wherein "X" denotes an LNA unit and "x" denotes a non-LNA unit. In an even more preferred embodiment, the substitution pattern for the nucleotides in positions three to eight, counting from the 3' end, is selected from the group consisting of xXxXxx, xXxxXx and xxXxXx, wherein "X" denotes an LNA unit and "x" denotes a non-LNA unit. In a most preferred embodiment, the substitution pattern for the nucleotides in positions three to eight, counting from the 3' end, is xXxXxx, wherein "X" denotes an LNA unit and "x" denotes a non-LNA unit.

In yet another embodiment, the miR-122 inhibiting oligonucleotide comprises at least three LNA units in positions three to eight, counting from the 3' end. In an embodiment thereof, the miR-122 inhibiting oligonucleotide comprises three LNA units in positions three to eight, counting from the 3' end. The substitution pattern for the nucleotides in positions three to eight, counting from the 3' end, may be selected from the group consisting of XXXxxx, xXXXxx, xxXXXx, xxxXXX, XXxXxx, XXxxXx, XXxxxX, xXXxXx, xXXxxX, xXxXxX, xXxxXX, XxXXxx, XxxXXx, XxxxXX, XxXxXx, XxXxxX, xxXXxX, xXxxXX, xXxXxX and XxXxXx, wherein "X" denotes an LNA unit and "x" denotes a non-LNA unit. In a preferred embodiment, the substitution pattern for the nucleotides in positions three to eight, counting from the 3' end, is selected from the group consisting of XXxxXx, XXxxxX, XXxxxX, xXXxXx, xXXxxX, xxXXxX, XxXXxx, XxxXXx, XxxxXX, xXxXXx, xXxxXX, xxXxXX, xXxXxX and XxXxXx, wherein "X" denotes an LNA unit and "x" denotes a non-LNA unit. In a more preferred embodiment, the substitution pattern for the nucleotides in positions three to eight, counting from the 3' end, is selected from the group consisting of xXXxXx, xXXxxX, xxXXxX, xXxXXx, xXxxXX and xXxXxX, wherein "X" denotes an LNA unit and "x" denotes a non-LNA unit. In an even more preferred embodiment, the substitution pattern for the nucleotides in positions three to eight, counting from the 3' end, is xXxXxX or XxXxXx, wherein "X" denotes an LNA unit and "x" denotes a non-LNA unit. In a most preferred embodiment, the substitution pattern for the nucleotides in positions three to eight, counting from the 3' end, is xXxXxX, wherein "X" denotes an LNA unit and "x" denotes a non-LNA unit.

In a further embodiment, the miR-122 inhibiting oligonucleotide according to the present invention comprises at least four LNA units in positions three to eight, counting from the 3' end. In an embodiment thereof, the miR-122 inhibiting oligonucleotide comprises four LNA units in positions three to eight, counting from the 3' end. The substitution pattern for the nucleotides in positions three to eight, counting from the 3' end, may be selected from the group consisting of xxXXXX, xXxXXX, xXXxXX, xXXXxX, xXXXXx, XxxXXX, XxXxXX, XxXXxX, XxXXXx, XXxxXX, XXxXxX, XXxXXx, XXXxxX, XXXxXx and XXXXxx, wherein "X" denotes an LNA unit and "x" denotes a non-LNA unit.

In yet a further embodiment, the miR-122 inhibiting oligonucleotide comprises at least five LNA units in positions three to eight, counting from the 3' end. In an embodiment thereof, the miR-122 inhibiting oligonucleotide comprises five LNA units in positions three to eight, counting from the 3' end. The substitution pattern for the nucleotides in positions three to eight, counting from the 3' end, may be selected from the group consisting of xXXXXX, XxXXXX, XXxXXX, XXXxXX, XXXXxX and XXXXXx, wherein "X" denotes an LNA unit and "x" denotes a non-LNA unit.

Preferably, the miR-122 inhibiting oligonucleotide comprises one or two LNA units in positions three to eight, counting from the 3' end. This is considered advantageous for the stability of the A-helix formed by the oligo:microRNA duplex, a duplex resembling an RNA:RNA duplex in structure.

In a preferred embodiment, said non-LNA unit is a DNA unit.

Variation of the Length of the Oligonucleotides

The length of the miR-122 inhibiting oligonucleotide need not match the length of the target microRNA-122 exactly. Indeed it is considered advantageous to have short oligonucleotides, such as between 10-17 or 10-16 nucleobases.

In one embodiment, the miR-122 inhibiting oligonucleotide has a length of from 8 to 24 nucleotides, such as 10 to 24, between 12 to 24 nucleotides, such as a length of 8, 9, 10, 11, 12, 13, 14, 15, 16, 17, 18, 19, 20, 21, 22, 23 or 24 nucleotides, preferably a length of from 10-22, such as between 12 to 22 nucleotides, such as a length of 10, 11, 12, 13, 14, 15, 16, 17, 18, 19, 20, 21 or 22 nucleotides, more preferably a length of from 10-20, such as between 12 to 20 nucleotides, such as a length of 10, 11, 12, 13, 14, 15, 16, 17, 18, 19 or 20 nucleotides, even more preferably a length of from 10 to 19, such as between 12 to 19 nucleotides, such as a length of 10, 11, 12, 13, 14, 15, 16, 17, 18 or 19 nucleotides, e.g. a length of from 10 to 18, such as between 12 to 18 nucleotides, such as a length of 10, 11, 12, 13, 14, 15, 16, 17 or 18 nucleotides, more preferably a length of from 10-17, such as from 12 to 17 nucleotides, such as a length of 10, 11, 12, 13, 14, 15, 16 or 17 nucleotides, most preferably a length of from 10 to 16, such as between 12 to 16 nucleotides, such as a length of 10, 11, 12, 13, 14, 15 or 16 nucleotides.

Modification of Nucleotides from Position 11, Counting from the 3' End, to the 5' End The substitution pattern for the nucleotides from position 11, counting from the 3' end, to the 5' end may include nucleotide analogue units (such as LNA) or it may not. In a preferred embodiment, the miR-122 inhibiting oligonucleotide comprises at least one nucleotide analogue unit (such as LNA), such as one nucleotide analogue unit, from position 11, counting from the 3° end, to the 5' end. In another preferred embodiment, the miR-122 inhibiting oligonucleotide comprises at least two nucleotide analogue units, such as LNA units, such as two nucleotide analogue units, from position 11, counting from the 3' end, to the 5' end.

In the following embodiments which refer to the modification of nucleotides in the nucleobases from position 11 to the 5' end of the oligonucleotide, the LNA units may be replaced with other nucleotide analogues, such as those referred to herein. "X" may, therefore be selected from the group consisting of 2'-O-alkyl-RNA unit, 2'-OMe-RNA unit, 2'-amino-DNA unit, 2'-fluoro-DNA unit, LNA unit, PNA unit, HNA unit, INA unit. "x" is preferably DNA or RNA, most preferably DNA.

In one embodiment, the miR-122 inhibiting oligonucleotide has the following substitution pattern, which is repeated from nucleotide eleven, counting from the 3' end, to the 5' end: xXxX or XxXx, wherein "X" denotes an LNA unit and "x" denotes a non-LNA unit. In another embodiment, the miR-122 inhibiting oligonucleotide has the following substitution pattern, which is repeated from nucleotide eleven, counting from the 3' end, to the 5' end: XxxXxx, xXxxXx or xxXxxX, wherein "X" denotes an LNA unit and "x" denotes a non-LNA unit. In yet another embodiment, miR-122 inhibiting oligonucleotide has the following substitution pattern, which is repeated from nucleotide eleven, counting from the 3' end, to the 5' end: XxxxXxxx, xXxxxXxx, xxXxxxXx or xxxXxxxX, wherein "X" denotes an LNA unit and "x" denotes a non-LNA unit.

The specific substitution pattern for the nucleotides from position 11, counting from the 3' end, to the 5' end depends on the number of nucleotides in the miR-122 inhibiting oligonucleotide. In a preferred embodiment, the miR-122 inhibiting oligonucleotide contains 12 nucleotides and the substitution pattern for positions 11 to 12, counting from the 3' end, is selected from the group consisting of xX and Xx, wherein "X" denotes an LNA unit and "x" denotes a non-LNA unit. In a more preferred embodiment thereof, the substitution pattern for positions 11 to 12, counting from the 3' end, is xX, wherein "X" denotes an LNA unit and "x" denotes a non-LNA unit. Alternatively, no LNA units are present in positions 11 to 12, counting from the 3' end, i.e. the substitution pattern is xx.

In another preferred embodiment, the miR-122 inhibiting oligonucleotide contains 13 nucleotides and the substitution pattern for positions 11 to 13, counting from the 3' end, is selected from the group consisting of Xxx, xXx, xxX, XXx, XxX, xXX and XXX, wherein "X" denotes an LNA unit and "x" denotes a non-LNA unit. In a more preferred embodiment thereof, the substitution pattern for positions 11 to 13, counting from the 3' end, is selected from the group consisting of xXx, xxX and xXX, wherein "X" denotes an LNA unit and "x" denotes a non-LNA unit. In a most preferred embodiment thereof, the substitution pattern for positions 11 to 13, counting from the 3' end, is xxX, wherein "X" denotes an LNA unit and "x" denotes a non-LNA unit. Alternatively, no LNA units are present in positions 11 to 13, counting from the 3' end, i.e. the substitution pattern is xxx.

In yet another preferred embodiment, the miR-122 inhibiting oligonucleotide contains 14 nucleotides and the substitution pattern for positions 11 to 14, counting from the 3' end, is selected from the group consisting of Xxxx, xXxx, xxXx, xxxX, XXxx, XxXx, XxxX, xXXx, xXxX and xxXX, wherein "X" denotes an LNA unit and "x" denotes a non-LNA unit. In a preferred embodiment thereof, the substitution pattern for positions 11 to 14, counting from the 3' end, is selected from the group consisting of xXxx, xxXx, xxxX, xXxX and xxXX, wherein "X" denotes an LNA unit and "x" denotes a non-LNA unit. In a more preferred embodiment thereof, the substitution pattern for positions 11 to 14, counting from the 3' end, is xXxX, wherein "X" denotes an LNA unit and "x" denotes a non-LNA unit. Alternatively, no LNA units are present in positions 11 to 14, counting from the 3' end, i.e. the substitution pattern is xxxx In a further preferred embodiment, the miR-122 inhibiting oligonucleotide contains 15 nucleotides and the substitution pattern for positions 11 to 15, counting from the 3' end, is selected from the group consisting of Xxxxx, xXxxx, xxXxx, xxxXx, xxxxX, XXxxx, XxXxx, XxxXx, XxxxX, xXXxx, xXxXx, xXxxX, xxXXx, xxXxX, xxxXX and XxXxX, wherein "X" denotes an LNA unit and "x" denotes a non-LNA unit. In a preferred embodiment thereof, the substitution pattern for positions 11 to 15, counting from the 3' end, is selected from the group consisting of xxXxx, XxXxx, XxxXx, xXxXx, xXxxX and xxXxX, wherein "X" denotes an LNA unit and "x" denotes a non-LNA unit. In a more preferred embodiment thereof, the substitution pattern for positions 11 to 15, counting from the 3' end, is selected from the group consisting of xxXxx, xXxXx, xXxxX and xxXxX, wherein "X" denotes an LNA unit and "x" denotes a non-LNA unit. In an even more preferred embodiment thereof, the substitution pattern for positions 11 to 15, counting from the 3' end, is selected from the group consisting of xXxxX and xxXxX, wherein "X" denotes an LNA unit and "x" denotes a non-LNA unit. In a most preferred embodiment, the substitution pattern for positions 11 to 15, counting from the 3' end, is xxXxX, wherein "X" denotes an LNA unit and "x" denotes a non-LNA unit. Alternatively, no LNA units are present in positions 11 to 15, counting from the 3' end, i.e. the substitution pattern is xxxxx In yet a further preferred embodiment, the miR-122 inhibiting oligonucleotide contains 16 nucleotides and the substitution pattern for positions 11 to 16, counting from the 3' end, is selected from the group consisting of Xxxxxx, xXxxxx, xxXxxx, xxxXxx, xxxxXx, xxxxxX, XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX, xxxxXX, XXXxxx, XXxXxx, XXxxXx, XXxxxX, XxXXxx, XxXxXx, XxXxxX, XxxXXx, XxxXxX, XxxxXX, xXXXxx, xXXxXx, xXXxxX, xXxXXx, xXxXxX, xXxxXX, xxXXXx, xxXXxX, xxXxXX and xxxXXX, wherein "X" denotes an LNA unit and "x" denotes a non-LNA unit. In a preferred embodiment thereof, the substitution pattern for positions 11 to 16, counting from the 3' end, is selected from the group consisting of XxxXxx, xXxXxx, xXxxXx, xxXxXx, xxXxxX, XxXxXx, XxXxxX, XxxXxX, xXxXxX, xXxxXX and xxXxXX, wherein "X" denotes an LNA unit and "x" denotes a non-LNA unit. In a more preferred embodiment thereof, the substitution pattern for positions 11 to 16, counting from the 3' end, is selected from the group consisting of xXxXxx, xXxxXx, xxXxXx, xxXXxx, xXxXxX, xXxxXX and xxXxXX, wherein "X" denotes an LNA unit and "x" denotes a non-LNA unit. In an even more preferred embodiment thereof, the substitution pattern for positions 11 to 16, counting from the 3' end, is selected from the group consisting of xxXxxX, xXxXxX, xXxxXX and xxXxXX, wherein "X" denotes an LNA unit and "x" denotes a non-LNA unit. In a still more preferred embodiment thereof, the substitution pattern for positions 11 to 16, counting from the 3' end, is selected from the group consisting of xxXxxX and xXxXxX, wherein "X" denotes an LNA unit and "x" denotes a non-LNA unit. In a most preferred embodiment thereof, the substitution pattern for positions 11 to 16, counting from the 3' end, is xxXxxX, wherein "X" denotes an LNA unit and "x" denotes a non-LNA unit. Alternatively, no LNA units are present in positions 11 to 16, counting from the 3' end, i.e. the substitution pattern is xxxxxx In a preferred embodiment of the invention, the miR-122 inhibiting oligonucleotide contains an LNA unit at the 5' end. In another preferred embodiment, the miR-122 inhibiting oligonucleotide contains an LNA unit at the first two positions, counting from the 5' end.

In a particularly preferred embodiment, the miR-122 inhibiting oligonucleotide contains 13 nucleotides and the substitution pattern, starting from the 3' end, is XXxXxXxxxXXxxX, wherein "X" denotes an LNA unit and "x" denotes a non-LNA unit. The preferred sequence for this embodiment, starting from the 3' end, is CCtCaCacTGttA, wherein a capital letter denotes a nitrogenous base in an LNA-unit and a small letter denotes a nitrogenous base in a non-LNA unit.

In another particularly preferred embodiment, the miR-122 inhibiting oligonucleotide contains 15 nucleotides and the substitution pattern, starting from the 3' end, is XXxXxXxxxXXxxXxX, wherein "X" denotes an LNA unit and "x" denotes a non-LNA unit. The preferred sequence for this embodiment, starting from the 3' end, is CCtCaCacTGtAcC, wherein a capital letter denotes a nitrogenous base in an LNA-unit and a small letter denotes a nitrogenous base in a non-LNA unit.

Modification of the Internucleoside Linkage Group

Typical internucleoside linkage groups in oligonucleotides are phosphate groups, but these may be replaced by internucleoside linkage groups differing from phosphate. In a further interesting embodiment of the invention, miR-122 inhibiting oligonucleotide is modified in its internucleoside linkage group structure, i.e. the modified oligonucleotide comprises an internucleoside linkage group which differs from phosphate.

Specific examples of internucleoside linkage groups which differ from phosphate (—O—P(O)$_2$—O—) include —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$—OO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is hydrogen or C$_{1-4}$-alkyl.

When the internucleoside linkage group is modified, the internucleoside linkage group is preferably a phosphorothioate group (—O—P(O,S)—O—). In a preferred embodiment, all internucleoside linkage groups of the oligonucleotides according to the present invention are phosphorothioate.

Designs for Specific microRNAs

The following table provides examples of miR-122 inhibiting oligonucleotide, such as those used in pharmaceutical compositions, as compared to prior art type of molecules.

| Oligo #, target microRNA, oligo sequence | Design | SEQ ID |
|---|---|---|
| target: hsa-miR-122a MIMAT0000421 | | |
| uggagugugacaauggguguuugu | | SEQ ID NO 58 |
| screened in HUH-7 cell line expressing miR-122 | | |
| miR-122 5'-ACAAacaccattgtcacacTCCA-3' | Full complement, gap | SEQ ID NO 67 |
| miR-122 5'-acaaacACCATTGTcacactcca-3' | Full complement, block | SEQ ID NO 68 |

-continued

| Oligo #, target microRNA, oligo sequence | Design | SEQ ID |
|---|---|---|
| miR-122 5'-acAaaCacCatTgtCacActCca-3' | Full complement, LNA_3 | SEQ ID NO 69 |
| miR-122 5'-CcAttGTcaCaCtCC-3' | New design | SEQ ID NO 63 |
| miR-122 5'-CcAtTGTcaCACtCC-3' | Enhanced new design | SEQ ID NO 70 |
| miR-122 5'-ATTGTcACACtCC-3' | ED - 13mer | SEQ ID NO 71 |
| miR-122 5'-TGTcACACtCC-3' | ED - 11mer | SEQ ID NO 72 |
| miR-122 5' CC$^M$AT$^M$T$^M$GTC$^M$A$^M$CA$^M$CT$^M$CC-3' | New design - 2'MOE | SEQ ID NO 73 |
| miR-122 5' CC$^F$AT$^F$T$^F$GTC$^F$A$^F$CA$^F$CT$^F$CC-3' | New design - 2'Fluoro | SEQ ID NO 74 |

Capital Letters without a superscript M or F, refer to LNA units. Lower case=DNA, except for lower case in bold =RNA. The LNA cytosines may optionally be methylated). Capital letters followed by a superscript M refer to 2'OME RNA units, Capital letters followed by a superscript F refer to 2' fluoro DNA units, lowercase letter refer to DNA. The above oligos may in one embodiment be entirely phosphorothioate, but other nucleobase linkages as herein described bay be used. In one embodiment the nucleobase linkages are all phosphodiester. It is considered that for use within the brain/spinal cord it is preferable to use phosphodiester linkages, for example for the use of antimiRs targeting miR21.

The miR-122 inhibiting oligonucleotide, in one embodiment, have a sequence of nucleobases 5'-3' selected form the group consisting of:
  LdLddLLddLdLdLL (New design)
  LdLdLLLLddLLLdLL (Enhanced new design)
  LMLMMLLMMMLMLMLL (New design—2'MOE)
  LMLMLLLMMLLLMLL (Enhanced new design—2'MOE)
  LFLFFLLFFLFLFLL (New design—2' Fluoro)
  LFLFLLLLFFLLLLFLL (Enhanced new design—2' Fluoro)
  LddLddLddL(d)(d)(L)(d)(d)(L)(d) 'Every third'
  dLddLddLdd(L)(d)(d)(L)(d)(d)(L) 'Every third'
  ddLddLddLd(d)(L)(d)(d)(L)(d)(d) 'Every third'
  LMMLMMLMML(M)(M)(L)(M)(M)(L)(M) 'Every third'
  MLMMLMMLMM(L)(M)(M)(L)(M)(M)(L) 'Every third'
  MMLMMLMMLM(M)(L)(M)(M)(L)(M)(M) 'Every third'
  LFFLFFLFFL(F)(F)(L)(F)(F)(L)(F) 'Every third'
  FLFFLFFLFF(L)(F)(F)(L)(F)(F)(L) 'Every third'
  FFLFFLFFLF(F)(L)(F)(F)(L)(F)(F) 'Every third'
  dLdLdLdLdL(d)(L)(d)(L)(d)(L)(d) 'Every second'
  LdLdLdLdL(d)(L)(d)(L)(d)(L)(d)(L) 'Every second'
  MLMLMLMLML(M)(L)(M)(L)(M)(L)(M) 'Every second'
  LMLMLMLML(M)(L)(M)(L)(M)(L)(M)(L) 'Every second'
  FLFLFLFLFL(F)(L)(F)(L)(F)(L)(F) 'Every second'
  LFLFLFLFL(F)(L)(F)(L)(F)(L)(F)(L) 'Every second'
Wherein L=LNA unit, d=DNA units, M=2'MOE RNA, F=2'Fluoro and residues in brackets are optional Specific examples of miR-122 inhibiting oligonucleotides may be selected from the group consisting of:

| SEQ ID NO: | Sequence |
|---|---|
| 75 | tgCatGgaTttGcaCa |
| 76 | tgCatGgaTttGcaC |
| 77 | CatGgaTttGcaC |
| 78 | tGcAtGgAtTtGcAc |
| 79 | cAtGgAtTtGcAc |
| 80 | CatGGatTtGcAC |
| 81 | TgCatGGatTtGcAC |
| 82 | TgCaTgGaTTtGcACa |
| 83 | cCatTgtCacActCca |
| 84 | cCatTgtAacTctCca |
| 85 | ccAttGtcAcaCtcCa |
| 86 | cCatTgtCacActCc |
| 87 | atTgtCacActCc |
| 88 | ccAttGtcAcaCtcC |
| 89 | AttGtcAcaCtcC |
| 90 | aTtGtcAcaCtCc |
| 91 | AttGTcaCaCtCC |
| 92 | CcAttGTcaCaCtCC |
| 93 | CcaTtgTcacActcCa |
| 94 | CCAttgtcacacTCCa |
| 95 | tCacGatTagCatTaa |
| 96 | aTcaCgaTtaGcaTta |
| 97 | TcAcGaTtAgCaTtAa |
| 98 | AtcAcGaTtAgCaTta |
| 99 | gAgcCgaAcgAacAa |
| 100 | gcCgaAcgAacAa |

-continued

| SEQ ID NO: | Sequence |
|---|---|
| 101 | GaGcCgAaCgAaCaA |
| 102 | GcCgAaCgAaCaA | wherein a lowercase letter identifies the nitrogenous base of a DNA unit and an uppercase letter identifies the nitrogenous base of an LNA unit, with uppercase C referring to $^{Me}C$.

It will be recognised that the design of LNA/DNA nucleobases in the above specific examples may be applied to other oligonucleotides according to the invention.

Conjugates

The invention also refers to conjugates comprising the miR-122 inhibiting oligonucleotide.

In one embodiment the oligomeric (oligonucleotide) compound is linked to ligands/conjugates, which may be used, e.g. to increase the cellular uptake of antisense oligonucleotides. This conjugation can take place at the terminal positions 5'/3'-OH but the ligands may also take place at the sugars and/or the bases. In particular, the growth factor to which the antisense oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/ligands are cholesterol moieties, duplex intercalators such as acridine, poly-L-lysine, "end-capping" with one or more nuclease-resistant linkage groups such as phosphoromonothioate, and the like. The invention also provides for a conjugate comprising the compound according to the invention as herein described, and at least one non-nucleotide or non-polynucleotide moiety covalently attached to said compound. Therefore, in one embodiment where the compound of the invention consists of s specified nucleic acid, as herein disclosed, the compound may also comprise at least one non-nucleotide or non-polynucleotide moiety (e.g. not comprising one or more nucleotides or nucleotide analogues) covalently attached to said compound. The non-nucleobase moiety may for instance be or comprise a sterol such as cholesterol.

Therefore, it will be recognised that the oligonucleotide of the invention, such as the oligonucleotide used in pharmaceutical (therapeutic) formulations may comprise further non-nucleobase components, such as the conjugates herein defined.

Terms

When used herein, the term "nucleotide analogue" refers to a non-natural occurring nucleotide wherein, for example in one preferred embodiment, either the ribose unit is different from 2-deoxyribose and/or the nitrogenous base is different from A, C, T and G and/or the internucleoside phosphate linkage group is different. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Schemes 1

The terms "corresponding nucleoside/nucleotide analogue" and "corresponding nucleoside/nucleotide" are intended to indicate that the nitrogenous base in the nucleoside/nucleotide analogue and the nucleoside/nucleotide is identical. For example, when the 2-deoxyribose unit of the nucleotide is linked to an adenine, the "corresponding nucleoside analogue" contains a pentose unit (different from 2-deoxyribose) linked to an adenine.

The term "nucleic acid" is defined as a molecule formed by covalent linkage of two or more nucleotides. The terms "nucleic acid" and "polynucleotide" are used interchangeably herein. For example, DNA and RNA are nucleic acids.

A preferred nucleotide analogue is LNA, such as beta-D-oxy-LNA, alpha-L-oxy-LNA, beta-D-amino-LNA and beta-D-thio-LNA, most preferred beta-D-oxy-LNA. The compounds of the invention are typically those wherein said nucleotides comprise a linkage group selected from the group consisting of a phosphate group, a phosphorothioate group and a boranophosphate group, the internucleoside linkage may be —O—P(O)$_2$—O—, —O—P(O,S)—O—, in particular a phosphate group and/or a phosphorothioate group. In a particular embodiment, all nucleotides comprise a phosphorothioate group. In one embodiment, some or all of the nucleotides are linked to each other by means of a phosphorothioate group. Suitably, all nucleotides are linked to each other by means of a phosphorothioate group.

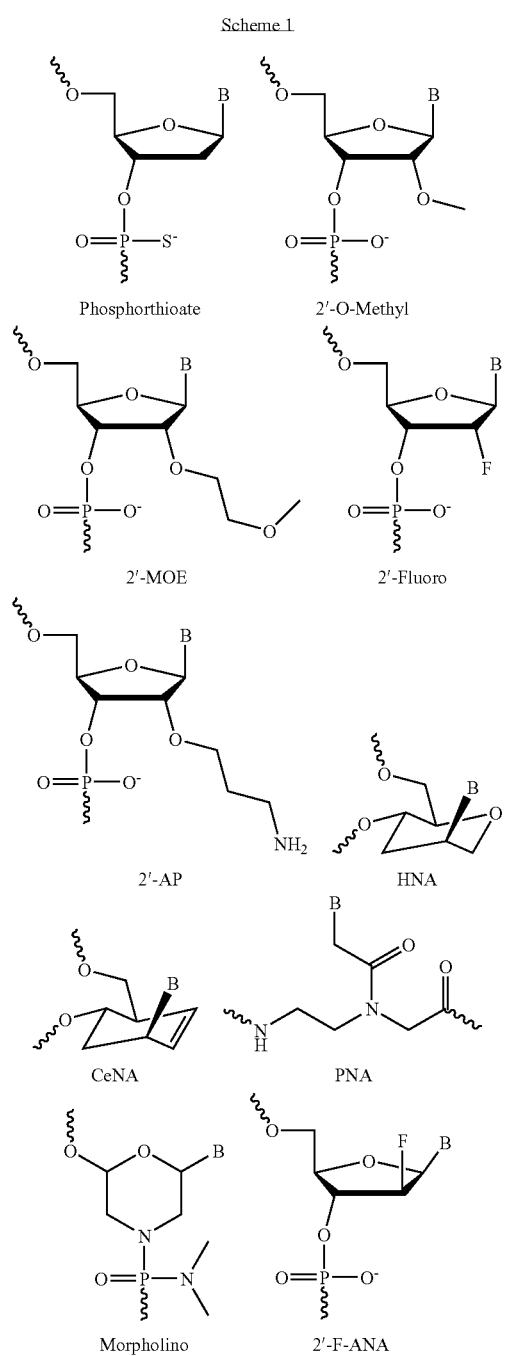

Scheme 1

Phosphorthioate

2'-O-Methyl

2'-MOE

2'-Fluoro

2'-AP

HNA

CeNA

PNA

Morpholino

2'-F-ANA

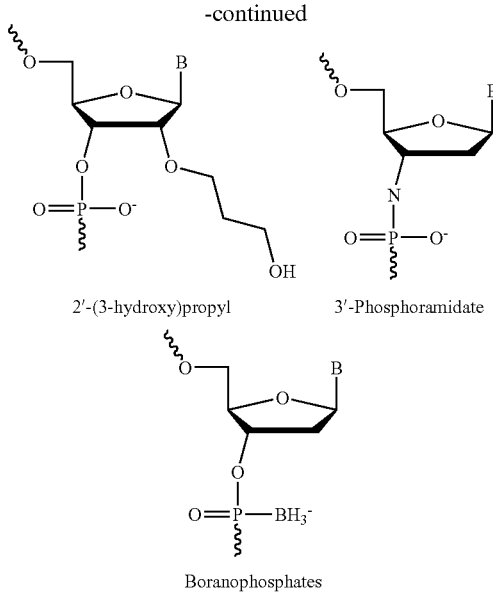

2'-(3-hydroxy)propyl     3'-Phosphoramidate

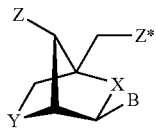

Boranophosphates

In an interesting embodiment, the compounds comprise of from 3-8 nucleotide analogues, e.g. 6 or 7 nucleotide analogues. In the by far most preferred embodiments, at least one of said nucleotide analogues is a locked nucleic acid (LNA), such as at least 3 or at least 4, or at least 5, or at least 6, or at least 7, or 8, of the nucleotide analogues may be LNA, in one embodiment all the nucleotides analogues may be LNA.

The term "LNA" refers to a nucleotide analogue containing one bicyclic nucleotide analogue, also referred to as a LNA monomer.

The term "LNA" when used in the context of a "LNA oligonucleotides" refers to an oligonucleotide containing one or more bicyclic nucleoside analogues. The Locked Nucleic Acid (LNA) used in the oligonucleotide compounds of the invention has the structure of the general formula X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected form hydrogen and C$_{1-4}$-alkyl; Z and Z* are independently selected among an internucleoside linkage, a terminal group or a protecting group; B constitutes a natural or non-natural nucleobase; and the asymmetric groups may be found in either orientation.

Preferably, the Locked Nucleic Acid (LNA) used in the oligonucleotide compound of the invention comprises at least one Locked Nucleic Acid (LNA) unit according any of the formulas

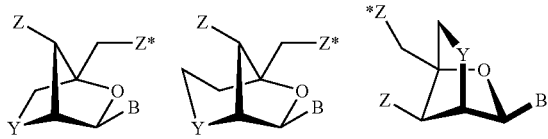

wherein Y is —O—, —S—, —NH—, or N(R$^H$); Z and Z* are independently selected among an internucleoside linkage, a terminal group or a protecting group; B constitutes a natural or non-natural nucleobase, and R$^H$ is selected form hydrogen and C$_{1-4}$-alkyl.

Preferably, the Locked Nucleic Acid (LNA) used in the oligonucleotide compound of the invention comprises at internucleoside linkages selected from the group consisting of —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR")—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected form hydrogen and C$_{1-4}$-alkyl.

As stated, in an interesting embodiment of the invention, the oligonucleotide compounds contain at least one unit of chemistry termed LNA (Locked Nucleic Acid).

Specifically preferred LNA units are shown in scheme 2.

Scheme 2

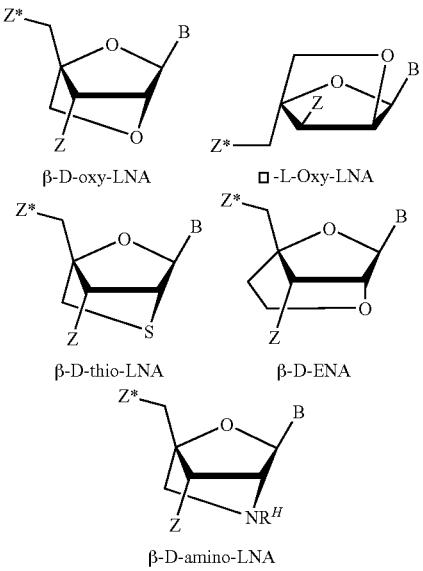

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above —N(H)—, N(R)—, CH$_2$—N(H)—, —CH$_2$—N(R)— where R is selected form hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the nucleobase B).

In a preferred embodiment LNA is selected from beta-D-oxy-LNA, alpha-L-oxy-LNA, beta-D-amino-LNA and beta-D-thio-LNA, in particular beta-D-oxy-LNA. The nucleosides and/or LNAs are typically linked together by means of phosphate groups and/or by means of phosphorothioate groups The term "at least [an integer]" comprises the integers larger than or equal to said integer, such as 1, 2, 3, 4, 5, 6, 7, 8, 9, 10, 11, 12, 13, 14, 15, 16, 17, 18, 19, 20, 21 and so forth.

As used herein, the term "target nucleic acid" encompasses DNA encoding the a VLDL assembly pathway protein, including Apo-B100, and miR-122. RNA (including pre-mRNA and mRNA and mRNA edit) transcribed from such DNA, and also cDNA derived from such RNA.

The "target protein" is mammalian apolipoprotein B, preferably human apolipoprotein B. It will be recognised that as ApoB-100 and ApoB-48 both originate from the same genetic sequence, that the oligomeric compounds according to the invention may be used for down-regulation of either, or both forms of apolipoprotein B, and both ApoB-100 encoding mRNA, and the RNA edited form, which encodes Apo-B48.

As used herein, the term "gene" means the gene including exons, introns, non-coding 5' and 3' regions and regulatory elements and all currently known variants thereof and any further variants, which may be elucidated.

As used herein, the term "mRNA" means the presently known mRNA transcript(s) of a targeted gene, and any further transcripts, which may be identified.

As used herein, the term "modulation" means either an increase (stimulation) or a decrease (inhibition) in the expression of a gene. In the present invention, inhibition is the preferred form of modulation of gene expression and mRNA is a preferred target.

As used herein, the term "targeting" an antisense compound to a particular target nucleic acid means providing the antisense oligonucleotide to the cell, animal or human in such a way that the antisense compound are able to bind to and modulate the function of its intended target.

In an interesting embodiment, the 3' end of the compound of the invention comprises a nucleotide, rather than a nucleotide analogue.

Preferably, the oligomeric compound, such as an antisense oligonucleotide, according to the invention comprises at least one Locked Nucleic Acid (LNA) unit, such as 1, 2, 3, 4, 5, 6, 7, or 8 Locked Nucleic Acid (LNA) units, preferably between 4 to 8 LNA units, such as 4-6 LNA units, most preferably 4, 5 or 6 LNA units. Suitably, the oligomeric compound may comprise both beta-D-oxy-LNA, and one or more of the following LNA units: thio-LNA, amino-LNA, oxy-LNA, ena-LNA and/or alpha-LNA in either the D-beta or L-alpha configurations or combinations thereof.

Preferably, the oligomeric compound, such as an antisense oligonucleotide, may comprise both LNA and DNA units. Preferably the combined total of LNA and DNA units is between 10-15.

In one embodiment, within the oligomeric compound according to the invention, such as an antisense oligonucleotide, which comprises LNA, all LNA C residues are 5' methyl-Cytosine.

Preparation of Oligonucleotide Compounds

The LNA nucleotide analogue building blocks (β-D-oxy-LNA, 3-D-thio-LNA, β-D-amino-LNA and α-L-oxy-LNA) can be prepared following published procedures and references cited therein, see, e.g., WO 03/095467 A1; D. S. Pedersen, C. Rosenbohm, T. Koch (2002) Preparation of LNA Phosphoramidites, Synthesis 6, 802-808; M. D. Sørensen, L. Kværnø, T. Bryld, A. E. Håakansson, B. Verbeure, G. Gaubert, P. Herdewijn, J. Wengel (2002) α-L-ribo-configured Locked Nucleic Acid (α-l-LNA): Synthesis and Properties, J. Am. Chem. Soc., 124, 2164-2176; S. K. Singh, R. Kumar, J. Wengel (1998) Synthesis of Novel Bicyclo[2.2.1] Ribonucleosides: 2'-Amino- and 2'-Thio-LNA Monomeric Nucleosides, J. Org. Chem. 1998, 63, 6078-6079; C. Rosenbohm, S. M. Christensen, M. D. Sørensen, D. S. Pedersen, L. E. Larsen, J. Wengel, T. Koch (2003) Synthesis of 2'-amino-LNA: a new strategy, Org. Biomol. Chem. 1, 655-663; and WO 2004/069991 A2.

One particular example of a thymidine LNA monomer is the (1S,3R, 4R, 7S)-7-hydroxy-1-hydroxymethyl-3-(thymin-1yl)-2,5-dioxa-bicyclo[2:2:1]heptane.

The LNA oligonucleotides can be prepared as described in the Examples and in WO 99/14226, WO 00/56746, WO 00/56748, WO 00/66604, WO 00/125248, WO 02/28875, WO 2002/094250 and WO 03/006475. Thus, the LNA oligonucleotides may be produced using the oligomerisation techniques of nucleic acid chemistry well-known to a person of ordinary skill in the art of organic chemistry. Generally, standard oligomerisation cycles of the phosphoramidite approach (S. L. Beaucage and R. P. Iyer, *Tetrahedron,* 1993, 49, 6123; S. L. Beaucage and R. P. Iyer, *Tetrahedron,* 1992, 48, 2223) are used, but e.g. H-phosphonate chemistry, phosphotriester chemistry can also be used.

For some monomers, longer coupling time, and/or repeated couplings and/or use of more concentrated coupling reagents may be necessary or beneficial.

The phosphoramidites employed couple typically with satisfactory >95% step-wise yields. Oxidation of the Phosphorous(III) to Phosphorous(V) is normally done with e.g. iodine/pyridine/-$H_2O$. This yields after deprotection the native phosphorodiester internucleoside linkage. In the case that a phosphorothioate internucleoside linkage is prepared a thiolation step is performed by exchanging the normal, e.g. iodine/pyridine/$H_2O$, oxidation used for synthesis of phosphorodiester internucleoside linkages with an oxidation using the ADTT reagent (xanthane hydride (0.01 M in acetonitrile:pyridine 9:1; v/v)). Other thiolation reagents are also possible to use, such as Beaucage and PADS. The phosphorothioate LNA oligonucleotides were efficiently synthesized with stepwise coupling yields >=98%.

LNA oligonucleotides comprising β-D-amino-LNA, 6-D-thio-LNA, and/or α-L-LNA can also efficiently be synthesized with step-wise coupling yields ≧98% using the phosphoramidite procedures.

Purification of LNA oligonucleotides was can be accomplished using disposable reversed phase purification cartridges and/or reversed phase HPLC and/or precipitation from ethanol or butanol. Capillary gel electrophoresis, reversed phase HPLC, MALDI-MS, and ESI-MS were used to verify the purity of the synthesized LNA oligonucleotides.

Salts

The Oligomeric compound can be employed in a variety of pharmaceutically acceptable salts. As used herein, the term refers to salts that retain the desired biological activity of the LNA oligonucleotide and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or combinations, e.g., a zinc tannate salt or the like.

Such salts are formed, from the Oligomeric compound which possess phosphorodiester group and/or phosphorothioate groups, and are, for example, salts with suitable bases. These salts include, for example, nontoxic metal salts which are derived from metals of groups Ia, Ib, IIa and IIb of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl) amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts. Lithium salts, sodium salts, magnesium salts, zinc salts or potassium salts are preferred, with sodium salts being particularly preferred.

Prodrugs

In one embodiment, the LNA oligonucleotide may be in the form of a prodrug. Oligonucleotides are by virtue negatively charged ions. Due to the lipophilic nature of cell membranes, the cellular uptake of oligonucleotides is reduced compared to neutral or lipophilic equivalents. This polarity "hindrance" can be avoided by using the prodrug approach (see e.g. Crooke, R. M. (1998) in Crooke, S. T. *Antisense research and Application*. Springer-Verlag, Berlin, Germany, vol. 131, pp. 103-140). In this approach, the Oligomeric compound are prepared in a protected manner so that the Oligomeric compound are neutral when it is administered. These protection groups are designed in such a way that they can be removed when the LNA oligonucleotide is taken up by the cells. Examples of such protection groups are S-acetylthioethyl (SATE) or S-pivaloylthioethyl (t-butyl-SATE). These protection groups are nuclease resistant and are selectively removed intracellulary.

Conjugates

In one embodiment of the invention, the oligonucleotide may be linked to ligands/conjugates, which may be used, e.g. to increase the cellular uptake of the oligonucleotide. This conjugation can take place at the terminal positions 5'/3'-OH but the ligands may also take place at the sugars and/or the bases. The 3'—OH is preferred site for cholesterol conjugation.

In a preferred embodiment, the oligonucleotide of the invention is conjugated with a moiety which improvise the in vivo uptake of the RNA complex, such as cholesterol.

The invention also provides for a conjugate comprising the oligonucleotide according to the invention as herein described, and at least one non-nucleotide or non-polynucleotide moiety covalently attached to said oligonucleotide.

Thus, the Oligomeric compound may, e.g., be conjugated or form chimera with non-nucleotide or non-polynucleotide moieties including Peptide Nucleic Acids (PNA), proteins (e.g. antibodies for a target protein), macromolecules, low molecular weight drug substances, fatty acid chains, sugar residues, glycoproteins, polymers (e.g. polyethylene glycol), micelle-forming groups, antibodies, carbohydrates, receptor-binding groups, steroids such as cholesterol, polypeptides, intercalating agents such as an acridine derivative, a long-chain alcohol, a dendrimer, a phospholipid and other lipophilic groups or combinations thereof, etc., just as the Oligomeric compound may be arranged in dimeric or dendritic structures. The Oligomeric compound or conjugates may also be conjugated or further conjugated to active drug substances, for example, aspirin, ibuprofen, a sulfa drug, an antidiabetic, an antibacterial agent, a chemotherapeutic compound or an antibiotic.

Pharmaceutical Composition

A particularly interesting aspect of the invention is directed to a pharmaceutical composition comprising a compound as defined herein or a conjugate as defined herein, and a pharmaceutically acceptable diluent, carrier or adjuvant. In a particularly interesting embodiment, the pharmaceutical composition is adapted for oral administration.

Directions for the preparation of pharmaceutical compositions can be found in "Remington: The Science and Practice of Pharmacy" by Alfonso R. Gennaro, and in the following.

It should be understood that the present invention also particularly relevant for a pharmaceutical composition, which comprises a least one antisense oligonucleotide construct of the invention as an active ingredient. It should be understood that the pharmaceutical composition according to the invention optionally comprises a pharmaceutical carrier, and that the pharmaceutical composition optionally comprises further antisense compounds, chemotherapeutic agents, cholesterol lowering agents, anti-inflammatory compounds, antiviral compounds and/or immuno-modulating compounds.

As stated, the pharmaceutical composition of the invention may further comprise at least one therapeutic/prophylactic compound. The compound is typically selected from the group consisting of bile salt sequestering resins (e.g., cholestyramine, colestipol, and colesevelam hydrochloride), HMGCoA-reductase inhibitors (e.g., lovastatin, cerivastatin, prevastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), implitapide, inhibitors of bile acid transporters (apical sodium-dependent bile acid transporters), regulators of hepatic CYP7a, estrogen replacement therapeutics (e.g., tamoxifen), and anti-inflammatories (e.g., glucocorticoids).

The oligonucleotide compound or conjugate comprised in this invention can be employed in a variety of pharmaceutically acceptable salts. As used herein, the term refers to salts that retain the desired biological activity of the herein identified compounds and exhibit minimal undesired toxicological effects, cf. "Conjugates"

In one embodiment of the invention the oligonucleotide compound or conjugate may be in the form of a prodrug, cf. "Prodrugs".

The invention also includes the formulation of one or more oligonucleotide compound or conjugate as disclosed herein. Pharmaceutically acceptable binding agents and adjuvants may comprise part of the formulated drug. Capsules, tablets and pills etc. may contain for example the following compounds: microcrystalline cellulose, gum or gelatin as binders; starch or lactose as excipients; stearates as lubricants; various sweetening or flavoring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellular emulsion. Such formulations are particularly useful for oral administration.

An oligonucleotide of the invention may be mixed with any material that do not impair the desired action, or with material that supplement the desired action. These could include other drugs including other nucleotide compounds.

For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment the active LNA oligonucleotide is administered IV, IP, orally, topically or as a bolus injection or administered directly in to the target organ.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to liver tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27).

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In a certain embodiment, the present invention provides pharmaceutical compositions containing (a) one or more antisense compounds and (b) one or more other cholesterol lowering agents which function by a non-antisense mechanism. When used with the compounds of the invention, such cholesterol lowering agents may be used individually (e.g. atorvastatin and oligonucleotide), sequentially (e.g. atorvastatin and oligonucleotide for a period of time followed by another agent and oligonucleotide), or in combination with one or more other such cholesterol lowering agents. All cholesterol lowering agents known to a person skilled in the art are here incorporated as combination treatments with compound according to the invention.

Anti-inflammatory drugs, including but not limited to nonsteroidal anti-inflammatory drugs and corticosteroids, antiviral drugs, and immuno-modulating drugs may also be combined in compositions of the invention. Two or more combined compounds may be used together or sequentially.

In another embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

Dosing is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient.

Optimum dosages may vary depending on the relative potency of individual oligonucleotides. Generally it can be estimated based on $EC_{50}$s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state. The assessment of an effective dosage regimen of a particular oligonucleotide is routine for the person skilled in the art, using knowledge known in the art, and the information given in this application, and will not require undue experimentation.

Method of Treatment

A person skilled in the art will appreciate that VLDL assembly inhibitors such as apoB-100 inhibitors or MTP inhibitors may be used together with miR-122 inhibitory compounds in a method of treatment of HCV.

The Following Embodiments Relating to miR-122 Antisense Compounds, that May be Combined with VLDL Assembly Inhibitors for the Treatment of HCV as Described Herein.

1. An oligonucleotide having a length of from 12 to 26 nucleotides having a core DNA sequence from positions two to seven or from positions three to eight, counting from the 3' end: acgttt, wherein at least one, such as one, preferably at least two, such as two or three, DNA units in said sequence have been substituted by their corresponding LNA unit; or a conjugate thereof.

2. An oligonucleotide having a length of from 12 to 26 nucleotides having a core DNA sequence from positions two to seven or from positions three to eight, counting from the 3' end: ctcaca, wherein at least one, such as one, preferably at least two, such as two or three, DNA units in said sequence have been substituted by their corresponding LNA unit; or a conjugate thereof.

3. An oligonucleotide having a length of from 12 to 26 nucleotides having a core DNA sequence from positions two to seven or from positions three to eight, counting from the 3' end: ttacga, wherein at least one, such as one, preferably at least two, such as two or three, DNA units in said sequence have been substituted by their corresponding LNA unit; or a conjugate thereof.

4. An oligonucleotide having a length of from 12 to 26 nucleotides having a core DNA sequence from positions two to seven or from positions three to eight, counting from the 3' end: acaagc; wherein at least one, such as one, preferably at least two, such as two or three, DNA units in said sequence have been substituted by their corresponding LNA unit; or a conjugate thereof.

5. The oligonucleotide according to any one of embodiments 1 to 4 or a conjugate thereof, wherein at least two, such as two or three, DNA units from positions one to six, two to seven or three to eight, counting from the 3' end, have been substituted by their corresponding LNA unit and wherein the LNA units are separated by at least one DNA unit.

6. The oligonucleotide according to embodiment 5 or a conjugate thereof, wherein the number of consecutive DNA units from positions one to six, two to seven or three to eight, counting from the 3' end, is at most two.

7. The oligonucleotide according to embodiment 6 or a conjugate thereof, wherein every second nucleotide from positions one to six, two to seven or three to eight, counting from the 3' end, is an LNA unit.

8. The oligonucleotide according to embodiment 6 or a conjugate thereof, wherein every third nucleotide from positions one to six, two to seven or three to eight, counting from the 3' end, is an LNA unit.

9. The oligonucleotide according to embodiment 6 or a conjugate thereof, wherein the substitution pattern for the nucleotides in positions one to six, two to seven or three to eight, counting from the 3' end, is selected from the group consisting of: xxXxxX, xxXxXx, xXxxXx, xXxXxx, XxxXxx, xXxXxX, XxXxXx, XxxXxX, and XxXxxX; wherein "X" denotes an LNA unit and "x" denotes a DNA unit.

10. The oligonucleotide according to embodiment 9 or a conjugate thereof, wherein the substitution pattern for the nucleotides in positions one to six, two to seven or three to eight, counting from the 3' end, is selected from the group consisting of xxXxxX, xXxxXx, XxxXxx, xXxXxX, and XxXxXx; wherein "X" denotes an LNA unit and "x" denotes a DNA unit.

11. The oligonucleotide according to embodiment 1 or a conjugate thereof having a DNA sequence from positions one to seven, two to eight or three to nine, counting from the 3' end: acgttta, wherein at least one, such as one, preferably at least two, such as two, more preferably at least three, such as three or four, DNA units in said sequence have been substituted by their corresponding LNA unit.

12. The oligonucleotide according to embodiment 2 or a conjugate thereof having a DNA sequence from positions one to seven, two to eight or three to nine, counting from the 3' end: ctcacac, wherein at least one, such as one, preferably at least two, such as two, more preferably at least three, such as three or four, DNA units in said sequence have been substituted by their corresponding LNA unit.

13. The oligonucleotide according to embodiment 3 or a conjugate thereof having a DNA sequence from positions one to seven, two to eight or three to nine, counting from the 3' end: ttacgat, wherein at least one, such as one, preferably at least two, such as two, more preferably at least three, such as three or four, DNA units in said sequence have been substituted by their corresponding LNA unit.

14. The oligonucleotide according to embodiment 4 or a conjugate thereof having a DNA sequence from positions one to seven, two to eight or three to nine, counting from the 3' end: acaagca, wherein at least one, such as one, preferably at least two, such as two, more preferably at least three, such as three or four, DNA units in said sequence have been substituted by their corresponding LNA unit.

15. The oligonucleotide according to any one of embodiments 11 to 14 or a conjugate thereof, wherein at least two, such as two, three or four, DNA units from positions one to seven, two to eight or three to nine, counting from the 3' end, have been substituted by their corresponding LNA unit and wherein the LNA units are separated by at least one DNA unit.

16. The oligonucleotide according to embodiment 15 or a conjugate thereof, wherein the number of consecutive DNA units from positions one to seven, two to eight or three to nine, counting from the 3' end, is at most two.

17. The oligonucleotide according to embodiment 16 or a conjugate thereof, wherein every second nucleotide from positions one to seven, two to eight or three to nine, counting from the 3' end, is an LNA unit.

18. The oligonucleotide according to embodiment 16 or a conjugate thereof, wherein every third nucleotide from positions one to seven, two to eight or three to nine, counting from the 3' end, is an LNA unit.

19. The oligonucleotide according to embodiment 16 or a conjugate thereof, wherein the substitution pattern for the nucleotides in positions one to seven, two to eight or three to nine, counting from the 3' end, is selected from the group consisting of xxXxxXx, xxXxXxx, xXxxXxx, xxXxXxX, xXxxXxX, xXxXxxX, xXxXxXx, XxxXxxX, XxxXxXx, XxXxxXx, XxXxXxx, and XxXxXxX; wherein "X" denotes an LNA unit and "x" denotes a DNA unit.

20. The oligonucleotide according to embodiment 19 or a conjugate thereof, wherein the substitution pattern for the nucleotides in positions one to seven, two to eight or three to nine, counting from the 3' end, is selected from the group consisting of xxXxxXx, xXxxXxx, XxxXxxX, xXxXxXx, XxXxXxX, and XxXxXxx; wherein "X" denotes an LNA unit and "x" denotes a DNA unit.

21. The oligonucleotide according to embodiment 11 or a conjugate thereof having a DNA sequence from positions one to eight, two to nine or three to ten, counting from the 3' end: acgtttag, wherein at least one, such as one, preferably at least two, such as two, more preferably at least three, such as three or four, DNA units in said sequence have been substituted by their corresponding LNA unit.

22. The oligonucleotide according to embodiment 12 or a conjugate thereof having a DNA sequence from positions one to eight, two to nine or three to ten, counting from the 3' end: ctcacact, wherein at least one, such as one, preferably at least two, such as two, more preferably at least three, such as three or four, DNA units in said sequence have been substituted by their corresponding LNA unit.

23. The oligonucleotide according to embodiment 13 or a conjugate thereof having a DNA sequence from positions one to eight, two to nine or three to ten, counting from the 3' end: ttacgatt, wherein at least one, such as one, preferably at least two, such as two, more preferably at least three, such as three or four, DNA units in said sequence have been substituted by their corresponding LNA unit.

24. The oligonucleotide according to embodiment 14 or a conjugate thereof having a DNA sequence from positions one to eight, two to nine or three to ten, counting from the 3' end: acaagcaa, wherein at least one, such as one, preferably at least two, such as two, more preferably at least three, such as three or four, DNA units in said sequence have been substituted by their corresponding LNA unit.

25. The oligonucleotide according to any one of embodiments 21 to 24 or a conjugate thereof, wherein at least two, such as two, three or four, DNA units from positions one to eight, two to nine or three to ten, counting from the 3' end, have been substituted by their corresponding LNA unit and wherein the LNA units are separated by at least one DNA unit.

26. The oligonucleotide according to embodiment 25 or a conjugate thereof, wherein the number of consecutive DNA units from positions one to eight, two to nine or three to ten, counting from the 3' end, is at most two.

27. The oligonucleotide according to embodiment 26 or a conjugate thereof, wherein every second nucleotide from positions one to eight, two to nine or three to ten, counting from the 3' end, is an LNA unit.

28. The oligonucleotide according to embodiment 26 or a conjugate thereof, wherein every third nucleotide from positions one to eight, two to nine or three to ten, counting from the 3' end, is an LNA unit.

29. The oligonucleotide according to embodiment 26 or a conjugate thereof, wherein the substitution pattern for the nucleotides in positions one to eight, two to nine or three to ten, counting from the 3' end, is selected from the group consisting of xxXxxXxx, xxXxxXxX, xxXxXxxX, xxXxXxXx, xXxxXxxX, xXxxXxXx, xXxXxxXx, xXxXxXxx, XxxXxxXx, XxxXxXxx, XxXxxXxx, xXxXxXxX, XxxXxxXX, XxXxxXxX, XxxXxXxX, and XxXxXxXx; wherein "X" denotes an LNA unit and "x" denotes a DNA unit.

30. The oligonucleotide according to embodiment 29 or a conjugate thereof, wherein the substitution pattern for the nucleotides in positions one to eight, two to nine or three to ten, counting from the 3' end, is selected from the group consisting of xxXxxXxx, xXxxXxxX, XxxXxxXx, xXxXxXxX, XxXxXxXx, and XxXxXxxX; wherein "X" denotes an LNA unit and "x" denotes a DNA unit.

31. The oligonucleotide according to embodiment 21 or a conjugate thereof having a DNA sequence from positions one to nine, two to ten or three to eleven, counting from the 3' end: acgtttagg, wherein at least one, such as one, preferably at least two, such as two, more preferably at least three, such as three, even more preferably at least four, such as four or five, DNA units in said sequence have been substituted by their corresponding LNA unit.

32. The oligonucleotide according to embodiment 22 or a conjugate thereof having a DNA sequence from positions one to nine, two to ten or three to eleven, counting from the 3' end: ctcacactg, wherein at least one, such as one, preferably at least two, such as two, more preferably at least three, such as three, even more preferably at least four, such as four or five, DNA units in said sequence have been substituted by their corresponding LNA unit.

33. The oligonucleotide according to embodiment 23 or a conjugate thereof having a DNA sequence from positions one to nine, two to ten or three to eleven, counting from the 3' end: ttacgatta, wherein at least one, such as one, preferably at least two, such as two, more preferably at least three, such as three, even more preferably at least four, such as four or five, DNA units in said sequence have been substituted by their corresponding LNA unit.

34. The oligonucleotide according to embodiment 24 or a conjugate thereof having a DNA sequence from positions one to nine, two to ten or three to eleven, counting from the 3' end: acaagcaag, wherein at least one, such as one, preferably at least two, such as two, more preferably at least three, such as three, even more preferably at least four, such as four or five, DNA units in said sequence have been substituted by their corresponding LNA unit.

35. The oligonucleotide according to any one of embodiments 21 to 24 or a conjugate thereof, wherein at least two, such as two, three, four or five, DNA units from positions one to nine, two to ten or three to eleven, counting from the 3' end, have been substituted by their corresponding LNA unit and wherein the LNA units are separated by at least one DNA unit.

36. The oligonucleotide according to embodiment 35 or a conjugate thereof, wherein the number of consecutive DNA units from positions one to nine, two to ten or three to eleven, counting from the 3' end, is at most two.

37. The oligonucleotide according to embodiment 36 or a conjugate thereof, wherein every second nucleotide from positions one to nine, two to ten or three to eleven, counting from the 3' end, is an LNA unit.

38. The oligonucleotide according to embodiment 36 or a conjugate thereof, wherein every third nucleotide from positions one to nine, two to ten or three to eleven, counting from the 3' end, is an LNA unit.

39. The oligonucleotide according to embodiment 36 or a conjugate thereof, wherein the substitution pattern for the nucleotides in positions one to nine, two to ten or three to eleven, counting from the 3' end, is selected from the group consisting of xxXxxXxxX, xxXxxXxXx, xxXxXxxXx, xxXxXxXxx, xXxxXxxXx, xXxxXxXxx, xXxXxxXxx, XxxXxxXxx, xxXxxXxxX, xXxxXxxX, xXxXxxXxX, xXxXxXxxX, xXxXxXxXx, XxxXxxXxX, XxxXxxXxX, XxxXxXxxX, XxxXxXxXx, XxXxxXxxX, XxXxxXxXx, XxXxXxxXx, XxXxXxXxx, and XxXxXxXxX; wherein "X" denotes an LNA unit and "x" denotes a DNA unit.

40. The oligonucleotide according to any of the preceding embodiments or a conjugate thereof, wherein said nucleotide has a length of from 12 to 24 nucleotides, such as a length of from 12 to 22 nucleotides, preferably a length of from 12 to 20 nucleotides, such as a length of from 12 to 19 nucleotides, more preferably a length of from 12 to 18 nucleotides, such as a length of from 12 to 17 nucleotides, even more preferably a length of from 12 to 16 nucleotides.

41. The oligonucleotide according to embodiment 1 having a sequence selected from the group consisting of tg$^{Me}$CatG-gaTttGca$^{Me}$Ca, tg$^{Me}$CatGgaTttGca$^{Me}$C, $^{Me}$CatGga TttGca$^{Me}$C, tGcAtGgAtTtGcAc, cAtGgAtTtGcAc, $^{Me}$CatG-GatTtGcA$^{Me}$C, Tg$^{Me}$CatGGatTtGcA$^{Me}$C, and Tg$^{Me}$CaTg-GaTTtGcACa; wherein a lowercase letter identifies the nitrogenous base of a DNA unit and an uppercase letter identifies the nitrogenous base of an LNA unit; or a conjugate thereof. (SEQ IDs NO 75-82)

42. The oligonucleotide according to embodiment 2 having a sequence selected from the group consisting of c$^{Me}$CatTgt-CacAct$^{Me}$Cca, c$^{Me}$CatTgtAacTct$^{Me}$Cca, ccAttGtcAca$^{Me}$Ctc$^{Me}$Ca, c$^{Me}$CatTgt$^{Me}$CacAct$^{Me}$Cc, atTgt$^{Me}$CacAct$^{Me}$Cc, ccAttGtcAca$^{Me}$Ctc$^{Me}$C, AttGtcAca$^{Me}$Ctc$^{Me}$C, aTtGt$^{Me}$Ca Ca$^{Me}$Ct$^{Me}$Cc, AttGTca$^{Me}$Ca$^{Me}$Ct$^{Me}$C$^{Me}$C, $^{Me}$CcAtt GTca$^{Me}$Ca$^{Me}$$_{Ct}$$^{Me}$C$^{Me}$C, $^{Me}$CcaTtgTcacActc$^{Me}$Ca, and $^{Me}$C$^{Me}$CAttgtcacacT$^{Me}$C$^{Me}$$_{Ca}$; wherein a lowercase letter identifies aTtGt$^{Me}$CaCa$^{Me}$Ct$^{Me}$Cc, AttGTca$^{Me}$Ca$^{Me}$Ct$^{Me}$C the nitrogenous base of a DNA unit and an uppercase letter identifies the nitrogenous base of an LNA unit; or a conjugate thereof. (SEQ IDs NO 83-94)

43. The oligonucleotide according to embodiment 3 having a sequence selected from the group consisting of t$^{Me}$Cac-GatTag$^{Me}$CatTaa, aTca$^{Me}$CgaTtaGcaTta, TcAcGaTtAg$^{Me}$-CaTtAa, AtcAcGaTtAg$^{Me}$CaTta; wherein a lowercase letter identifies the nitrogenous base of a DNA unit and an uppercase letter identifies the nitrogenous base of an LNA unit; or a conjugate thereof. (SEQ IDs NO 95-98).

44. The oligonucleotide according to embodiment 4 having a sequence selected from the group consisting of gAgc$^{Me}$C-gaAcgAacAa, gc$^{Me}$CgaAcgAacAa, GaGc$^{Me}$CgAa$^{Me}$Cg Aa$^{Me}$CaA, and Gc$^{Me}$CgAa$^{Me}$CgAa$^{Me}$CaA; wherein a lowercase letter identifies the nitrogenous base of a DNA unit and an uppercase letter identifies the nitrogenous base of an LNA unit; or a conjugate thereof. (SEQ IDs NO 99-102).

45. The oligonucleotide according to any of the preceding embodiments or a conjugate thereof, wherein the oligonucleotide comprises at least one internucleoside linkage group which differs from phosphodiester.

46. The oligonucleotide according to embodiment 45 or a conjugate thereof, wherein said internucleoside linkage group, which differs from phosphodiester, is phosphorothioate.

47. The oligonucleotide according to embodiment 46 or a conjugate thereof, wherein all internucleoside linkage groups are phosphorothioate.

48. The oligonucleotide according to any of the preceding embodiments or a conjugate thereof, wherein said LNA units are independently selected from the group consisting of thio-LNA units, amino-LNA units and oxy-LNA units.

49. The oligonucleotide according to embodiment 48 or a conjugate thereof, wherein said LNA units are in the beta-D-form.

50. The oligonucleotide according to embodiment 48 or a conjugate thereof, wherein said LNA units are oxy-LNA units in the beta-D-form.

51. The oligonucleotide according to any of the preceding embodiments or a conjugate thereof for use as a medicament.

52. The oligonucleotide

53. A pharmaceutical composition comprising an oligonucleotide according to any of embodiments 1-52 or a conjugate thereof and a pharmaceutically acceptable carrier.

54. The composition according to embodiment 53, wherein said carrier is saline or buffered saline.

Specific Embodiments Relating to the Use of a Combination of Compounds for Treatment of HCV:

1. A medicament for the treatment of HCV infection, comprising a miR-122 inhibitor and an inhibitor of VLDL assembly.

2. A miR-122 inhibitor as a medicament for the treatment of HCV infection in patients treated with an inhibitor of VLDL assembly.

3. An inhibitor of VLDL assembly as a medicament for the treatment of HCV infection in patients treated with a miR-122 inhibitor.

4. An inhibitor of VLDL assembly according to any one of embodiments 1-3, wherein the VLDL assembly inhibitor to be used in combination with a miR-122 inhibitor, is an inhibitor of a molecule important for VLDL assembly, such as in non limiting example apoB-48, apoB-100, apoC, apoE, MTP (microsomal transfer protein), TGH (triacylglycerol hydrolase), ACAT2 (liver and intestine acyl-COA:cholesterol acyl transferase), Phospholipase D, iPLA2 (cytosolic calcium-independent phospholipase A2).

5. An inhibitor of VLDL assembly according to embodiment 4, wherein the inhibitor is an inhibitor of ApoB-100, and the compound is any one of SEQ ID NO: 31, SEQ ID NO: 26 or SEQ ID NO: 103 or any one of the compounds disclosed in table 1.

6. A miR-122 inhibitor according to any one of claims 1-3, wherein the miR-122 inhibitor is any one of SEQ ID NO: 60-63, 66-74 or 75-102.

7. The use of any one of embodiments 1-6, wherein the medicament is for the prevention of post transplantation reinfection.

8. The use of any one of embodiments 1-6, wherein the medicament is for prophylactic treatment.

9. The use of any one of embodiments 1-6, wherein the medicament is for treatment of patients infected with HCV (wherein not 4 or 5).

10. The use of any one of embodiments 1-9, wherein the medicament is made for treatment of patients that are resistant to other existing treatment, such as interferon and/or ribavirin treatment.

11. The use of any one of embodiments 1-10, wherein the APOB-100 or MTP antagonist, is an oligonucleotide complementary to all or part of the APOB-100 mRNA sequence or to the MTP mRNA sequence.

12. The use of embodiment 11, wherein the oligonucleotide contains one or more LNA residues.

13. The use of any one of embodiments 1-12, wherein the miR-122 inhibitor is an oligonucleotide that is complementary to all or part of the miR-122 mRNA sequence.

14. The use of embodiment 13, wherein the oligonucleotide contains one or more LNA residues.

15. The use of any one of embodiments 1-13, wherein the medicament is administered parentally.

15. The use of any one of claims embodiments 1-14, wherein the medicament is administered intravenously or intramuscularly or intraperitoneally.

16. The use of any one of embodiments 1-15, wherein the miR-122 inhibitor and the APOB-100 inhibitor are administered simultaneously in a combined dosage regimen.

17. The use of any one of embodiments 1-15, wherein the miR-122 inhibitor and the APOB-100 inhibitor are administered simultaneously in separate dosage regimens.

18. The use of any one of embodiments 1-17, wherein the miR-122 inhibitor and the ApoB__100 inhibitor are to be administered separately in two different dosage forms.

19. The use of any one of embodiments 1-18, wherein effective dosages of the compounds are provided to the patient in order to obtain the desired clinical outcome.

20. A method of treatment, wherein an effective dosage of a medicament according to any one of embodiments 1-6 is provided to a patient, who is infected or at risk of getting infected with HCV, in order to obtain a desired clinical outcome, or to prevent infection or reinfection.

EXAMPLES

Example 1

Monomer Synthesis

The LNA monomer building blocks and derivatives thereof were prepared following published procedures and references cited therein, see:

WO 03/095467 A1

D. S. Pedersen, C. Rosenbohm, T. Koch (2002) Preparation of LNA Phosphoramidites, Synthesis 6, 802-808.

M. D. Sørensen, L. Kværnø, T. Bryld, A. E. Håkansson, B. Verbeure, G. Gaubert, P. Herdewijn, J. Wengel (2002) α-L-ribo-configured Locked Nucleic Acid (α-I-LNA): Synthesis and Properties, J. Am. Chem. Soc., 124, 2164-2176.

S. K. Singh, R. Kumar, J. Wengel (1998) Synthesis of Novel Bicyclo[2.2.1] Ribonucleosides: 2'-Amino- and 2'-Thio-LNA Monomeric Nucleosides, J. Org. Chem. 1998, 63, 6078-6079.

C. Rosenbohm, S. M. Christensen, M. D. Sørensen, D. S. Pedersen, L. E. Larsen, J. Wengel, T. Koch (2003) Synthesis of 2'-amino-LNA: a new strategy, Org. Biomol. Chem. 1, 655-663.

D. S. Pedersen, T. Koch (2003) Analogues of LNA (Locked Nucleic Acid). Synthesis of the 2'-Thio-LNA Thymine and 5-Methyl Cytosine Phosphoramidites, Synthesis 4, 578-582.

Example 2

Oligonucleotide Synthesis

Oligonucleotides were synthesized according to the method described in WO07/031,081.

Table 1 apoB-100 Oligonucleotide Compounds of the Invention

In SEQ ID NOS: 1-57, Regions A and C are in bold, regions B and where present D, are not in bold. A superscript $^m$ prior to the base letter C, refers to methyl-cytosine; a subscript $_s$ after the base letter, refers to a phosphorothioate linkage; a superscript $^o$ after the base letter refers to oxy-LNA, particularly beta-D-oxy-LNA.

TABLE 1

| Test substance | Sequence | Size | |
|---|---|---|---|
| SEQ ID NO: 1 | 5'-CAGC ATTG GTAT TCAG-3' | 16 | Antisense motif |
| SEQ ID NO: 2 | 5'-CAGC ATTG GTAT TCA-3' | 15 | Antisense motif |
| SEQ ID NO: 3 | 5'-AGCA TTGG TATT CAG-3' | 15 | Antisense motif |
| SEQ ID NO: 4 | 5'-CAGC ATTG GTAT TC-3' | 14 | Antisense motif |
| SEQ ID NO: 5 | 5'-AGCA TTGG TATT CA-3' | 14 | Antisense motif |
| SEQ ID NO: 6 | 5'-GCAT TGGT ATTC AG-3' | 14 | Antisense motif |
| SEQ ID NO: 7 | 5'-CAGC ATTG GTAT T-3' | 13 | Antisense motif |
| SEQ ID NO: 8 | 5'-AGCA TTGG TATT C-3' | 13 | Antisense motif |
| SEQ ID NO: 9 | 5'-GCAT TGGT ATTC A-3' | 13 | Antisense motif |
| SEQ ID NO: 10 | 5'-CATT GGTA TTCA G-3' | 13 | Antisense motif |
| SEQ ID NO: 11 | 5'-CAGC ATTG GTAT-3' | 12 | Antisense motif |
| SEQ ID NO: 12 | 5'-AGCA TTGG TATT-3' | 12 | Antisense motif |
| SEQ ID NO: 13 | 5'-GCAT TGGT ATTC-3' | 12 | Antisense motif |
| SEQ ID NO: 14 | 5'-CATT GGTA TTCA-3' | 12 | Antisense motif |
| SEQ ID NO: 15 | 5'-ATTG GTAT TCAG-3' | 12 | Antisense motif |
| SEQ ID NO: 16 | 5'-A$_s$G$_s$$^{Me}$C$_s$a$_s$t$_s$t$_s$g$_s$g$_s$t$_s$a$_s$t$_s$T$_s$$^{Me}$C$_s$A$_s$g-3' | 16 | Motif #1 |
| SEQ ID NO: 17 | 5'-A$_s$G$_s$$^{Me}$C$_s$a$_s$t$_s$t$_s$g$_s$g$_s$t$_s$a$_s$t$_s$T$_s$$^{Me}$C$_s$A-3' | 14 | Motif #5 |
| SEQ ID NO: 18 | 5'-AG$_s$$^{Me}$C$_s$a$_s$t$_s$t$_s$g$_s$g$_s$t$_s$a$_s$t$_s$T$_s$$^{Me}$C$_s$A-3' | 14 | Motif #5 |
| SEQ ID NO: 19 | 5'-A$_s$G$^{Me}$C$_s$a$_s$t$_s$t$_s$g$_s$g$_s$t$_s$a$_s$t$_s$T$_s$$^{Me}$C$_s$A-3' | 14 | Motif #5 |
| SEQ ID NO: 20 | 5'-A$_s$G$_s$$^{Me}$Ca$_s$t$_s$t$_s$g$_s$g$_s$t$_s$a$_s$t$_s$T$_s$$^{Me}$C$_s$A-3' | 14 | Motif #5 |
| SEQ ID NO: 21 | 5'-A$_s$G$_s$$^{Me}$C$_s$a$_s$t$_s$t$_s$g$_s$g$_s$t$_s$a$_s$tT$_s$$^{Me}$C$_s$A-3' | 14 | Motif #5 |
| SEQ ID NO: 22 | 5'-A$_s$G$_s$$^{Me}$C$_s$a$_s$t$_s$t$_s$g$_s$g$_s$t$_s$a$_s$t$_s$T$^{Me}$C$_s$A-3' | 14 | Motif #5 |
| SEQ ID NO: 23 | 5'-A$_s$G$_s$$^{Me}$C$_s$a$_s$t$_s$t$_s$g$_s$g$_s$t$_s$a$_s$t$_s$T$^{Me}$$_s$CA-3' | 14 | Motif #5 |
| SEQ ID NO: 24 | 5'-AG$_s$$^{Me}$C$_s$a$_s$t$_s$t$_s$g$_s$g$_s$t$_s$a$_s$t$_s$T$_s$$^{Me}$CA-3' | 14 | Motif #5 |
| SEQ ID NO: 25 | 5'-AG$^{Me}$C$_s$a$_s$t$_s$t$_s$g$_s$g$_s$t$_s$a$_s$t$_s$T$^{Me}$CA-3' | 14 | Motif #5 |
| SEQ ID NO: 26 | 5'-G$_s$$^{Me}$C$_s$a$_s$t$_s$t$_s$g$_s$g$_s$t$_s$a$_s$t$_s$T$_s$$^{Me}$C$_s$A-3' | 13 | Motif #9 |
| SEQ ID NO: 27 | 5'-G$^{Me}$C$_s$a$_s$t$_s$t$_s$g$_s$g$_s$t$_s$a$_s$t$_s$T$_s$$^{Me}$C$_s$A-3' | 13 | Motif #9 |
| SEQ ID NO: 28 | 5'-G$_s$$^{Me}$Ca$_s$t$_s$t$_s$g$_s$g$_s$t$_s$a$_s$t$_s$T$_s$$^{Me}$C$_s$A-3' | 13 | Motif #9 |
| SEQ ID NO: 29 | 5'-G$_s$$^{Me}$C$_s$a$_s$t$_s$t$_s$g$_s$g$_s$t$_s$a$_s$tT$_s$$^{Me}$C$_s$A-3' | 13 | Motif #9 |
| SEQ ID NO: 30 | 5'-G$_s$$^{Me}$C$_s$a$_s$t$_s$t$_s$g$_s$g$_s$t$_s$a$_s$t$_s$T$^{Me}$C$_s$A-3' | 13 | Motif #9 |
| SEQ ID NO: 31 | 5'-G$_s$$^{Me}$C$_s$a$_s$t$_s$t$_s$g$_s$g$_s$t$_s$a$_s$t$_s$T$^{Me}$$_s$CA-3' | 13 | Motif #9 |
| SEQ ID NO: 32 | 5'-G$^{Me}$C$_s$a$_s$t$_s$t$_s$g$_s$g$_s$t$_s$a$_s$t$_s$T$_s$$^{Me}$CA-3' | 13 | Motif #9 |
| SEQ ID NO: 33 | 5'-G$^{Me}$C$_s$a$_s$t$_s$t$_s$g$_s$g$_s$t$_s$a$_s$t$_s$T$^{Me}$CA-3' | 13 | Motif #9 |
| SEQ ID NO: 34 | 5'-G$_s$$^{Me}$C$_s$a$_s$t$_s$t$_s$g$_s$g$_s$t$_s$a$_s$t$_s$T$_s$$^{Me}$C-3' | 12 | Motif #13 |

TABLE 1-continued

| Test substance | Sequence | Size | |
|---|---|---|---|
| SEQ ID NO: 35 | 5'-G$^{Me}$C$_s$a$_s$t$_s$t$_s$g$_s$g$_s$t$_s$a$_s$t$_s$T$_s$$^{Me}$C-3' | 12 | Motif #13 |
| SEQ ID NO: 36 | 5'-G$_s$$^{Me}$Ca$_s$t$_s$t$_s$g$_s$g$_s$t$_s$a$_s$t$_s$T$_s$$^{Me}$C-3' | 12 | Motif #13 |
| SEQ ID NO: 37 | 5'-G$_s$$^{Me}$C$_s$a$_s$t$_s$t$_s$g$_s$g$_s$t$_s$a$_s$tT$_s$$^{Me}$C-3' | 12 | Motif #13 |
| SEQ ID NO: 38 | 5'-G$_s$$^{Me}$C$_s$a$_s$t$_s$t$_s$g$_s$g$_s$t$_s$a$_s$t$_s$T$^{Me}$C-3' | 12 | Motif #13 |
| SEQ ID NO: 39 | 5'-G$^{Me}$C$_s$a$_s$t$_s$t$_s$g$_s$g$_s$t$_s$a$_s$t$_s$T$^{Me}$C-3' | 12 | Motif #13 |
| SEQ ID NO: 40 | 5'-G$^{Me}$Ca$_s$t$_s$t$_s$g$_s$g$_s$t$_s$a$_s$tT$^{Me}$C-3' | 12 | Motif #13 |
| SEQ ID NO: 41 | 5'-mCso Aso Gso cs as ts ts gs gs ts as ts Tso mCso Ao-3' | 15 | Motif #2 |
| SEQ ID NO: 42 | 5'-Aso Gso cs as ts ts gs gs ts as ts Tso mCso a-3' | 14 | Motif #5 |
| SEQ ID NO: 43 | 5'-Aso Gso cs as ts ts gs gs ts as Tso Tso mCso a-3' | 14 | Motif #5 |
| SEQ ID NO: 44 | 5'-Aso Gso mCso as ts ts gs gs ts as Tso Tso mCso a-3' | 14 | Motif #5 |
| SEQ ID NO: 45 | 5'-Gso cs as ts ts gs gs ts as ts Tso mCo-3' | 12 | Motif #13 |
| SEQ ID NO: 46 | 5'-Gso mCso as ts ts gs gs ts as Tso Tso mCo-3' | 12 | Motif #13 |
| SEQ ID NO: 47 | 5'-Gso cs as ts ts gs gs ts as To-3' | 10 | |
| SEQ ID NO: 48 | 5'-Gso mCso as ts ts gs gs ts Aso To-3' | 10 | |
| SEQ ID NO: 49 | 5'-Gso mCso as ts ts gs gs Tso Aso To-3' | 10 | |
| SEQ ID NO: 50 | 5'-AGcattggtatTCa-3' | 14 | |
| SEQ ID NO: 51 | 5'-AGcattggtaTTCa-3' | 14 | |
| SEQ ID NO: 52 | 5'-AGCattggtaTTCa-3' | 14 | |
| SEQ ID NO: 53 | 5'-AGCattggtatTCA-3' | 14 | |
| SEQ ID NO: 54 | 5'-GcattggtatTC-3' | 12 | |
| SEQ ID NO: 55 | 5'-GCattggtatTC-3' | 12 | |
| SEQ ID NO: 56 | 5'-GCattggtaTTC-3' | 12 | |
| SEQ ID NO: 57 | 5'-GcattggtaT-3' | 10 | |

Example 3
Design of the LNA Anti-miR Oligonucleotides and Melting Temperatures Target microRNA:

SEQ ID NO: 58
miR-122a: 5'-uggagugugacaauggcguuugu-3'

SEQ ID NO: 59
miR-122a 3' to 5': 3'-uguuugugguaacagugugaggu-5'

Table 2 LNA Anti-miR-122 Oligonucleotide Sequences and $T_m$:

TABLE 2

| SEQ ID | Sequence: | | Tm (° C.) |
|---|---|---|---|
| SEQ ID 60 | XxxX design 5'-cCatTgtCacActCca-3' | PS backbone | 75 |
| SEQ ID 61 | XxxX design 5'-ccAttGtcAcaCtcCa-3' | PS backbone | 69 |
| SEQ ID 62 | Gapmer 5'-CCAttgtcacacTCCa-3' | PS backbone | 69 |

TABLE 2-continued

| SEQ ID | | Sequence: | | Tm (° C.) |
|---|---|---|---|---|
| SEQ ID 63 | 15-mer | 5'-CcAttGTcaCaCtCC-3' | PS backbone | 78 |
| SEQ ID 64 | mismatch control | 5'-CcAtt<u>C</u>T<u>g</u>aC<u>c</u>Ct<u>A</u>C-3' | PS backbone | 32 |
| SEQ ID 65 | mismatch control | 5'-ccAttGtc<u>T</u>ca<u>A</u>tcCa-3' | PS backbone | 46 |
| SEQ ID 66 | 13-mer | 5'-AttGTcaCaCtCC-3' | PS backbone | | lower case: DNA, uppercase: LNA (all LNA C were methylated), underlined: mismatch The melting temperatures were assessed towards the mature miR-122a sequence, using a synthetic miR-122a RNA oligonucleotide with phosphorothioate linkaged.

The LNA anti-miR/miR-122a oligo duplex was diluted to 3 µM in 500 µl RNase free $H_2O$, which was then mixed with 500 µl 2× dimerization buffer (final oligo/duplex conc. 1.5 µM, 2× Tm buffer: 200 mM NaCl, 0.2 mM EDTA, 20 mM NaP, pH 7.0, DEPC treated to remove RNases). The mix was first heated to 95 degrees for 3 minutes, then allowed to cool at room temperature (RT) for 30 minutes.

Following RT incubation $T_m$ was measured on Lambda 40 UV/VIS Spectrophotometer with peltier temperature progammer PTP6 using PE Templab software (Perkin Elmer). The temperature was ramped up from 20° C. to 95° C. and then down again to 20° C., continuously recording absorption at 260 nm. First derivative and local maximums of both the melting and annealing was used to assess melting/annealing point ($T_m$), both should give similar/same $T_m$ values. For the first derivative 91 points was used to calculate the slope.

By substituting the antimir oligonucleotide and the complementary RNA molecule, the above assay can be used to determine the $T_m$ of other oligonucleotides such as the oligonucleotides according to the invention.

However, in one embodiment the $T_m$ may be made with a complementary DNA (phosphorothioate linkages) molecule. Typically the $T_m$ measured against a DNA complementary molecule is about 10° C. lower than the $T_m$ with an equivalent RNA complement. The $T_m$ measured using the DNA complement may therefore be used in cases where the duplex has a very high $T_m$.

Melting temperature ($T_m$) measurements:

| | $T_m$ |
|---|---|
| oligo to miR-122 RNA complement | |
| SEQ ID NO: 61 + miR-122a, RNA | 69° C. |
| SEQ ID NO: 66 + miR-122a, RNA | 74° C. |
| SEQ ID NO: 63 + miR-122a, RNA | 79° C. |
| oligo to DNA complement | |
| SEQ ID NO: 61 + 122R, DNA | 57° C. |
| SEQ ID NO: 63 + 122R, DNA | 66° C. |

It is recognised that for oligonucleotides with very high $T_m$, the above $T_m$ assays may be insufficient to determine the $T_m$. In such an instance the use of a phosphorothioated DNA complementary molecule may further lower the $T_m$.

The use of formamide is routine in the analysis of oligonucleotide hybridisation (see Hutton 1977, NAR 4 (10) 3537-3555). In the above assay the inclusion of 15% formamide typically lowers the $T_m$ by about 9° C., and the inclusion of 50% formamide typically lowers the $T_m$ by about 30° C. Using these ratios, it is therefore possible to determine the comparative $T_m$ of an oligonucleotide against its complementary RNA (phosphodiester) molecule, even when the $T_m$ of the duplex is, for example higher than 95° C. (in the absence of formamide).

For oligonucleotides with a very high $T_m$, an alternative method of determining the $T_m$, is to make titrations and run it out on a gel to see single strand versus duplex and by those concentrations and ratios determine Kd (the dissociation constant) which is related to deltaG and also $T_m$.

Example 4

Cholesterol Levels in Plasma

Total cholesterol level is measured in plasma using a colometric assay Cholesterol CP from ABX Pentra. The cholesterol is measured following enzymatic hydrolysis and oxidation. 21.5 µL water was added to 1.5 µL plasma. 250 µL reagent is added and within 5 min the cholesterol content is measured at a wavelength of 540 nM. Measurements on each animal was made in duplicates. The sensitivity and linearity was tested with 2 fold diluted control compound (ABX Pentra N control). The relative Cholesterol level was determined by subtraction of the background and presented relative to the cholesterol levels in plasma of saline treated mice.

Example 5

Measurements of mRNA Levels

Antisense modulation of Apo-B100 expression can be assayed in a variety of ways known in the art. For example, Apo-B100 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA. Methods of RNA isolation and RNA analysis such as Northern blot analysis is routine in the art and is taught in, for example, Current Protocols in Molecular Biology, John Wiley and Sons.

Real-time quantitative (PCR) can be conveniently accomplished using the commercially iQ Multi-Color Real Time PCR Detection System available from BioRAD. Real-time Quantitative PCR is a technique well known in the art and is taught in for example Heid et al. Real time quantitative PCR, Genome Research (1996), 6: 986-994.

Example 6

In Vitro Model: Cell Culture

The effect of LNA oligonucleotides on target nucleic acid expression (amount) can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis (including microRNA northern), Quantitative PCR (including microRNA qPCR), Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

15PC3: The human prostate cancer cell line 15PC3 was kindly donated by Dr. F. Baas, Neurozintuigen Laboratory, AMC, The Netherlands and was cultured in DMEM (Sigma)+10% fetal bovine serum (FBS)+Glutamax I+gentamicin.

PC3: The human prostate cancer cell line PC3 was purchased from ATCC and was cultured in F12 Coon's with glutamine (Gibco)+10% FBS+gentamicin.

518A2: The human melanoma cancer cell line 518A2 was kindly donated by Dr. B. Jansen, Section of experimental Oncology, Molecular Pharmacology, Department of Clinical Pharmacology, University of Vienna and was cultured in DMEM (Sigma)+10% fetal bovine serum (FBS)+Glutamax I+gentamicin.

HeLa: The cervical carcinoma cell line HeLa was cultured in MEM (Sigma) containing 10% fetal bovine serum gentamicin at 37° C., 95% humidity and 5% $CO_2$.

MPC-11: The murine multiple myeloma cell line MPC-11 was purchased from ATCC and maintained in DMEM with 4 mM Glutamax+10% Horse Serum.

DU-145: The human prostate cancer cell line DU-145 was purchased from ATCC and maintained in RPM with Glutamax+10% FBS.

RCC-4+/− VHL: The human renal cancer cell line RCC4 stably transfected with plasmid expressing VHL or empty plasmid was purchased from ECACC and maintained according to manufacturers instructions.

786-0: The human renal cell carcinoma cell line 786-0 was purchased from ATCC and maintained according to manufacturers instructions HUVEC: The human umbilical vein endothelial cell line HUVEC was purchased from Camcrex and maintained in EGM-2 medium.

K562: The human chronic myelogenous leukaemia cell line K562 was purchased from ECACC and maintained in RPMI with Glutamax+10% FBS. U87MG: The human glioblastoma cell line U87MG was purchased from ATCC and maintained according to the manufacturers instructions.

B16: The murine melanoma cell line B16 was purchased from ATCC and maintained according to the manufacturers instructions.

LNCap: The human prostate cancer cell line LNCap was purchased from ATCC and maintained in RPMI with Glutamax+10% FBS Huh-7: Human liver, epithelial like cultivated in Eagles MEM with 10% FBS, 2 mM Glutamax I, 1× non-essential amino acids, Gentamicin 25 µg/ml L428: (Deutsche Sammlung für Mikroorganismen (DSM, Braunschweig, Germany)): Human B cell lymphoma maintained in RPMI 1640 supplemented with 10% FCS, L-glutamine and antibiotics.

L1236: (Deutsche Sammlung für Mikroorganismen (DSM, Braunschweig, Germany)): Human B cell lymphoma maintained in RPMI 1640 supplemented with 10% FCS, L-glutamine and antibiotics.

Example 7

Stability of LNA Oligonucleotides in Human or Rat Plasma

LNA oligonucleotide stability was tested in plasma from human or rats (it could also be mouse, monkey or dog plasma). In 45 µl plasma, 5 µl LNA oligonucleotide is added (at a final concentration of 20 µM). The LNA oligonucleotides are incubated in plasma for times ranging from 0 to 96 hours at 37° C. (the plasma is tested for nuclease activity up to 96 hours and shows no difference in nuclease cleavage-pattern).

At the indicated time the sample were snap frozen in liquid nitrogen. 2 µL (equals 40 µmol) LNA oligonucleotide in plasma was diluted by adding 15 µL of water and 3 µL 6× loading dye (Invitrogen). As marker a 10 bp ladder (Invitrogen, USA 10821-015) is used. To 1 µl ladder, 1 µl 6× loading and 4 µl water is added. The samples are mixed, heated to 65° C. for 10 min and loaded to a pre-run gel (16% acrylamide, 7 M UREA, 1×TBE, pre-run at 50 Watt for 1 h) and run at 50-60 Watt for 2% hours. Subsequently, the gel is stained with 1× SyBR gold (molecular probes) in 1×TBE for 15 min. The bands were visualised using a phosphoimager from BioRad.

Example 8

Screening of Oligonucleotides Targeting ApoB-100 mRNA (Dosing 3*5 mg/kg)

In this study 5 mg/kg/dose were dosed on 3 consecutive days (one dose/day i.v.) and animals were sacrificed 24 hours after last dosing. At sacrifice, liver and retro orbital sinus blood was sampled. Serum was prepared from blood for analysis of cholesterol. RNA was isolated from the liver and the expression of ApoB-100 mRNA was measured.

The effect of dosing three doses at 5 mg/kg/dose of oligoes of different length on ApoB-100 mRNA expression is shown in FIG. 1. SEQ ID NO 16 (Table 1) down regulated ApoB-100 mRNA with about 25-30%, whereas the 14-mer SEQ ID NO 17 (Table 1) and 12-mer SEQ ID NO 34 (Table 1) was much more potent and equally potent—down regulated ApoB-100 mRNA with about 75% after dosing 3 times 5 mg/kg.

Figure 2A:
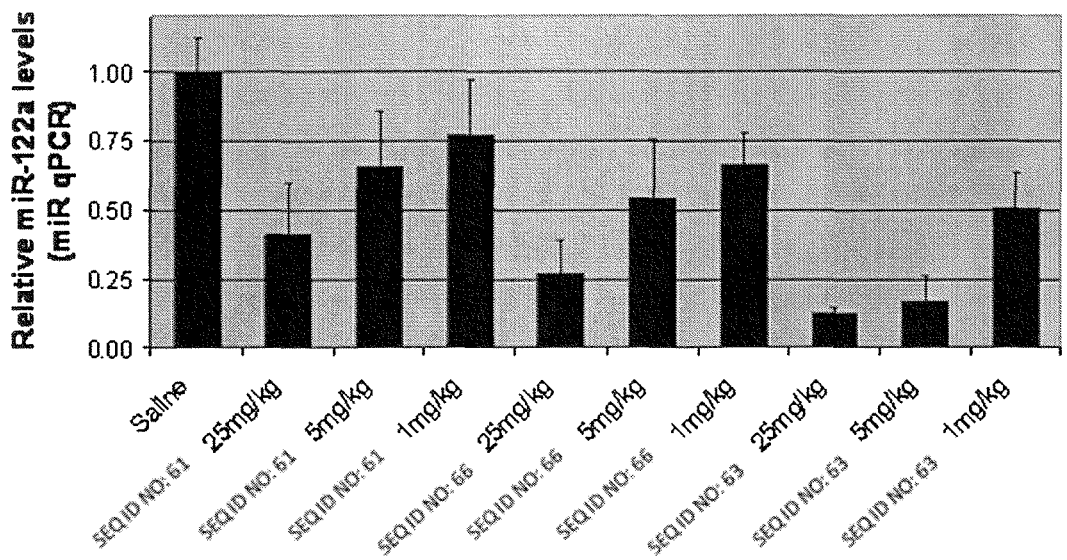
FIG. 2. Assessment of LNA anti-miR-122a knock-down dose-response for SEQ ID NO: 66 and SEQ ID NO: 63 in comparison with SEQ ID NO: 61 in vivo in mice livers using miR-122a real-time RT-PCR.
FIG. 2b miR-122 levels in the mouse liver after treatment with different LNA-antimiRs. The LNA-antimiR molecules SEQ ID NO: 61 and SEQ ID NO: 63 were administered into normal mice by three i.p. injections on every second day over a six-day-period at indicated doses and sacrificed 48 hours after last dose. Total RNA was extracted from the mice livers and miR-122 was measured by miR-122 specific qPCR.

Total cholesterol was measured in serum at sacrifice, day 3 (FIG. 2). Similar to the results from the qPCR the best or the most potent effect was obtained with the 12-mer SEQ ID NO 34 followed by the 14-mer SEQ ID NO 17 (Table 1). The 16-mer (SEQ ID NO 16) (Table 1) reduced total cholesterol with about 18%.

Example 9

Dose Response and Duration of Action of SEQ ID NO 17 and SEQ ID NO 34 in C57BL/6 Female Mice In this study three different concentrations (10, 15 and 25 mg/kg) of SEQ ID NO 17 (Table 1) and SEQ ID NO 34 (Table 1) were examined for duration of action on ApoB-100 mRNA expression and serum cholesterol level. SEQ ID NO 17 and SEQ ID NO 34 were given as a single dose of 10, 15 or 25 mg/kg to C57BL/6 female mice. Mice were sacrificed at different time points (1, 3, 5 and 8 days) after dosing; liver and serum were examined for ApoB-100 mRNA expression, liver oligonucleotide concentration and cholesterol and ALT, respectively.

Analysis of Target mRNA Down Regulation

Liver sampled at sacrifice was analysed for ApoB-100 mRNA expression by qPCR. Data was normalized to Gapdh and presented relative to the data obtained by dosing saline. One dose of 10, 15 or 25 mg/kg of SEQ ID NO 17 or SEQ ID NO 34 was very effective to down regulate ApoB-100 mRNA in liver (FIG. 3). Twenty-four hours after dosing, down regulation of 90-95% was obtained with SEQ ID NO 34, whereas dosing of SEQ ID NO 17 resulted in 70-85% lower ApoB mRNA levels than in the saline control group.

Serum Cholesterol

Blood serum used to measure cholesterol was sampled at sacrifice. Twenty-four hours after dosing SEQ ID NO 17 serum total cholesterol was reduced 25-40%, and dosing SEQ ID NO 34 gave 40-55% reduction in total cholesterol. At day 3, the total cholesterol level was further reduced: SEQ ID NO 17 gave 70-90% reduction in a dose dependent manner after doing 10, 15 or 25 mg/kg. SEQ ID NO 34 reduced total cholesterol with 90-95% relative to the saline control group. At day 5-8 the total cholesterol level increased in all groups except the group dosed SEQ ID NO 17 at 10 mg/kg. (FIG. 4.).

Example 10

Dose Response and Duration of Action of SEQ ID NO 17 and SEQ ID NO 34 in C57BL/6 Female Mice A single dose of SEQ ID NO 17 (Table 1) and SEQ ID NO 34 (Table 1) at different concentrations was administered to C57BL/6J mice to find ED50 values for cholesterol. Duration of action was also included in this study, because we previously have seen that maximum effect of a single dose not always was achieved 24 hours after dosing. In Example 6, we completely down-regulated ApoB-100 mRNA after dosing 10, 15 or 25 mg/kg SEQ ID NO 34 and 25 mg/kg SEQ ID NO 17. In this study we therefore have chosen lower concentrations (1, 2.5 and 5 mg/kg).

Analysis of ApoB-100 mRNA Down Regulation

Figure 5:
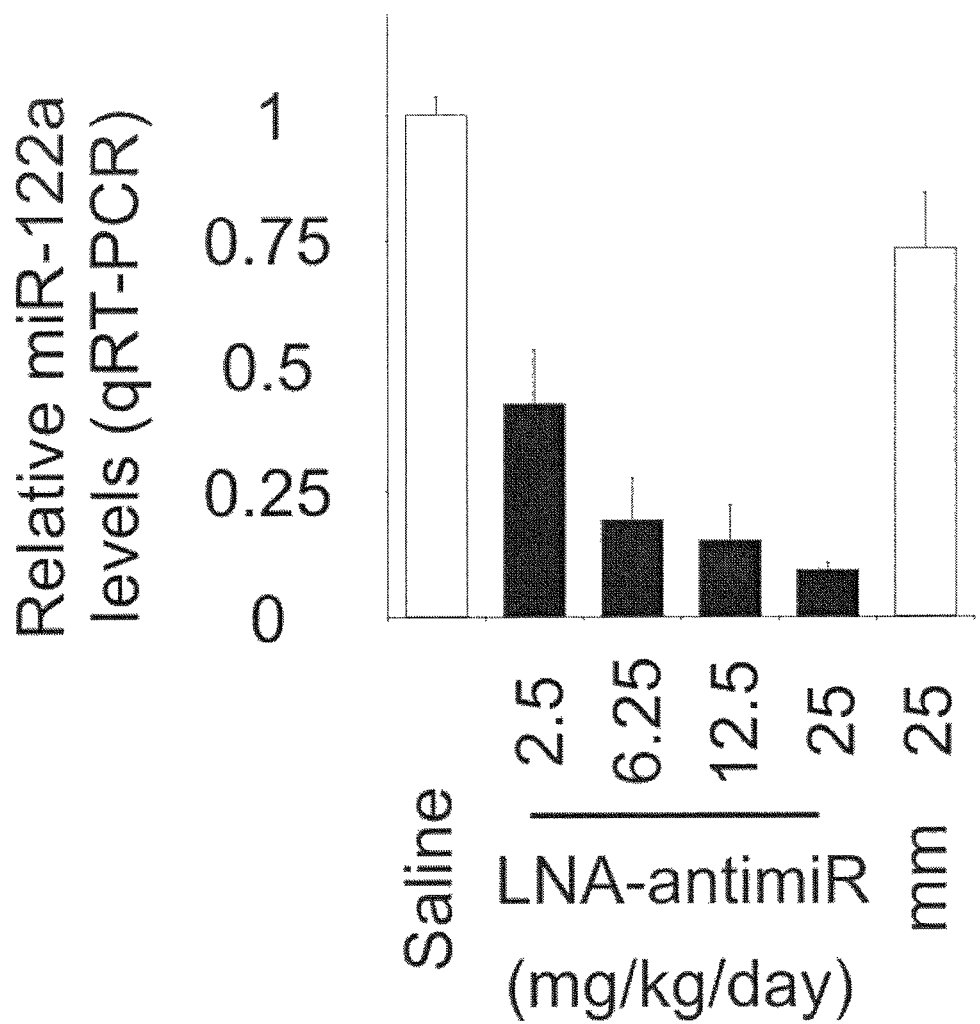
FIG. 5. Assessment of LNA-antimiR™-122a knock-down dose-response in vivo in mice livers using miR-122a real-time RT-PCR. Six groups of animals (5 mice per group) were treated in the following manner. Group 1 animals were injected with 0.2 ml saline by i.v. on 3 successive days, Group 2 received 2.5 mg/kg SEQ ID NO: 61, Group 3 received 6.25 mg/kg, Group 4 received 12.5 mg/kg and Group 5 received 25 mg/kg, while Group 6 received 25 mg/kg SEQ ID NO: 65 (mismatch LNA-antimiR™ oligonucleotide), all in the same manner. The experiment was repeated (therefore n=10) and the combined results are shown.

Liver sampled at sacrifice was analysed for ApoB-100 mRNA expression by qPCR. Data was normalized to Gapdh and presented relative to the data obtained by dosing saline. One dose of 10, 15 or 25 mg/kg of SEQ ID NO 17 or SEQ ID NO 34 was very effective to down regulate ApoB-100 mRNA in liver (FIG. 5). A single dose of SEQ ID NO 17 of 1, 2.5 or 5 mg/kg resulted in a dose dependent down regulation of ApoB-100 mRNA with a duration of 5 days. Similar results were obtained with SEQ ID NO 34. At day 8 both oligonucleotides resulted in ApoB-100 mRNA expression that was similar after dosing 2.5 SEQ ID NO 34 and 5 mg/kg SEQ ID NO 17, reduction of 75%. At day 16 the mRNA level had increased again in all groups, except after dosing 5 mg/kg SEQ ID NO 34 with ApoB-100 mRNA down regulation of 75% similar to that at days 5 and 8.

Serum Cholesterol

Blood serum was sampled at sacrifice and used to measure cholesterol. The serum total cholesterol level reflected the mRNA expression of ApoB-100; dose dependent reduction with best effect at 5 days after dosing SEQ ID NO 17 at 1 and 2.5 mg/kg and similar effect at days 3, 5 and 8 after dosing 5 mg/kg (50% reduction). Dose dependent effect was also obtained after dosing SEQ ID NO 34 with best effect at day 3 after dosing 5 mg/kg (70% reduction) with following increase in cholesterol level (60% reduction at day 8 and 45% at day 16). However, the cholesterol levels in the groups dosed SEQ ID NO 34 did not follow the mRNA reductions in the groups dosed 2.5 and 5 mg/kg, e.g. dosing 5 mg/kg gave about 75% down regulation of ApoB-100 mRNA days 5-16 whereas the cholesterol level after dosing 2.5 mg/kg and 5 mg/kg increased from day 3 to day 16 from a 70% reduction to 45% reduction.

Example 11

Screening of Oligonucleotides Targeting ApoB-100 mRNA (Dosing 3*1 or 5 mg/kg i.v. Three Consecutive Days)

The effect on ApoB-100 mRNA was examined at different days after dosing 1.0 or 5.0 mg/kg (one dose day 0) of the three LNA antisense oligonucleotides 12-mer SEQ ID NO 34 (Table 1), SEQ ID NO 26 (Table 1) 13-mer and 14-mer SEQ ID NO 17 (Table 1) all targeting ApoB mRNA.

Analysis of Target mRNA Down Regulation

Figure 7:
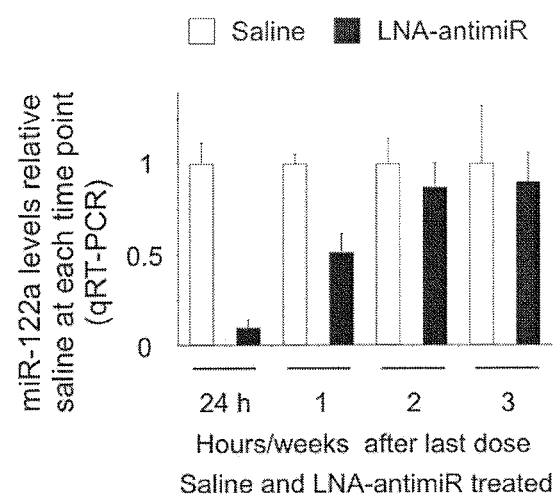
FIG. 7. Mice were treated with 25 mg/kg/day LNA-anti-miR or saline for three consecutive days and sacrificed 1, 2 or 3 weeks after last dose. Included are also the values from the animals sacrificed 24 hours after last dose (example 11 "old design"). miR-122 levels were assessed by qPCR and normalized to the mean of the saline group at each individual time point. Included are also the values from the animals sacrificed 24 hours after last dose (shown mean and SD, n=7, 24 h n=10). Sacrifice day 9, 16 or 23 corresponds to sacrifice 1, 2 or 3 weeks after last dose.).

Liver sampled at sacrifice was analysed for ApoB-100 mRNA expression by qPCR. Data was normalized to Gapdh and presented relative to the data obtained by dosing saline. Dosing 3* 1 or 5 mg/kg of SEQ ID NO 34, SEQ ID NO 17 or SEQ ID NO 26 was very effective to down regulate ApoB-100 mRNA in liver (FIG. 7). Dosing 1 mg/kg SEQ ID NO 34 or SEQ ID NO 26 down regulated ApoB-100 mRNA with 60% and 5 mg/kg resulted in 90% down regulation similar for both compounds. SEQ ID NO 17 dosed 3* 1 mg/kg/dose or 5 mg/kg/dose down regulated target mRNA with 50% and 70% respectively.

Serum Cholesterol

At sacrifice blood for serum was sampled and used to measure cholesterol. Similar to the results for the mRNA expression, the SEQ ID NO 34 and SEQ ID NO 26 gave similar results: 60% reduction after dosing 3*1 mg/kg and about 85-90% after 3*5 mg/kg/dose. The SEQ ID NO 17 was a little less potent and reduced serum cholesterol with 40% and 70% after dosing 3* 1 or 5 mg/kg/dose, respectively.

Example 12

In Vitro Model: Treatment with LNA Anti-miR Antisense Oligonucleotide

The miR-122a expressing cell line Huh-7 was transfected with LNA anti-miR5 at 1 and 100 nM concentrations according to optimized lipofectamine 2000 (LF2000, Invitrogen) protocol (as follows).

Huh-7 cells were cultivated in Eagles MEM with 10% FBS, 2 mM Glutamax I, 1× non-essential amino acids, Gentamicin 25 μg/ml. The cells were seeded in 6-well plates (300000 cells per well), in a total vol. of 2.5 ml the day before transfection. At the day of transfection a solution containing LF2000 diluted in Optimem (Invitrogen) was prepared (1.2 ml optimem+3.75 μl LF2000 per well, final 2.5 μg LF2000/ml, final tot vol 1.5 ml).

LNA Oligonucleotides (LNA anti-miRs) were also diluted in optimem. 285 μl optimem+15 μl LNA oligonucleotide (10 μM oligonucleotide stock for final concentration 100 nM and 0.1 μM for final concentration 1 nM) Cells were washed once in optimem then the 1.2 ml optimem/LF2000 mix were added to each well. Cells were incubated 7 min at room temperature in the LF2000 mix where after the 300 μl oligonucleotide optimem solution was added.

Cell were further incubated for four hours with oligonucleotide and lipofectamine-2000 (in regular cell incubator at 37°

C., 5% CO2). After these four hours the medium/mix was removed and regular complete medium was added. Cells were allowed to grow for another 20 hours. Cells were harvested in Trizol (Invitrogen) 24 hours after transfection. RNA was extracted according to a standard Trizol protocol according to the manufacturer's instructions (Invitrogen), especially to retain the microRNA in the total RNA extraction.

Example 13

In Vitro and In Vivo Model: Analysis of Oligonucleotide Inhibition of miR Expression by microRNA Specific Quantitative PCR miR-122a levels in the RNA samples were assessed on an ABI 7500 Fast real-time PCR instrument (Applied Biosystems, USA) using a miR-122a specific qRT-PCR kit, mirVana (Ambion, USA) and miR-122a primers (Ambion, USA). The procedure was conducted according to the manufacturers protocol.

Results:

The miR-122a-specific new LNA anti-miR oligonucleotide design (ie SEQ ID NO: 63 (also referred to as SEQ ID NO:63)), was more efficient in inhibiting miR-122a at 1 nM compared to previous design models, including "every-third" and "gap-mer" (SEQ ID NO: 60, SEQ ID NO: 61 SEQ ID NO: 61, SEQ ID NO: 62) motifs were at 100 nM. The mismatch control was not found to inhibit miR-122a (SEQ ID NO: 64). Results are shown in FIG. 1.

Example 14

Assessment of LNA Antago-mir Knock-Down Specificity Using miRNA Microarray Expression Profiling A) RNA Labeling for miRNA Microarray Profiling Total RNA was extracted using Trizol reagent (Invitrogen) and Tend labeled using T4 RNA ligase and Cy3- or Cy5-labeled RNA linker (5"-PO4-rUrUrU-Cy3/dT-3" or 5"-PO4-rUrUrU-Cy5/dT-3"). The labeling reactions contained 2-5 µg total RNA, 15 µM RNA linker, 50 mM Tris-HCl (pH 7.8), 10 mM MgCl2, 10 mM DTT, 1 mM ATP, 16% polyethylene glycol and 5 unit T4 RNA ligase (Ambion, USA) and were incubated at 30° C. for 2 hours followed by heat inactivation of the T4 RNA ligase at 80° C. for 5 minutes.

B) Microarray Hybridization and Post-Hybridization Washes

LNA-modified oligonucleotide capture probes comprising probes for all annotated miRNAs annotated from mouse (*Mus musculus*) and human (*Homo sapiens*) in the miRBase MicroRNA database Release 7.1 including a set of positive and negative control probes were purchased from Exiqon (Exiqon, Denmark) and used to print the microarrays for miRNA profiling. The capture probes contain a 5"-terminal C6-amino modified linker and were designed to have a Tm of 72° C. against complementary target miRNAs by adjustment of the LNA content and length of the capture probes. The capture probes were diluted to a final concentration of 10 µM in 150 mM sodium phosphate buffer (pH 8.5) and spotted in quadruplicate onto Codelink slides (Amersham Biosciences) using the MicroGrid II arrayer from BioRobotics at 45% humidity and at room temperature. Spotted slides were post-processed as recommended by the manufacturer.

Labeled RNA was hybridized to the LNA microarrays overnight at 65° C. in a hybridization mixture containing 4×SSC, 0.1% SDS, 1 µg/µl Herring Sperm DNA and 38% formamide. The hybridized slides were washed three times in 2×SSC, 0.025% SDS at 65° C., followed by three times in 0.08×SSC and finally three times in 0.4×SSC at room temperature.

C) Array Scanning, Image Analysis and Data Processing

The microarrays were scanned using the ArrayWorx scanner (Applied Precision, USA) according to the manufacturer's recommendations. The scanned images were imported into TIGR Spotfinder version 3.1 (Saeed et al., 2003) for the extraction of mean spot intensities and median local background intensities, excluding spots with intensities below median local background+4× standard deviations. Background-correlated intensities were normalized using variance stabilizing normalization package version 1.8.0 (Huber et al., 2002) for R (www.r-project.org). Intensities of replicate spots were averaged using Microsoft Excel. Probes displaying a coefficient of variance >100% were excluded from further data analysis.

Example 15

Detection of microRNAs by In Situ Hybridization. Detection of microRNAs in Formalin-Fixed Paraffin-Embedded Tissue Sections by In Situ Hybridization A) Preparation of the Formalin-Fixed, Paraffin-Embedded Sections for In Situ Hybridization Archival paraffin-embedded samples are retrieved and sectioned at 5 to 10 mm sections and mounted in positively-charged slides using floatation technique. Slides are stored at 4° C. until the in situ experiments are conducted.

B) In Situ Hybridization

Sections on slides are deparaffinized in xylene and then rehydrated through an ethanol dilution series (from 100% to 25%). Slides are submerged in DEPC-treated water and subject to HCl and 0.2% Glycine treatment, re-fixed in 4% paraformaldehyde and treated with acetic anhydride/triethanolamine; slides are rinsed in several washes of 1×PBS in-between treatments. Slides are pre-hybridized in hyb solution (50% formamide, 5×SSC, 500 mg/mL yeast tRNA, 1×Denhardt) at 50° C. for 30 min. Then, 3 µmol of a FITC-labeled LNA probe (Exiqon, Denmark) complementary to each selected miRNA is added to the hyb. solution and hybridized for one hour at a temperature 20-25° C. below the predicted Tm of the probe (typically between 45-55° C. depending on the miRNA sequence). After washes in 0.1× and 0.5×SCC at 65° C., a tyramide signal amplification reaction was carried out using the Genpoint Fluorescein (FITC) kit (DakoCytomation, Denmark) following the vendor's recommendations. Finally, slides are mounted with Prolong Gold solution. Fluorescence reaction is allowed to develop for 16-24 hr before documenting expression of the selected miRNA using an epifluorescence microscope.

Detection of microRNAs by Whole-Mount In Situ Hybridization of Zebrafish, *Xenopus* and Mouse Embryos.

All washing and incubation steps are performed in 2 ml eppendorf tubes. Embryos are fixed overnight at 4° C. in 4% paraformaldehyde in PBS and subsequently transferred through a graded series (25% MeOH in PBST (PBS containing 0.1% Tween-20), 50% MeOH in PBST, 75% MeOH in PBST) to 100% methanol and stored at −20° C. up to several months. At the first day of the in situ hybridization embryos are rehydrated by successive incubations for 5 min in 75% MeOH in PBST, 50% MeOH in PBST, 25% MeOH in PBST and 100% PBST (4×5 min).

Fish, mouse and *Xenopus* embryos are treated with proteinaseK (10 µg/ml in PBST) for 45 min at 37° C., refixed for 20 min in 4% paraformaldehyde in PBS and washed 3×5 min with PBST. After a short wash in water, endogenous alkaline phosphatase activity is blocked by incubation of the embryos in 0.1 M tri-ethanolamine and 2.5% acetic anhydride for 10 min, followed by a short wash in water and 5×5 min washing in PBST. The embryos are then transferred to hybridization buffer (50% Formamide, 5×SSC, 0.1% Tween, 9.2 mM citric acid, 50 ug/ml heparin, 500 ug/ml yeast RNA) for 2-3 hour at the hybridization temperature. Hybridization is performed in fresh pre-heated hybridization buffer containing 10 nM of 3' DIG-labeled LNA probe (Roche Diagnostics) complementary to each selected miRNA. Post-hybridization washes are done at the hybridization temperature by successive incubations for 15 min in HM-(hybridization buffer without heparin and yeast RNA), 75% HM-/25% 2×SSCT (SSC containing 0.1% Tween-20), 50% HM-/50% 2×SSCT, 25% HM-/75% 2×SSCT, 100% 2×SSCT and 2×30 min in 0.2×SSCT.

Subsequently, embryos are transferred to PBST through successive incubations for 10 min in 75% 0.2×SSCT/25% PBST, 50% 0.2×SSCT/50% PBST, 25% 0.2×SSCT/75% PBST and 100% PBST. After blocking for 1 hour in blocking buffer (2% sheep serum/2 mg:ml BSA in PBST), the embryos are incubated overnight at 4° C. in blocking buffer containing anti-DIG-AP FAB fragments (Roche, 1/2000). The next day, zebrafish embryos are washed 6×15 min in PBST, mouse and *X. tropicalis* embryos are washed 6×1 hour in TBST containing 2 mM levamisole and then for 2 days at 4° C. with regular refreshment of the wash buffer.

After the post-antibody washes, the embryos are washed 3×5 min in staining buffer (100 mM tris HCl pH9.5, 50 mM MgCl2, 100 mM NaCl, 0.1% tween 20). Staining was done in buffer supplied with 4.5 µl/ml NBT (Roche, 50 mg/ml stock) and 3.5 µl/ml BCIP (Roche, 50 mg/ml stock). The reaction is stopped with 1 mM EDTA in PBST and the embryos are stored at 4° C. The embryos are mounted in Murray's solution (2:1 benzylbenzoate:benzylalcohol) via an increasing methanol series (25% MeOH in PBST, 50% MeOH in PBST, 75% MeOH in PBST, 100% MeOH) prior to imaging.

Example 16

In Vitro Model: Isolation and Analysis of mRNA Expression (Total RNA Isolation and cDNA Synthesis for mRNA Analysis)

Total RNA was isolated either using RNeasy mini kit (Qiagen) or using the Trizol reagent (Invitrogen). For total RNA isolation using RNeasy mini kit (Qiagen), cells were washed with PBS, and Cell Lysis Buffer (RTL, Qiagen) supplemented with 1% mercaptoethanol was added directly to the wells. After a few minutes, the samples were processed according to manufacturer's instructions.

For in vivo analysis of mRNA expression tissue samples were first homogenised using a Retsch 300mM homogeniser and total RNA was isolated using the Trizol reagent or the RNeasy mini kit as described by the manufacturer.

First strand synthesis (cDNA from mRNA) was performed using either OmniScript Reverse Transcriptase kit or M-MLV Reverse transcriptase (essentially described by manufacturer (Ambion)) according to the manufacturer's instructions (Qiagen). When using OmniScript Reverse Transcriptase 0.5 µg total RNA each sample, was adjusted to 12 µl and mixed with 0.2 µl poly (dT)$_{12-18}$ (0.5 µg/µl) (Life Technologies), 2 µl dNTP mix (5 mM each), 2 µl 10×RT buffer, 0.5 µl RNA-guard™ RNase Inhibitor (33 units/ml, Amersham) and 1 µl OmniScript Reverse Transcriptase followed by incubation at 37° C. for 60 min. and heat inactivation at 93° C. for 5 min.

When first strand synthesis was performed using random decamers and M-MLV-Reverse Transcriptase (essentially as described by manufacturer (Ambion)) 0.25 µg total RNA of each sample was adjusted to 10.8 µl in H$_2$O. 2 µl decamers and 2 µl dNTP mix (2.5 mM each) was added. Samples were heated to 70° C. for 3 min. and cooled immediately in ice water and added 3.25 µl of a mix containing (2 µl 10×RT buffer; 1 µl M-MLV Reverse Transcriptase; 0.25 µl RNAase inhibitor). cDNA is synthesized at 42° C. for 60 min followed by heating inactivation step at 95° C. for 10 min and finally cooled to 4° C. The cDNA can further be used for mRNA quantification by for example Real-time quantitative PCR.

mRNA expression can be assayed in a variety of ways known in the art. For example, mRNA levels can be quantitated by, e.g., Northern blot analysis, competitive polymerase chain reaction (PCR), Ribonuclease protection assay (RPA) or real-time PCR. Real-time quantitative PCR is presently preferred. RNA analysis can be performed on total cellular RNA or mRNA.

Methods of RNA isolation and RNA analysis such as Northern blot analysis are routine in the art and is taught in, for example, Current Protocols in Molecular Biology, John Wiley and Sons.

Real-time quantitative (PCR) can be conveniently accomplished using the commercially available iQ Multi-Color Real Time PCR Detection System available from BioRAD. Real-time Quantitative PCR is a technique well-known in the art and is taught in for example Heid et al. Real time quantitative PCR, Genome Research (1996), 6: 986-994.

Example 17

LNA Oligonucleotide Uptake and Efficacy In Vivo

In vivo study: Six groups of animals (5 mice per group) were treated in the following manner. Group 1 animals were injected with 0.2 ml saline by i.v. on 3 successive days, Group 2 received 2.5 mg/kg SEQ ID NO: 61 SEQ ID NO: 61, Group 3 received 6.25 mg/kg, Group 4 received 12.5 mg/kg and Group 5 received 25 mg/kg, while Group 6 received 25 mg/kg SEQ ID NO:65 (mismatch LNA-antimiR™ oligonucleotide), all in the same manner. All doses were calculated from the Day 0 body weights of each animal.

Before dosing (Day 0) and 24 hour after last dose (Day 3), retro-orbital blood was collected in tubes containing EDTA and the plasma fraction harvested and stored frozen −80° C. for cholesterol analysis. At sacrifice livers were dissected and one portion was cut into 5 mm cubes and immersed in 5 volumes of ice-cold RNAlater. A second portion was snap frozen in liquid nitrogen and stored for cryo-sectioning.

Total RNA was extracted from liver samples as described above and analysed for miR-122a levels by microRNA specific QPCR. FIG. 5 demonstrates a clear dose-response obtained with SEQ ID NO: 61SEQ ID NO: 61 with an IC50 at ca 3-5 mg/kg, whereas no miR-122a inhibition was detected using the mismatch LNA antago-mir SEQ ID NO:65 for miR-122a.

Example 18

LNA-AntimiR-122a Dose-Response In Vivo in C57/BL/J Female Mice

In vivo study: Ten groups of animals (female C57/BL6; 3 mice per group) were treated in the following manner. Group 1 animals were injected with 0.2 ml saline by i.p. on day 0, day 2 and day 4. Groups 2-10 were dosed by i.p. with three different conc. (25 mg/kg, 5 mg/kg and 1 mg/kg) of either LNA antimiR-122a/SEQ ID NO: 61 (group 2-4), LNA antimir-122a/SEQ ID NO: 66 (group 5-7) or LNA antimir-122a/ SEQ ID NO: 63 (group 8-10); the LNA antimir-122a sequences are given in the Table 1. All three LNA antimiR-122a oligonucleotides target the liver-specific miR-122a. The doses were calculated from the Day 0 body weights of each animal.

The animals were sacrificed 48 hours after last dose (Day 6), retro-orbital blood was collected in tubes containing EDTA and the plasma fraction harvested and stored frozen −80° C. for cholesterol analysis. At sacrifice livers were dissected and one portion was cut into 5 mm cubes and immersed in 5 volumes of ice-cold RNAlater. A second portion was snap frozen in liquid nitrogen and stored for cryo-sectioning.

Total RNA was extracted from liver samples using Trizol reagent according to the manufacturer's recommendations (Invitrogen, USA) and analysed for miR-122a levels by microRNA-specific QPCR according to the manufacturer's recommendations (Ambion, USA). FIG. 2 demonstrates a clear dose-response obtained with all three LNA antimir-122a molecules (SEQ ID NO: 61, SEQ ID NO: 66, SEQ ID NO:63). Both SEQ ID NO: 66 and SEQ ID NO:63 show significantly improved efficacy in vivo in miR-122a silencing (as seen from the reduced miR-122a levels) compared to SEQ ID NO: 61, with SEQ ID NO:63 being most potent ($IC_{50}$ ca 1 mg/kg).

Figure 2B:
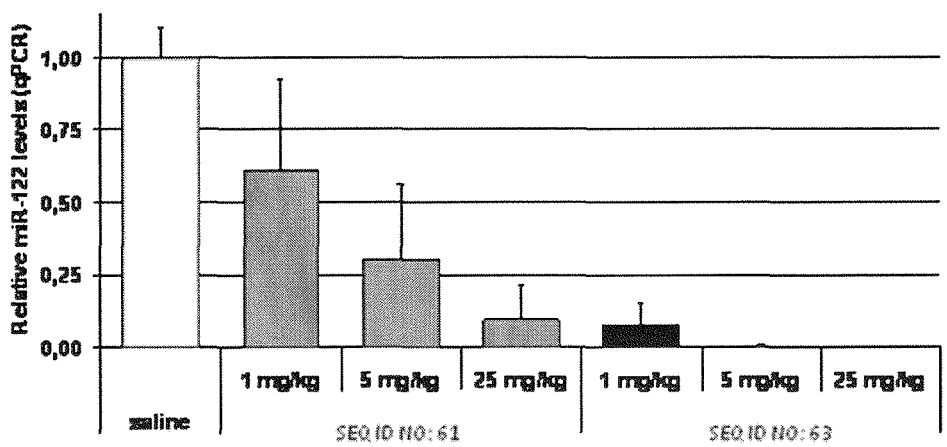

The above example was repeated using SEQ ID NO: 61 and SEQ ID NO:63 using 5 mice per group and the data combined (total of eight mice per group) is shown in FIG. 2b.

Example 19

Northern Blot

MicroRNA specific northern blot showing enhanced miR-122 blocking by SEQ ID NO:63 compared to SEQ ID NO: 61 in LNA-antimiR treated mouse livers.

Oligos Used in this Example:

| SEQ ID NO: | | |
|---|---|---|
| 63 | 5'-CcAttGTcaCaCtCC-3' | New design |
| 61 | 5'-CcAttGtcAcaCtcCa-3' | Old design |

Figure 6:
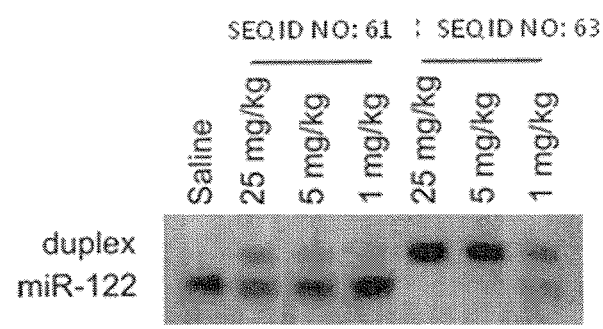
FIG. 6. Northern blot comparing SEQ ID NO: 63 with SEQ ID NO: 61. Total RNA from one mouse in each group were subjected to miR-122 specific northern blot. Mature miR-122 and the duplex (blocked microRNA) formed between the LNA-antimiR and miR-122 is indicated.

We decided to assess the effect of SEQ ID NO:63 on miR-122 miRNA levels in the livers of SEQ ID NO: 63-treated mice. The LNA-antimiRs SEQ ID NO:63 and SEQ ID NO: 61 were administered into mice by three i.p. injections on every second day over a six-day-period at indicated doses followed by sacrificing the animals 48 hours after the last dose. Total RNA was extracted from the livers. miR-122 levels were assessed by microRNA specific northern blot (FIG. 6)

Treatment of normal mice with SEQ ID NO:63 resulted in dramatically improved, dose-dependent reduction of miR-122. MicroRNA specific northern blot comparing SEQ ID NO:63 with SEQ ID NO: 61 was performed (FIG. 6). SEQ ID NO:63 completely blocked miR-122 at both 5 and 25 mg/kg as seen by the absence of mature single stranded miR-122 and only the presence of the duplex band between the LNA-antimiR and miR-122. Comparing duplex versus mature band on the northern blot SEQ ID NO:63 seem equally efficient at 1 mg/kg as SEQ ID NO: 61SEQ ID NO: 61 at 25 mg/kg.

Example 20

Assessment of Cholesterol Levels in Plasma in LNA Anti-miR122 Treated Mice

Total cholesterol level was measured in plasma using a colometric assay Cholesterol CP from ABX Pentra. Cholesterol was measured following enzymatic hydrolysis and oxidation (2,3). 21.5 µl water was added to 1.5 µl plasma. 250 µl reagent was added and within 5 min the cholesterol content measured at a wavelength of 540 nM. Measurements on each animal were made in duplicate. The sensitivity and linearity was tested with 2-fold diluted control compound (ABX Pentra N control). The cholesterol level was determined by subtraction of the background and presented relative to the cholesterol levels in plasma of saline treated mice.

FIG. 3 demonstrates a markedly lowered level of plasma cholesterol in the mice that received SEQ ID NO: 66 and SEQ ID NO: 63 compared to the saline control at Day 6.

Example 21

Assessment of miR-122a Target mRNA Levels in LNA AntimiR-122a Treated Mice

Figure 4A:
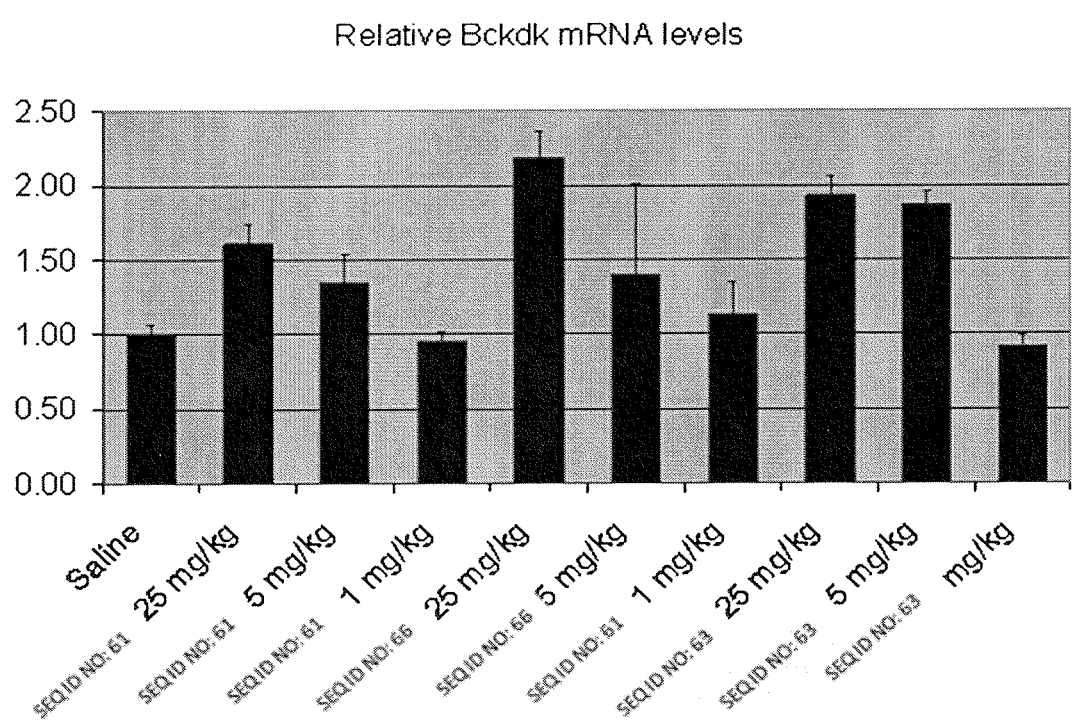
FIG. 4a. Assessment of relative Bckdk mRNA levels in LNA antimiR-122a treated mice in comparison with saline control mice using real-time quantitative RT-PCR.
Figure 4B:
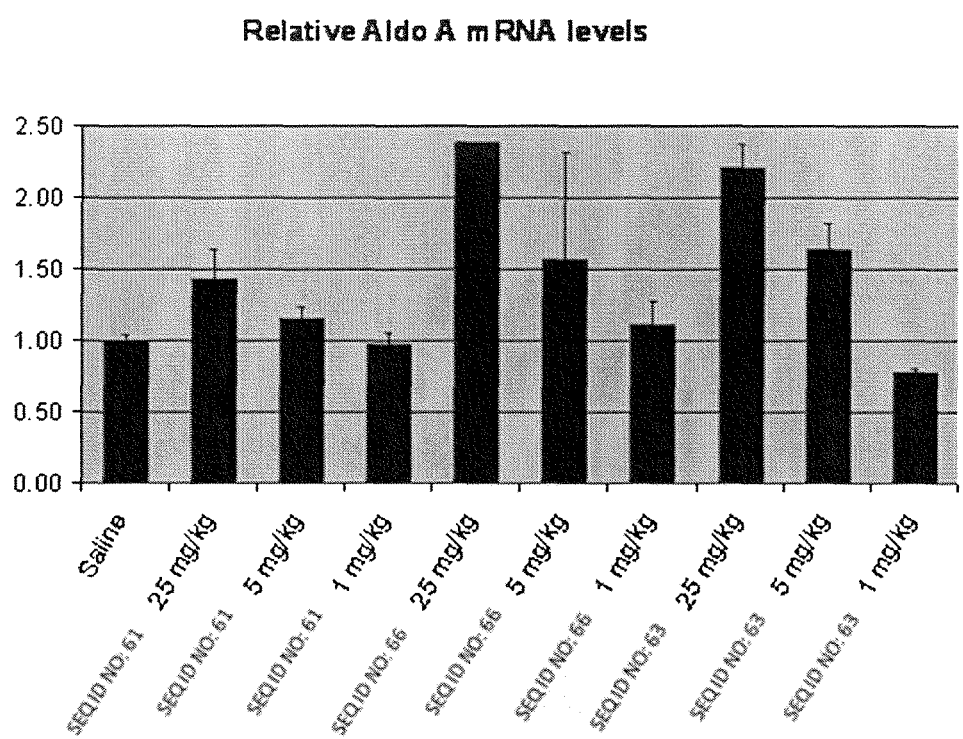
FIG. 4b. Assessment of relative aldolase A mRNA levels in LNA antimiR-122a treated mice in comparison with saline control mice using real-time quantitative RT-PCR.
Figure 4C:
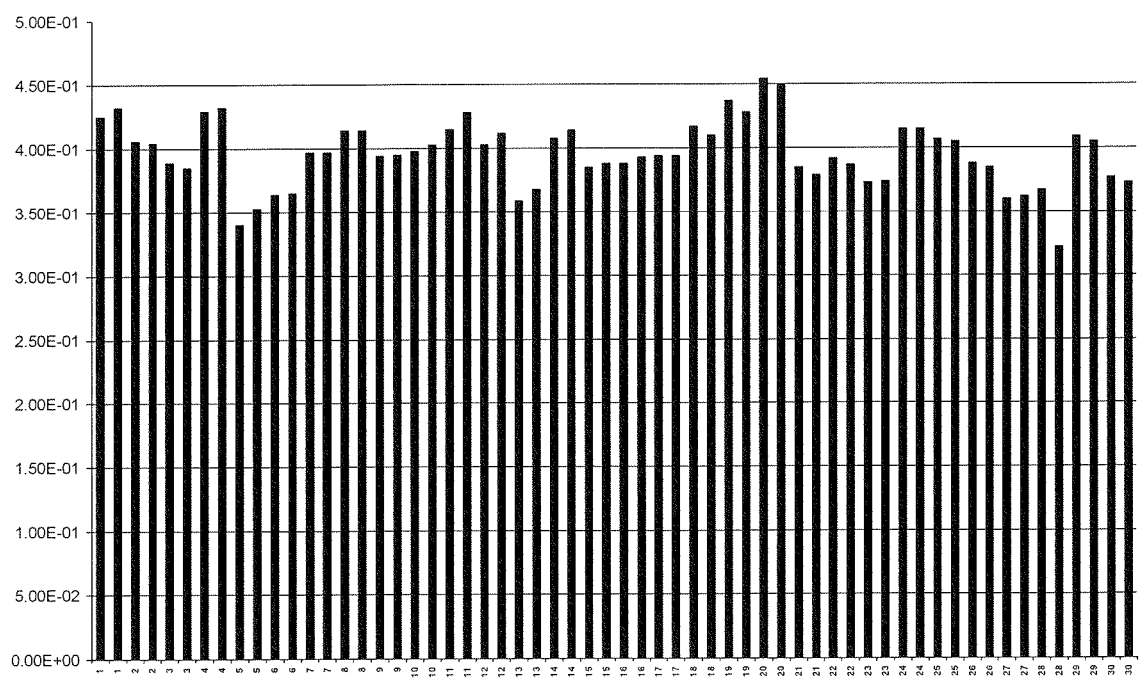
FIG. 4c. Assessment of GAPDH mRNA levels in LNA antimiR-122a treated mice (animals 4-30) in comparison with saline control mice (animals 1-3) using real-time quantitative RT-PCR.

The saline control and different LNA-antimiR-122a treated animals were sacrificed 48 hours after last dose (Day 6), and total RNA was extracted from liver samples as using Trizol reagent according to the manufacturer's recommendations (Invitrogen, USA). The mRNA levels were assessed by real-time quantitative RT-PCR for two miR-122a target genes, Bckdk (branched chain ketoacid dehydrogenase kinase, ENSMUSG00000030802) and aldolase A (aldoA, ENSMUSG00000030695), respectively, as well as for GAPDH as control, using Taqman assays according to the manufacturer's instructions (Applied biosystems, USA). FIGS. 4a and 4b demonstrate a clear dose-dependent upregulation of the two miR-122a target genes, Bckdk and AldoA, respectively, as a response to treatment with all three LNA antimiR-122a molecules (SEQ ID NO: 61SEQ ID NO: 61, SEQ ID NO: 66, SEQ ID NO: 63). In contrast, the qPCR assays for GAPDH control did not reveal any differences in the GAPD mRNA levels in the LNA-antimiR-122a treated mice compared to the saline control animals (FIG. 4c). The Bckdk and AldoA mRNA levels were significantly higher in the SEQ ID NO: 66 and SEQ ID NO: 63 treated mice compared to the SEQ ID NO: 61SEQ ID NO: 61 treated mice (FIGS. 4a and 4b), thereby demonstrating their improved in vivo efficacy.

Example 22

LNA Oligonucleotide Duration of Action In Vivo

In vivo study: Two groups of animals (21 mice per group) were treated in the following manner. Group 1 animals were injected with 0.2 ml saline by i.v. on 3 successive days, Group 2 received 25 mg/kg SEQ ID NO: 61SEQ ID NO: 61 in the same manner. All doses were calculated from the Day 0 body weights of each animal.

After last dose (Day 3), 7 animals from each group were sacrificed on Day 9, Day 16 and Day 23, respectively. Prior to this, on each day, retro-orbital blood was collected in tubes containing EDTA and the plasma fraction harvested and stored frozen −80° C. for cholesterol analysis from each day. At sacrifice livers were dissected and one portion was cut into 5 mm cubes and immersed in 5 volumes of ice-cold RNAlater. A second portion was snap frozen in liquid nitrogen and stored for cryo-sectioning.

Total RNA was extracted from liver samples as described above and analysed for miR-122a levels by microRNA specific QPCR. FIG. 7 (Sacrifice day 9, 16 or 23 correspond to sacrifice 1, 2 or 3 weeks after last dose) demonstrates a two-fold inhibition in the mice that received SEQ ID NO: 61SEQ ID NO: 61 compared to the saline control, and this inhibition could still be detected at Day 16, while by Day 23 the mi122a levels approached those of the saline group.

Example 22

LNA Oligonucleotide Duration of Action In Vivo

In vivo study: Two groups of animals (21 mice per group) were treated in the following manner. Group 1 animals were injected with 0.2 ml saline by i.v. on 3 successive days, Group 2 received 25 mg/kg SEQ ID NO: 61SEQ ID NO: 61 in the same manner. All doses were calculated from the Day 0 body weights of each animal.

After last dose (Day 3), 7 animals from each group were sacrificed on Day 9, Day 16 and Day 23, respectively. Prior to this, on each day, retro-orbital blood was collected in tubes containing EDTA and the plasma fraction harvested and stored frozen −80° C. for cholesterol analysis from each day. At sacrifice livers were dissected and one portion was cut into 5 mm cubes and immersed in 5 volumes of ice-cold RNAlater. A second portion was snap frozen in liquid nitrogen and stored for cryo-sectioning.

Figure 8:
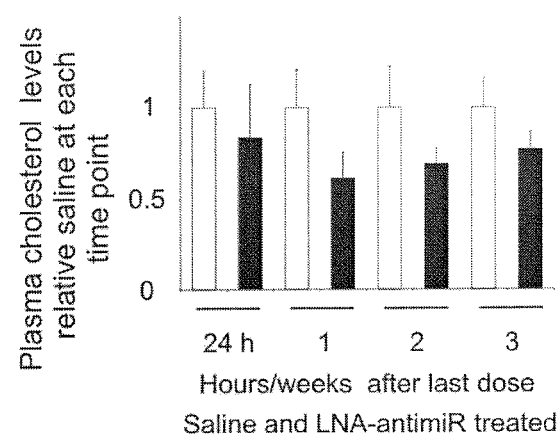
FIG. 8. Mice were treated with 25 mg/kg/day LNA-anti-miR or saline for three consecutive days and sacrificed 1, 2 or 3 weeks after last dose. Included are also the values from the animals sacrificed 24 hours after last dose (example 11 "old design"). Plasma cholesterol was measured and normalized to the saline group at each time point (shown mean and SD, n=7, 24 h n=10).

Total RNA was extracted from liver samples as described above and analysed for miR-122a levels by microRNA specific QPCR. FIG. 8 demonstrates a two-fold inhibition in the mice that received SEQ ID NO: 61SEQ ID NO: 61 compared to the saline control, and this inhibition could still be detected at Day 16, while by Day 23 the miR-122a levels approached those of the saline group.

As to Examples 17-22, the Following Procedures Apply:

NMRI mice were administered intravenously with SEQ ID NO: 61 SEQ ID NO: 61 using daily doses ranging from 2.5 to 25 mg/kg for three consecutive days. Animals were sacrificed 24 hours, 1, 2 or 3 weeks after last dose. Livers were harvested divided into pieces and submerged in RNAlater (Ambion) or snap-frozen. RNA was extracted with Trizol reagent according to the manufacturer's instructions (Invitrogen) from the RNAlater tissue, except that the precipitated RNA was washed in 80% ethanol and not vortexed. The RNA was used for mRNA TaqMan qPCR according to manufacturer (Applied biosystems) or northern blot (see below). The snap-frozen pieces were cryo-sectioned for in situ hybridizations.

Further, as to FIGS. 9-14, SEQ ID NO: 61SEQ ID NO: 61 is designated LNA-antimiR and SEQ ID NO: 65 (the mismatch control) is designated "mm".

Example 23

Figure 9:
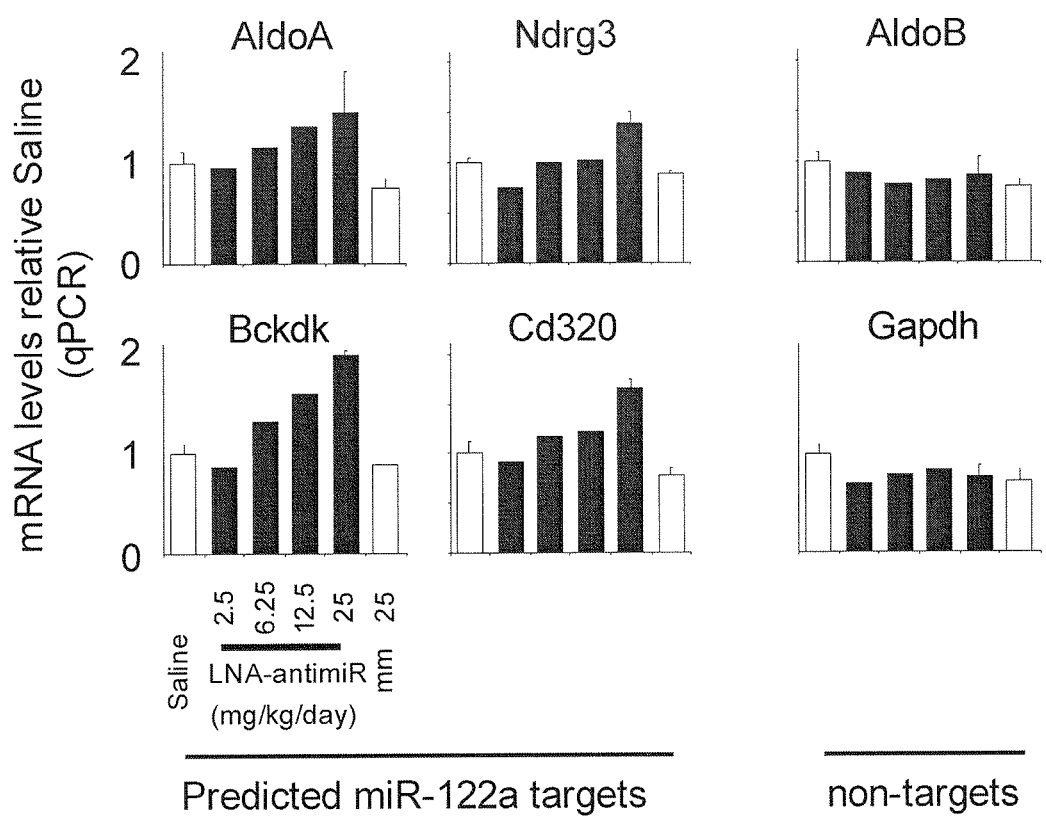
FIG. 9. Dose dependent miR-122a target mRNA induction by SEQ ID NO: 61 inhibition of miR-122a. Mice were treated with different SEQ ID NO: 61 doses for three consecutive days, as described above and sacrificed 24 hours after last dose. Total RNA extracted from liver was subjected to qPCR. Genes with predicted miR-122 target site and observed to be upregulated by microarray analysis were investigated for dose-dependent induction by increasing SEQ ID NO: 61 doses using qPCR. Total liver RNA from 2 to 3 mice per group sacrificed 24 hours after last dose were subjected to qPCR for the indicated genes. Shown in FIG. 9 is mRNA levels relative to Saline group, n=2-3 (2.5-12.5 mg/kg/day: n=2, no SD). Shown is also the mismatch control (m, SEQ ID NO: 65)

Dose Dependent miR-122a Target mRNA Induction by SEQ ID NO: 61SEQ ID NO: 61 Inhibition of miR-122a Mice were treated with different SEQ ID NO: 61 SEQ ID NO: 61 doses for three consecutive days, as described above and sacrificed 24 hours after last dose. Total RNA extracted from liver was subjected to qPCR. Genes with predicted miR-122 target site and observed to be upregulated by microarray analysis were investigated for dose-dependent induction by increasing SEQ ID NO: 61 SEQ ID NO: 61 doses using qPCR. Total liver RNA from 2 to 3 mice per group sacrificed 24 hours after last dose were subjected to qPCR for the indicated genes. Shown in FIG. 9 is mRNA levels relative to Saline group, n=2-3 (2.5-12.5 mg/kg/day: n=2, no SD). Shown is also the mismatch control (m, SEQ ID NO: 65).

Assayed genes: Nrdg3 Aldo A, Bckdk, CD320 with predicted miR-122 target site. Aldo B and Gapdh do not have a predicted miR-122a target site.

A clear dose-dependent induction was seen of the miR-122a target genes after treatment with different doses of SEQ ID NO: 61 SEQ ID NO: 61.

Example 24

Transient Induction of miR-122a Target mRNAs Following SEQ ID NO: 61SEQ ID NO: 61 Treatment NMRI female mice were treated with 25 mg/kg/day SEQ ID NO: 61SEQ ID NO: 61 along with saline control for three consecutive days and sacrificed 1, 2 or 3 weeks after last dose, respectively. RNA was extracted from livers and mRNA levels of predicted miR-122a target mRNAs, selected by microarray data were investigated by qPCR. Three animals from each group were analysed.

Assayed genes: Nrdg3 Aldo A, Bckdk, CD320 with predicted miR-122 target site. Gapdh does not have a predicted miR-122a target site.

Figure 10:
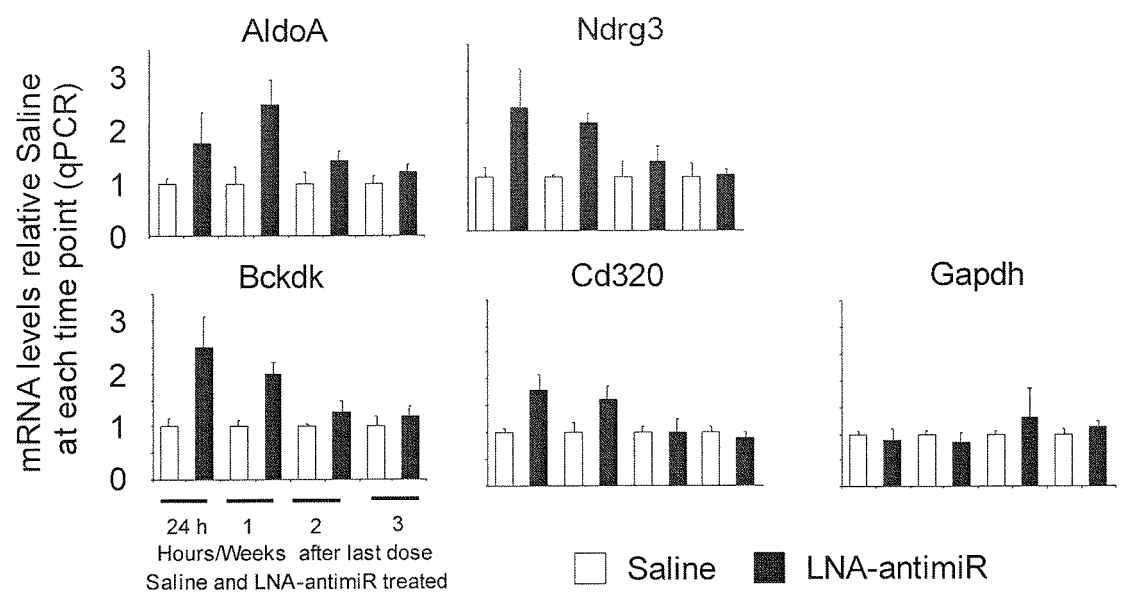
FIG. 10. Transient induction of miR-122a target mRNAs following SEQ ID NO: 61 treatment. NMRI female mice were treated with 25 mg/kg/day SEQ ID NO: 61 along with saline control for three consecutive days and sacrificed 1, 2 or 3 weeks after last dose, respectively. RNA was extracted from livers and mRNA levels of predicted miR-122a target mRNAs, selected by microarray data were investigated by qPCR. Three animals from each group were analysed.

A transient induction followed by a restoration of normal expression levels in analogy with the restoration of normal miR-122a levels was seen (FIG. 10).

mRNA levels are normalized to the individual GAPDH levels and to the mean of the Saline treated group at each individual time point. Included are also the values from the animals sacrificed 24 hours after last dose. Shown is mean and standard deviation, n=3 (24 h n=3)

Example 25

Induction of Vldlr in Liver by SEQ ID NO: 61 Treatment

The same liver RNA samples as in previous example were investigated for Vldlr induction.

Figure 11:
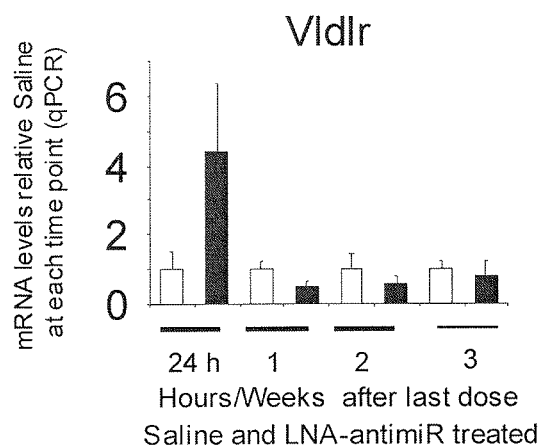
FIG. 11. Induction of Vldlr in liver by SEQ ID NO: 61 treatment. The same liver RNA samples as in previous example (FIG. 10) were investigated for Vldlr induction.

A transient up-regulation was seen after SEQ ID NO: 61 treatment, as with the other predicted miR-122a target mRNAs (FIG. 11)

Example 26

Stability of miR-122a/SEQ ID NO: 61 Duplex in Mouse Plasma

Figure 12:
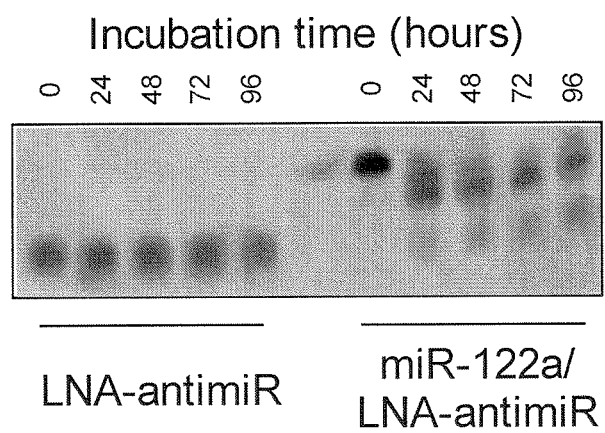
FIG. 12. Stability of miR-122a/SEQ ID NO: 61 duplex in mouse plasma. Stability of SEQ ID NO: 61 and SEQ ID NO: 61/miR-122a duplex were tested in mouse plasma at 37° C. over 96 hours. Shown in FIG. 12 is a SYBR-Gold stained PAGE.

Stability of SEQ ID NO: 61 and SEQ ID NO: 61/miR-122a duplex were tested in mouse plasma at 37° C. over 96 hours. Shown in FIG. 12 is a SYBR-Gold stained PAGE.

SEQ ID NO: 61 was completely stable over 96 hours. The SEQ ID NO: 61/miR-122a duplex was immediately truncated (degradation of the single stranded miR-122a region not covered by SEQ ID NO: 61) but thereafter almost completely stable over 96 hours.

The fact that a preformed SEQ ID NO: 61/miR-122 duplex showed stability in serum over 96 hours together with the high thermal duplex stability of SEQ ID NO: 61 molecule supported our notion that inhibition of miR-122a by SEQ ID NO: 61 was due to stable duplex formation between the two molecules, which has also been reported in cell culture (Naguibneva et al. 2006).

Example 27

Sequestering of Mature miR-122a by SEQ ID NO: 61 Leads to Duplex Formation

Figure 13:
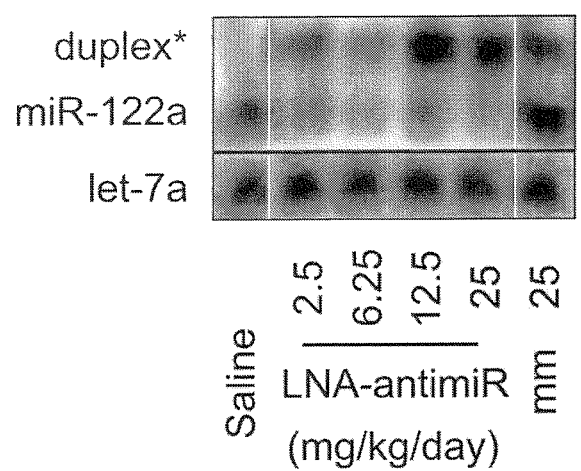
FIG. 13. Sequestering of mature miR-122a by SEQ ID NO: 61 leads to duplex formation. Shown in FIG. 13 is a membrane probed with a miR-122a specific probe (upper panel) and re-probed with a Let-7 specific probe (lower panel). With the miR-122 probe, two bands could be detected, one corresponding to mature miR-122 and one corresponding to a duplex between SEQ ID NO: 61 and miR-122.

The liver RNA was also subjected to microRNA Northern blot. Shown in FIG. 13 is a membrane probed with a miR-122a specific probe (upper panel) and re-probed with a Let-7 specific probe (lower panel). With the miR-122 probe, two bands could be detected, one corresponding to mature miR-122 and one corresponding to a duplex between SEQ ID NO: 61 and miR-122.

To confirm silencing of miR-122, liver RNA samples were subjected to small RNA northern blot analysis, which showed significantly reduced levels of detectable mature miR-122, in accordance with our real-time RT-PCR results. By comparison, the levels of the let-7a control were not altered. Interestingly, we observed dose-dependent accumulation of a shifted miR-122/SEQ ID NO: 61 heteroduplex band, suggesting that SEQ ID NO: 61 does not target miR-122 for degradation, but rather binds to the microRNA, thereby sterically hindering its function.

Northern blot analysis was performed as follows:
Preparation of northern membranes was done as described in Sempere et al. 2002, except for the following changes: Total RNA, 10 µg per lane, in formamide loading buffer (47.5% formamide, 9 mM EDTA, 0.0125% Bromophenol Blue, 0.0125% Xylene Cyanol, 0.0125% SDS) was loaded onto a 15% denaturing Novex TBE-Urea polyacrylamide gel (Invitrogen) without preheating the RNA. The RNA was electrophoretically transferred to a GeneScreen plus Hybridization Transfer Membrane (PerkinElmer) at 200 mA for 35 min. Membranes were probed with 32P-labelled LNA-modified oligonucleotides complimentary to the mature microRNAs*. The LNA oligonucleotides were labelled and hybridized to the membrane as described in (Válóczi et al. 2004) except for the following changes: The prehybridization and hybridization solutions contained 50% formamide, 0.5% SDS, 5×SSC, 5×Denhardt's solution and 20 µg/ml sheared denatured herring sperm DNA. Hybridizations were performed at 45° C. The blots were visualized by scanning in a Storm 860 scanner. The signal of the background membrane was subtracted from the radioactive signals originating from the miRNA bands. The values of the miR-122 signals were corrected for loading differences based on the let-7a signal. To determine the size of the radioactive signals the Decade Marker System (Ambion) was used according to the suppliers' recommendations.

Figure 14:
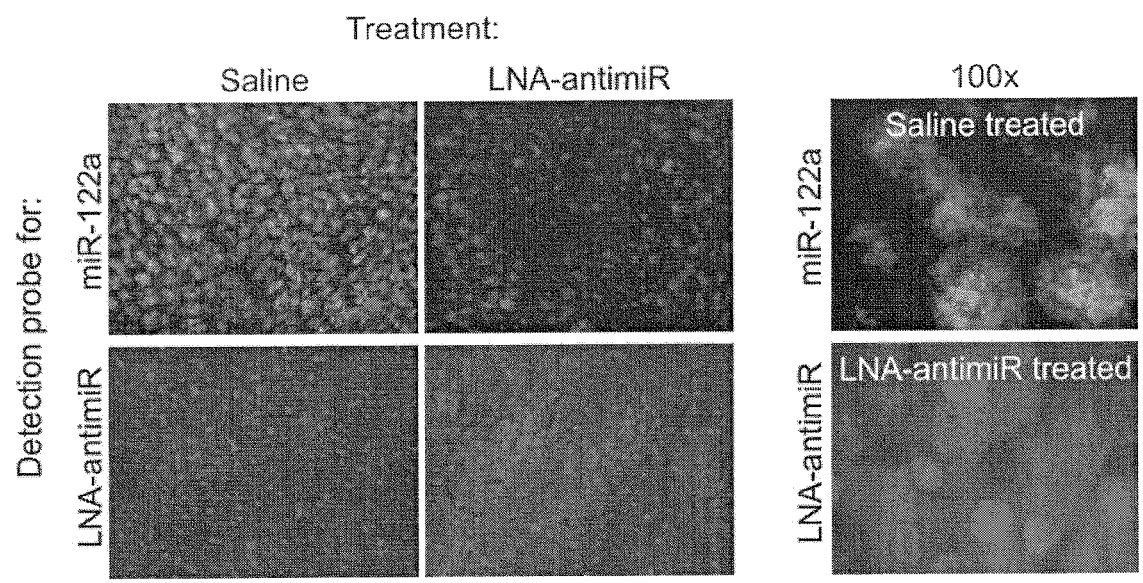
FIG. 14. miR-122a sequestering by SEQ ID NO: 61 along with SEQ ID NO: 61 distribution assessed by in situ hybridization of liver sections. Liver cryo-sections from treated animals were FIG. 15. Liver gene expression in miR-122 LNA-antimiR treated mice. Saline and LNA-antimiR treated mice were compared by genome-wide expression profiling using Affymetrix Mouse Genome 430 2.0 arrays. (a,1) Shown is number of probes displaying differentially expression in liver samples of LNA-antimiR-122 treated and saline treated mice 24 hours post treatment. (b,2) The occurrence of miR-122 seed sequence in differentially expressed genes. The plot shows the percentage of transcripts with at least one miR-122 seed recognition sequence in their 3' UTR. Random: Random sequences were generated and searched for miR-122 seed recognition sequences. Temporal liver gene expression profiles in LNA-antimiR treated mice. Mice were treated with 25 mg/kg/day LNA-antimiR or saline for three consecutive days and sacrificed 1, 2 or 3 weeks after last dose. Included are also the values from the animals sacrificed 24 hours after last dose. (c,3) RNA samples from different time points were also subjected to expression profiling. Hierarchical cluster analysis of expression profiles of genes identified as differentially expressed between LNA-antimiR and saline treated mice 24 hours, one week or three weeks post treatment. (d,4) Expression profiles of genes identified as differentially expressed between LNA-antimiR and saline treated mice 24 hours post treatment were followed over time. The expression ratios of up- and down-regulated genes in LNA-antimiR treated mice approach 1 over the time-course, indicating a reversible effect of the LNA-antimiR treatment.

Example 28 miR-122a Sequestering by SEQ ID NO: 61 Along with SEQ ID NO: 61 Distribution Assessed by In Situ Hybridization of Liver Sections Liver cryo-sections from treated animals were subjected to in situ hybridizations for detection and localization of miR-122 and SEQ ID NO: 61 (FIG. 14). A probe complementary to miR-122 could detect miR-122a. A second probe was complementary to SEQ ID NO: 61. Shown in FIG. 14 is an overlay, in green is distribution and apparent amounts of miR-122a and SEQ ID NO: 61 and blue is DAPI nuclear stain, at 10× magnification. 100× magnifications reveal the intracellular distribution of miR-122a and SEQ ID NO: 61 inside the mouse liver cells.

The liver sections from saline control animals showed a strong miR-122 staining pattern over the entire liver section, whereas the sections from SEQ ID NO: 61 treated mice showed a significantly reduced patchy staining pattern. In contrast, SEQ ID NO: 61 molecule was readily detected in SEQ ID NO: 61 treated liver, but not in the untreated saline control liver. Higher magnification localized miR-122a to the cytoplasm in the hepatocytes, where the miR-122 in situ pattern was clearly compartmentalized, while SEQ ID NO: 61 molecule was evenly distributed in the entire cytoplasm.

Example 29

Micro Array Analysis

Figure 15:
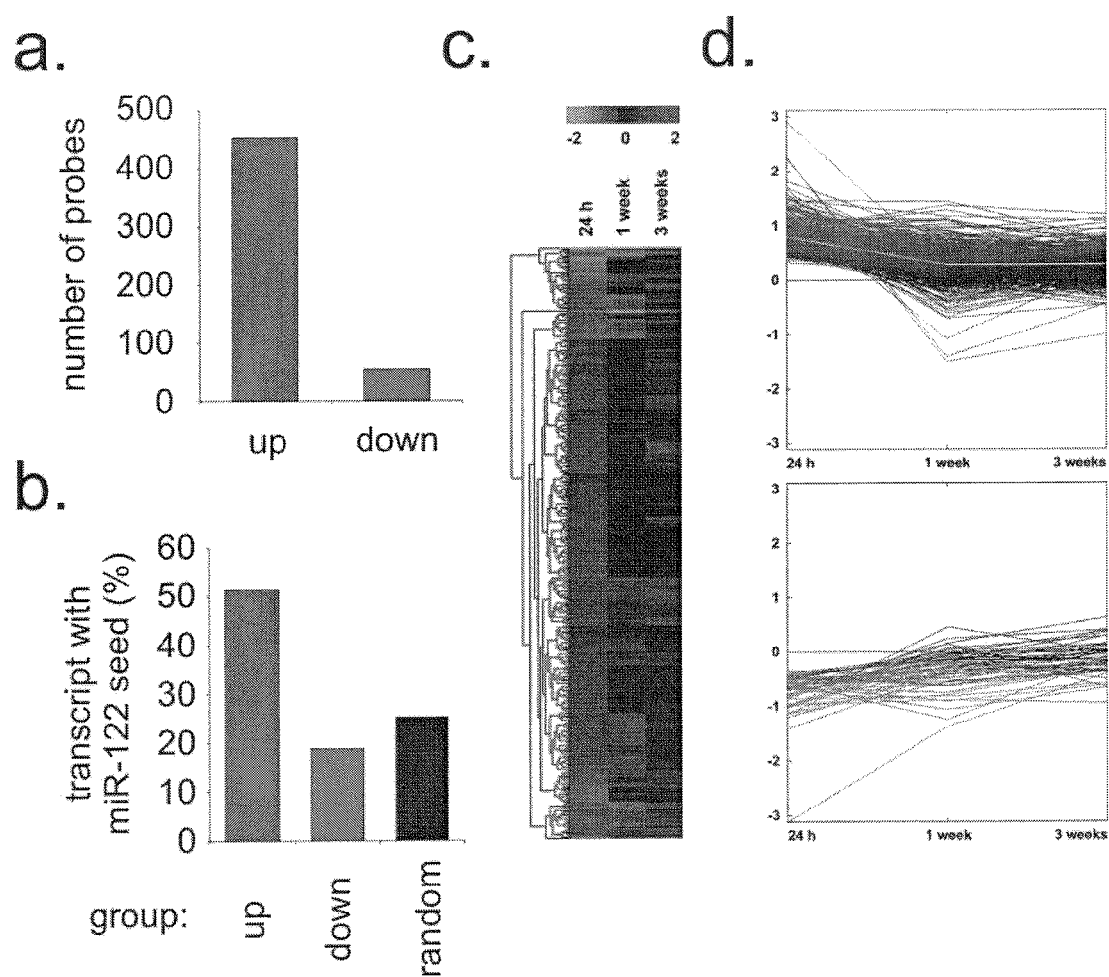

We carried out genome-wide expression profiling of total RNA samples from saline LNA-antimiR-122 treated and LNA mismatch control treated mice livers 24 hours after the last dose using Affymetrix Mouse Genome 430 2.0 arrays. Analysis of the array data revealed 455 transcripts that were upregulated in the LNA-antimiR treated mice livers compared to saline and LNA mismatch controls, while 54 transcripts were downregulated (FIG. 15a). A total of 415 of the upregulated and 53 downregulated transcripts could be identified in the Ensembl database. We subsequently examined the 3' untranslated regions (UTRs) of the differentially expressed mRNAs for the presence of the 6 nt sequence CACTCC, corresponding to the reverse complement of the nucleotide 2-7 seed region in mature miR-122. The number of transcripts having at least one miR-122 recognition sequence was 213 (51%) among the upregulated transcripts, and 10 (19%) within the downregulated transcripts, while the frequency in a random sequence population was 25%, implying that a significant pool of the upregulated mRNAs represent direct miR-122 targets in the liver (FIG. 15b).

The LNA-antimiR treatment showed maximal reduction of miR-122 levels at 24 hours, 50% reduction at one week and matched saline controls at three weeks after last LNA dose (Example 12 "old design"). This coincided with a markedly reduced number of differentially expressed genes between the two mice groups at the later time points. Compared to the 509 mRNAs 24 hours after the last LNA dose we identified 251 differentially expressed genes after one week, but only 18 genes after three weeks post treatment (FIGS. 15c and 15d). In general genes upregulated 24 hours after LNA-antimiR treatment then reverted towards control levels over the next two weeks (FIG. 15d).

In conclusion, a large portion of up-regulated/de-repressed genes after LNA-antimiR treatment are miR-122 targets, indicating a very specific effect for blocking miR-122. Also genes up-regulated/de-repressed approach normal levels 3 weeks after end of treatment, suggest a relative long therapeutic effect, but however not cause a permanent alteration, ie the effect is reversible.

Methods:
Gene Expression Profiling of LNA-antimiR Treated Mice. Expression profiles of livers of saline and LNA-antimiR treated mice were compared. NMRI female mice were treated with 25 mg/kg/day of LNA-antimiR along with saline control for three consecutive days and sacrificed 24 h, 1, 2 or 3 weeks after last dose. Additionally, expression profiles of livers of mice treated with the mismatch LNA control oligonucleotide 24 h after last dose were obtained. Three mice from each group were analyzed, yielding a total of 21 expression profiles. RNA quality and concentration was measured using an Agilent 2100 Bioanalyzer and Nanodrop ND-1000, respectively. Total RNA was processed following the GeneChip Expression 3'-Amplification Reagents One-cycle cDNA synthesis kit instructions (Affymetrix Inc, Santa Clara, Calif., USA) to produce double-stranded cDNA. This was used as a template to generate biotin-labeled cRNA following manufacturer's specifications. Fifteen micrograms of biotin-labeled cRNA was fragmented to strands between 35 and 200 bases in length, of which 10 micrograms were hybridised onto Affymetrix Mouse Genome 430 2.0 arrays overnight in the GeneChip Hybridisation oven 6400 using standard procedures. The arrays were washed and stained in a GeneChip Fluidics Station 450. Scanning was carried out using the GeneChip Scanner 3000 and image analysis was performed using GeneChip Operating Software. Normalization and statistical analysis were done using the LIMMA software package for the R programming environment27. Probes reported as absent by GCOS software in all hybridizations were removed from the dataset. Additionally, an intensity filter was applied to the dataset to remove probes displaying background-corrected intensities below 16. Data were normalized using quantile normalization28. Differential expression was assessed using a linear model method. P values were adjusted for multiple testing using the Benjamini and Hochberg. Tests were considered to be significant if the adjusted p values were p<0.05. Clustering and visualization of Affymetrix array data were done using the MultiExperiment Viewer software29.

Target Site Prediction

Transcripts with annotated 3' UTRs were extracted from the Ensembl database (Release 41) using the EnsMart data mining tool30 and searched for the presence of the CACTCC sequence which is the reverse complement of the nucleotide 2-7 seed in the mature miR-122 sequence. As a background control, a set of 1000 sequences with a length of 1200 nt, corresponding to the mean 3' UTR length of the up- and downregulated transcripts at 24 h after last LNA-antimiR dose, were searched for the 6 nucleotide miR-122 seed matches. This was carried out 500 times and the mean count was used for comparison Example 30

Dose-Dependent Inhibition of miR-122 in Mouse Liver by LNA-antimiR is Enhanced as Compared to Antagomir Inhibition of miR-122

NMRI female mice were treated with indicated doses of LNA-antimiR (SEQ ID NO: 61) along with a mismatch control (m, SEQ ID NO: 65), saline and antagomir (SPC3595) for three consecutive days and sacrificed 24 hours after last dose (as in example 11 "old design", n=5). miR-122 levels were analyzed by qPCR and normalized to the saline treated group. Genes with predicted miR-122 target site and up regulated in the expression profiling (AldoA, Nrdg3, Bckdk and CD320) showed dose-dependent de-repression by increasing LNA-antimiR doses measured by qPCR.

Figure 16:
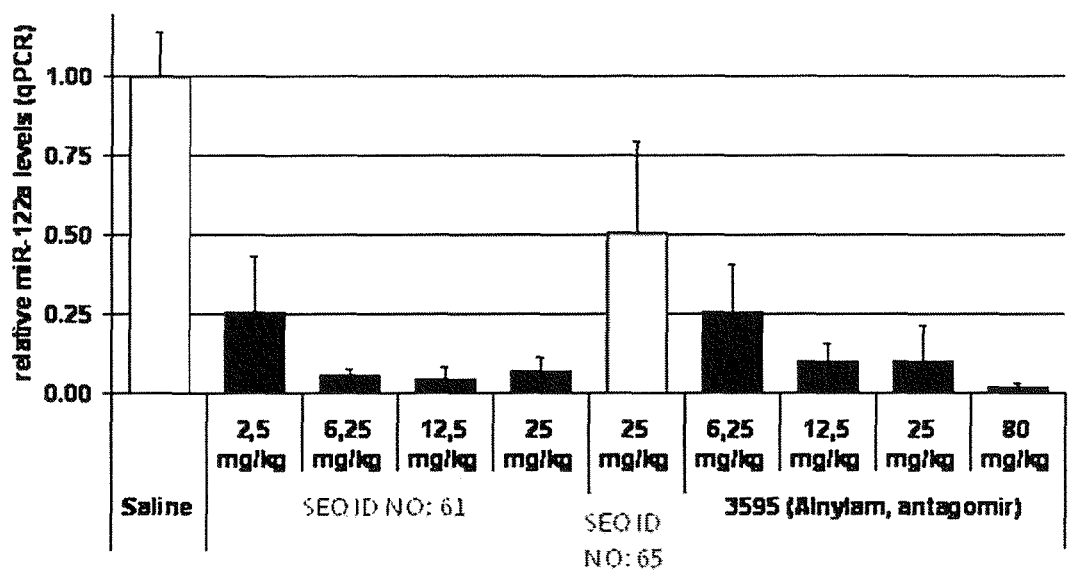
FIG. 16. The effect of treatment with SEQ ID NO: 61 and 3595 on miR-122 levels in mice livers.
Figure 17:
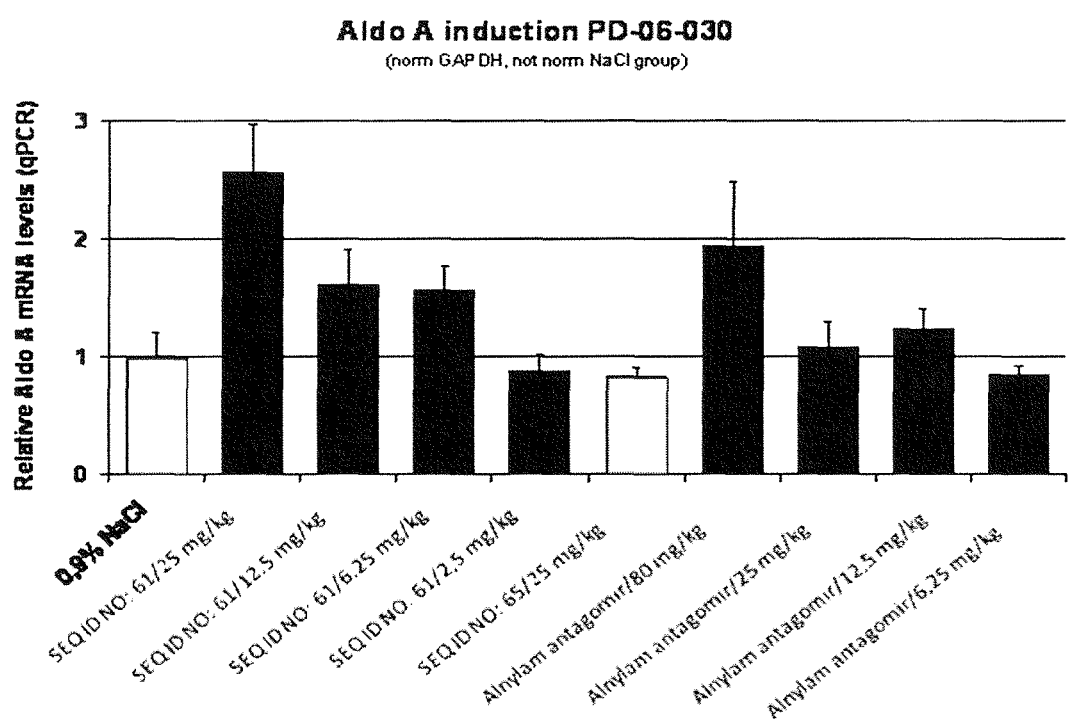
FIG. 17. The effect of treatment with SEQ ID NO: 61 and 3595 on Aldolase A levels in mice livers.
Figure 18:
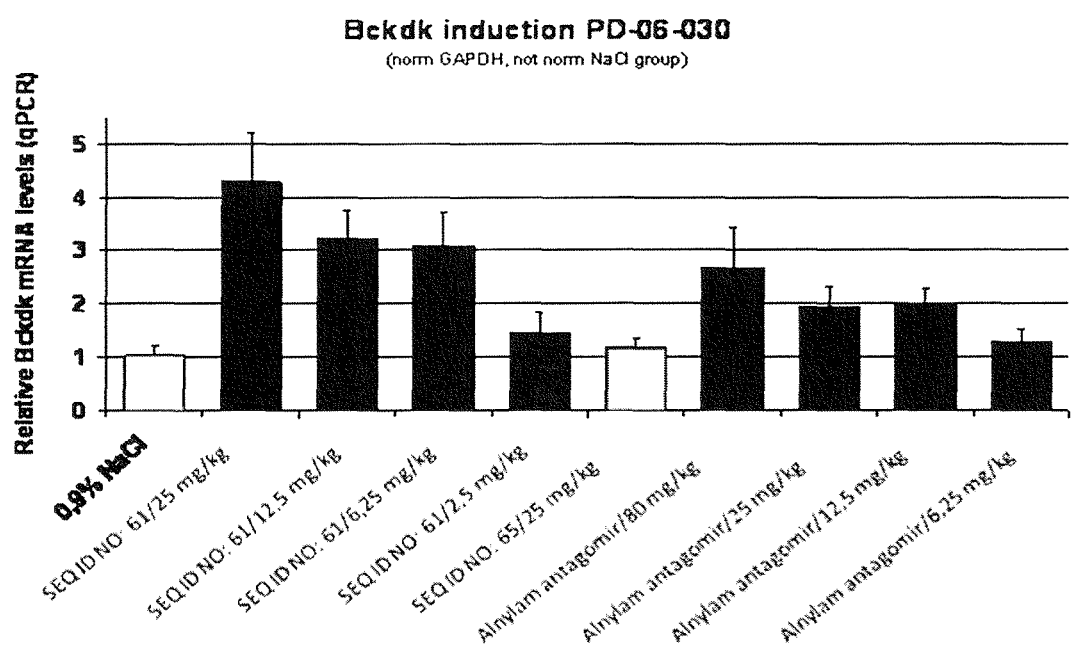
FIG. 18. The effect of treatment with SEQ ID NO: 61 and 3595 on Bckdk levels in mice livers.
Figure 19:
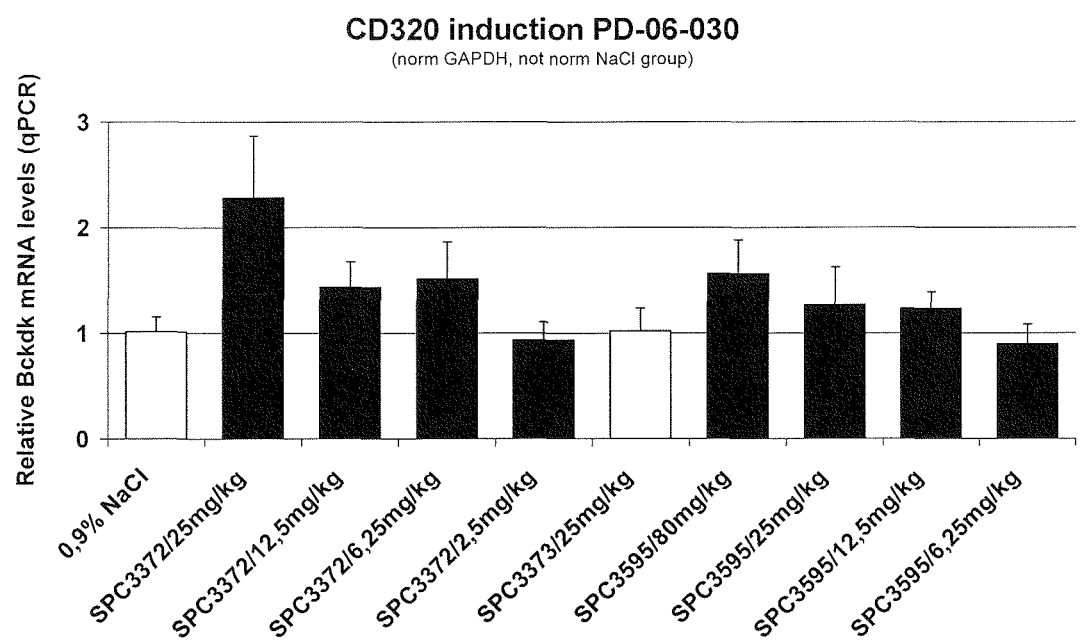
FIG. 19. The effect of treatment with SEQ ID NO: 61 and 3595 on CD320 levels in mice livers.
Figure 20:
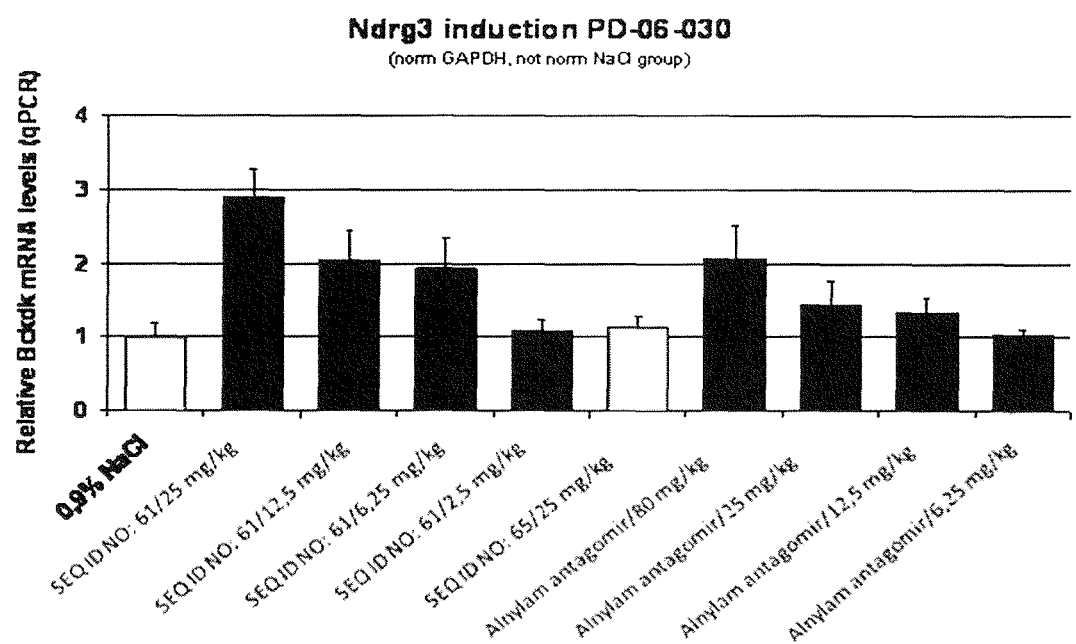
FIG. 20. The effect of treatment with SEQ ID NO: 61 and 3595 on Ndrg3 levels in mice livers.

The de-repression was consistently higher on all tested miR-122 target mRNAs (AldoA, Bckdk, CD320 and Nrdg3 FIG. 17, 18, 19, 20) in LNA-antimiR treated mice compared to antagomir treated mice. This was also indicated when analysing the inhibition of miR-122 by miR-122 specific qPCR (FIG. 16). Hence LNA-antimiRs give a more potent functional inhibition of miR-122 than corresponding dose antagomir.

Example 31

Inhibition of miR-122 by LNA-AntimiR in Hypercholesterolemic Mice Along with Cholesterol Reduction and miR-122 Target mRNA De-Repression C57BL/6J female mice were fed on high fat diet for 13 weeks before the initiation of the SEQ ID NO: 63 treatment. This resulted in increased weight to 30-35 g compared to the weight of normal mice, which was just under 20 g, as weighed at the start of the LNA-antimiR treatment. The high fat diet mice lead to significantly increased total plasma cholesterol level of about 130 mg/dl, thus rendering the mice hypercholesterolemic compared to the normal level of about 70 mg/dl. Both hypercholesterolemic and normal mice were treated i.p. twice weekly with 5 mg/kg SEQ ID NO: 63 and the corresponding mismatch control for a study period of 5½ weeks. Blood samples were collected weekly and total plasma cholesterol was measured during the entire course of the study. Upon sacrificing the mice, liver and blood samples were prepared for total RNA extraction, miRNA and mRNA quantification, assessment of the serum transaminase levels, and liver histology.

Figure 21:
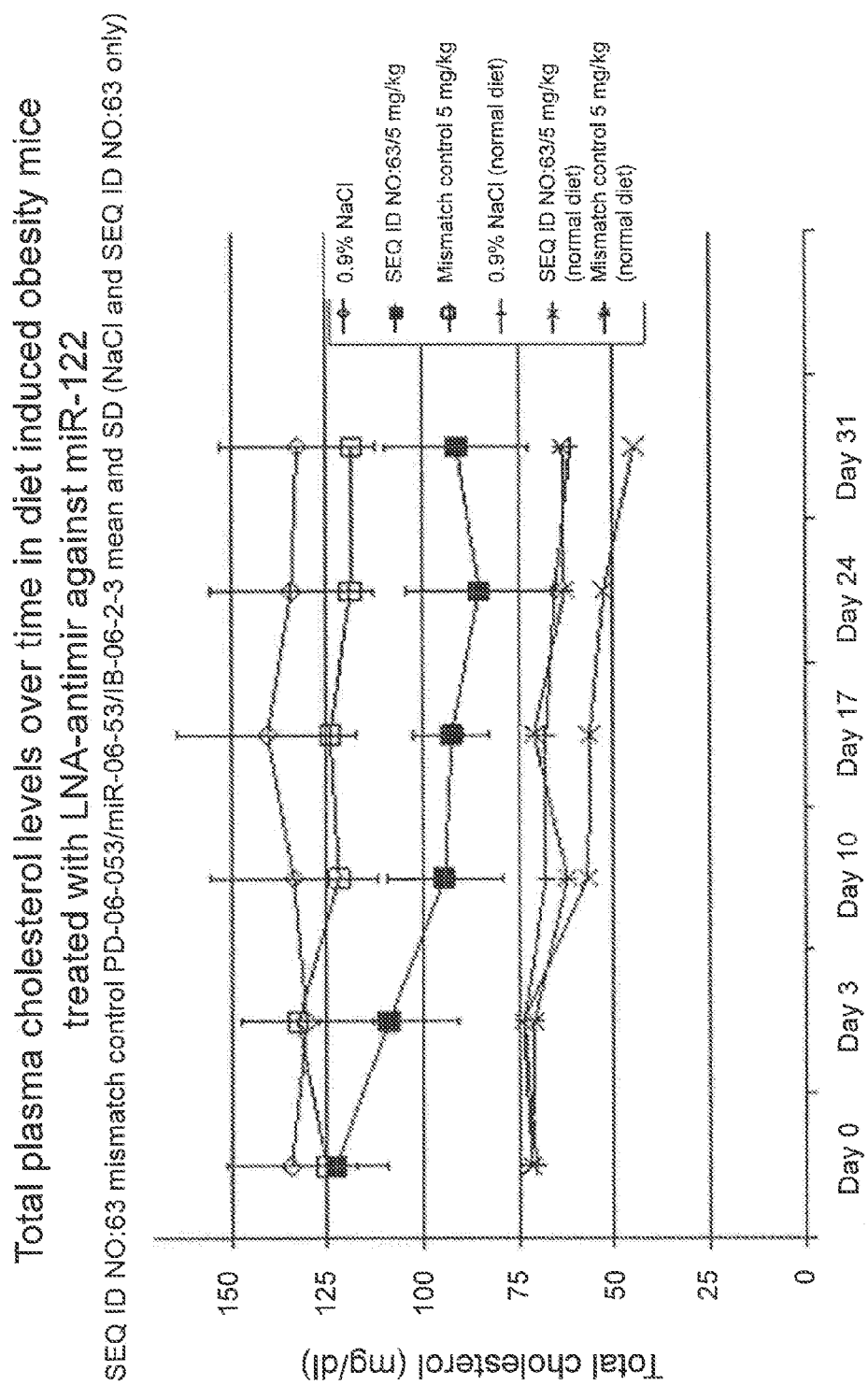
FIG. 21. The effect of long-term treatment with SEQ ID NO: 63 on total plasma cholesterol in hypercholesterolemic and normal mice. Weekly samples of blood plasma were obtained from the SEQ ID NO: 63 treated and saline control mice once weekly followed by assessment of total plasma cholesterol. The mice were treated with 5 mg/kg SEQ ID NO: 63, mismatch control or saline twice weekly. Normal mice given were treated in parallel.

Treatment of hypercholesterolemic mice with SEQ ID NO: 63 resulted in reduction of total plasma cholesterol of about 30% compared to saline control mice already after 10 days and sustained at this level during the entire study (FIG. 21). The effect was not as pronounced in the normal diet mice. By contrast, the mismatch control did not affect the plasma cholesterol levels in neither hypercholesterolemic nor normal mice.

Figure 22:
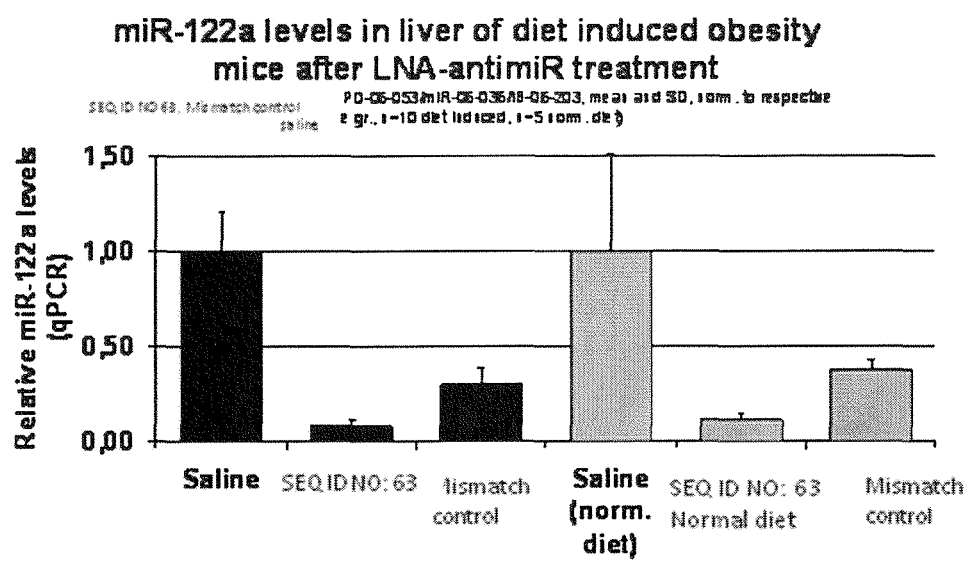
FIG. 22. The effect of long-term treatment with SEQ ID NO: 63 on miR-122 levels in hypercholesterolemic and normal mice.
Figure 23:
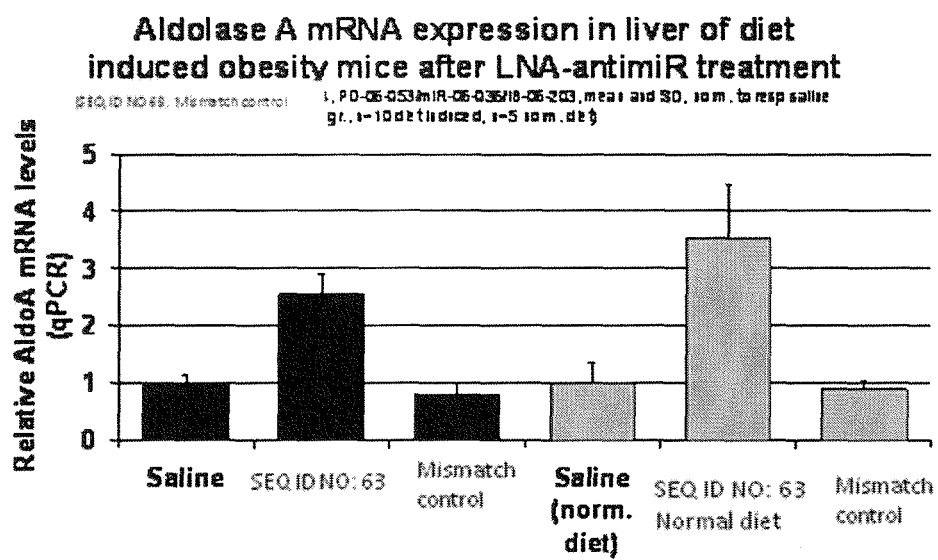
FIG. 23. The effect of long-term treatment with SEQ ID NO: 63 on Aldolase A levels in hypercholesterolemic and normal mice.
Figure 24:
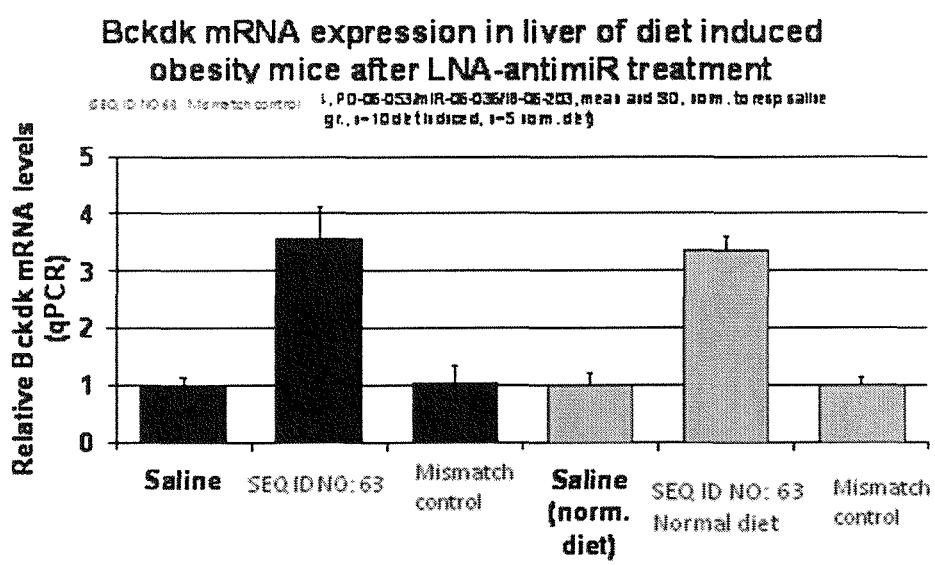
FIG. 24. The effect of long-term treatment with SEQ ID NO: 63 on Bckdk levels in hypercholesterolemic and normal mice.

Quantification of miR-122 inhibition and miR-122 target gene mRNA de-repression (AldoA and Bckdk) after the long-term treatment with SEQ ID NO: 63 revealed a comparable profile in both hypercholesterolemic and normal mice (FIG. 22, 23, 24), thereby demonstrating the potency of SEQ ID NO: 63 in miR-122 antagonism in both animal groups. The miR-122 qPCR assay indicated that also the mismatch control had an effect on miR-122 levels in the treated mice livers, albeit to a lesser extent compared to SEQ ID NO: 63. This might be a reduction associated with the stem-loop qPCR. Consistent with this notion, treatment of mice with the mismatch control did not result in any functional de-repression of the direct miR-122 target genes (FIGS. 23 and 24) nor reduction of plasma cholesterol (FIG. 21), implying that SEQ ID NO: 63-mediated antagonism of miR-122 is highly specific in vivo.

Figure 25:
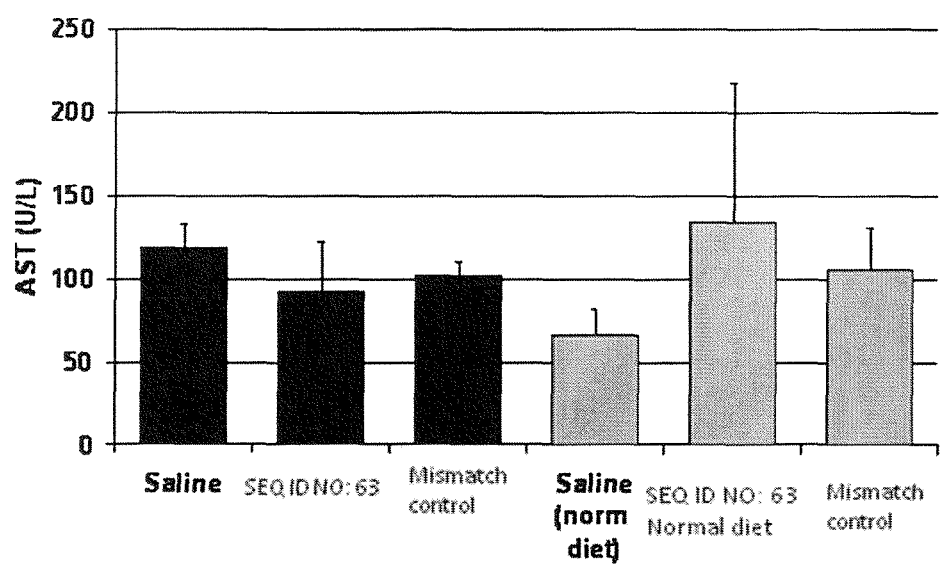
FIG. 25. The effect of long-term treatment with SEQ ID NO: 63 on AST levels in hypercholesterolemic and normal mice.
Figure 26:
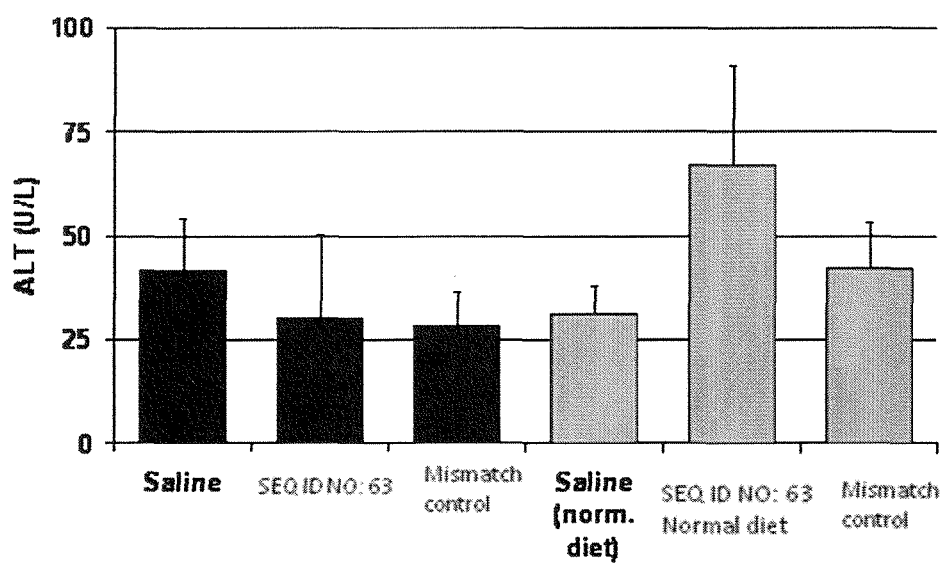
FIG. 26. The effect of long-term treatment with SEQ ID NO: 63 on ALT levels in hypercholesterolemic and normal mice.
Figure 27:
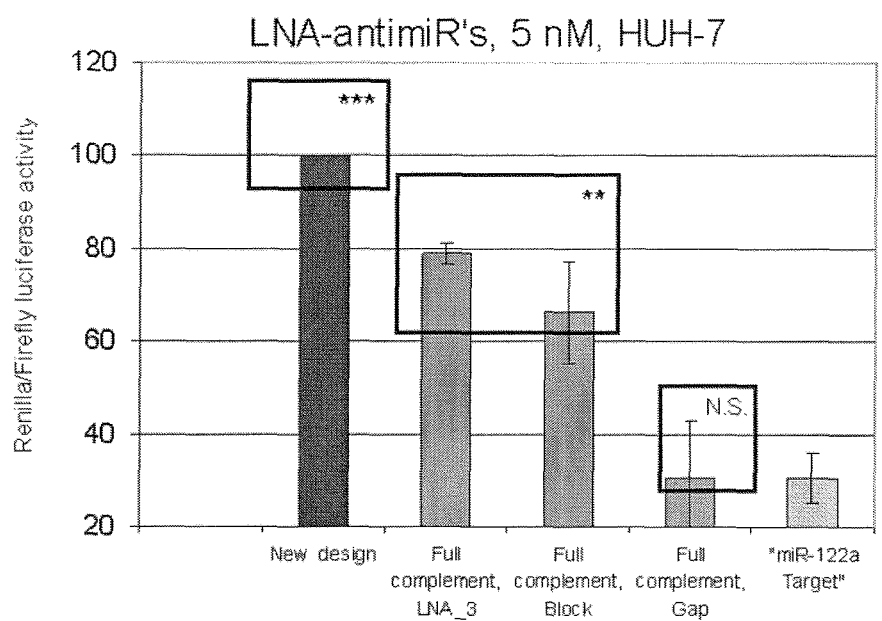
FIG. 27. Functional de-repression of *renilla* luciferase with miR-122 target by miR-122 blocking oligonucleotides in an endogenously miR-122 expressing cell line, Huh-7. "miR-122 target" is the corresponding plasmid with miR-122 target but not co-transfected with oligo blocking miR-122 and hence represent fully miR-122 repressed renilla luciferace expression.
Figure 28:
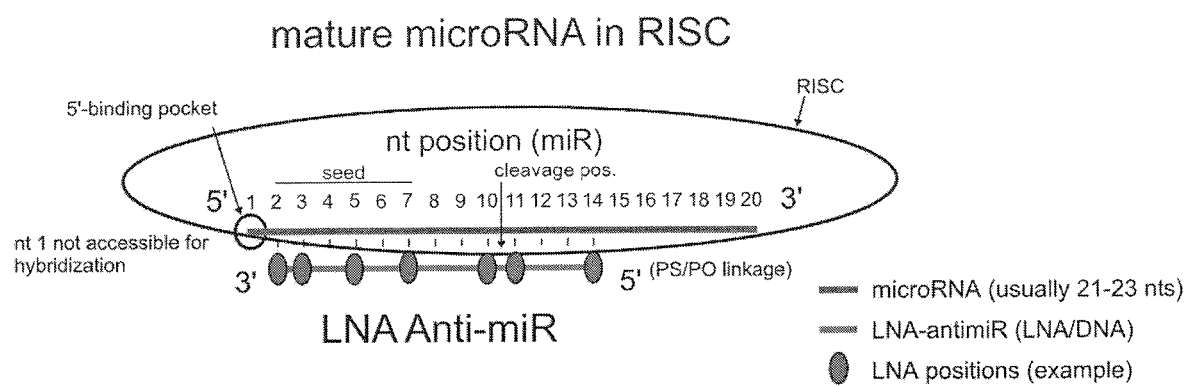
FIG. 28. Diagram illustrating the alignment of an oligonucleotide according to the invention and a microRNA target (miR-122).
Figure 29:
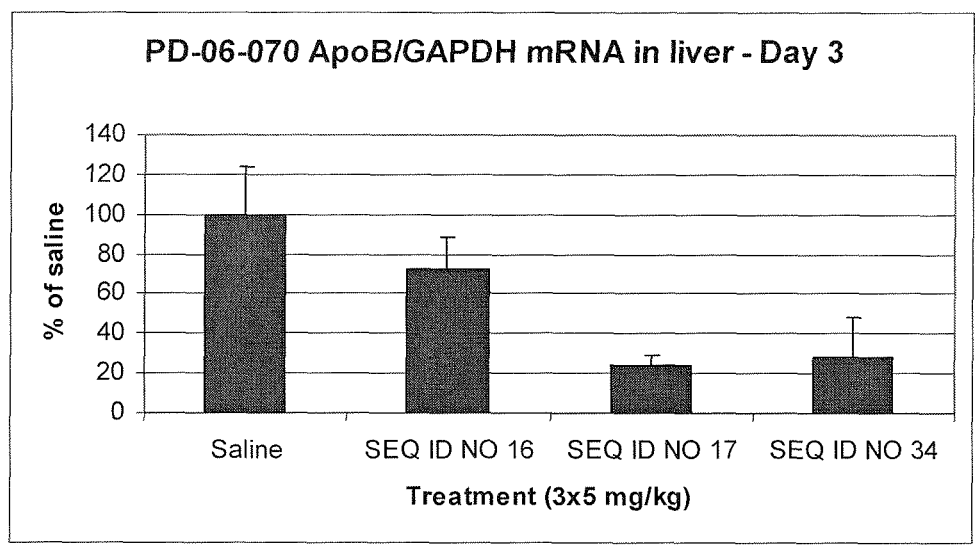
FIG. 29. The apoB-100 mRNA expression was measured by qPCR normalized to the house keeping gene GAPDH and presented relative to the saline group. Mice (n=3 or 5) were dosed 3 consecutive days and sacrifice 24 hours after the last dosing, liver was isolated and analysed. SEQ ID NO refers to those listed in Table 1 of example 2.
Figure 30:
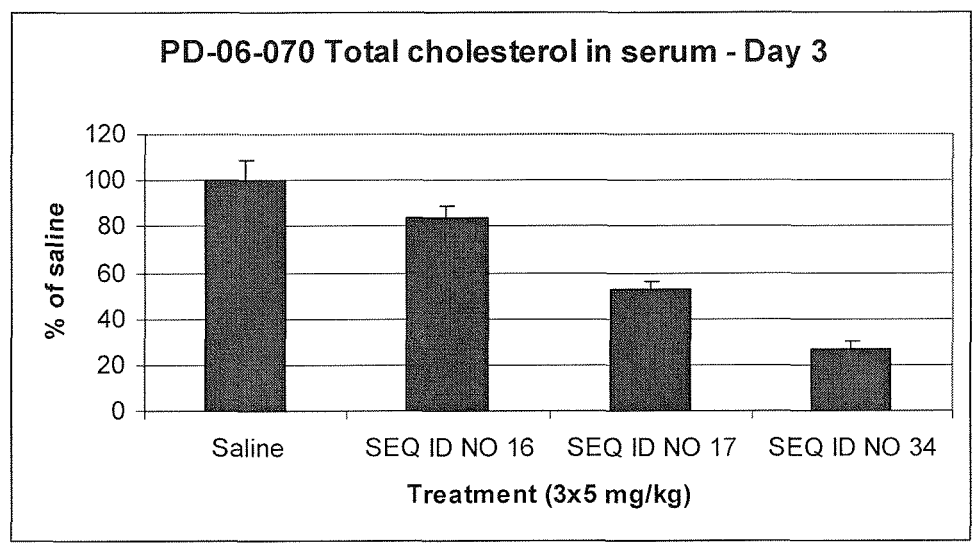
FIG. 30. Serum cholesterol levels at sacrifice (day 3) after dosing of apoB-100 antisense oligo nucleotides of different length. SEQ ID NO refers to those listed in Table 1 of example 2.
Figure 31:
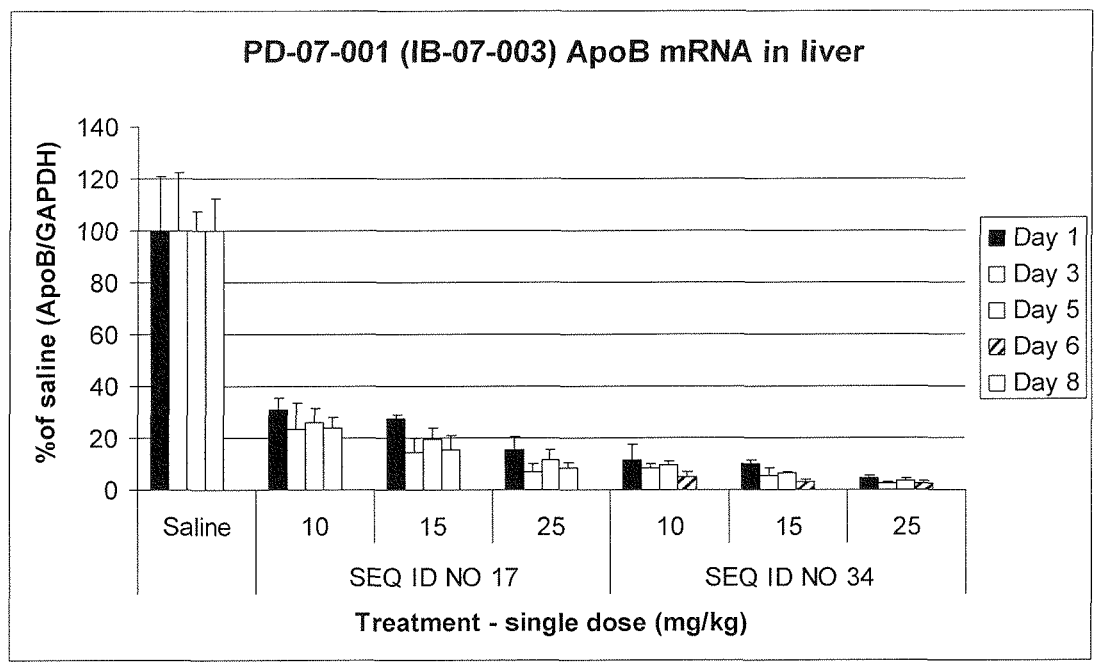
FIG. 31. The apoB-100 mRNA expression was measured by qPCR normalized to the house keeping gene GAPDH and presented relative to the saline group. Mice (n=5) were dosed once and sacrifice different days after dosing, liver was isolated and analysed. SEQ ID NO refers to those listed in Table 1 of example 2.
Figure 32:
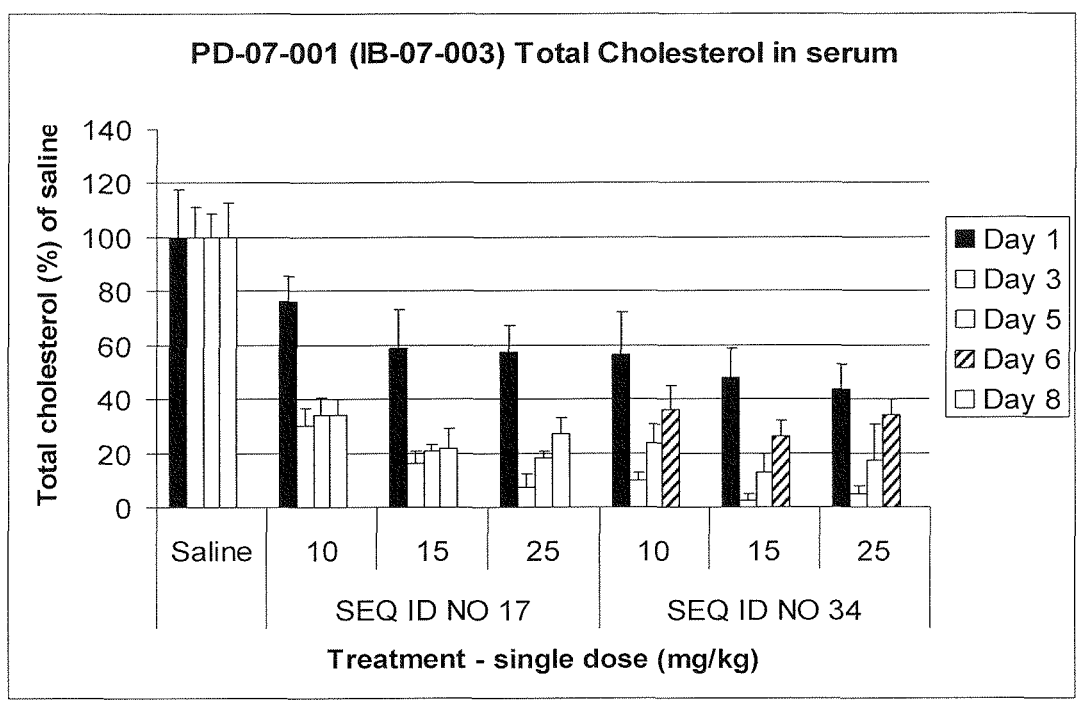
FIG. 32. Serum total cholesterol measured at sacrifice (days 1, 3, 5, 6 and 8 after administration of apoB100 oligo) using a ABX pentra kit., n=5. SEQ ID NO refers to those listed in Table 1 of example 2.
Figure 33:
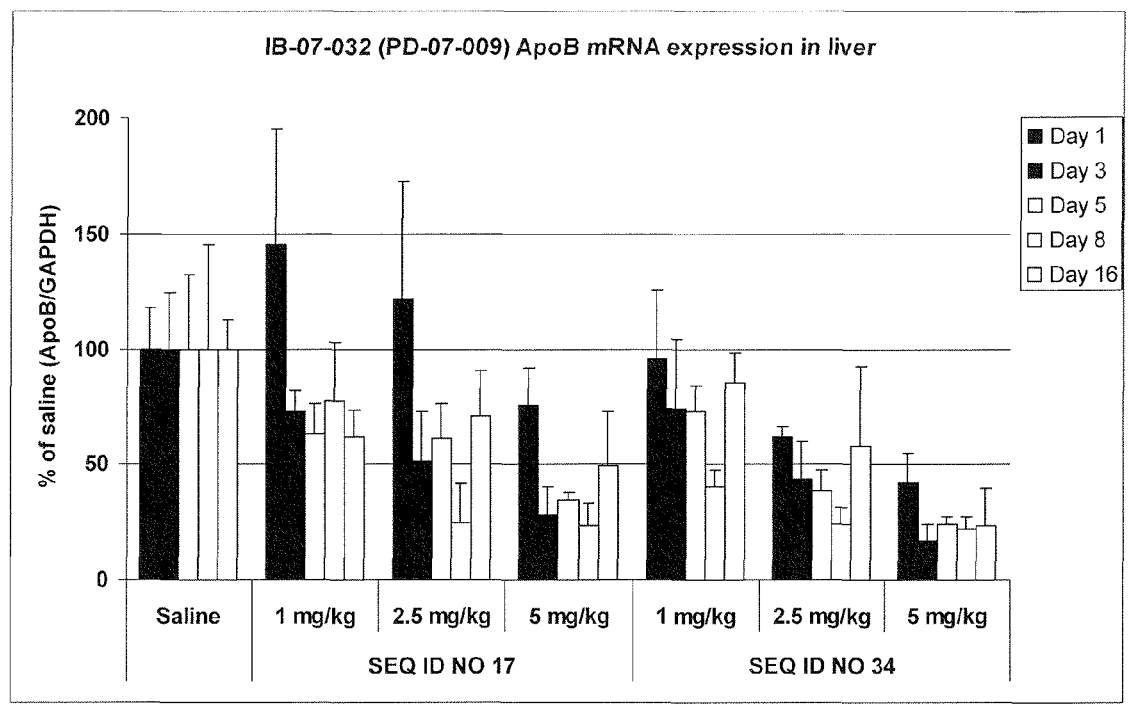
FIG. 33. The apoB-100 mRNA expression was measured by qPCR normalized to the house keeping gene GAPDH and presented relative to the saline group. Mice (n=5) were dosed once and sacrifice different days after dosing, liver was isolated and analysed. SEQ ID NO refers to those listed in Table 1 of example 2.
Figure 34:
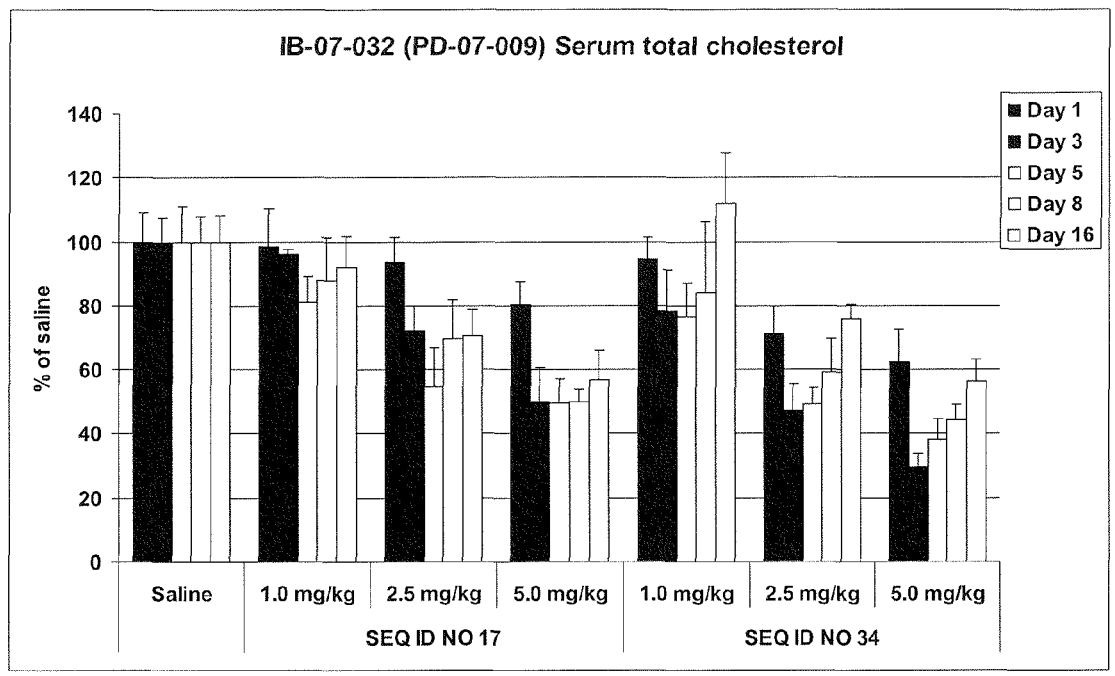
FIG. 34. Serum total cholesterol measured at sacrifice (days 1, 3, 5, 6, 8 and 16 upon apoB-100 antisense oligo administration) using a ABX pentra kit, n=5. SEQ ID NO refers to those listed in Table 1 of example 2.
Figure 35:
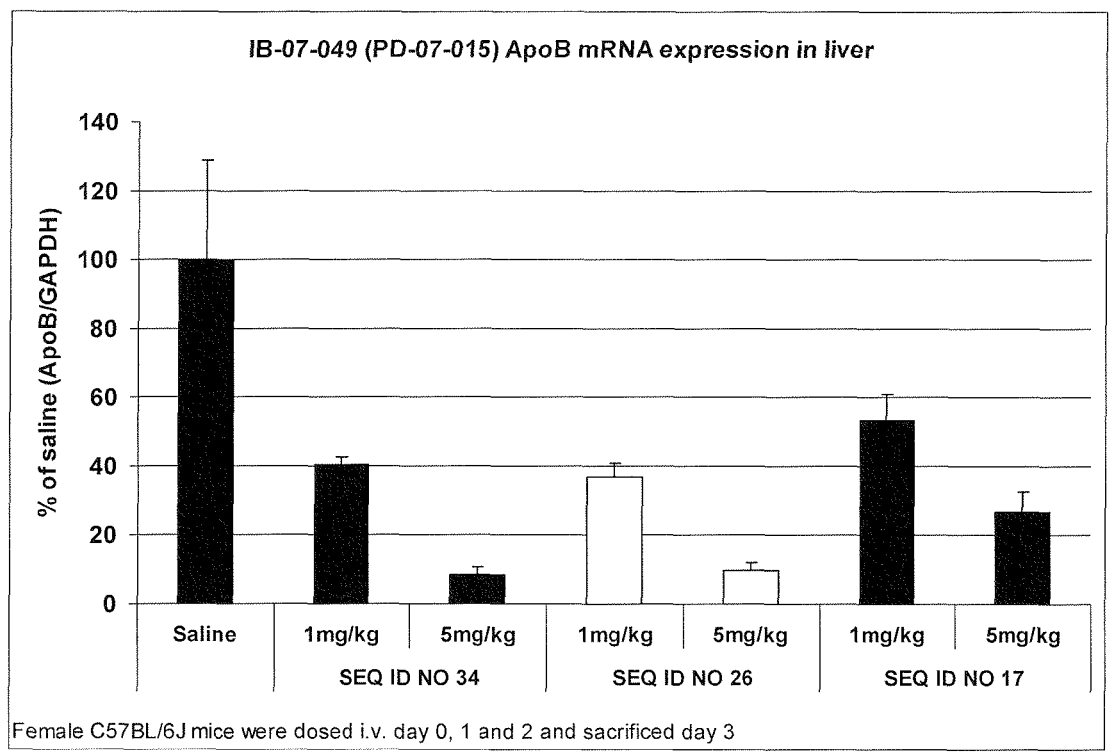
FIG. 35. The apoB-100 mRNA expression was measured by qPCR normalized to the house keeping gene GAPDH and presented relative to the saline group. Mice (n=5) were dosed 1 or 5 mg/kg 3 consecutive days and sacrificed 24 hours after last dosing (day 3), liver was isolated and analysed. SEQ ID NO refers to those listed in Table 1 of example 2.
Figure 36:
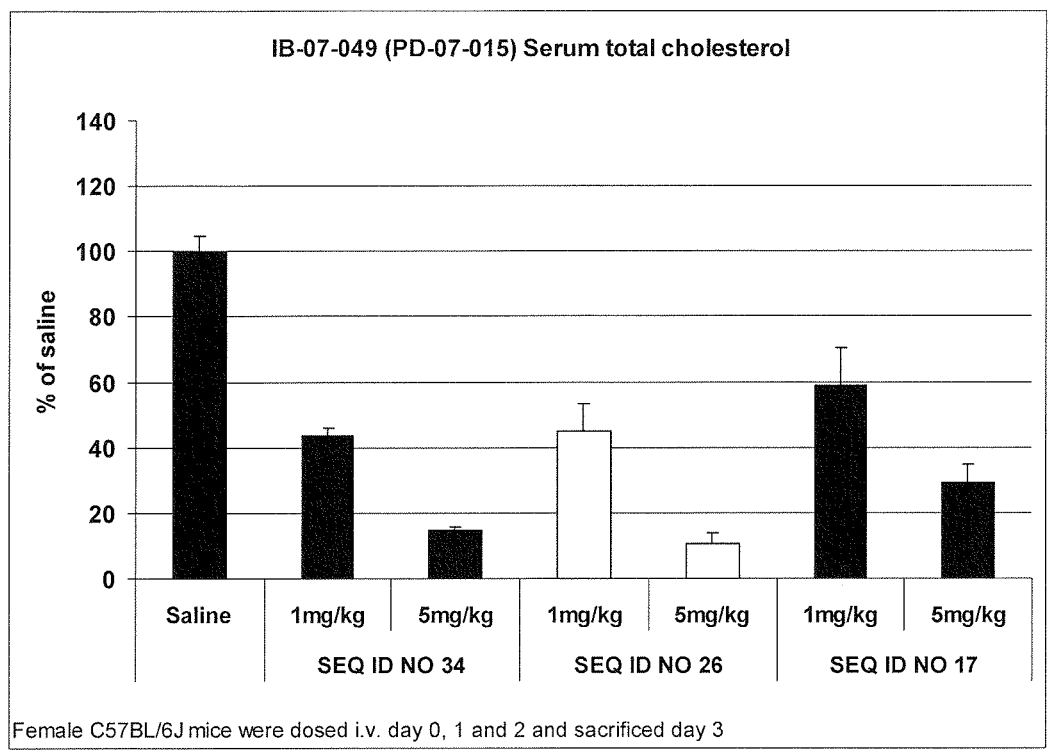
FIG. 36. Serum total cholesterol measured at sacrifice (day 3 after apoB-100 administration) using a ABX pentra kit., n=5. SEQ ID NO refers to those listed in Table 1 of example 2.

Liver enzymes in hypercholesterolemic and normal mice livers were assessed after long term SEQ ID NO: 63 treatment. No changes in the alanine and aspartate aminotransferase (ALT and AST) levels were detected in the SEQ ID NO: 63 treated hypercholesterolemic mice compared to saline control mice (FIGS. 25 and 26). A possibly elevated ALT level was observed in the normal mice after long-term treatment with SEQ ID NO: 63 (FIG. 26).

Example 32

Methods for Performing the LNA-antimiR/Hypercholesterolemic Experiment and Analysis Mice and Dosing.

C57BL/6J female mice (Taconic M&B Laboratory Animals, Ejby, Denmark) were used. All substances were formulated in physiological saline (0.9% NaCl) to final concentration allowing the mice to receive an intraperitoneal injection volume of 10 ml/kg.

In the diet induced obesity study, the mice received a high fat (60EN %) diet (D12492, Research Diets) for 13 weeks to increase their blood cholesterol level before the dosing started. The dose regimen was stretched out to 5½ weeks of 5 mg/kg LNA-antimiR™ twice weekly. Blood plasma was collected once a week during the entire dosing period. After completion of the experiment the mice were sacrificed and RNA extracted from the livers for further analysis. Serum was also collected for analysis of liver enzymes.

Total RNA Extraction.

The dissected livers from sacrificed mice were immediately stored in RNA later (Ambion). Total RNA was extracted with Trizol reagent according to the manufacturer's instructions (Invitrogen), except that the precipitated RNA pellet was washed in 80% ethanol and not vortexed.

MicroRNA-Specific Quantitative RT-PCR.

The miR-122 and let-7a microRNA levels were quantified with TaqMan microRNA Assay (Applied Biosystems) following the manufacturer's instructions. The RT reaction was diluted ten times in water and subsequently used for real time PCR amplification according to the manufacturer's instructions. A two-fold cDNA dilution series from liver total RNA of a saline-treated animal or mock transfected cells cDNA reaction (using 2.5 times more total RNA than in samples) served as standard to ensure a linear range (Ct versus relative copy number) of the amplification. Applied Biosystems 7500 or 7900 real-time PCR instrument was used for amplification.

Quantitative RT-PCR mRNA quantification of selected genes was done using standard Tag Man assays (Applied Biosystems). The reverse transcription reaction was carried out with random decamers, 0.5 µg total RNA, and the M-MLV RT enzyme from Ambion according to a standard protocol. First strand cDNA was subsequently diluted 10 times in nuclease-free water before addition to the RT-PCR reaction mixture. A two-fold cDNA dilution series from liver total RNA of a saline-treated animal or mock transfected cells cDNA reaction (using 2.5 times more total RNA than in samples) served as standard to ensure a linear range (Ct versus relative copy number) of the amplification. Applied Biosystems 7500 or 7900 real-time PCR instrument was used for amplification.

Metabolic Measurements.

Immediately before sacrifice retro-orbital sinus blood was collected in EDTA-coated tubes followed by isolation of the plasma fraction. Total plasma cholesterol was analysed using ABX Pentra Cholesterol CP (Horiba Group, Horiba ABX Diagnostics) according to the manufacturer's instructions.

Liver Enzymes (ALT and AST) Measurement

Serum from each individual mouse was prepared as follows: Blood samples were stored at room temperature for 2 h before centrifugation (10 min, 3000 rpm at room temperature). After centrifugation, serum was harvested and frozen at −20° C.

ALT and AST measurement was performed in 96-well plates using ALT and AST reagents from ABX Pentra according to the manufacturer's instructions. In short, serum samples were diluted 2.5 fold with $H_2O$ and each sample was assayed in duplicate. After addition of 50 µl diluted sample or standard (multical from ABX Pentra) to each well, 200 µl of 37° C. AST or ALT reagent mix was added to each well. Kinetic measurements were performed for 5 min with an interval of 30 s at 340 nm and 37° C. using a spectrophotometer.

Example 33

Modulation of Hepatitis C Replication by LNA-AntimiR (SEQ ID NO: 63)

Oligos used in this example (uppercase: LNA, lowercase DNA, LNA Cs are methyl, and LNAs are preferably B-D-oxy (o subscript after LNA residue):

| SEQ ID NO: | | |
|---|---|---|
| 63 | 5'-$^mC_s^oc_sA_s^ot_st_sG_s^oT_s^oc_sa_s^mC_s^oa_s^mC_s^ot_s^mC_s^{om}C^o$-3' | LNA-antimiR targeting miR-122 |
| 66 | 5'-$A_s^ot_st_sG_s^oT_s^oc_sa_s^mC_s^oa_s^mC_s^ot_s^mC_s^{om}CO$-3' | LNA-antimiR targeting miR-122, |
| 64 | 5'-$^mC_s^oc_sA_s^ot_st_s^mC_s^oT_s^og_sa_s^mC_s^oc_s^mC_s^ot_sA_s^{om}CO$-3' | 4 nt mismatch control to SEQ ID 63 |
| | 2'OMe anti-122: full length (23 nt) 2'OMe modified oligo complementary to miR-122 | |
| | 2'OMe Ctrl: scrambled 2'OMe modified control | |

Hepatitis C (HCV) replication has been shown to be facilitated by miR-122 and consequently, antagonizing miR-122 has been demonstrated to affect HCV replication in a hepatoma cell model in vitro. We assess the efficacy of SEQ ID NO: 63 reducing HCV replication in the Huh-7 based cell model. Preliminary data on SEQ ID NO: 63 along with its truncated version SEQ ID NO: 66 (13-mer LNA-antimiR) and 4 nt mismatch control from inhibiting HCV replication in the Huh-7 cell line transfected with a HCV replicon (NNeo/C-5B). The different LNA-antimiR molecules along with a 2' OMe antisense and scramble oligonucleotide were transfected into Huh-7 cells, HCV was allowed to replicate for 48 hours. Total RNA samples extracted from the Huh-7 cells were subjected to Northern blot analysis.

A significant reduction of HCV RNA was observed in cells treated with SEQ ID NO: 63 as compared to the mock and mismatch control. The inhibition was clearly dose-dependent with both SEQ ID NO: 63 and SEQ ID NO: 66. Interestingly, using a 2'OMe oligonucleotide fully complementary to miR-122 at 50 nM was much less efficient than SEQ ID NO: 63 at the same final concentration. Notably, the 13 nt SEQ ID NO: 66 LNA-antimiR showed comparable efficacy with SEQ ID NO: 63 (Elmen et al. *Nature* 452, 896-899 (17 Apr. 2008)).

Example 34

Luciferase Reporter Assay for Assessing Functional Inhibition of microRNA by LNA-antimiRs and Other microRNA Targeting Oligos Generalisation of New and Enhanced New Design as Preferred Design for Blocking MicroRNA Function Oligos used in this example (uppercase: LNA, lowercase: DNA) to assess LNA-antimiR de-repressing effect on luciferase reporter with microRNA target sequence cloned by blocking respective microRNA:

| SEQ ID NO | target microRNA, oligo sequence | Design |
|---|---|---|
| | target: hsa-miR-122a MIMAT0000421 | |
| 58 | uggagugugacaaugguguuugu | |
| | screened in HUH-7 cell line expressing miR-122 | |
| 67 | miR-122 5'-ACAAacaccattgtcacacTCCA-3' | Full complement, gap |
| 68 | miR-122 5'-acaaacACCATTGTcacactcca-3' | Full complement, block |
| 69 | miR-122 5'-acAaaCacCatTgtCacActCca-3' | Full complement, LNA_3 |
| 63 | miR-122 5'-CcAttGTcaCaCtCC-3' | New design |
| 70 | miR-122 5'-CcAtTGTcaCACtCC-3' | Enhanced new design |

Example 35

Combination Inhibition of the Two Steps (Genomic Replication and Assembly/Secretion) in HCV Lifecycle and Reduction of Complete Viral Replication by Co-Transfecting the LNA Oligo Combination in an In Vitro HCV Replication Modelsystem A cell culture system allowing full HCV replication (genomic and particle assembly release), Huh-7.5 infected with FL-J6/JFH are transfected, using lipofectamine 2000 (Invitrogen) with LNA-antimiR-122 along with LNA-apoB-antisense.

HCV genomic RNA is assessed both intracellularly and extracellularly by HCV specific real-time RT-PCR or northern blot. As well as viral titer excreted from the cells.

Example 36

Inhibition of these Two Steps in HCV Lifecycle and Reduction of Viral Replication By Administrating the LNA Oligo Combination in an In Vivo HCV Replication Modelsystem SCID mice grafted with human hepatocytes replicate HCV. The mice are given i.p. injections with dose combination in the range of but not limited to 5-25 mg/kg LNA-antimiR-122 together with 0.5-2.5 mg/kg or lower LNA-apoB-antisense. Reduced viral production is assesses by measuring HCV RNA (HCV specifice real-time RT-PCR) and infectious particles in the blood, HCV RNA is also assessed in the liver of infected mice (RNA extraction from grafted human hepatocytes and subsequently HCV specifice real-time RT-PCR and northern blot).

Example 37

Inhibition of these Two Steps in HCV Lifecycle and Reduction of Viral Replication by Administrating the LNA Oligo Combination in an In Vivo HCV Replication Modelsystem Chronically HCV infected chimpanzees are injected with a combination of LNA-antimiR-122 and LNA-apoB100 antisense oligonucleotide, with dose ratio such as but not limited to 3-10 mg/kg of LNA-antimiR-122 and 0.1-3 mg/kg of LNA-apoB100 antisense oligonucleotide.

Reduced viral production is assessed by measuring HCV RNA (HCV specifice real-time RT-PCR) and infectious particles in the blood, HCV RNA is also assessed in the liver of infected mice (RNA extraction from grafted human hepatocytes and subsequently HCV specifice real-time RT-PCR and northern blot).

Example 38

A Proposed Treatment Against HCV could Consist of LNA-antimir-122 and LNA-apoB-antisense Using a Weekly i.v. Dosing Such as but not Limited to 1-5 mg/kg LNA-antimiR and 0.1-1 mg/kg LNA-apoB-antisense

Example 39

Measurement of Liver Enzymes (AST and ALT) in a Patient May be Used as a Means of Assessing Efficacy of Treatment. Assessment of Disease Progression and Response to Treatment During the acute phase of HCV infection serum liver transaminases (alanine aminotransferase, ALT/aspartate amino transeferase, AST) are elevated and are measured by colorometric assays (for example, ABX pentra, (Horiba ABX, Montpellier France), the kit is used according to protocol). These levels can still be over normal levels if chronic infection is established.

Example 40

Measuring the Efficacy of the Treatment in Patients (Virus Count)

Methods for diagnosis of HCV infection are standard procedures that are well known in the art for the skilled artisan.

Additional assessment of HCV disease progression and response to treatment:

During the acute phase of HCV infection high virus load can be detected in the blood. The viral load goes down after the acute phase but is more sensitive than liver transaminases. Viral load is assessed by quantitative real-time PCR (for example available from Quest Diagnostics, Lyndhurst, N.J., USA).

The invention claimed is:

1. A method of treating Hepatitis C (HCV) infection in a subject infected with HCV, said method comprising the administration of
   (i) an effective amount of an inhibitor of miR-122, wherein the inhibitor of miR-122 is an oligonucleotide of sequence 5%-CcAttGTcaCaCtCC-3 (SEQ ID NO: 63), wherein an uppercase letter identifies a beta-D-oxy LNA unit, a lowercase letter identifies a DNA unit, a C identifies a 5-methylcytosine LNA unit, and all internucleoside linkages are phosphorothioate; and,
   (ii) an effective amount of an inhibitor of VLDL (very-low-density lipoprotein) assembly.

2. The method according to claim 1, wherein the inhibitor of VLDL assembly is an inhibitor of ApoB (apolipoprotein B).

3. The method according to claim 2, wherein the inhibitor of assembly is an antisense compound which targets ApoB.

4. The method according to claim 1, wherein the inhibitor of VLDL assembly is an inhibitor of MTP (microsomal transfer protein).

5. The method according to claim 1, wherein the inhibitor of VLDL assembly is a statin.

6. The method according to claim 3, wherein the inhibitor of VLDL assembly is an antisense oligonucleotide which comprises a nucleobase sequence which is complementary to a corresponding region of an mRNA which encodes a molecule involved in VLDL assembly.

7. The method according to claim 6, wherein the antisense oligonucleotide which inhibits VLDL assembly has a length of between 9 and 25 nucleobases.

8. The method according to claim 7, wherein the antisense oligonucleotide which inhibits VLDL assembly is a gapmer oligonucleotide which consists of a nucleobase sequence that is 5' A-B-C 3' or 5' A-B-C-D 3', wherein:
   (i) A comprises between 1 and 5 nucleotide analogue units;
   (ii) B comprises 7, 8, 9, 10, 11 or 12 nucleotide units which, when formed in a duplex with a complementary mRNA are capable of recruiting RNAseH;
   (iii) C comprises between 1 and 5 nucleotide analogue units; and
   (iv) D consists of 1, 2, or 3 DNA units.

9. The method according to claim 8, wherein all the nucleotide analogue units present in A and C are independently selected from the group consisting of 2'-O-alkyl-RNA units, 2'-OMe-RNA units, 2'-amino-DNA units, 2' fluoro-DNA units, LNA units, PNA units, HNA units, and INA units.

10. The method according to claim 9, wherein the nucleotide analogue units present in A and C are all the same.

11. The method according to claim 1, wherein the miR-122 inhibitor is administered together with the inhibitor of VLDL assembly.

12. The method according to claim 1, wherein the miR-122 inhibitor and the inhibitor of VLDL assembly are administered separately.

13. The method according to claim 7, wherein the antisense oligonucleotide which inhibits VLDL assembly has a length of 9, 10, 11, 13, 14, 15, 16, 17, 18, 19, 20, 21, 22, 23, 24, or 25 nucleobases.

14. The method according to claim 10, wherein the nucleotide analogue units present in A and C are all LNA units.

* * * * *

UNITED STATES PATENT AND TRADEMARK OFFICE
CERTIFICATE OF CORRECTION

PATENT NO. : 8,440,637 B2  Page 1 of 1
APPLICATION NO. : 12/681591
DATED : May 14, 2013
INVENTOR(S) : Joacim Elmen It is certified that error appears in the above-identified patent and that said Letters Patent is hereby corrected as shown below:

In the Claims:

In claim 1, at column 149, line 16, replace "5%-CcAttGTcaCaCtCC-3" with --5'-CcAttGTcaCaCtCC-3'--.

In claim 3, at column 149, line 27, replace "assembly" with --VLDL assembly--.

In claim 13, at column 150, line 35, replace "11, 13" with --11, 12, 13--.

Signed and Sealed this
Second Day of July, 2013

Teresa Stanek Rea
*Acting Director of the United States Patent and Trademark Office*